(12) United States Patent
Zheng et al.

(10) Patent No.: US 7,826,982 B2
(45) Date of Patent: Nov. 2, 2010

(54) METHOD OF IDENTIFYING INHIBITORS USING A 3-D STRUCTURE OF RAC-1 GTPASE

(75) Inventors: Yi Zheng, Cincinnati, OH (US); Nicolas Nassar, Coram, NY (US); Karlheinz R. Skowronek, Huntington Station, NY (US)

(73) Assignees: Children's Hospital Medical Center, Cincinnati, OH (US); The Research Foundation of State University of New York, Stony Brook, NY (US)

( * ) Notice: Subject to any disclaimer, the term of this patent is extended or adjusted under 35 U.S.C. 154(b) by 58 days.

(21) Appl. No.: 11/496,959

(22) Filed: Jul. 31, 2006
(Under 37 CFR 1.47)

(65) Prior Publication Data
US 2007/0155766 A1    Jul. 5, 2007

Related U.S. Application Data

(60) Provisional application No. 60/703,587, filed on Jul. 29, 2005.

(51) Int. Cl.
*G01N 31/00* (2006.01)
*G06G 7/58* (2006.01)

(52) U.S. Cl. ............................................ 702/27; 703/11

(58) Field of Classification Search ........................ None
See application file for complete search history.

(56) References Cited

U.S. PATENT DOCUMENTS

| | | |
|---|---|---|
| 5,141,851 A | 8/1992 | Brown et al. |
| 5,238,922 A | 8/1993 | Graham et al. |
| 5,420,245 A | 5/1995 | Brown et al. |
| 5,420,334 A | 5/1995 | Singh et al. |
| 5,436,128 A | 7/1995 | Harpold et al. |
| 5,447,922 A | 9/1995 | Lawrence et al. |
| 5,470,832 A | 11/1995 | Gibbs et al. |
| 5,482,954 A | 1/1996 | Kohn et al. |
| 5,510,510 A | 4/1996 | Patel et al. |
| 5,523,430 A | 6/1996 | Patel et al. |
| 5,567,841 A | 10/1996 | Magnin et al. |
| 5,574,025 A | 11/1996 | Anthony et al. |
| 5,602,098 A | 2/1997 | Sebti et al. |
| 5,618,964 A | 4/1997 | Cheng et al. |
| 5,629,302 A | 5/1997 | Eugster et al. |
| 5,631,401 A | 5/1997 | Stein et al. |
| 5,705,686 A | 1/1998 | Sebti et al. |
| 5,756,528 A | 5/1998 | Anthony et al. |
| 5,773,455 A | 6/1998 | Dong et al. |
| 5,786,193 A | 7/1998 | Greene et al. |
| 5,817,678 A | 10/1998 | Kim et al. |
| 5,830,868 A | 11/1998 | Bolton et al. |
| 5,834,434 A | 11/1998 | Sebti et al. |
| 5,843,941 A | 12/1998 | Marsters, Jr. et al. |
| 5,928,924 A | 7/1999 | Greene et al. |
| 5,929,077 A | 7/1999 | Leftheris |
| 6,011,029 A | 1/2000 | Ding et al. |
| 6,083,979 A | 7/2000 | Sebti et al. |
| 6,156,746 A | 12/2000 | Leftheris et al. |
| 6,166,067 A | 12/2000 | Kriimer et al. |
| 6,191,147 B1 | 2/2001 | Brown et al. |
| 6,194,438 B1 | 2/2001 | Yang et al. |
| 6,197,771 B1 | 3/2001 | Bigge et al. |
| 6,211,193 B1 | 4/2001 | Remiszewski et al. |
| 6,214,827 B1 | 4/2001 | Afonso et al. |
| 6,214,828 B1 | 4/2001 | Doll et al. |
| 6,218,401 B1 | 4/2001 | Afonso et al. |
| 6,225,322 B1 | 5/2001 | Cooper et al. |
| 6,228,856 B1 | 5/2001 | Njoroge et al. |
| 6,228,865 B1 | 5/2001 | Doll et al. |
| 6,239,140 B1 | 5/2001 | Cooper et al. |
| 6,242,433 B1 | 6/2001 | Balsamo et al. |
| 6,242,458 B1 | 6/2001 | Bishop et al. |
| 6,248,756 B1 | 6/2001 | Anthony et al. |
| 6,258,824 B1 | 7/2001 | Yang |
| 6,262,110 B1 | 7/2001 | Shaikenov et al. |

(Continued)

FOREIGN PATENT DOCUMENTS

WO    WO 2004/076445    9/2004

(Continued)

OTHER PUBLICATIONS

Grizot et al., "Crystal Structure of the Rac1-RhoGDI Complex Involved in NADPH Oxidase Activation", Biochemistry 40:10007-10013, 2001.*

(Continued)

*Primary Examiner*—David J Steadman
(74) *Attorney, Agent, or Firm*—Knobbe Martens Olson & Bear, LLP

(57) ABSTRACT

The preferred embodiments generally relate to methods and compositions that affect the GTP-binding activity of members of the Rho family GTPases, preferably Rac (Rac1, Rac2 and/or Rac3), such compositions include compounds that modulate the GTP/GDP exchange activity, along with uses for the compounds including screening for compounds which recognize Rac GTPase, and methods of treating pathological conditions associated or related to a Rho family GTPase, including Rac. The preferred embodiments also relate to methods of using such compounds, or derivatives thereof, e.g., in therapeutics, diagnostics, and as research tools.

1 Claim, 6 Drawing Sheets

U.S. PATENT DOCUMENTS

| | | | |
|---|---|---|---|
| 6,265,382 | B1 | 7/2001 | Doherty et al. |
| 6,268,394 | B1 | 7/2001 | Shaikenov et al. |
| 6,277,854 | B1 | 8/2001 | Njoroge et al. |
| 6,294,552 | B1 | 9/2001 | Lyssikatos et al. |
| 6,316,462 | B1 | 11/2001 | Bishop et al. |
| 6,329,376 | B1 | 12/2001 | Bergman |
| 6,358,968 | B1 | 3/2002 | Remiszewski et al. |
| 6,362,188 | B1 | 3/2002 | Guzi et al. |
| 6,372,747 | B1 | 4/2002 | Taveras et al. |
| 6,376,496 | B1 | 4/2002 | Hartman et al. |
| 6,387,903 | B1 | 5/2002 | Dinsmore et al. |
| 6,387,905 | B2 | 5/2002 | Njoroje et al. |
| 6,387,926 | B1 | 5/2002 | Bhide et al. |
| 6,387,948 | B1 | 5/2002 | Kwon et al. |
| 6,399,615 | B1 | 6/2002 | Guzi et al. |
| 6,403,581 | B1 | 6/2002 | Ayral-Kaloustian et al. |
| 6,410,541 | B2 | 6/2002 | Remiszewski et al. |
| 6,423,751 | B1 | 7/2002 | Liao |
| 6,426,352 | B1 | 7/2002 | Njoroge et al. |
| 6,432,959 | B1 | 8/2002 | Cooper et al. |
| 6,440,974 | B2 | 8/2002 | Doll et al. |
| 6,440,989 | B2 | 8/2002 | Afonso et al. |
| 6,441,017 | B1 | 8/2002 | Bell et al. |
| 6,451,812 | B1 | 9/2002 | End et al. |
| 6,458,783 | B1 | 10/2002 | Ding et al. |
| 6,458,935 | B1 | 10/2002 | Burns et al. |
| 6,492,381 | B1 | 12/2002 | Bishop et al. |
| 6,495,564 | B1 | 12/2002 | Lyssikatos et al. |
| 6,500,841 | B1 | 12/2002 | DeSolms et al. |
| 6,511,800 | B1 | 1/2003 | Singh |
| 6,528,523 | B2 | 3/2003 | Njoroge et al. |
| 6,535,820 | B1 | 3/2003 | Strickland et al. |
| 6,539,309 | B1 | 3/2003 | Strickland et al. |
| 6,545,020 | B1 | 4/2003 | Van Ginckel et al. |
| 6,572,850 | B1 | 6/2003 | Mandeville, III et al. |
| 6,576,639 | B1 | 6/2003 | Doll et al. |
| 6,579,887 | B2 | 6/2003 | Lyssikatos et al. |
| 6,586,447 | B1 | 7/2003 | Lyssikatos et al. |
| 6,586,461 | B1 | 7/2003 | Gibbs |
| 6,596,735 | B1 | 7/2003 | Yang |
| 6,615,359 | B2 | 9/2003 | Eyres et al. |
| 6,649,638 | B1 | 11/2003 | Brown et al. |
| 6,897,028 | B1 * | 5/2005 | Makowski et al. .............. 506/4 |
| 6,998,233 | B2 * | 2/2006 | Wells et al. ...................... 435/6 |
| 2004/0137518 | A1 * | 7/2004 | Lambert et al. .............. 435/7.1 |
| 2005/0049294 | A1 | 3/2005 | Palladino et al. |
| 2005/0069553 | A1 | 3/2005 | Zheng et al. |
| 2005/0238666 | A1 | 10/2005 | Williams et al. |
| 2006/0004032 | A1 | 1/2006 | Zheng et al. |
| 2006/0135532 | A1 | 6/2006 | Bryant et al. |

FOREIGN PATENT DOCUMENTS

| | | |
|---|---|---|
| WO | WO 2005/051392 | 6/2005 |
| WO | WO 2006/055833 | 5/2006 |

OTHER PUBLICATIONS

Fiegen et al., "Alternative Splicing of Rac1 Generates Rac1b, a Self-activating GTPase", J. Biol. Chem. 279:4743-4749, 2004.*
Flower, "Drug Design, Cutting Edge Approaches," Royal Society of Chemistry, Cambridge, UK, 2002, p. 25.*
Nasser et al., Curr. Top. Med. Chem. 6:109-1116, 2006.*
Deininger et al., Blood, vol. 96(10), 3343-3356, (2000).
Groffen et al., "Two candidate breast cancer genes on chromosome", Grant #: 1RB-0001, 3 pages, (1995), www.bcrp.org.
International Search Report issued on the corresponding PCT Application No. PCT/US06/29873, dated Jun. 4, 2008.
Macherla, V.R. et al., "Structure-Activity Relationship Studies of Salinosporamide A (NPI-0052), a Novel Marine Derived Proteasome Inhibitor", J. Med. Chem., 48:3684-3687, (2005).
Silver, P. (Dana-Farber Cancer Ins.), May 2004, 1 page, Defense Technical Information Center (DTIC) Accession No. ADA 426138.
U.S. Appl. No. 60/523,599, filed Nov. 20, 2003.
U.S. Appl. No. 60/629,380, filed Nov. 19, 2004.
U.S. Appl. No. 60/703,587, filed Jul. 29, 2004.
File History of the related U.S. Appl. No. 10/994,165, for the period of May 3, 2008-Sep. 30, 2008.
File History of the related U.S. Appl. No. 11/283,556, for the period of Jul. 27,2006-Sep. 30, 2008.
Akbar, H. et al., "Rac2 GTPase plays a critical role in platelet adhesion as well as in sustenance and perpetuation of platelet aggregation." Blood (ASH Annual Meeting Abstracts) 104, Abstract 3523, 2004.
Arikawa, K. et al., "Ligand-dependent inhibition of B16 melanoma cell migration and invasion via endogenous S1P2 G protein-coupled receptor. Requirement of inhibition of cellular RAC activity." J Biol Chem., Aug. 29, 2003 278(35):32841-51. Epub Jun. 16, 2003.
Bastola, D. R. et al., "Downregulation of PTEN/MMAC/TEP1 expression in human prostate cancer cell line DU145 by growth stiluli." Mol. Cell Biochem., 236:75-81, 2002.
Blan, A.D. et al., "Platelet activation in hypertension." J. Hum. Hypertens., 11:607-609, 1997.
Broijersen, A. et al., "Platelet activity in vivo in hyperlipoproteinemia-importance of combined hyperlipidemia." Thromb. Haemost., 79:268-275, 2001.
Cancelas et al., Nat Med. Aug. 2005;11(8):886-91. Epub Jul. 17, 2005.
ISR issued on PCT/US04/39090, Apr. 5, 2005, Children's Hospital Medical Center.
ISR issued on PCT/US05/41949, Jun. 27, 2006, Children's Hospital Medical Center.
Clark, R.D. et al., "Consensus scoring for ligand/protein interactions." J. Mol. Graph. Model. 20:281-295, 2002.
Del Pozo, M. A. et al., "Adhesion to the extracellular matrix regulates the coupling of the small GTPase Rac to its effector PAK." EMBO J., 19:2008-2014, 2000.
Dunbrack, Jr. et al., Bayesian statistical analysis of protein side-chain rotamer preferences, Protein Science, 6:1661-1681, 1997.
Engers, R. et al., "Tiaml mutations in human renal-cell carcinomas." Int. J. Cancer, 88:369-376, 2000.
Etienne-Manneville, S. et al., "Rho GTPases in Cell Biology," Nature, vol. 420, 629-635, Dec. 2002.
Fitzgerald, D.J. et al., "Platelet activation in unstable coronary heart disease." N. Engl.J. Med., 315:983-989, 1996.
Fritz, G. et al., "Rho GTPases are over-expressed in human tumors." Int. J. Cancer, 81:682-687, 1999.
Gao, Y. et al., "Trp(56) of rac1 specifies interaction with a subset of guanine nucleotide exchange factors." J. Biol. Chem., 276:47530:-47541, 2001.
Gao, Y. et al., "Rational design and characterization of a Rac GTPase-specific small molecula inhibitor." Proc. Natl. Acad. Sci. U.S.A., 101;7618-7623, 2004.
Gawaz, M. "Role of platelets in coronary thrombosis and reperfusion of ischemic myocardium." Cardiovas. Res., 61;498-511, 2004.
Goodford, J. Med. Chem., 28:849-857, 1985.
Gruneberg, S. et al., "Subnanomolar Inhibitors from Computer Screening: A Model Study Using Human Carbonic Anhydrase II Agnew." Chem. Int. Ed Engl., 40:389-393, 2001.
Gu, Y. et al., Science, 302;445-449, 2003.
Guo, F. et al., "P19arf-p53 tumor suppressor pathway regulates cell motility by suppression of PI3 kinase and Rac1 GTPase activities." J. Biol. Chem. Paper in press, 2003.
Guyatt, G. et al., "Grades of recommendation for antithrombotic agents." Chest, 119:3S-7S, 2001.
Haszon, I. et al., "Platelet aggregation, blood viscosity and serum lipids in hypertensive and obese children." Eur. J. Pediatr., 162:385-390, 2003.
Hawkins, P. T. et al., "PDGF stimulates an increase in GTP-Rac via activation of phosphoinostitide 3-kinase." Curr. Biol. 5:393-403, 1995.
Heeschen, C. et al., "Soluble CD40 ligand in acute coronary syndromes." N. Engl. J. Med., 348;1104-1111, 2003.

Huo, Y. et al., "role of platelets in development of atherosclerosis." *Trends Cardiovasc. Med.*, 14:18-22, 2004.

Hurst, T. "Flexible 3D searching: the directed tweak technique." *J. Chem. Inf. Comput. Sci.*, 34:190-196, 1994.

Kaempchen, K. et al., "Upregulation of the Rac1/JNK signaling pathway in primary human schwannoma cells." *Hum Mol Genet.* May 2003, 3(5):483-95.

Kaighn, M. E. et al., "Establishment and characterization of a human prostatic carcinoma cell line (PC-3)." *Invest Urol.*, 17:16-23, 1979.

Kamai, T. et al., "Overexpression of RhoA mRNA is associated with advanced stage in testicular germ cell tumor." *BJU. Int.*, 87:227-231, 2001.

Karnoub et al., "Molecular basis for Rac1 recognition by guanine nucleotide exchange factors." *Nat. Struct. Biol.*, 8:1037-1041, 2001.

Kato-Stankiewicz, J. et al., "Inhibitors of Ras/Raf-1 interaction identified by two-hybrid screening revert Ras-dependent transformation phenotypes in human cancer cells." 99:14398-13303, 2002.

Khosravi-Far et al., "Activation of Rac1, RhoA, and mitogen-activated protein kinases is required for Ras transformation." *Mol. Cell Biol.*, 15:6443-6453, 1995.

Lang, S.H. et al., "Enhanced expression of vimentin in momtile prostate cell lines in poorly differntiated and metastatic prostate carcinoma." *Prostate*, 52:253-263, 2002.

Liliental, J. et al., "Genetic deletion of the Pten tumor suppressor gene promotes cell motility by activation of Rac1 and Cdc42 GTPases." *Curr. Bio.*, 10:401-404, 2000.

Manduteanu, I. et al., "Increased adhesion of human diabetic platelets to cultured valvular endothelial cells." *J. Submicrosc. Cytol. Pathol.*, 24;539-547, 1992.

Mira, J. P. et al., "Endogenous, Hyperactive Rac3 controls proliferation of breast cancer cells by a p21-activated kinase-dependent pathway." *Proc. Natl. Acad. Sci. U.S.A.*, 97:185-189, 2000.

Movilla, N. et al., "How Vav proteins discriminate the GTPases Rac1 and RhoA from Cdc42." *Oncogene*, 20:8057-8065, 2001.

Narumiya, S. et al., *Cell Signal*, 5:9-19, 1993.

Nityanand, S. et al., "Platelets in essential hypertension." *Thromb. Res.*, 72:447-454, 1993.

Perola, E. et al., "Successful virtual screening of a chemical database for farnesyltransferase inhibitor leads." *J. Med. Chem.*, 43:401-408, 2000.

Preston, R. A., et al., "Effects of severe hypertension on endothelial and platelet microparticles." *Hypertension*, 41:211-217, 2003.

Qiu et al., "Cdc42 regulates anchorage-independent growth and is necessary for Ras transformation." *Mol. Cell Biol.*, 17:3449-3458, 1997.

Rarey et al., "A fast flexible docking method using an incremental construction algorithm." *J. Mol. Biol.*, 261:470-489, 1996.

Ridley et al., "The small GTP-binding protein rac regulates growth factor-induced membrane ruffling." *Cell*, 70:401-410, 1992.

Roberts, A. W. et al., *Immunity*, 10;183-196, 1999.

Sahai, E. et al., "Differing modes of tumor cell invasion have distinct requirements for Rho/ROCK signalling and extracellular proteolysis.", *Nat Cell Biol.*, Aug. 2003, 5(8):711-9.

Sahai, E., "Rho-GTPases and cancer." *Nature Reviews Cancer*, 2:133-142, 2002.

Schmidt, A. et al., "Guanine nucleotide exchange factors for Rho GTPases: turning on the switch." *Genes Dev.*, 16:1587-1609, 2002.

Schmitz, A. A. et al., "Rho GtPases: signaling, migration, and invasion." *Exp. Cell Res.*, 261:1-12, 2000.

Schnelzer, A. et al., "Rac1 in human breast cancer: overexpression, mutation analysis, and characterization of a new isoform, Rac1b." *Oncogene*, 19:3013-3020, 2000.

Sekine, A. et al., *J. Biol. Chem.*, 264:8602-8605, 1989.

Serebruany, V. L. et al., "Increased soluble platelet/endothelial cellular adhesion molecule01 and osteonectin leveles in patients with severe congestive heart failure. Independence of . . . " *Eur. J. Heart Failure*, 1;243-249, 1999.

Skorski, T. et al., "BCR/ABL-mediated leukemogenesis requires the activity of the small GTP-binding protein Rac." *Proc Natl Acad Sci U S A.* 95(20):11858-62, 1998.

Sorof, J. et al., "Obesity hypertension in children. A problem of epidemic proportions." *Hypertension*, 40: 441-447, 2002.

Stepan, V. M. et al., "Gastrin induces c-fos gene transcription via multiple signaling pathways." *Am. J. Physiol*, 276:G415-G424, 1999.

Suwa, H. et al., "Overexpression of the rhoC gene correlates with progression of ductal adenocarcinoma of the pancreas." *Br. J. Cancer*, 77:147-152, 1998.

Symons, M., "Adhesion signaling: PAK meets Rac on solid ground." *Curr. Biol.*, 10:R535-R537, 2000.

The SALT collaborative group, "Swedish Aspirin Low Dose Trial of 75 mg aspirin as secondary prophylaxis after cerebrovasular ischemic events." *Lancet*, 338;1345-1349, 1991.

Tschoepe, D. et al., "Platelets in diabetes: the role in hemosstatic regulation in atherosclerosis." *Semin. Thromb. Hemost.*, 19:122-128, 1993.

Van Aelst, L. et al., "Rho GTPases and signaling networks." *Genes Dev.*, 11:2295-2322, 1997.

Waszkowycz, B., "Large-scale virtual screening for discovering leads in the postgenomic era." *IBM systems J.*, 40:360-376, 2001.

Winocour, P.D., "Platelet abnormalities in diabetes mellitus." *Diabetes*, 41 (Suppl 2):26-31, 1992.

Worthylake, D. K. et al., "Crystal structure of Rac1 in complex with the guanine nucleotide exchange region of Tiam1." *Nature*, 408:682-688, 2000.

Zhao JJ, et al., "Human mammary epithelial cell transformation through the activation of phosphatidylinositol 3-kinase." *Cancer Cell.*, May 2003, 3(5):483-95.

Zheng, Y., "Dbl family guanine nucleotide exchante factors." *Trends Biochem. Sci.*, 26:724-732, 2001.

Zheng, Y. et al., "Direct involvement of the small GTP-binding protein Rho in Ibc oncogene function." *J. Biol. Chem.*, 270:9031-9034, 1995.

File History for U.S. Appl. No. 10/994,165, filed Nov. 19, 2004.
File History for U.S. Appl. No. 11/283,556, filed Nov. 18, 2005.

\* cited by examiner

METHOD OF IDENTIFYING INHIBITORS USING A 3-D STRUCTURE OF RAC-1 GTPASE

CROSS REFERENCE TO RELATED APPLICATIONS

This patent application claims priority under 35 U.S.C. §119(e) to U.S. Provisional Patent No. 60/703,587, filed Jul. 29, 2005, which is incorporated herein by reference in its entirety.

STATEMENT REGARDING FEDERALLY SPONSORED RESEARCH

This invention was made in part with Government support under Grant No. R01 GM60523 and No. R01 GM53943 awarded by the National Institutes of Health. The Government can have certain rights in this invention.

BACKGROUND OF THE INVENTION

1. Field of the Invention

The present invention generally relates to methods and compositions that affect the GTP-binding activity of members of the Ras superfamily GTPases, along with uses for the compounds including screening for compounds that recognize Rac GTPase, and methods of treating pathological conditions associated or related to a Ras superfamily GTPase.

2. Description of the Related Art

Rho family GTPases are molecular switches that control signaling pathways regulating cytoskeleton reorganization, gene expression, cell cycle progression, cell survival, and other cellular processes (Etienne-Manneville, 2002), which is incorporated herein by reference in its entirety.

Rho family proteins constitute one of three major branches of the Ras superfamily. Rho proteins share approximately 30 percent amino acid identity with the Ras proteins. At least 14 mammalian Rho family proteins have been identified thus far, including RhoA, RhoB, RhoC, RhoD, RhoE/Rnd3, Rnd1/Rho6, Rnd2/Rho7, RhoG, Rac1, Rac2, Rac3, Cdc42, TC10, and TTF.

SUMMARY OF THE INVENTION

The preferred embodiments provide compounds that are potent and selective inhibitors of Rho GTPases. Specifically, these compounds can be used to inhibit Rho-related Rac GTPase. These inhibitors can be used to treat diseases associated with Rac disregulation. Furthermore, these compounds can be used to treat cancers associated with Rac disregulation. In view of their activity, these compounds can also be used in treating other disorders responding to the inhibition of Rac.

One embodiment comprises a method for treating an indication mediated by mammalian Rho family proteins, comprising administering to a subject in need of such treatment a safe and effective amount of at least one compound having the formula (IIa):

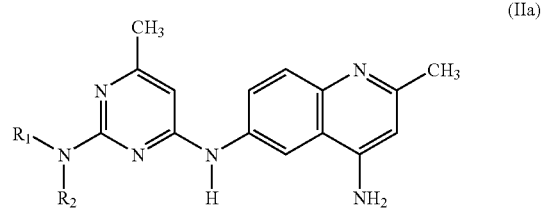

wherein:

$R_1$ to $R_2$ are independently selected from the group consisting of H, —X-Alk, —X-Alk-X', and —X—Y—X'; wherein X is —$CR_7R_8$; X' is —$CHR_7R_8$; Alk is a $C_2$-$C_{18}$ substituted or unsubstituted hydrocarbon chain; Y is a $C_2$-$C_8$ substituted or unsubstituted alkylene chain; $R_6$ is H or (C1-C4) alkyl; and $R_7$ and $R_8$ are independently selected from the group consisting of H or (C1-C4) alkyl or a salt of a compound of formula (IIa). In some such methods, Alk is substituted with halo, halo (C1-C4) alkoxy, (C3-C8) cycloalkyl, hydroxy, or acetyl. In some such methods, Y is substituted with an NR6 group.

One embodiment comprises a method for treating an indication mediated by mammalian Rho family proteins, comprising administering to a subject in need of such treatment a safe and effective amount of at least one compound having the formula (III):

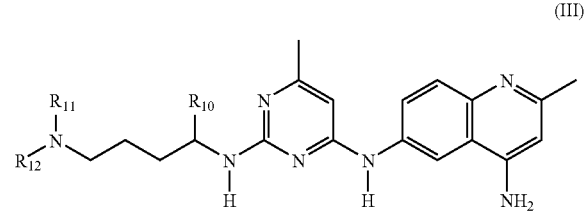

wherein:

$R_{10}$ to $R_{12}$ are independently selected from the group consisting of H, halo, (C1-C4) alkyl, branched (C3-C4) alkyl, halo (C1-C4) alkyl, (C1-C4) alkoxy, $NO_2$, and $NH_2$; or a salt of a compound of formula (III). In some such methods, $R_{10}$ to $R_{12}$ are independently selected from the group consisting of H, (C1-C4) alkyl, or branched (C3-C4) alkyl.

One embodiment comprises a method for treating an indication mediated by mammalian Rho family proteins comprising administering to a subject in need of such treatment a safe and effective amount of at least one compound having the formula (IV):

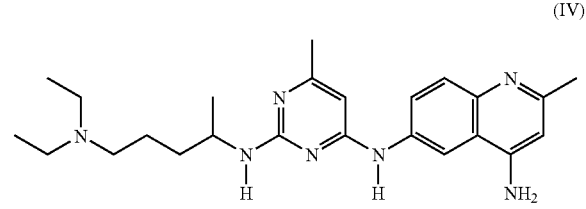

or pharmaceutically acceptable salts thereof. In some such methods, the compound is N6-(2-((4-(diethylamino) 1-methylbutyl)amino)-6-methyl-4-pyrimidinyl)-2-methyl-4,6-quinolinediamine. In some such methods, the mammalian Rho family GTPase is selected from the group consisting of RhoA, RhoB, RhoC, RhoD, RhoE/Rnd3, Rnd1/Rho6, Rnd2/Rho7, RhoG, Rac1, Rac2, Rac3, Cdc42, TC10, TTF/RhoH, RhoL, Chp, WRCH1, TCL, RIF, and combinations thereof. In some such methods, the Rho GTPase is selected from the group comprising Rac1, Rac2, Rac3, and combinations thereof. In some such methods, the Rho GTPase is Rac1. In some such methods, the compound interacts with the Rho regulatory pathway via interaction with a Rac GTPase. In some such methods, the Rac GTPase is selected from the group consisting of Rac1, Rac2, and Rac3. In some such methods, the Rac GTPase is Rac1. In some such methods, the indication is selected from the group consisting of leukemia, prostate cancer, ovarian cancer, pancreas cancer, lung cancer, breast cancer, liver cancer, head and neck cancer, colon cancer, bladder cancer, non-Hodgkin's lymphoma cancer and melanoma. In some such methods, the indication is abnormal cell proliferation. In some such methods, the indication is cancer cell proliferation. In some such methods, the indication is selected from the group consisting of hypertension, atherosclerosis, restenosis, cerebral ischemia, cerebral vasospasm, neuronal degeneration, spinal cord injury, cancer of the breast, colon, prostate, ovaries, brain or lung, thrombotic disorders, asthma, glaucoma, osteoporosis and erectile dysfunction.

One embodiment comprises a pharmaceutical composition comprising N6-(2-((4-(diethylamino)-1-methylbutyl)amino)-6-methyl-4-py-rimidinyl)-2-methyl-4,6-quino-linediamine and a pharmaceutically-acceptable carrier. In some such pharmaceutical compositions, N6-(2-((4-(diethylamino)-1-methylbutyl)amino)-6-methyl-4-pyrimidinyl)-2-methyl-4,6-quinolinediamine compound is at least 1% by weight. Some such pharmaceutical compositions further comprise an additional pharmaceutically active agent. In some such pharmaceutical compositions, the second pharmaceutically active agent is selected from the group consisting of farnesyl protein transferase inhibitors, prenyl protein transferase inhibitors, geranylgeranyl-protein transferase inhibitors, toxins and combinations thereof.

One embodiment comprises a crystal of Rac-1 GTPase having a space group $P2_1$ and unit cell dimensions of about a=41.8 Angstroms, b=40.0 Angstroms, c=52.1 Angstroms, and β=105.93°. In some such crystals, Rac-1 GTPase is complexed with a compound having the formula (IIa):

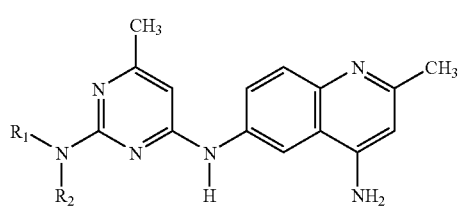

(IIa)

wherein:
$R_1$ to $R_2$ are independently selected from the group consisting of H, —X-Alk, —X-Alk-X', and —X—Y—X'; wherein
X is —$CR_7R_8$;
X' is —$CHR_7R_8$;
Alk is a $C_2$-$C_{18}$ substituted or unsubstituted hydrocarbon chain;
Y is a $C_2$-$C_8$ substituted or unsubstituted alkylene chain;
$R_6$ is H or (C1-C4) alkyl; and
$R_7$ and $R_8$ are independently selected from the group consisting of H or (C1-C4) alkyl;
or a salt of a compound of formula (IIa).

One embodiment comprises a crystal Rac-1 GTPase, wherein said crystal has a three-dimensional structure characterized by the atomic structure coordinates of Table 1 or Table 2. In some such crystals, Rac-1 GTPase is complexed with a compound having the formula (IIa):

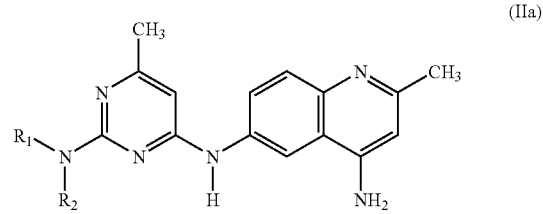

(IIa)

wherein:
$R_1$ to $R_2$ are independently selected from the group consisting of H, —X-Alk, —X-Alk-X', and —X—Y—X'; wherein
X is —$CR_7R_8$;
X' is —$CHR_7R_8$;
Alk is a $C_2$-$C_{18}$ substituted or unsubstituted hydrocarbon chain;
Y is a $C_2$-$C_8$ substituted or unsubstituted alkylene chain;
$R_6$ is H or (C1-C4) alkyl; and
$R_7$ and $R_8$ are independently selected from the group consisting of H or (C1-C4) alkyl;
or a salt of a compound of formula (IIa).

One embodiment comprises a method of making a crystal comprising Rac-1 GTPase, wherein the crystal Rac-1 GTPase comprises at least amino acid residues 1 through 185 of the sequence of SEQ ID NO:1; wherein the crystal effectively diffracts X-rays for the determination of the atomic coordinates to a resolution of greater than 5.0 Angstroms; and wherein said crystal has a space group $P2_1$ and unit cell dimensions of about a=41.8 Angstroms, b=40.0 Angstroms, c=52.1 Angstroms, and β=105.93°, said method comprising growing a crystal by hanging drop method using a buffer that comprises 20% PEG 8000, 5% Ethylene Glycol, 15% DMSO, 0.1 M HEPES, pH 7.0, 10 mM DTT, and 1 mM NSC23766 at 20° C.; and equilibrating the crystal in a drop comprising 18% PEG 8000, 3.5% Ethylene Glycol, 10.7% DMSO, 0.1 M HEPES, pH 7.0, 10 mM DTT, 14.3 mM NSC23766 over a reservoir containing a buffer comprising 25% PEG 8000, 5% Ethylene Glycol, 15% DMSO 0.1M HEPES, pH 7.0, 10 mM DTT.

One embodiment comprises a method of identifying an agent that interacts with Rac-1 GTPase comprising:
  (a) obtaining a crystal of a complex comprising Rac-1 GTPase;
  (b) obtaining the atomic coordinates of the crystal; and
  (c) using the atomic coordinates and one or more molecular modeling techniques to identify an agent that interacts with Rac-1 GTPase.

One embodiment comprises a method for evaluating the potential of a chemical entity to associate with:
  a) a molecule or molecular complex comprising a binding pocket defined by structure coordinates of Rac-1 GTPase Trp-56, Lys-5, Val-7, Ser-71, Ile-36, Tyr-64, Arg-68, and Pro-73; or b) a homologue of said molecule or molecular complex, wherein said homologue comprises a binding pocket that has a root mean square deviation from the backbone atoms of said amino acids of not more than about 1.5 Angstrom comprising the steps of:

i) employing computational means to perform a fitting operation between the chemical entity and the binding pocket of the molecule or molecular complex; and ii) analyzing the results of said fitting operation to quantify the association between the chemical entity and the binding pocket.

One embodiment comprises a compound for inhibiting activity of Rac-1 GTPase, whose active site presents a three-dimensional structure from a crystal of Rac-1 GTPase having a space group $P2_1$ and unit cell dimensions of about a=41.8 Angstroms, b=40.0 Angstroms, c=52.1 Angstroms, and β=105.93°.

One embodiment is directed to a crystal of Rac-1 GTPase bound to GDP.

One embodiment is directed to a crystal Rac-1 GTPase, wherein said crystal has a three-dimensional structure characterized as having atomic coordinates with a root-mean-squared deviation of 6 Å or less, 5 Å or less, 4 Å or less, 3 Å or less, 2 Å or less, 1 Å or less, relative to atoms of amino acids 30-39 and 59-73 of Table 1 or Table 2. In some such embodiments, the of amino acids 30-39 and 59-73 of Table 1 or Table 2 are peptide backbone atoms.

One embodiment is directed to atomic coordinates with a root-mean-squared deviation of 6 Å or less, 5 Å or less, 4 Å or less, 3 Å or less, 2 Å or less, 1 Å or less, relative to atoms of amino acids 30-39 and 59-73 of Table 1 or Table 2.

In some such embodiments, the of amino acids 30-39 and 59-73 of Table 1 or Table 2 are peptide backbone atoms.

One embodiment is directed to a method of characterizing the three-dimensional structure of Rac-1 GTPase comprising: (a) obtaining a crystal of a GDP-bound Rac-1 GTPase; and (b) obtaining the atomic coordinates of the crystallized GDP-bound Rac-1 GTPase.

One embodiment is directed to a method of characterizing the three-dimensional structure of a ligand bound to a Rac-1 GTPase comprising: (a) obtaining a crystal of a ligand bound to a GDP-bound Rac-1 GTPase; and (b) obtaining the atomic coordinates of the crystallized ligand and GDP-bound Rac-1 GTPase.

One embodiment is directed to a method of identifying an agent that interacts with Rac-1 GTPase comprising: (a) obtaining a crystal of a GDP-bound Rac-1 GTPase; and (b) obtaining the atomic coordinates of the crystallized GDP-bound Rac-1 GTPase; and (c) using the atomic coordinates and one or more molecular modeling techniques to identify an agent that interacts with GDP-bound Rac-1 GTPase.

One embodiment is directed to a method of designing a Rac-1 GTPase inhibitor comprising accessing at least a portion the data of Table 1 or Table 2 and modeling the binding of one or more compounds to a Rac-1 GTPase utilizing said data. In some such embodiments, the modeling comprises predicting the likelihood of a compound to bind to Rac-1 GTPase by modeling the interaction of a compound with a Rac-1 GTPase activation site. Some such embodiments further comprise utilizing said data to identify one or more interactions between a Rac-1 GTPase and a ligand. In some such embodiments, said one or more interactions are selected from the group consisting of one or more hydrogen bonds between ligand and protein; one or more electrostatic interactions between ligand and protein; one or more hydrophobic interactions; one or more covalent bonds between ligand and protein; one or more changes in the positions of protein atoms, such as amino acid side chains upon ligand binding; one or more changes in atoms whose positions are well defined to a conformation that may maintain flexibility; one or more hydrogen bonding networks; one or more structural changes to the hydrogen bond network, one or more structural changes to the interactions with Mg2+, one or more structural changes to the interactions with GDP, and one or more structural changes to the interactions with GTP.

A method identifying a Rac-1 GTPase inhibitor comprising obtaining data comprising the one or more of the above interactions and modeling a compound to interact with a Rac-1 GTPase, wherein the compound comprises one or more of the above interactions or improvements of one or more of the above interactions.

One embodiment is directed to a method of designing a Rac-1 GTPase inhibitor comprising obtaining an X-ray crystal structure coordinate of a GDP-bound Rac-1 GTPase and identifying a compound that inhibits a Rac-1 GTPase activation.

Some such embodiments comprise identifying a compound that inhibits Thr35 binding of Mg2+.

Some such embodiments comprise identifying a compound that inhibits conformational change in the loop containing amino acid residues 60-64.

Some such embodiments comprise identifying a compound that inhibits Ala59 from displacing Mg2+.

In some such methods, said compound hydrogen bonds to Ala59.

Some such embodiments comprise identifying a compound that inhibits a RAC-specific GEF from binding to RAC Some such embodiments comprise identifying a compound that inhibits RAC-specific GEF from dissociating from RAC.

Some such embodiments comprise identifying a compound that inhibits conformational change in the amino acids of switch I.

Some such embodiments comprise identifying a compound that inhibits conformational change in the amino acids of switch II In some such methods, said compound is identified as hydrogen bonding to Leu70 or Ser71, or both.

In some such methods, said compound is identified as hydrogen bonding to Leu67, Gln74, Asp57, or Ser71, or combinations thereof.

In some such methods, said compound is identified as being in van der Waals contact with Val36, Trp56, Ala59, Tyr64, Leu67, Leu70, Ser71 or Pro73, or combinations thereof.

One embodiment is directed to a method of identifying a Rac-1 GTPase inhibitor comprising accessing one or more of the coordinates of Table 1 or Table 2 and identifying a compound that occupies a position within a range of about 1.0 to 2.0 angstroms or about 2.5 to 5.0 angstroms of one or more of the coordinates of the ligand in Table 1 or Table 2.

In some such methods, the compound occupies a position within about 1.2 to 1.7 or about 2.6 to 3.5 angstroms of one or more of the coordinates of the ligand in at least one of Tables 1-5.

One embodiment is directed to a method of identifying a Rac-1 GTPase inhibitor comprising:

(a) identifying one or more interactions between a ligand and a Rac-1 GTPase; and (b) changing a substituent on the ligand in order to modify the interaction between the ligand the subunit.

In some such methods, the ligand is NSC23766.

One embodiment is directed to a method of screening a set of one or more compounds to identify compounds most likely to bind to a Rac-1 GTPase comprising the steps of: (a) computationally determining the docking energy of each of one or more compounds in an activation site of a Rac-1 GTPase, wherein each respective docking energy indicates the likelihood of said compound binding to said Rac-1 GTPase activation site; (b) selecting one or more compounds indicated as having a likelihood of binding to said Rac-1 GTPase activation site above a threshold value.

One embodiment is directed to a method of identifying a compound that is likely to bind an activation site of a Rac-1 GTPase comprising the steps of: (a) computationally determining the docking energy of each of one or more compounds in an activation site of a Rac-1 GTPase, wherein each respective docking energy indicates the likelihood of said compound binding to said Rac-1 GTPase activation site; (b) selecting one or more compounds indicated as having a likelihood of binding to said Rac-1 GTPase activation site above a threshold value.

In some such methods, said activation site comprises one or more of the protein atoms of Table 1 or Table 2.

One embodiment is directed to atomic coordinates that have a root-mean-squared deviation of 6.0 Å or less, 5.5 Å or less, 5.0 Å or less, 4.5 Å or less, 4.0 Å or less, 3.5 Å or less, 3.0 Å or less, 2.5 Å or less, 2.0 Å or less, 1.7 Å or less, 1.5 Å or less, 1.4 Å or less, 1.3 Å or less, 1.2 Å or less, 1.1 Å or less, 1.0 Å or less, 0.9 Å or less, 0.8 Å or less, 0.7 Å or less, 0.6 Å or less, 0.5 Å or less, 0.4 Å or less, 0.3 Å or less, 0.2 Å or less, or 0.1 Å or less, relative to atoms of the atomic coordinates provided in Table 1 or Table 2.

In some of the disclosed methods, said activation site comprises protein atoms having atomic coordinates that have a root-mean-squared deviation of 6.0 Å or less, 5.5 Å or less, 5.0 Å or less, 4.5 Å or less, 4.0 Å or less, 3.5 Å or less, 3.0 Å or less, 2.5 Å or less, 2.0 Å or less, 1.7 Å or less, 1.5 Å or less, 1.4 Å or less, 1.3 Å or less, 1.2 Å or less, 1.1 Å or less, 1.0 Å or less, 0.9 Å or less, 0.8 Å or less, 0.7 Å or less, 0.6 Å or less, 0.5 Å or less, 0.4 Å or less, 0.3 Å or less, 0.2 Å or less, or 0.1 Å or less, relative to atoms of the atomic coordinates provided in Table 1 or Table 2.

In some of the disclosed atomic coordinates or methods, the atoms of the atomic coordinates provided in Table 1 or Table 2 include at least one atom from an amino acid of switch I and at least one atom from an amino acid of switch II.

In some of the disclosed atomic coordinates or methods, the atoms of the atomic coordinates provided in Table 1 or Table 2 include at least one atom from an amino acid selected from amino acids 30-39 of Rac-1 GTPase (see SEQ ID NO:1) and at least one atom from an amino acid selected from amino acids 56-74 of Rac-1 GTPase (see SEQ ID NO:1).

In some of the disclosed atomic coordinates or methods, the atoms of the atomic coordinates provided in Table 1 or Table 2 include at least one atom from an amino acid selected from Gly30, Tyr32, Ile33, Pro34, Thr35, Val36, Phe37 and Asp38 of Rac-1 GTPase and at least one atom from an amino acid selected from amino acids 56-74 of Rac-1 GTPase.

In some of the disclosed atomic coordinates or methods, the atoms of the atomic coordinates provided in Table 1 or Table 2 include at least one atom from an amino acid selected from Gly30, Tyr32, Ile33, Pro34, Val36 and Phe37 of Rac-1 GTPase and at least one atom from an amino acid selected from amino acids 56-74 of Rac-1 GTPase.

In some of the disclosed atomic coordinates or methods, the atoms of the atomic coordinates provided in Table 1 or Table 2 include at least one atom from an amino acid selected from Thr35 and Val36 of Rac-1 GTPase and at least one atom from an amino acid selected from amino acids 56-74 of Rac-1 GTPase.

In some of the disclosed atomic coordinates or methods, the atoms of the atomic coordinates provided in Table 1 or Table 2 include at least one atom from Trp56 of Rac-1 GTPase and at least one atom from an amino acid selected from amino acids 30-39 of Rac-1 GTPase.

In some of the disclosed atomic coordinates or methods, the atoms of the atomic coordinates provided in Table 1 or Table 2 include at least one atom from an amino acid selected from Trp56 and Leu70 of Rac-1 GTPase and at least one atom from an amino acid selected from amino acids 30-39 of Rac-1 GTPase.

In some of the disclosed atomic coordinates or methods, the atoms of the atomic coordinates provided in Table 1 or Table 2 include at least one atom from an amino acid selected from Trp56, Leu70 and Ser71 of Rac-1 GTPase and at least one atom from an amino acid selected from amino acids 30-39 of Rac-1 GTPase.

In some of the disclosed atomic coordinates or methods, the atoms of the atomic coordinates provided in Table 1 or Table 2 include at least one atom from an amino acid selected from Trp56, Tyr64, Leu67 and Leu70 of Rac-1 GTPase and at least one atom from an amino acid selected from amino acids 30-39 of Rac-1 GTPase.

In some of the disclosed atomic coordinates or methods, the atoms of the atomic coordinates provided in Table 1 or Table 2 include at least one atom from an amino acid selected from Trp56, Ala59, Tyr64, Leu67, Leu70, Ser71 and Pro73 and at least one atom from an amino acid selected from amino acids 30-39 of Rac-1 GTPase.

In some of the disclosed atomic coordinates or methods, the atoms of the atomic coordinates provided in Table 1 or Table 2 include at least one atom from an amino acid selected from Gly30, Tyr32, Ile33, Pro34, Thr35, Val36, Phe37 or Asp38 of Rac-1 GTPase and at least one atom from an amino acid selected from amino acids 56-70 of Rac-1 GTPase.

In some of the disclosed atomic coordinates or methods, the atoms of the atomic coordinates provided in Table 1 or Table 2 include at least one atom from an amino acid selected from Gly30, Tyr32, Ile33, Pro34, Val36 and Phe37 of Rac-1 GTPase and at least one atom from an amino acid selected from Trp56, Ala59, Tyr64, Leu67, Leu70, Ser71 and Pro73 of Rac-1 GTPase.

In some of the disclosed atomic coordinates or methods, the atoms of the atomic coordinates provided in Table 1 or Table 2 include at least one atom from an amino acid selected from Thr35 and Val36 of Rac-1 GTPase and at least one atom from an amino acid selected from Trp56, Ala59, Tyr64, Leu67, Leu70, Ser71 and Pro73 of Rac-1 GTPase.

In some of the disclosed atomic coordinates or methods, the atoms of the atomic coordinates provided in Table 1 or Table 2 include the Mg2+ atom.

In some of the disclosed atomic coordinates or methods, the atoms are selected from the group consisting of all atoms of a selected amino acid, backbone atoms only of a selected amino acid, and alpha carbon atoms only of a selected amino acid.

Some of the disclosed methods further comprise determining the conformation of said compound in said activation site.

In some methods disclosed herein, said step of determining the docking energy further comprises a step of generating a grid-based receptor field representation of said activation site.

In some methods disclosed herein, said step of determining the docking energy further comprises a step of determining the optimal conformation of said compound in said activation site.

In some methods disclosed herein, said step of determining the docking energy further comprises a step of building atoms of said compound into said activation site to thereby match said activation site.

A computer readable media comprising the atomic coordinates disclosed herein.

Some embodiments of the computer readable media comprise the atomic coordinates of the protein atoms of Table 1 or Table 2.

A computer readable media comprising the atomic coordinates for a ligand of Table 1 or Table 2.

In some embodiments of the computer readable media, the ligand is NSC23766.

A computer readable media comprising at least a portion of the atomic coordinates for a GDP-bound Rac-1 GTPase.

Some embodiments of the computer readable media comprise amino acids 1-185 of Rac-1 GTPase.

Some embodiments of the computer readable media comprise at least a portion of the atomic coordinates of a non-GDP ligand of Rac-1 GTPase.

In some embodiments of the computer readable media, the coordinates are less than the coordinates for amino acids 1-185 of Rac-1 GTPase.

A computer system comprising the coordinates disclosed herein.

In some embodiments, the computer system is capable of generating structures and/or performing rational drug design for a Rac-1 GTPase/ligand complex.

BRIEF DESCRIPTION OF THE DRAWINGS

The novel features of the preferred embodiments are set forth with particularity in the appended claims. The preferred embodiments, however, both as to organization and methods of operation, together with further objects and advantages thereof, can best be understood by reference to the following description, taken in conjunction with the accompanying drawings in which:

Figure 1:
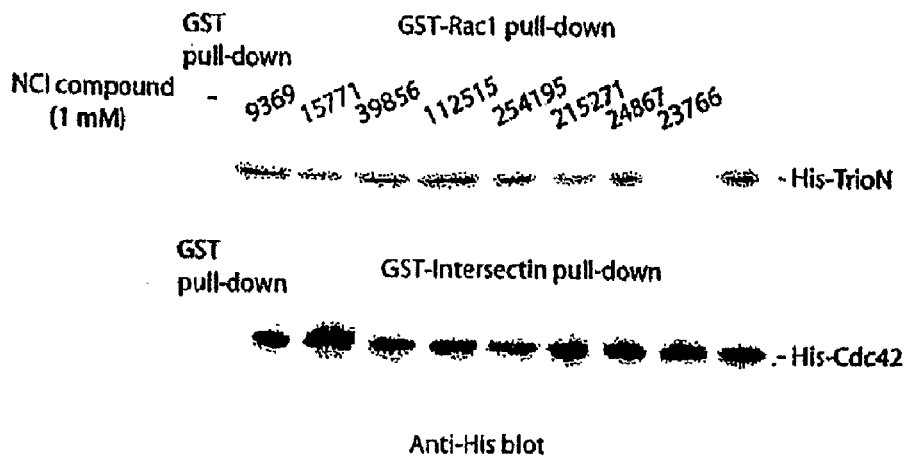
FIG. 1. shows identification of NSC23766 as an inhibitor of Rac1-Trio interaction.

In the following description of the illustrated embodiments, references are made to the accompanying drawings, which form a part hereof, and in which is shown by way of illustration various embodiments in which the invention can be practiced. It is to be understood that other embodiments can be utilized, and structural and functional changes can be made without departing from the scope of the preferred embodiments.

DETAILED DESCRIPTION OF THE PREFERRED EMBODIMENT

Throughout this document, all temperatures are given in degrees Celsius, and all percentages are weight percentages unless otherwise stated. The following are definitions of terms used in this specification. The initial definition provided for a group or term herein applies to that group or term throughout the present specification, individually or as part of another group, unless otherwise indicated. The following definitions, unless otherwise defined, apply to preferred embodiments:

The terms "active compounds" or "active agents" refer to any one of the agents described by formula I, II, IIa, III, IIIa or IV.

The term "alkyl" refers to straight or branched chain hydrocarbon groups having 1 to 12 carbon atoms, or more, preferably 1 to 8 carbon atoms. Lower alkyl groups, that is, alkyl groups of 1 to 4 carbon atoms, are most preferred.

The term "substituted alkyl" refers to an alkyl group as defined above having at least one substituent, such as halo, amino, cyano, hydroxy, alkoxy, alkylthio, —NH(alkyl), —NH(cycloalkyl), —N(alkyl)$_2$, —C(=O)H, —CO$_2$H, —CO$_2$-alkyl, cycloalkyl, substituted cycloalkyl, aryl, heteroaryl, or heterocycle The term "substituted alkyl" also includes an alkyl group as defined above substituted with N(substituted alkyl) or N(substituted alkyl)$_2$, or in other words, the groups (CH$_2$), NHR' and (CH$_2$)n NR'R", wherein each of R' and R" comprises a substituted alkyl or R' and R" together form a heterocyclo ring.

The term "alkoxy" refers to an alkyl group as defined above bonded through an oxygen (—O—). The term "alkylthio" refers to an alkyl group as defined above bonded through a sulfur (—S—).

The term "cycloalkyl" refers to fully saturated and partially unsaturated hydrocarbon rings of at least 3, preferably 3 to 9, more preferably 3 to 7, carbon atoms as well as such rings having a fused aryl ring such as indan.

The term "substituted cycloalkyl" refers to such rings having one, two or three substituents, preferably one, such as alkyl, substituted alkyl, alkoxy, alkylthio, halo, hydroxy, cyano, amino, —NH(alkyl), —NH(cycloalkyl), —N(alkyl)$_2$, —CO$_2$H, —CO$_2$-lower alkyl, aryl, heterocyclo, heteroaryl, keto, =N—OH, =N—O-lower alkyl, and a five or six membered ketal, i.e. 1,3-dioxolane or 1,3-dioxane.

The term "halo" refers to fluoro, chloro, bromo and iodo.

The term "aryl" refers to phenyl, 1-naphthyl and 2-naphthyl, with phenyl being preferred. The term "aryl" includes such rings having from zero, one, two or three substituents, such as alkyl, substituted alkyl, alkoxy, alkylthio, halo, hydroxy, nitro, cyano, amino, —NH(alkyl), —NH(cycloalkyl), —N(alkyl)$_2$, —CO$_2$H, —(C=O)alkyl, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, phenyl, benzyl, phenylethyl, phenyloxy, phenylthio, heterocyclo, and heteroaryl.

The term "heterocyclo" refers to substituted and unsubstituted non-aromatic 3 to 7 membered monocyclic groups, 7 to 11 membered bicyclic groups, and 10 to 15 membered tricyclic groups which have at least one heteroatom (O, S or N) in at least one of the rings. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing the bicyclic and tricyclic groups may contain only carbon atoms and can be saturated, partially saturated, or unsaturated. The nitrogen and sulfur atoms can optionally be oxidized and the nitrogen atoms can optionally be quaternized. The heterocyclic group can be attached at any available nitrogen or carbon atom. The heterocyclic ring can contain one, two or three substituents, such as halo, amino, cyano, alkyl, substituted alkyl, —NH(alkyl), —NH(cycloalkyl), —N(alkyl)$_2$, alkoxy, alkylthio, hydroxy, nitro, phenyl, benzyl, phenylethyl, phenyloxy, phenylthio, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, heterocyclo, heteroaryl, keto, =N—OH, =N—O-lower alkyl, and a five or six membered ketal, i.e., 1,3-dioxolane or 1,3-dioxane.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolidinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups can contain only carbon atoms and can be saturated, partially saturated, or unsaturated. The nitrogen and sulfur atoms can optionally be oxidized and the nitrogen atoms can optionally be quaternized. Heteroaryl groups which are bicyclic or tricyclic must include at least one fully aromatic ring but the other fused ring or rings can be aromatic or non-aromatic. The heteroaryl group can be attached at any available nitrogen or carbon atom of any ring. The heteroaryl ring system can contain one, two or three substituents, such as halo, amino, cyano, alkyl, substituted alkyl, —NH(alkyl), —NH(cycloalkyl), —N(alkyl)$_2$, alkoxy, alkylthio, hydroxy, nitro, phenyl, benzyl, phenylethyl, phenyloxy, phenylthio, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, heterocyclo, and heteroaryl.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "substituted imidazole" refers to an imidazole, an aryl-fused imidazole such as benzimidazole, or a heteroaryl-fused imidazole such as a pyridoimidazole which contain one or two substituents, such as hydrogen, alkyl, substituted alkyl, alkoxy, alkylthio, halo, hydroxy, nitro, cyano, amino, —NH(alkyl), —NH(cycloalkyl), —N(alkyl)$_2$, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, phenyl, benzyl, phenylethyl, phenyloxy, phenylthio, heterocyclo, and heteroaryl.

The term "substituted triazole" refers to a triazole having at least one substituent, such as alkyl, substituted alkyl, alkoxy, alkylthio, halo, hydroxy, nitro, cyano, amino, —NH(alkyl), —NH(cycloalkyl), —N(alkyl)$_2$, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, phenyl, benzyl, phenylethyl, phenyloxy, phenylthio, heterocyclo, and heteroaryl.

The terms "(C1-C3) alkyl", "(C1-C4) alkyl", and "(C1-C10) alkyl", when used alone, refer to straight chain alkyl radicals.

The terms "branched (C3-C4) alkyl", and "branched (C3-C6) alkyl" refer to all alkyl isomers containing the designated number of carbon atoms, excluding the straight chain isomers.

The terms "(C1-C4) alkoxy" and "(C1-C7) alkoxy" refer to straight or branched chain alkoxy groups.

The term "halo (C1-C7) alkyl" refers to a (C1-C7) alkyl group, straight chain or branched, substituted with one or more halo groups.

The term "substituted phenyl" used alone or in combination with other terms, as in "substituted phenylthio" or "substituted phenylsulfonyl", refers to phenyl substituted with up to three groups, such as halo, I, (C1-C10) alkyl, branched (C3-C6) alkyl, halo (C1-C7) alkyl, hydroxy (C1-C7) alkyl, (C1-C7) alkoxy, halo (C1-C7) alkoxy, phenoxy, phenyl, NO$_2$, OH, CN, (C1-C4) alkanoyloxy, or benzyloxy.

The term "substituted phenoxy" refers to phenoxy substituted with at least one group, such as halo, I, (C1-C10) alkyl, branched (C3-C6) alkyl, halo (C1-C7) alkyl, hydroxy (C1-C7) alkyl, (C1-C7) alkoxy, halo (C1-C7) alkoxy, phenoxy, phenyl, NO$_2$, OH, CN, (C1-C4) alkanoyloxy, or benzyloxy.

The terms "substituted naphthyl", "substituted pyridyl" and "substituted furanyl" refer to these ring systems substituted with at least one group such as, halo, halo (C1-C4) alkyl, CN, NO$_2$, (C1-C4) alkyl, (C3-C4) branched alkyl, phenyl, (C1-C4) alkoxy, or halo (C1-C4) alkoxy.

The term "unsaturated hydrocarbon chain" refers to a hydrocarbon chain containing one or two sites of unsaturation.

The preferred embodiments provide quinoline compounds of the following formula (I) or salts thereof, for use as inhibitors of RhoGTPases, especially Rac1GTPase:

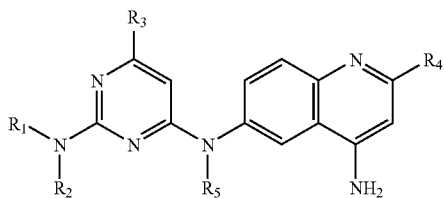

(I)

wherein: $R_1$ to $R_5$ are independently: H, halo, (C1-C4) alkyl, branched (C3-C4) alkyl, halo (C1-C4) alkyl, (C1-C4) alkoxy, $NO_2$, $NH_2$, —X-Alk, —X-Alk-X, —X—Y—X, —$NR_6$ or O—$R_6$, wherein X is O, $NR_6$, or $CR_7R_8$;

Alk is a C2-C18 saturated or unsaturated hydrocarbon chain, straight chain or branched, optionally substituted with halo, halo (C1-C4) alkoxy, (C3-C8) cycloalkyl, hydroxy, or acetyl;

Y is an alkylene chain 2 to 8 carbon atoms long, that optionally includes an O, S, SO, $SO_2$, or $NR_6$ group, and optionally includes a saturated or unsaturated carbocyclic ring comprising three to seven carbon atoms, and optionally is substituted with (C1-C3) alkyl, (C2-C4) phenyl, (C3-C8) cycloalkyl, hydroxy, halo, or (C1-C4) acyl; and Ar is 1,3-benzodioxolyl fluorenyl, pyridyl substituted pyridyl, indolyl, furanyl, substituted furanyl, thienyl, optionally substituted with $CH_2$ or Cl, thiazolyl, cyclopentyl, 1-methylcyclopentyl, cyclohexenyl(tetrahydrophenyl), cyclohexyl(hexahydrophenyl), naphthyl, substituted naphthyl, dihydronaphthyl, tetrahydronaphthyl, or decahydronaphthyl;

$R_6$ is H, (C1-C4) alkyl, or acetyl;

$R_7$ and $R_8$ are independently H, (C1-C4) alkyl, (C1-C4) acyl, halo, —OH, O—Y—Ar, or —$NR_9$—Y—Ar; and $R_9$ is H, (C1-C4) alkyl, or acetyl.

or a salt of a compound of formula (I), provided, however, that this specifically excludes compounds that are known per se or that could be considered similar to known compounds.

Preferably at least two of $R_1$ to $R_5$ being H or $CH_3$, and at least one of $R_1$ to $R_2$ is —X-Alk, —X-Alk-X or —X—Y—X, —$NR_6$ or O—$R_6$ and the rest of $R_1$ to $R_5$ are H or $CH_3$; wherein:

X is O, $NR_6$, or $CR_7R_8$;

Alk is a C2-C18 saturated or unsaturated hydrocarbon chain, straight chain or branched, optionally substituted with halo, halo (C1-C4) alkoxy, (C3-C8) cycloalkyl, hydroxy, or acetyl;

Y is an alkylene chain 2 to 8 carbon atoms long, that optionally includes an O, S, SO, $SO_2$, or $NR_6$ group, and optionally includes a saturated or unsaturated carbocyclic ring comprising three to seven carbon atoms, and optionally is substituted with (C1-C3) alkyl, (C2-C4) phenyl, (C3-C8) cycloalkyl, hydroxy, halo, or (C1-C4) acyl; and Ar is 1,3-benzodioxolyl fluorenyl, pyridyl substituted pyridyl, indolyl, furanyl, substituted furanyl, thienyl, optionally substituted with $CH_2$ or Cl, thiazolyl, cyclopentyl, 1-methylcyclopentyl, cyclohexenyl(tetrahydrophenyl), cyclohexyl(hexahydrophenyl), naphthyl, substituted naphthyl, dihydronaphthyl, tetrahydronaphthyl, or decahydronaphthyl;

$R_6$ is H, (C1-C4) alkyl, or acetyl;

$R_7$ and $R_8$ are independently H, (C1-C4) alkyl, (C1-C4) acyl, halo, —OH, O—Y—Ar, or —$NR_9$—Y—Ar; and $R_9$ is H, (C1-C4) alkyl, or acetyl.

Preferably, the preferred embodiments provide compounds of the formula (II) or salts thereof, for use as inhibitors of RhoGTPases:

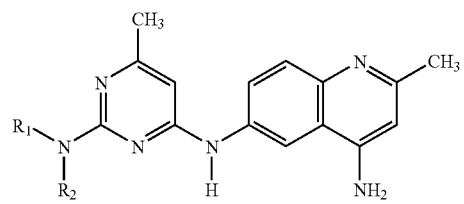

(II)

wherein:

$R_1$ to $R_2$ are independently: H, halo, (C1-C4) alkyl, branched (C3-C4) alkyl, halo (C1-C4) alkyl, (C1-C4) alkoxy, $NO_2$, $NH_2$, —X-Alk, —X-Alk-X, —X—Y—X, —$NR_6$ or O—$R_6$, wherein X is O, $NR_6$, or $CR_7R_8$;

Alk is a C2-C18 saturated or unsaturated hydrocarbon chain, straight chain or branched, optionally substituted with halo, halo (C1-C4) alkoxy, (C3-C8) cycloalkyl, hydroxy, or acetyl;

Y is an alkylene chain 2 to 8 carbon atoms long, that optionally includes an O, S, SO, $SO_2$, or $NR_6$ group, and optionally includes a saturated or unsaturated carbocyclic ring comprising three to seven carbon atoms, and optionally is substituted with (C1-C3) alkyl, (C2-C4) phenyl, (C3-C8) cycloalkyl, hydroxy, halo, or (C1-C4) acyl; and Ar is 1,3-benzodioxolyl fluorenyl, pyridyl substituted pyridyl, indolyl, furanyl, substituted furanyl, thienyl, optionally substituted with $CH_2$ or Cl, thiazolyl, cyclopentyl, 1-methylcyclopentyl, cyclohexenyl(tetrahydrophenyl), cyclohexyl(hexahydrophenyl), naphthyl, substituted naphthyl, dihydronaphthyl, tetrahydronaphthyl, or decahydronaphthyl;

$R_6$ is H, (C1-C4) alkyl, or acetyl;

$R_7$ and $R_8$ are independently H, (C1-C4) alkyl, (C1-C4) acyl, halo, —OH, O—Y—Ar, or —$NR_9$—Y—Ar; and $R_9$ is H, (C1-C4) alkyl, or acetyl.

or a salt of a compound of formula (II).

Preferably, the preferred embodiments provide compounds of the formula (IIa) or salts thereof, for use as inhibitors of RhoGTPases:

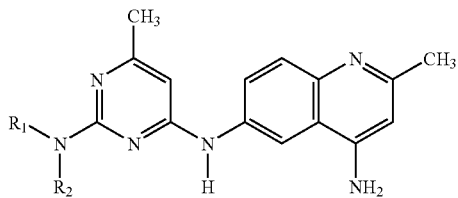

(IIa)

wherein:

$R_1$ to $R_2$ are independently: H, —X-Alk, —X-Alk-X', or —X—Y—X', wherein

X is —$CR_7R_8$;

X' is —$CHR_7R_8$;

Alk is a C2-C18 saturated or unsaturated hydrocarbon chain, straight chain or branched, optionally substituted with halo, halo (C1-C4) alkoxy, (C3-C8) cycloalkyl, hydroxy, or acetyl;

Y is an alkylene chain 2 to 8 carbon atoms long, that optionally includes an $NR_6$ group;

$R_6$ is H or (C1-C4) alkyl; and
$R_7$ and $R_8$ are independently H or (C1-C4) alkyl;
or a salt of a compound of formula (IIa).

The preferred embodiments provide compounds of the formula (III) or salts thereof, for use as inhibitors of Rho GTPases:

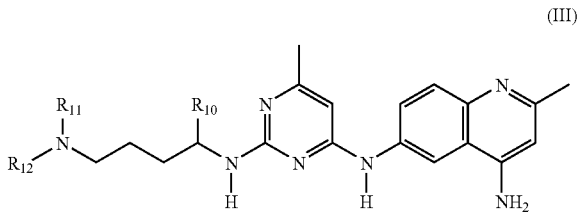

(III)

wherein:

$R_{10}$ to $R_{12}$ are independently: H, halo, (C1-C4) alkyl, branched (C3-C4) alkyl, halo (C1-C4) alkyl, (C1-C4) alkoxy, $NO_2$, or $NH_2$;

or a salt of a compound of formula (III).

The preferred embodiments provide compounds of the formula (IIIa) or salts thereof, for use as inhibitors of Rho GTPases:

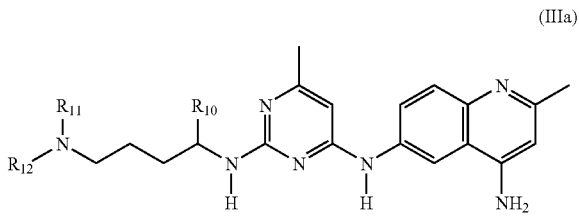

(IIIa)

wherein:

$R_{10}$ to $R_{12}$ are independently: H, (C1-C4) alkyl, or branched (C3-C4) alkyl;

or a salt of a compound of formula (IIIa).

The preferred embodiments provide compounds of the formula (IV) or salts thereof, for use as inhibitors of Rho GTPases:

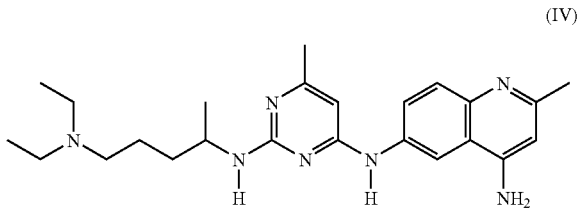

(IV)

or a salt of a compound of formula (IV).

The pharmaceutical compositions of the preferred embodiments comprise a disease inhibiting and pharmaceutically acceptable amount of a compound of formula I, II, IIa, III, IIIa or IV, or N6-(2-((4-(diethylamino)-1-methylbutyl)amino)-6-methyl-4-pyrimidinyl)-2-methyl-4,6-quinolinediamine, in combination with a pharmaceutically-acceptable carrier.

The pharmaceutical compositions of the preferred embodiments comprise at least 1% by weight of a compound of formula I, II, IIa, III, IIIa or IV, or N-6-(2-((4-(diethylamino)-1-methylbutyl)amino)-6-methyl-4-pyrimidinyl)-2-methyl-4,6-quinolinediamine (e.g., formula IV, chemical compound 23766).

The pharmaceutical compositions of the preferred embodiments comprise a compound of formula I, II, IIa, III, IIIa or IV, or $N^6$-(2-((4-(diethylamino)-1-methylbutyl)amino)-6-methyl-4-pyrimidinyl)-2-methyl-4,6-quinolinediamine (e.g., formula IV, chemical compound 23766) further comprising a pharmaceutically active compound. For example, the additional pharmaceutically active compound can be a compound that is useful for inhibiting cell proliferation. For example, the additional pharmaceutically active compound can be a compound selected from the group consisting of farnesyl protein transferase inhibitors, prenyl-protein transferase inhibitors, geranylgeranyl-protein transferase inhibitors, toxins and combinations thereof.

The pharmaceutical combinations of the preferred embodiments comprise at least 1% by weight of a compound of formula I, II, IIa, III, IIIa or IV, or $N^6$-(2-((4-(diethylamino)-1-methylbutyl)amino)-6-methyl-4-pyrimidinyl)-2-methyl-4,6-quinolinediamine (e.g., formula IV, chemical compound 23766), in combination with a second pharmaceutical compound.

In another embodiment, the pharmaceutical combinations of the preferred embodiments comprise at least 1% by weight of a Rho family GTPase-regulating active compound further comprising additional cancer treatment pharmaceutical agent and, preferably, in combination with a pharmaceutically-acceptable carrier.

The pharmaceutical compositions of the preferred embodiments comprise a cancer prevention amount of a Rho family GTPase-regulating active compound in combination with a pharmaceutically-acceptable carrier.

The pharmaceutical methods of the preferred embodiments comprise administering N6-(2-((4-(diethylamino)-1-methylbutyl)amino)-6-methyl-4-pyrimidinyl)-2-methyl-4,6-quinolinediamine to a subject in need of such treatment with a therapeutic amount of a compound of formula I, II, IIa, III, IIIa or IV, or of a combination described above.

Rac is one of the most important members of a family of proteins known as the Rho GTPases. This family of proteins binds to a small metabolic product called GTP, which acts as a critical regulator of Rho GTPase activity. This enables Rac to regulate a wide variety of cellular functions that span the entire gamut of a cell's life, from its initial growth and differentiation, to its movement and division, and finally to its death. They are important for gene expression, and they play crucial roles in the ability of innate immune cells to make lethal responses to bacterial infections, of skin cells to cover wounds during the healing process, of vascular cells to make new blood vessels, of cancer cells to metastasize, and of neurons to develop and make proper connections in the brain.

The inactive form of Rac-1 GTPase is the GDP-bound form. Provided herein is the three-dimensional structure of the inactive GDP-bound form, which contains conformational differences relative to the GTP-bound form of Rac-1 GTPase.

The present embodiments relate to crystalline protein corresponding to GDP-bound Rac-1 GTPase. Preferably, the crystalline protein is of sufficient quality to allow for the determination of the three-dimensional X-ray diffraction structure. The structural coordinates of a crystalline protein corresponding to Rac-1 GTPase is given in Table 1 or Table 2 below.

In one embodiment, a crystal structure of Rac-1 GTPase complexed with

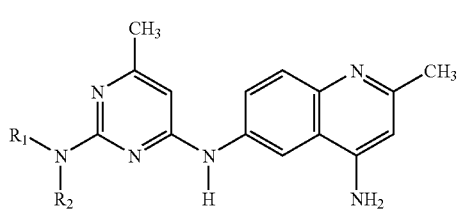

(IIa)

wherein:

$R_1$ to $R_2$ are independently selected from the group consisting of H, —X-Alk, —X-Alk-X', and —X—Y—X'; wherein X is —$CR_7R_8$; X' is —$CHR_7R_8$; Alk is a C2-C18 substituted or unsubstituted hydrocarbon chain; Y is a C2-C8 substituted or unsubstituted alkylene chain; $R_6$ is H or (C1-C4) alkyl; and $R_7$ and $R_8$ are independently selected from the group consisting of H or (C1-C4) alkyl; or a salt of a compound of formula (IIa) is obtained. In one embodiment, the compound of Formula IIa is

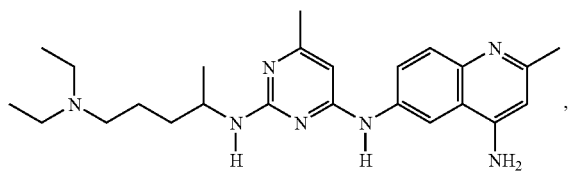

Formula (IV). In the crystal structure of Rac-1 GTPase complexed with a compound of Formula IV, the compound of Formula IV makes contacts with any of Trp-56, Lys-5, Val-7, Ser-71, Ile-36, Tyr-64, Arg-68, and Pro-73 of Rac-1 GTPase.

The embodiments also relate to methods for preparing and crystallizing the protein. Crystals of Rac-1 GTPase can be grown by a number of techniques known by those in the art, including batch crystallization, vapor diffusion (either by sitting drop or hanging drop) and by microdialysis. Seeding of the crystals in some instances is required to obtain X-ray quality crystals. Standard micro and/or macro seeding of crystals may therefore be used. An initial crystal can be allowed to grow over several hours to several months at about 4° C. to about 20° C. from a hanging drop. Crystals then can be subsequently grown by macroseeding from the initial crystal.

Once a crystal of the preferred embodiments is grown, X-ray diffraction data can be collected. A MAR imaging plate detector for X-ray diffraction data collection can be used for example. Crystals can be characterized by using X-rays produced in a conventional source (such as a sealed tube or a rotating anode) or using a synchrotron source. In the example below, diffraction data was measured at National Synchrotron Light Source (Brookhaven, Upton, N.Y.).

Methods of characterization include, but are not limited to, precession photography, oscillation photography, Laue diffraction photography, and diffractometer data collection. As exemplified below, heavy atom derivatives can be obtained by soaking crystals in stabilization solution with 1 mM $Na_2OsCl_6$ for about 12 hours, with 10 mM $KAu(CN)_2$ for about 12 hours, with 10 mM $Pb(OAc)_2$ for about 1 hour, and with 10 mM $UO_2(NO_3)_2$ for about 4 hours.

The protein itself, as well as information derived from the crystal structure can be used to analyze and modify protein activity as well as to identify compounds that interact with a catalytic domain. Once the three-dimensional structure of a crystal comprising a Rac-1 GTPase is determined, (e.g., see the coordinates in Table 1 or Table 2) a potential modulator of Rac-1 GTPase activity, can be examined through the use of computer modeling using a docking program such as, but not limited to, GRAM, DOCK, or AUTODOCK [Dunbrack et al., 1997, supra], to identify potential modulators of Rac-1 GTPase. This procedure can include computer fitting of potential modulators to Rac-1 GTPase to ascertain how well the shape and the chemical structure of the potential modulator will bind to a binding region of Rac-1 GTPase. Computer programs can also be employed to estimate the attraction, repulsion, and steric hindrance of the two binding partners. Generally the tighter the fit, the lower the steric hindrances, and the greater the attractive forces, the more potent the potential modulator since these properties are consistent with a tighter binding constant. Furthermore, the more specificity in the design of a potential drug the more likely that the drug will not interact as well with other proteins. This will minimize potential side-effects due to unwanted interactions with other proteins.

"Computer readable media" as used herein means any media which can be read and accessed directly by a computer e.g., so that the media is suitable for use in the above-mentioned computer system. The media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

"Computer system" as used herein means the hardware means, software means and data storage means used to analyze atomic coordinate data. The minimum hardware means of the computer-based systems of the present invention comprises a central processing unit (CPU), input means, output means and data storage means. Desirably a monitor is provided to visualize structure data. The data storage means may be RAM or means for accessing computer readable media of the invention. Examples of such systems are microcomputer workstations available from Silicon Graphics Incorporated and Sun Microsystems running Unix based, Windows NT or IBM OS/2 operating systems.

Some embodiments relate to methods of identifying or designing GTPase inhibitors. The methods can include the step of accessing at least a portion the data of Table 1 or Table 2, and modeling one or more compounds utilizing said data. The modeling can include, for example, predicting the likelihood of a compound to bind to the Rac-1 GTPase by modeling the interaction of a compound with a GTPase activation site of the Rac-1 GTPase. The methods further can include utilizing the data to identify one or more interactions between a Rac-1 GTPase and a ligand. For example, the interactions can include one or more hydrogen bonds between ligand and protein; one or more electrostatic interactions between ligand and protein; one or more hydrophobic interactions; one or more covalent bonds between ligand and protein; one or more changes in the positions of protein atoms; such as amino acid side chains upon ligand binding; one or more atoms whose positions are well defined versus those that may maintain flexibility in the complex; one or more hydrogen bonding networks; one or more interactions that are important to the catalytic mechanism of the protein/enzyme; one or more structural changes to the hydrogen bond network or the interactions which occur in the presence of the ligand; one or more interactions between the ligand and the protein that interfere with or prevent activation of Rac-1 GTPase; one or more key interactive forces between the ligand and the protein based on the collective data; one or more modifications to the existing ligand that enhance binding to the protein. The modification to the existing ligand can include, for example, adding the potential for electrostatic interactions, reducing steric interactions, increasing hydrophobic interactions, and increasing the surface area of the interaction. Also, the methods can include modeling a compound or compounds to include the interactions described above, or improvements of the interactions.

Some embodiments relate to methods of designing inhibitors, with or without accessing the data of Table 1 or Table 2, by identifying a compound that prevents activation of Rac-1 GTPase. Typically, a compound that prevents activation of Rac-1 GTPase acts by one or more of the following mechanisms: inhibits Thr35 binding of $Mg^{2+}$, inhibits conformational change in the loop containing amino acid residues 60-64, inhibits Ala59 from displacing $Mg^{2+}$, inhibits a RAC-specific GEF from binding to RAC, inhibits RAC-specific GEF from dissociating from RAC, inhibits conformational change in the amino acids of switch I, or inhibits conformational change in the amino acids of switch II.

New compounds can be designed which inhibit Rac-1 GTPase by binding the region between switch I and switch II on Rac-1. Some embodiments relate to methods of identifying a Rac-1 GTPase inhibitor comprising accessing one or more of the coordinates of Table 1 or Table 2 and identifying a compound that occupies a position within about 5, 4.5, 4, 3.5, 3, 2.5, 2, 1.5 or 1 angstroms of one or more of the atomic coordinates of the ligand (DRG) in said Table. For example, a Rac-1 GTPase inhibitor can be identified as a compound that occupies a position between about 5 and about 2.5 angstroms, about 4.5 and about 3 angstroms, about 3.5 and about 2.6 angstroms, or about 3.2 and about 2.6 angstroms from one or more of the atomic coordinates of amino acids Thr35, Val36, Trp56, Ala59, Tyr64, Leu67, Leu70, Ser71 and Pro73, and the $Mg^{2+}$ ion as provided in Table 1 or Table 2. For example, a Rac-1 GTPase inhibitor can be identified as a compound that is involved in hydrophobic contact, van der Waals contact, hydrogen bond formation, salt bridge formation, or other physical interaction with one or more of the atomic coordinates of amino acids Thr35, Val36, Trp56, Ala59, Tyr64, Leu67, Leu70, Ser71 and Pro73, and the $Mg^{2+}$ ion as provided in Table 1 or Table 2. In another example, a Rac-1 GTPase inhibitor can be identified as a compound that occupies a position between about 2 and about 1 angstroms, about 1.7 and about 1.2 angstroms, or about 1.6 and about 1.3 angstroms from one or more of the atomic coordinates of amino acids Thr35, Val36, Trp56, Ala59, Tyr64, Leu67, Leu70, Ser71 and Pro73 as provided in any Table 1 or Table 2. For example, a Rac-1 GTPase inhibitor can be identified as a compound that is covalently bound to one or more of the atomic coordinates of amino acids Thr35, Val36, Trp56, Ala59, Tyr64, Leu67, Leu70, Ser71 and Pro73 as provided in Table 1 or Table 2. The method can include identifying a distance between an atom of the Rac-1 GTPase and an atom of an inhibitor, and substituting the inhibitor atom with a different atom or with a functional group to result in a modified interaction. For example, the modified interaction can be a decreased distance between the ligand and the Rac-1 GTPase, which can permit, e.g., hydrophobic interactions, van der Waals interactions, hydrogen bonding or electrostatic interactions. Thus, some aspects can relate to methods of identifying a Rac-1 GTPase inhibitor that include the steps of identifying one or more interactions between a ligand and Rac-1 GTPase; and changing a substituent on the ligand in order to modify the interaction between the ligand the subunit. An exemplary ligand for which a substituent can be modified is NSC23766.

Still some embodiments relate to methods of screening a set of one or more compounds to identify compounds most likely to bind to a Rac-1 GTPase. The methods can include the steps of: (a) computationally determining the docking energy of each of one or more compounds in a GTPase activation site of a Rac-1 GTPase, wherein each respective docking energy indicates the likelihood of said compound binding to said Rac-1 GTPase activation site; and (b) selecting one or more compounds indicated as having the highest likelihood of binding to said Rac-1 GTPase activation site.

Also, some embodiments relate to methods of identifying a compound that is likely to bind the active site of a Rac-1 GTPase, which methods can include the steps of: (a) computationally determining the docking energy of each of one or more compounds in a GTPase activation site of a Rac-1 GTPase, wherein each respective docking energy indicates the likelihood of said compound binding to said Rac-1 GTPase activation site; and (b) selecting one or more compounds indicated as having the highest likelihood of binding to said Rac-1 GTPase activation site.

Some embodiments relate to methods of screening compounds that bind to the Rac-1 GTPase so as to inhibit GTPase activity of the Rac-1 GTPase. Such methods can include predicting the likelihood of a candidate compound to bind a Rac-1 GTPase activation site. An exemplary Rac-1 GTPase activation site is a region located between switch I and switch II of the Rac-1 GTPase. Another exemplary Rac-1 GTPase activation site comprises at least one amino acid of switch I and at least one amino acid of switch II. Another exemplary Rac-1 GTPase activation site comprises at least one amino acid selected from amino acids 30-39 of Rac-1 GTPase (see SEQ ID NO:1) and at least one amino acid selected from amino acids 56-74 of Rac-1 GTPase (see SEQ ID NO:1). Another exemplary Rac-1 GTPase activation site comprises at least one amino acid selected from Gly30, Tyr32, Ile33, Pro34, Thr35, Val36, Phe37 and Asp38 of Rac-1 GTPase and at least one amino acid selected from amino acids 56-74 of Rac-1 GTPase. Another exemplary Rac-1 GTPase activation site comprises at least one amino acid selected from Gly30, Tyr32, Ile33, Pro34, Val36 and Phe37 of Rac-1 GTPase and at least one amino acid selected from amino acids 56-74 of Rac-1 GTPase. Another exemplary Rac-1 GTPase activation site comprises at least one amino acid selected from Thr35 and Val36 of Rac-1 GTPase and at least one amino acid selected from amino acids 56-74 of Rac-1 GTPase. Another exemplary Rac-1 GTPase activation site comprises Trp56 of Rac-1 GTPase and at least one amino acid selected from amino acids 30-39 of Rac-1 GTPase. Another exemplary Rac-1 GTPase activation site comprises at least one amino acid selected from Trp56 and Leu70 of Rac-1 GTPase and at least one amino acid selected from amino acids 30-39 of Rac-1 GTPase. Another exemplary Rac-1 GTPase activation site comprises at least one amino acid selected from Trp56, Leu70 and Ser71 of Rac-1 GTPase and at least one amino acid selected from amino acids 30-39 of Rac-1 GTPase. Another exemplary Rac-1 GTPase activation site comprises at least one amino acid selected from Trp56, Tyr64, Leu67 and Leu70 of Rac-1 GTPase and at least one amino acid selected from amino acids 30-39 of Rac-1 GTPase. Another exemplary Rac-1 GTPase activation site comprises at least one amino acid selected from Trp56, Ala59, Tyr64, Leu67, Leu70, Ser71 and Pro73 and at least one amino acid selected from amino acids 30-39 of Rac-1 GTPase. Another exemplary Rac-1

GTPase activation site comprises at least one amino acid selected from Gly30, Tyr32, Ile33, Pro34, Thr35, Val36, Phe37 or Asp38 of Rac-1 GTPase and at least one amino acid selected from amino acids 56-70 of Rac-1 GTPase. Another exemplary Rac-1 GTPase activation site comprises at least one amino acid selected from Gly30, Tyr32, Ile33, Pro34, Val36 and Phe37 of Rac-1 GTPase and at least one amino acid selected from Trp56, Ala59, Tyr64, Leu67, Leu70, Ser71 and Pro73 of Rac-1 GTPase. Another exemplary Rac-1 GTPase activation site comprises at least one amino acid selected from Thr35 and Val36 of Rac-1 GTPase and at least one amino acid selected from Trp56, Ala59, Tyr64, Leu67, Leu70, Ser71 and Pro73 of Rac-1 GTPase. An exemplary Rac-1 GTPase activation site such as those above also can comprise the $Mg^{2+}$ atom.

Methods for predicting the likelihood of a candidate compound to bind a particular site of a protein are known in the art, and any of these known methods can be used in accordance with the teachings provided herein to evaluate compounds for their ability to bind a Rac-1 GTPase activation site so as to inhibit Rac-1 GTPase activation. As provided herein, inhibition of Rac-1 GTPase activity can be accomplished by inhibiting Thr35 binding of $Mg^{2+}$, inhibiting conformational change in the loop containing amino acid residues 60-64, inhibits Ala59 from displacing $Mg^{2+}$, inhibiting a RAC-specific GEF from binding to RAC, inhibiting RAC-specific GEF from dissociating from RAC, inhibiting conformational change in the amino acids of switch I, or inhibiting conformational change in the amino acids of switch II. Using the three dimensional atomic structure of the Rac-1 GTPase alone or in complex with NSC23766 (see Table 1 or 2) and known modeling methods, it is possible to screen candidate compounds for their ability to bind to a Rac-1 GTPase activation site, such as those recited above.

The ability of a potential compound to bind a Rac-1 GTPase activation site can be examined through the use of computer modeling using a known docking program such as Hammerhead, FlexX, MCDOCK, ICM-dock, QXP, GOLD, CHARMM, GRAM, DOCK, or AUTODOCK (see, e.g., Walters et al., Drug Discovery Today, Vol. 3, No. 4, (1998), 160-178, and Dunbrack et al., Folding and Design, 2, (1997), 27-42). This procedure can include computer fitting of potential ligands to the Rac-1 GTPase activation site formed by the residues of the activation site, such as those recited above, to ascertain how well the shape and the chemical structure of the potential ligand will match the corresponding active site. The docking methods used in the art can function using any of a variety of different algorithms and optimizations, however generally, these methods function by indicating the goodness of fit of a compound in the binding site of the protein (e.g., the activation site of a Rac-1 GTPase). The goodness of fit can be expressed, for example, as a docking energy of a compound with a protein binding site. In such instances, docking energy can be a quantitative indicator of the likelihood of the compound to bind the Rac-1 GTPase activation site. The goodness of fit, such as docking energy, can serve as a convenient basis for evaluating candidate compounds as potential lead compounds for Rac-1 GTPase activation site binding. For example, when two or more compounds are modeled for their ability to bind to a Rac-1 GTPase activation site, a threshold or cutoff can be used to identify a subset of the two or more compounds that can be further examined as potential lead compounds. A threshold can be a designated percentage of compounds with highest likelihood of binding to a Rac-1 GTPase activation site, where such a designated percentage can be the top 1%, the top 2%, the top 3%, the top 4%, the top 5%, the top 6%, the top 7%, the top 8%, the top 9%, or the top 10%. Another threshold can be relative to a known binder of a Rac-1 GTPase activation site; for example, a threshold can be set according to the ability of NSC23766 to bind a Rac-1 GTPase activation site. As an example, a compound predicted to bind to a Rac-1 GTPase activation site more readily than NSC23766 can be identified as a compound predicted to inhibit Rac-1 GTPase activity.

In some exemplary docking methods, a representation of a Rac-1 GTPase activation site is generated. Various types of representations of a protein binding site are known in the art, such as, for example, a grid-based field representation of a binding site. The representation of a Rac-1 GTPase activation site is typically based on the three dimensional coordinates of the atoms in the binding site. Three dimensional coordinates of the atoms in the binding site can be obtained from Table 1 or Table 2, where the atoms to be selected from Table 1 or Table 2 are selected from the atoms in the above-described exemplary Rac-1 GTPase activation sites, which will typically comprise at least one amino acid of switch I and at least one amino acid of switch II. In another example, a Rac-1 GTPase activation site representation can contain protein atoms within a designated distance from the location of a NSC23766 atom, where the designated distance can be, for example 5 Å, 6 Å, 7 Å, 8 Å, 9 Å, 10 Å, 11 Å, 12 Å, 13 Å, 14 Å, 15 Å, 16 Å, 17 Å, 18 Å, 19 Å, or 20 Å, as determined according to the atomic coordinates available in Table 1 and Table 2. A Rac-1 GTPase activation site representation also can include any water molecules observed in the Rac-1 GTPase activation site. The presence of water molecules in a Rac-1 GTPase activation site can be determined according to the atomic coordinates provided in Table 1 or Table 2. The number of atoms to include and the type of representation to be used can be determined according to the docking method used and the degree of accuracy versus computational efficiency desired.

While representations of Rac-1 GTPase activation sites can be determined according to the atomic coordinates provided in Table 1 or Table 2, one of skill in the art will recognize that the present embodiment also can encompass minor variations of the relative positions of the atoms in the representations of Rac-1 GTPase activation sites. For example, the root-mean-squared deviation (RMSD) between atoms of the activation site representation and the corresponding atoms of the atomic coordinates provided in Table 1 or Table 2 will typically be 6.0 Å or less, 5.5 Å or less, 5.0 Å or less, 4.5 Å or less, 4.0 Å or less, 3.5 Å or less, 3.0 Å or less, 2.5 Å or less, 2.0 Å or less, 1.7 Å or less, 1.5 Å or less, 1.4 Å or less, 1.3 Å or less, 1.2 Å or less, 1.1 Å or less, 1.0 Å or less, 0.9 Å or less, 0.8 Å or less, 0.7 Å or less, 0.6 Å or less, 0.5 Å or less, 0.4 Å or less, 0.3 Å or less, 0.2 Å or less, or 0.1 Å or less, as calculated for all atoms of the activation site representation or as calculated according to a subset of atoms used for the active site representation. When a subset of atoms is used to calculation the RMSD between atoms of the activation site representation and the corresponding atoms of the atomic coordinates provided in Table 1 or Table 2, the subset of atoms are typically those provided in the above-described exemplary Rac-1 GTPase activation sites. In particular, an exemplary set of atoms of the Rac-1 GTPase activation site for use in RMSD calculation includes at least one atom from an amino acid of switch I and at least one atom from an amino acid of switch II. Another exemplary set of atoms of the Rac-1 GTPase activation site for use in RMSD calculation includes at least one atom from an amino acid selected from amino acids 30-39 of Rac-1 GTPase (see SEQ ID NO:1) and at least one atom from an amino acid selected from amino acids 56-74 of Rac-1 GTPase (see SEQ ID NO:1). Another exemplary set of atoms of the Rac-1 GTPase activation site for use in RMSD calculation includes at least one atom from an amino acid selected from Gly30, Tyr32, Ile33, Pro34, Thr35, Val36, Phe37 and Asp38 of Rac-1 GTPase and at least one atom from an amino acid selected from amino acids 56-74 of Rac-1 GTPase. Another exemplary set of atoms of the Rac-1 GTPase activation site for use in RMSD calculation includes at least one atom from an amino acid selected from Gly30, Tyr32, Ile33, Pro34, Val36 and Phe37 of Rac-1 GTPase and at least one atom from an amino acid selected from amino acids 56-74 of Rac-1 GTPase. Another exemplary set of atoms of the Rac-1 GTPase activation site for use in RMSD calculation includes at least one atom from an amino acid selected from Thr35 and Val36 of Rac-1 GTPase and at least one atom from an amino acid selected from amino acids 56-74 of Rac-1 GTPase. Another exemplary set of atoms of the Rac-1 GTPase activation site for use in RMSD calculation includes at least one atom from Trp56 of Rac-1 GTPase and at least one atom from an amino acid selected from amino acids 30-39 of Rac-1 GTPase. Another exemplary set of atoms of the Rac-1 GTPase activation site for use in RMSD calculation includes at least one atom from an amino acid selected from Trp56 and Leu70 of Rac-1 GTPase and at least one atom from an amino acid selected from amino acids 30-39 of Rac-1 GTPase. Another exemplary set of atoms of the Rac-1 GTPase activation site for use in RMSD calculation includes at least one atom from an amino acid selected from Trp56, Leu70 and Ser71 of Rac-1 GTPase and at least one atom from an amino acid selected from amino acids 30-39 of Rac-1 GTPase. Another exemplary set of atoms of the Rac-1 GTPase activation site for use in RMSD calculation includes at least one atom from an amino acid selected from Trp56, Tyr64, Leu67 and Leu70 of Rac-1 GTPase and at least one atom from an amino acid selected from amino acids 30-39 of Rac-1 GTPase. Another exemplary set of atoms of the Rac-1 GTPase activation site for use in RMSD calculation includes at least one atom from an amino acid selected from Trp56, Ala59, Tyr64, Leu67, Leu70, Ser71 and Pro73 and at least one atom from an amino acid selected from amino acids 30-39 of Rac-1 GTPase. Another exemplary set of atoms of the Rac-1 GTPase activation site for use in RMSD calculation includes at least one atom from an amino acid selected from Gly30, Tyr32, Ile33, Pro34, Thr35, Val36, Phe37 or Asp38 of Rac-1 GTPase and at least one atom from an amino acid selected from amino acids 56-70 of Rac-1 GTPase. Another exemplary set of atoms of the Rac-1 GTPase activation site for use in RMSD calculation includes at least one atom from an amino acid selected from Gly30, Tyr32, Ile33, Pro34, Val36 and Phe37 of Rac-1 GTPase and at least one atom from an amino acid selected from Trp56, Ala59, Tyr64, Leu67, Leu70, Ser71 and Pro73 of Rac-1 GTPase. Another exemplary set of atoms of the Rac-1 GTPase activation site for use in RMSD calculation includes at least one atom from an amino acid selected from Thr35 and Val36 of Rac-1 GTPase and at least one atom from an amino acid selected from Trp56, Ala59, Tyr64, Leu67, Leu70, Ser71 and Pro73 of Rac-1 GTPase. Another exemplary set of atoms of the Rac-1 GTPase activation site for use in RMSD calculation such as those above also can include the $Mg^{2+}$ atom. In such exemplary set of atoms above, the atoms can be selected from all atoms of a selected amino acid, backbone atoms only of a selected amino acid, or alpha carbon atoms only of a selected amino acid.

The x-ray crystal structures described herein in Tables 1 and 2 report the atomic coordinates of the heretofore unknown three-dimensional structure of the GDP-bound, inactive form of Rac-1 GTPase. This three-dimensional structure of the GDP-bound form was compared with the active or GTP-bound form of Rac-1 GTPase (PDB ID# 1MH1) to understand at the molecular level the switch mechanism or conformational change involved in Rac-1 GTPase activation.

The calculated root mean square deviation (rmsd) after superposition of all Cαs of both structures is 0.95 Å. Both structures superpose well outside one polypeptide spanning amino acid residues 30 to 40. This region is typically referred to as the switch I region. Another major difference between the two structures is in the way the $Mg^{2+}$ ion is coordinated. As in other GTP-binding proteins including Ras, in the GTP-bound form of Rac the $Mg^{2+}$ ion is coordinated by the hydroxyl side chain group of Thr35, which is also making a hydrogen bond with the γ-phosphate. The absence of the γ-phosphate in the GDP-bound form of Rac results in the change of conformation of Thr35, which in Rac•GDP projects into the solvent. This change of conformation of Thr35 results in the change of conformation of the switch I region of Rac. For example, the ψ angle of Pro29 changes by 150° between the two conformations. Table 3 below lists the changes in distance of the Cαs for the residues of switch I after superposition of both Rac-1 structures:

TABLE 3

| Residue | Change in Distance (Å) |
|---------|------------------------|
| Gly30   | 3.9                    |
| Glu31   | 0.74                   |
| Tyr32   | 5.6                    |
| Ile33   | 4.8                    |
| Pro34   | 5.1                    |
| Thr35   | 1.6                    |
| Val36   | 4.0                    |
| Phe37   | 6.0                    |
| Asp38   | 2.5                    |
| Asn39   | 0.7                    |

In some exemplary docking methods, the conformation of the compound in the Rac-1 GTPase activation site is calculated. Various methods for calculating the conformation of a ligand in a protein binding site are known for docking methods. These can include determining optimal conformation(s) of a compound outside of and within the active site. These also can include building the atoms into the active site such that the atoms match the binding site (sterically, chemically, electrically, or combinations thereof). Any such method can be performed in the docking methods provided herein.

Any of a variety of candidate compounds can be used in the modeling methods provided herein. Methods of predicting the ability of a candidate compound to bind to a Rac-1 GTPase activation site can be used to examine a plurality of candidate compounds in evaluating and comparing the ability of compounds of the plurality to bind to the Rac-1 GTPase activation site. A number of exemplary public and commercial sources of libraries of compound structures are available, for example the Cambridge Structural Database (CSD), the Chemical Directory (ACD) from the company MDL (US), ZINC (Irwin and Shoichet, J. Chem. Inf. Model. (2005) 45:177-82) as well as various electronic catalogues of publicly available compounds such as the National Cancer Institute (NCI, US) catalogue, ComGenex catalogue (Budapest, Hungary), and Asinex (Moscow, Russia). Such libraries may be used to allow computer-based docking of many compounds in order to identify those with potential to interact with the Rac-1 GTPase activation site described herein.

In some instances, methods can be used in which a determination can be made of whether or not a candidate compound is likely to block access of a RAC-specific GEF protein from a interacting with the Rac-1 GTPase activation site. While not intending to be limited by the following theory, it is postulated based on the present observations that Rac-1 GTPase can be activated by a RAC-specific GEF binding the Rac-1 GTPase activation site, and thus blocking access of a RAC-specific GEF to the Rac-1 GTPase activation site by a compound can increase the Rac-1 GTPase inhibiting activity of the compound. Methods for predicting the likelihood of blocking protein-protein interactions are known in the art, such as determination of steric blockage of protein-protein interaction, and can be used in conjunction with computerized modeling methods provided herein or otherwise known in the art, computer-assisted manual examination methods provided herein or otherwise known in the art, or with manual modeling and design of candidate compounds for binding a Rac-1 GTPase activation site.

In some instances, methods can be used in which a determination can be made of whether or not a candidate compound is likely to block dissociation of a RAC-specific GEF protein from the Rac-1 GTPase activation site. While not intending to be limited by the following theory, it is postulated based on the present observations that Rac-1 GTPase is not completely activated by GEF binding the Rac-1 GTPase activation site until dissociation of the GEF from Rac-1, and thus blocking dissociation of a GEF from the Rac-1 GTPase activation site by a compound can increase the Rac-1 GTPase inhibiting activity of the compound. Methods for predicting the likelihood of promoting protein-protein interactions are known in the art, and can be used in conjunction with computerized modeling methods provided herein or otherwise known in the art, computer-assisted manual examination methods provided herein or otherwise known in the art, or with manual modeling and design of candidate compounds for binding a Rac-1 GTPase activation site.

In some instances, methods can be used in which a determination can be made of whether or not a candidate compound is likely to inhibit Thr35 of Rac-1 GTPase binding to $Mg^{2+}$. While not intending to be limited by the following theory, it is postulated based on the present observations that Rac-1 GTPase activation includes Thr35 binding to $Mg^{2+}$, and thus blocking Thr35 binding to $Mg^{2+}$ by a compound can increase the Rac-1 GTPase inhibiting activity of the compound. Methods for predicting the likelihood of blocking amino acid-ion interactions are known in the art, and can be used in conjunction with computerized modeling methods provided herein or otherwise known in the art, computer-assisted manual examination methods provided herein or otherwise known in the art, or with manual modeling and design of candidate compounds for binding a Rac-1. GTPase activation site.

In some instances, methods can be used in which a determination can be made of whether or not a candidate compound is likely to inhibit conformational change in the loop containing amino acid residues 60-64. While not intending to be limited by the following theory, it is postulated based on the present observations that Rac-1 GTPase activation includes conformational change in the loop containing amino acid residues 60-64, and thus blocking such a conformational change by a compound can increase the Rac-1 GTPase inhibiting activity of the compound. Methods for predicting the likelihood of conformational changes of protein structural elements are known in the art, and can be used in conjunction with computerized modeling methods provided herein or otherwise known in the art, computer-assisted manual examination methods provided herein or otherwise known in the art, or with manual modeling and design of candidate compounds for binding a Rac-1 GTPase activation site.

In some instances, methods can be used in which a determination can be made of whether or not a candidate compound is likely to inhibit Ala59 from displacing $Mg2^+$. While not intending to be limited by the following theory, it is postulated based on the present observations that Rac-1 GTPase activation includes Ala59 from displacing $Mg2^+$ in exchanging GDP for GTP, and thus blocking Ala59 from displacing $Mg2^+$ by a compound can increase the Rac-1 GTPase inhibiting activity of the compound by increasing the inhibition of exchange of GDP to GTP. Methods for predicting the likelihood of blocking amino acid-ion interactions are known in the art, and can be used in conjunction with computerized modeling methods provided herein or otherwise known in the art, computer-assisted manual examination methods provided herein or otherwise known in the art, or with manual modeling and design of candidate compounds for binding a Rac-1 GTPase activation site.

In some instances, methods can be used in which a determination can be made of whether or not a candidate compound is likely to inhibit conformational change in the amino acids of switch I, in particular amino acids 30-39 of SEQ ID NO:1, such as amino acids Gly30, Tyr32, Ile33, Pro34, Thr35, Val36, Phe37 and Asp38. While not intending to be limited by the following theory, it is postulated based on the present observations that Rac-1 GTPase activation includes conformational change in amino acids of switch I, and thus blocking such a conformational change by a compound can increase the Rac-1 GTPase inhibiting activity of the compound. Methods for predicting the likelihood of conformational changes of protein structural elements are known in the art, and can be used in conjunction with computerized modeling methods provided herein or otherwise known in the art, computer-assisted manual examination methods provided herein or otherwise known in the art, or with manual modeling and design of candidate compounds for binding a Rac-1 GTPase activation site.

In some instances, methods can be used in which a determination can be made of whether or not a candidate compound is likely to inhibit conformational change in the amino acids of switch II. While not intending to be limited by the following theory, it is postulated based on the present observations that Rac-1 GTPase activation includes slight conformational change in amino acids of switch II, and thus blocking such a conformational change by a compound can increase the Rac-1 GTPase inhibiting activity of the compound. Methods for predicting the likelihood of conformational changes of protein structural elements are known in the art, and can be used in conjunction with computerized modeling methods provided herein or otherwise known in the art, computer-assisted manual examination methods provided herein or otherwise known in the art, or with manual modeling and design of candidate compounds for binding a Rac-1 GTPase activation site.

Also computer-assisted, manual examination of a Rac-1 GTPase activation site may be performed. The use of programs such as GRID (Goodford, J. Med. Chem., 28, (1985), 849-857)—a program that determines probable interaction between molecules with various functional groups and the protein surface—may also be used to analyze the binding site to predict partial structures of ligands for the site. Computer programs can be employed to estimate the attraction, repulsion, and steric hindrance of the candidate compound and the Rac-1 GTPase activation site described herein. Generally, the tighter the fit, the fewer the steric hindrances, and the greater the attractive forces, the more potent the potential ligand since these properties are consistent with a tighter binding constant. Furthermore, the more specificity in the design of a potential ligand, the more likely it is that the ligand will not interact with other proteins as well. This will tend to minimize potential side-effects due to unwanted interactions with other proteins.

Having designed or selected possible binding compounds, these can then be screened for activity. Exemplary methods for screening binding compounds are provided herein, and include, but are not limited to those described in Macherla et al., *J. Med. Chem.* 2005 and U.S. Patent Publication No. 2005/0049294, entitled "Methods of using [3.2.0] heterocyclic compounds and analogs thereof," filed on Jun. 18, 2004; both of which are hereby incorporated by reference in their entirety. Consequently, also provided herein are methods of evaluating a candidate compound predicted to bind to the Rac-1 GTPase activation site, where the method includes providing candidate compounds predicted to bind to the Rac-1 GTPase activation site in accordance with the methods described above, and contacting Rac-1 GTPase or a fragment thereof, with the candidate compound and determining whether the candidate compound bound to Rac-1 GTPase or fragment thereof. Also provided herein are methods of evaluating a candidate compound predicted to inhibit Rac-1 GTPase activity, where the method includes providing candidate compounds predicted to bind to Rac-1 GTPase in accordance with the methods described above, contacting a Rac-1 GTPase with the candidate compound, and determining whether the candidate compound inhibits Rac-1 GTPase activity.

The NSC23766 molecule described herein belongs to a new class of Rac-1 GTPase inhibitors, and acts by preventing activation of Rac-1 GTPase. The co-crystal structure of NSC23766 in complex with Rac-1 GTPase reveals that NSC23766 makes numerous van der Waals interactions with the switch I residue Val36 and the switch II residues Trp56, Ala59, Tyr64, Leu67, Leu70, Ser71 and Pro73 of Rac-1 GTPase. Hydrogen bonds were found involving the carbonyl of Leu70 and the side chain oxygen of Ser71. Further possible hydrogen bonds involving the carbonyl of Leu67, side chain of Gln74, the carbonyl of Asp57, and the carbonyl of Ser71 were identified.

Based upon these observations, an improved inhibitor can be made by adding to or modifying NSC23766 in order to have a configuration of moieties that can hydrogen bond with the carbonyl of Leu70, the side chain oxygen of Ser71, the carbonyl of Leu67, the side chain of Gln74, the carbonyl of Asp57, and the carbonyl of Ser71. It was also observed in the crystal structure of Rac-1 GTPase without NSC23766 bound that a DMSO molecule specifically interacted with the amide main chain group of Ala59. Thus, a further addition or modification to NSC23766 can include a moiety that can hydrogen bond with amide main chain group of Ala59. Exemplary moieties that can be added as hydrogen bond donors include amine, amide and hydroxyl moieties; exemplary moieties that can be added as hydrogen bond acceptors include hydroxyl, carbonyl, and ether moieties.

Further in regard to the co-crystal observations, an improved inhibitor can be made by adding to or modifying NSC23766 in order to have a configuration of moieties having improved van der Waals and/or hydrophobic interactions with the switch I residue Val36 and the switch II residues Trp56, Ala59, Tyr64, Leu67, Leu70, Ser71 and Pro73 of Rac-1 GTPase. Exemplary hydrophobic moieties that can be added include alkyl moieties, substituted alkyl moieties, aryl moieties and substituted aryl moieties.

Methods and compositions are described that affect the GTPase activity of members of the Ras superfamily, preferably Rac, such compositions include compounds that modulate the GTPase activity, along with uses for the compounds including screening for compounds which recognize Rac GTPase, and methods of treating pathological conditions associated or related to a Ras superfamily GTPase, including Rac. Another embodiment comprises binding to a Rho GTPase selected from the group consisting of Rac1, Rac2 and Rac3. Preferably, another embodiment comprises binding to a Rho GTPase that is Rac1. The preferred embodiments also relate to methods of using such compounds, or derivatives thereof, e.g. in therapeutics, diagnostics, and as research tools.

Methods and compositions are described that affect the GTPase activity of members of the Ras superfamily, preferably Rac; such compositions include compounds that modulate the GTPase activity. Preferably, the indication associated with GTPase activity is selected from the group consisting of hypertension, atherosclerosis, restenosis, cerebral ischemia, cerebral vasospasm, neuronal degeneration, spinal cord injury, cancer of the breast, colon, prostate, ovaries, brain or lung, thrombotic disorders, asthma, glaucoma, osteoporosis and erectile dysfunction.

The preferred embodiments also relate to methods of testing for and/or identifying agents that regulate Rac by measuring their effect on the ability of a Rho family GTPase-regulating active compound to regulate the action of Rac GTPase.

As used herein, the terms "Ras or Ras superfamily proteins" encompass a large family of GTP binding/GTP hydrolyzing monomeric proteins. Ras family includes the Ras, Rho, Rab, Arf, and Ran subfamilies of GTPases.

The terms "Rho GTPases" or "Rho family GTPases" refer to a subfamily of Ras superfamily and are small, membrane-bound, Ras-related GTP-binding proteins that function by binding and hydrolyzing GTP. Rho GTPases function as molecular switches, cycling between an inactive GDP-bound conformation and an active GTP-bound conformation and include RhoA, RhoB, RhoC, Cdc42, Rac1, Rac2, Rac3, TC10, RhoG, RhoD, Chp, WRCH1, TCL, and RIF.

A protein or polypeptide sequence of a Ras-related protein includes variants or fragments thereof derived from any species, particularly mammalian, including bovine, ovine, porcine, murine, equine, and preferably human, from any source whether natural, synthetic, semi-synthetic, or recombinant.

The terms "Rac GTPase" or "Rac protein or polypeptide" refer to Rac1, Rac2, and/or Rac3.

One embodiment provides for a method for reducing cancer cell proliferation by administering in a subject having cancer an effective amount of a Rho family GTPase-regulating active compound as defined herein.

Another embodiment provides for the use of an effective amount of a Rho family GTPase-regulating active compound as defined herein for the preparation of pharmaceutical composition for the treatment of a disease associated with abnormal cell proliferation.

Because of their cell proliferation inhibitory activity, the compounds of the preferred embodiments are suitable for treating a variety of diseases in a variety of conditions. In this regard, "treatment" or "treating" includes both therapeutic and prophylactic treatments. Accordingly, the compounds can be used at very early stages of a disease, or before early onset, or after significant progression, including metastasis. The term "treatment" or "treating" designates in particular a reduction of the burden in a patient, such as a reduction in cell proliferation rate, a destruction of diseased proliferative cells, a reduction of tumor mass or tumor size, a delaying of tumor progression, as well as a complete tumor suppression.

Typical examples of diseases associated with abnormal cell proliferation include cancers and restenosis, for instance. The compounds of the preferred embodiments are particularly suited for the treatment of cancers, such as solid tumors or lymphoid tumors. Specific examples include leukemia, prostate cancer, ovarian cancer, pancreas cancer, lung cancer, breast cancer, liver cancer, head and neck cancer, colon cancer, bladder cancer, non-Hodgkin's lymphoma cancer and melanoma.

The active compounds of the preferred embodiments can be administered according to various routes, typically by injection, such as local or systemic injection(s). Intratumoral injections are preferred for treating existing cancers. However, other administration routes can be used as well, such as intramuscular, intravenous, intradermic, subcutaneous, etc. Furthermore, repeated injections can be performed, if needed, although it is believed that limited injections will be needed in view of the efficacy of the compounds.

It is contemplated that such target cells can be located within an animal or human patient, in which case a safe and effective amount of the complex, in pharmacologically acceptable form, would be administered to the patient. Generally speaking, it is contemplated that useful pharmaceutical compositions of the preferred embodiments will include the selected active compound derivative in a convenient amount, e.g., from about 0.001% to about 10% (w/w) that is diluted in a pharmacologically or physiologically acceptable carrier, such as, for example, phosphate buffered saline. The route of administration and ultimate amount of material that is administered to the patient or animal under such circumstances will depend upon the intended application and will be apparent to those of skill in the art in light of the examples which follow.

Any composition chosen should be of low or non-toxicity to the cell. Toxicity for any given compound can vary with the concentration of compound used. It is also beneficial if the compound chosen is metabolized or eliminated by the body and if this metabolism or elimination is done in a manner that will not be harmfully toxic.

The examples are illustrative of the types of compounds to be used in the method claimed herein; the list is not exhaustive. Derivatives of the above compounds that fit the criteria of the claims are preferably also be considered when choosing an active compound.

The compound is preferably administered such that a therapeutically effective concentration of the compound is in contact with the affected cells of the body. The dose administered to an animal, particularly a human, in the context of the preferred embodiments is preferably sufficient to effect a therapeutic response in the animal over a reasonable period of time. The dose will be determined by the strength of the particular compound employed and the condition of the animal, as well as the body weight of the animal to be treated. The existence, nature, and extent of any adverse side effects that might accompany the administration of a particular compound also will determine the size of the dose and the particular route of administration employed with a particular patient. In general, the compounds of the preferred embodiments are therapeutically effective at low doses. The generally useful dose range is from about 0.001 mM, or less, to about 100 mM, or more. Preferably, the effective dose range is from about 0.01, 0.05, 0.1, 0.5, 0.6, 0.7, 0.8, or 0.9 mM, to about 1, 2, 3, 4, 5, 6, 7, 8, 9, or 10 mM. Accordingly, the compounds will be generally administered in low doses.

The compound can be administered in a pharmaceutically acceptable carrier. Pharmaceutically acceptable carriers are well-known to those who are skilled in the art. The choice of carrier will be determined in part by the particular compound, as well as by the particular method used to administer the composition. Accordingly, there is a wide variety of suitable formulations of the pharmaceutical composition of the preferred embodiments.

The compounds can be administered orally, topically, parenterally, by inhalation or spray, vaginally, rectally or sublingually in dosage unit formulations. The term "administration by injection" includes but is not limited to: intravenous, intraarticular, intramuscular, subcutaneous and parenteral injections, as well as use of infusion techniques. Dermal administration can include topical application or transdermal administration. One or more compounds can be present in association with one or more non-toxic pharmaceutically acceptable carriers and if desired other active ingredients.

Compositions intended for oral use can be prepared according to any suitable method known to the art for the manufacture of pharmaceutical compositions. Such compositions can contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions can also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example arachis oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Compounds of the preferred embodiments can also be administrated transdermally using methods known to those skilled in the art. For example, a solution or suspension of an active agent in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of an active agent can be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents can also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to about 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations can also include mixtures of one or more materials selected from monohydroxy or polyhydroxy alcohols, saturated or unsaturated C8-C18 fatty alcohols, saturated or unsaturated C8-C18 fatty acids, saturated or unsaturated fatty esters with up to 24 carbons, diesters of saturated or unsaturated dicarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates can also be used as matrix components. Additional additives, such as viscous resins or oils can be added to increase the viscosity of the matrix.

Pharmaceutical compositions of the preferred embodiments can also be in the form of oil-in-water emulsions. The oil phase can be a vegetable oil, for example olive oil or arachis oil, or a mineral oil, for example, liquid paraffin or mixtures of these. Suitable emulsifying agents can be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions can also contain sweetening and flavoring agents. Syrups and elixirs can be formulated with sweetening agents, for example glycerol, propylene glycol, sorbitol or sucrose. Such formulations can also contain a demulcent, a preservative and flavoring and coloring agents.

The compounds can also be administered in the form of suppositories for rectal or vaginal administration of the drug. These compositions can be prepared by mixing the drug with a suitable nonirritating excipient which is solid at ordinary temperatures but liquid at the rectal temperature or vaginal temperature and will therefore melt in the rectum or vagina to release the drug. Such materials include cocoa butter and polyethylene glycols.

For all regimens of use disclosed herein for active agent, the daily oral dosage regimen will preferably be from about 0.01 to about 200 mg/Kg of total body weight. Preferably, the daily oral dosage regimen will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. Preferably, the daily dosage for administration by injection, including intravenous, intramuscular, subcutaneous and parenteral injections, and use of infusion techniques will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily vaginal dosage regime will preferably be from 0.01 to 200 mg/Kg of total body weight. The daily topical dosage regimen will preferably be from 0.01 to 200 mg administered between one to four times daily. The concentration for vaginal dosage and topical dosage will preferably be that required to maintain a daily dose is of from 0.1 to 200 mg/Kg. Preferably, the daily oral dosage regimen will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily inhalation dosage regimen will preferably be from 0.01 to 10 mg/Kg of total body weight. Preferably, the daily inhalation dosage regimen will preferably be from about 0.01, 0.05, 0.1, 0.5, to about 1, 2, 3, 4, 5, or 10, mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of an active agent or a pharmaceutically acceptable salt thereof given for a defined number of days, can be ascertained by those skilled in the art using conventional treatment tests.

Another aspect of the preferred embodiments relates to the regulation of biological pathways in which a GTPase is involved, particularly pathological conditions, e.g., cell proliferation (e.g., cancer), growth control, morphogenesis, stress fiber formation, and integrin-mediated interactions, such as embryonic development, tumor cell growth and metastasis, programmed cell death, hemostasis, leucocyte homing and activation, bone resorption, clot retraction, and the response of cells to mechanical stress. Thus, the preferred embodiments relate to all aspects of a method of modulating an activity of a Rac polypeptide comprising, administering an effective amount of an active agent, an effective amount of a compound which modulates the activity of a Rac polypeptide, or combination thereof. The activity of Rac which is modulated can include: GTP binding, GDP binding, GEF binding, GTPase activity, integrin binding, coupling or binding of Rac to receptor or effector-like molecules (such as integrins, growth factor receptors, tyrosine kinases, PI-3K, PIP-5K, etc.). Increasing, reducing, antagonizing, or promoting Rac can modulate the activity. The modulation of Rac can be measured by assay for GTP hydrolysis, binding to Rac-GEF, etc. An effective amount is any amount which, when administered, modulates the Rac activity. The activity can be modulated in a cell, a tissue, a whole organism, in situ, in vitro (test tube, a solid support, etc.), in vivo, or in any desired environment.

The modulation of oncogenic transforming activity by an active agent, or derivatives thereof, can be measured according to various known procedures. A compound can be added at any time during the method (e.g., pretreatment of cells; after addition of GEF, etc.) to determine its effect on the oncogenic transforming activity of an active agent. Various cell lines can also be used.

Other assays for Rac-mediated signal transduction can be accomplished according to procedures known in the art, e.g., as described in U.S. Pat. Nos. 5,141,851; 5,420,334; 5,436,128; and 5,482,954, all of which are incorporated herein by reference in their entirety. In addition, peptides that inhibit the interaction, e.g., binding, between an active agent and a G-protein, such as Rac, can be identified.

The preferred embodiments also relate to a method of testing for and identifying an agent which modulates the activity of RacGTPase, or a biologically-active fragment thereof, or which modulates the binding between an active agent, or a biologically-active fragment thereof, and a GTPase, or a biologically-active fragment thereof, to which it binds. The method comprises contacting the active agent and Rac GTPase with an agent to be tested and then detecting the presence or amount of binding between the active agent and GTPase, or an activity of the active agent.

By modulating, it is meant that addition of the agent affects the activity or binding. The binding or activity modulation can be affected in various ways, including inhibiting, blocking, preventing, increasing, enhancing, or promoting it. The binding or activity effect does not have to be achieved in a specific way, e.g., it can be competitive, noncompetitive, allosteric, sterically hindered, via cross-linking between the agent and the GEF or GTPase, etc. The agent can act on either the active agent or GTPase. The agent can be an agonist, an antagonist, or a partial agonist or antagonist. The presence or amount of binding can be determined in various ways, e.g., directly or indirectly by assaying for an activity promoted or inhibited by the active agent, such as guanine nucleotide exchange, GTP hydrolysis, oncogenic transformation, etc. Such assays are described above and below, and are also known in the art. The agent can be obtained and/or prepared from a variety of sources, including natural and synthetic. It can comprise, e.g., amino acids, lipids, carbohydrates, organic molecules, nucleic acids, inorganic molecules, or mixtures thereof.

The agent can be added simultaneously or sequentially. For example, the agent can be added to the active agent and then the resultant mixture can be further combined with the GTPase. The method can be carried out in liquid on isolated components, on a matrix (e.g., filter paper, nitrocellulose, agarose), in cells, on tissue sections, etc.

The method further relates to obtaining or producing agents that have been identified according to the above-described method. The preferred embodiments also relate to products identified in accordance with such methods.

The preferred embodiments thus also relate to the treatment and prevention of diseases and pathological conditions associated with Rac-mediated signal transduction, e.g., cancer, diseases associated with abnormal cell proliferation, and the like. For example, the preferred embodiments relate to a method of treating cancer comprising administering, to a subject in need of treatment, an amount of a compound effective to treat the disease, where the compound is an active agent. Treating the disease can mean, delaying its onset, delaying the progression of the disease, improving or delaying clinical and pathological signs of disease. Similarly, the method also relates to treating diseases associated with inflammation, and/or the chemotactic ability of neutrophils. A regulator compound, or mixture of compounds, can be synthetic, naturally-occurring, or a combination. A regulator compound can comprise amino acids, nucleotides, hydrocarbons, lipids, polysaccharides, etc. A regulator compound is preferably a regulator of Rac GTPase. To treat the disease, the compound, or mixture, can be formulated into pharmaceutical composition comprising a pharmaceutically acceptable carrier and other excipients as apparent to the skilled worker. Such composition can additionally contain effective amounts of other compounds, especially for treatment of cancer.

Based on these data, one embodiment is an improved method for treatment of tumors comprising administration of a pharmaceutically effective quantity of active agent or its pharmaceutically acceptable salts or esters, active agent analogs or their pharmaceutically acceptable salts or esters, or a combination thereof.

The compositions and preparations described preferably contain at least 0.1% of active agent. The percentage of the compositions and preparations can, of course, be varied, and can contain between about 2% and 60% of the weight of the amount administered. Preferably, the percentage of the compositions and preparations can contain between about 2, 5, 10, or 15% and 30, 35, 40, 45, 50, 55, or 60% of the weight of the amount administered. The amount of active compounds in such pharmaceutically useful compositions and preparations is such that a suitable dosage will be obtained.

The active agent form salts, which are also within the scope of the preferred embodiments. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") can be formed and are included within the term "salt(s)" as used herein. Pharmaceutically acceptable (i.e., non-toxic, physiologically acceptable) salts are preferred, although other salts are also useful, e.g., in isolation or purification steps, which can be employed during preparation. Salts of the compounds of the active agent can be formed, for example, by reacting a compound of the active agent with an amount of acid or base, such as an equivalent amount, in a medium such as one in which the salt precipitates or in an aqueous medium followed by lyophilization.

The active agent which contain a basic moiety, such as, but not limited to an amine or a pyridine or imidazole ring, can form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The active agents which contain an acidic moiety, such as, but not limited to a carboxylic acid, can form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups can be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of the preferred embodiments are also contemplated herein. The term "prodrug", as employed herein, denotes a compound which, upon administration to a subject, undergoes chemical conversion by metabolic or chemical processes to yield a compound of the active agent, and/or a salt and/or solvate thereof. Solvates of the active agent are preferably hydrates.

Active agent, and salts thereof, can exist in their tautomeric form (for example, as an amide or imino ether). All such tautomeric forms are contemplated herein as part of the preferred embodiments.

All stereoisomers of the present compounds, such as those, for example, which can exist due to asymmetric carbons on any of the substituents, including enantiomeric forms (which can exist even in the absence of asymmetric carbons) and diastereomeric forms, are contemplated and within the scope of the preferred embodiments. Individual stereoisomers of the compounds of the preferred embodiments can, for example, be substantially free of other isomers, or can be admixed, for example, as racemates or with all other or other selected, stereoisomers. The chiral centers of the preferred embodiments can have the S or R configuration as defined by the IUPAC 1974 Recommendations.

When the compounds according to the preferred embodiments are in the forms of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts are prepared by reacting the active agent with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol, etc. Mixture of solvents can be used. Organic bases like lysine, arginine, diethanolamine, choline, guanidine and their derivatives etc. can also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents can also be used.

As indicated above, a further object of the preferred embodiments relates to a pharmaceutical composition comprising at least one compound of formula I, II, IIa, III, IIIa, or IV, as defined above, and a pharmaceutically acceptable vehicle or support.

The compounds can be formulated in various forms, including solid and liquid forms, such as tablets, gel, syrup, powder, aerosol, etc.

The compositions of the preferred embodiments can contain physiologically acceptable diluents, fillers, lubricants, excipients, solvents, binders, stabilizers, and the like. Diluents that can be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that can be used in the compositions include but are not limited to starch, gelatin and fillers such as sucrose, glucose, dextrose and lactose.

Natural and synthetic gums that can be used in the compositions include but are not limited to sodium alginate, ghatti gum, carboxymethyl cellulose, methyl cellulose, polyvinyl pyrrolidone and veegum. Excipients that can be used in the compositions include but are not limited to microcrystalline cellulose, calcium sulfate, dicalcium phosphate, starch, magnesium stearate, lactose, and sucrose. Stabilizers that can be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that can be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds of formula I, II, IIa, III, IIIa, or IV are administered will vary according to the dosage form, mode of administration, the condition being treated and particulars of the patient being treated. Accordingly, optimal therapeutic concentrations will be best determined at the time and place through routine experimentation.

The compounds according to the preferred embodiments can also be used enterally. Orally, the compounds according to the preferred embodiments are suitable administered at the rate of 100 μg to 100 mg per day per kg of body weight. Preferably, orally, the compounds according to the preferred embodiments are suitable administered at the rate of about 100, 150, 200, 250, 300, 350, 400, 450, or 500 μg to about 1, 5, 10, 25, 50, 75, 100 mg per day per kg of body weight. The required dose can be administered in one or more portions. For oral administration, suitable forms are, for example, tablets, gel, aerosols, pills, dragees, syrups, suspensions, emulsions, solutions, powders and granules; a preferred method of administration consists in using a suitable form containing from 1 mg to about 500 mg of active substance. Preferably, a method of administration consists in using a suitable form containing from about 1, 2, 5, 10, 25, or 50 mg to about 100, 200, 300, 400, 500 mg of active substance.

The compounds according to the preferred embodiments can also be administered parenterally in the form of solutions or suspensions for intravenous or intramuscular perfusions or injections. In that case, the compounds according to the preferred embodiments are generally administered at the rate of about 10 μg to 10 mg per day per kg of body weight; a preferred method of administration consists of using solutions or suspensions containing approximately from 0.01 mg to 1 mg of active substance per ml. Preferably, the compounds according to the preferred embodiments are generally administered at the rate of about 10, 20, 30, 40, 50, 60, 70, 80, 90, or 100 μg to 1, 2, 3, 4, 5, 6, 7, 8, 9, or 10 mg per day per kg of body weight; a preferred method of administration consists of using solutions or suspensions containing approximately from 0.01, 0.02, 0.03, 0.04, or 0.5 mg to 0.1, 0.2, 0.3, 0.4, 0.5, 0.6, 0.7, 0.8, 0.9, or 1 mg of active substance per ml.

The compounds of formula I, II, IIa, III, IIIa, or IV can be used in a substantially similar manner to other known anti-tumor agents for treating (both chemopreventively and therapeutically) various tumors. For the compounds of the preferred embodiments, the anti-tumor dose to be administered, whether a single dose, multiple dose, or a daily dose, will of course vary with the particular compound employed because of the varying potency of the compound, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment will be able to ascertain, without undue experimentation, appropriate protocols for the effective administration of the compounds of the preferred embodiments, such as by referring to the earlier published studies on compounds found to have anti-tumor properties.

The preferred embodiments relate to methods of treatment of disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjogren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Szary syndrome, and Hodgkin disease.

The compounds of preferred embodiments can be used in relation to diseases of the skin. Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma, tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

The compounds of preferred embodiments can be used in relation to disorders arising from bone marrow cells. In normal bone marrow, the myelocytic series (polymorphonuclear cells) make up approximately 60% of the cellular elements, and the erythrocytic series, 20-30%. Lymphocytes, monocytes, reticular cells, plasma cells and megakaryocytes together constitute 10-20%. Lymphocytes make up 5-15% of normal adult marrow. In the bone marrow, cell types are add mixed so that precursors of red blood cells (erythroblasts), macrophages (monoblasts), platelets (megakaryocytes), polymorphonuclear leukocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each are known to the person of ordinary skill in the art and are found, for example, in *Immunology, Immunopathology and Immunity*, Fifth Edition, Sell et al. Simon and Schuster (1996), which is incorporated herein by reference in its entirety. Accordingly, the preferred embodiments are directed to disorders arising from these cells. These disorders include but are not limited to the following: diseases involving hematopoietic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadenoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

The compounds of preferred embodiments can be used in relation to disorders involving the spleen. Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

The compounds of preferred embodiments can be used in relation to disorders involving blood vessels. Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

The compounds of preferred embodiments can be used in relation to disorders involving red cells. Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

The compounds of preferred embodiments can be used in relation to disorders involving B-cells. Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenstrom macroglobulinemia), mantle cell lymphoma, marginal zone lymphoma (MALToma), and hairy cell leukemia.

The compounds of preferred embodiments can be used in relation to disorders related to reduced platelet number. Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

The compounds of preferred embodiments can be used in relation to disorders involving precursor T-cell neoplasms. Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Szary syndrome, peripheral T-cell lymphoma, unspecified, angioimmunoblastic T-cell lymphoma, angiocentric lymphoma (NK/T-cell lymphoma4a), intestinal T-cell lymphoma, adult T-cell leukemia/lymphoma, and anaplastic large cell lymphoma.

The compounds of preferred embodiments can be used in relation to disorders of the bone. Bone-forming cells include the osteoprogenitor cells, osteoblasts, and osteocytes. The disorders of the bone are complex because they can have an impact on the skeleton during any of its stages of development. Hence, the disorders can have variable manifestations and can involve one, multiple or all bones of the body. Such disorders include, congenital malformations, achondroplasia and thanatophoric dwarfism, diseases associated with abnormal matrix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

The compounds of preferred embodiments can be used in relation to disorders involving the tonsils. Disorders involving the tonsils include, but are not limited to, tonsillitis, Peritonsillar abscess, squamous cell carcinoma, dyspnea, hyperplasia, follicular hyperplasia, reactive lymphoid hyperplasia, non-Hodgkin's lymphoma and B-cell lymphoma.

The compounds of preferred embodiments can be used in relation to disorders involving the liver. Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly, infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis, drug- and toxin-induced liver disease, such as alcoholic liver disease; inborn errors of metabolism and pediatric liver disease, such as hemochromatosis, Wilson disease, alpha.1-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

The compounds of preferred embodiments can be used in relation to disorders involving the colon. Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

The compounds of preferred embodiments can be used in relation to disorders involving the lung. Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors, pathologies of the pleura, including inflammatory pleural effusions, noninflammatory pleural effusions, pneumothorax, and pleural tumors, including solitary fibrous tumors (pleural fibroma) and malignant mesothelioma.

The active compounds can be incorporated into pharmaceutical compositions suitable for administration to a subject, e.g., a human. Such compositions typically comprise the nucleic acid molecule, protein, modulator or antibody and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the preferred embodiments. Supplementary active compounds can also be incorporated into the compositions. A pharmaceutical composition of the preferred embodiments is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid, buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes) can also be used as pharmaceutically acceptable carriers. These can be prepared according to methods known to those skilled in the art.

It is especially advantageous to formulate oral or parenteral compositions in dosage unit form for ease of administration and uniformity of dosage. "Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the preferred embodiments are dictated by and directly dependent on the unique characteristics of the active compound and the particular therapeutic effect to be achieved, and the limitations inherent in the art of compounding such an active compound for the treatment of individuals.

As used herein, the term "therapeutically effective amount" means the total amount of each active component of the pharmaceutical composition or method that is sufficient to show a meaningful patient benefit, e.g., healing of chronic conditions or in an increase in rate of healing of such conditions, or in a reduction in aberrant conditions. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the preferred embodiments, a therapeutically effective amount of one, two, or more of the active agents of the preferred embodiments is administered to a subject afflicted with a disease or disorder related to Rho family GTPases, or to a tissue which has such disease or disorder. The active agents of the preferred embodiments can be administered in accordance with the method of the preferred embodiments either alone of in combination with other known therapies. When co-administered with one or more other therapies, the active agents of the preferred embodiments can be administered either simultaneously with the other treatment(s), or sequentially. If administered sequentially, the attending physician will decide on the appropriate sequence of administering the active agents of the preferred embodiments in combination with the other therapy.

Generally, a therapeutically effective amount of active agent (i.e., an effective dosage) ranges from about 0.001 to 5000 mg/kg body weight, more preferably about 0.01 to 1000 mg/kg body weight, more preferably about 0.01 to 500 mg/kg body weight, more preferably about 0.01 to 250 mg/kg body weight, more preferably about 0.01 to 100 mg/kg body weight, more preferably about 0.001 to 60 mg/kg body weight, more preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors can influence the dosage required to effectively treat a subject, including but not limited to the severity of the disease or disorder, previous treatments, the general health and/or age of the subject, and other diseases present. Moreover, treatment of a subject with a therapeutically effective amount can include a single treatment or, preferably, can include a series of treatments. In a preferred example, a subject is treated in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage used for treatment can increase or decrease over the course of a particular treatment. Changes in dosage can result and become apparent from the results of diagnostic assays as described herein.

The preferred embodiments encompass one or more additional agents that modulate expression or activity of Rac GTPase. An agent can, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In one embodiment, the additional agent can be a prenylation inhibitor, such as disclosed by U.S. Pat. Nos. 6,649,638, 5,420,245; 5,574,025; 5,523,430; 5,602,098; 5,631,401; 5,705,686; 5,238,922; 5,470,832; and 6,191,147, all of which are incorporated herein by reference in their entirety.

In another embodiment, the additional agent comprises one or more inhibitor of farnesyl protein transferase (FPTase), prenyl-protein transferase or geranylgeranyl-protein transferase as described in U.S. Pat. Nos. 6,572,850; 6,458,783; 6,423,751; 6,387,926; 6,242,433; 6,191,147; 6,166,067; 6,156,746; 6,083,979; 6,011,029; 5,929,077; 5,928,924; 5,843,941; 5,786,193; 5,629,302; 5,618,964; 5,574,025; 5,567,841; 5,523,430; 5,510,510; 5,470,832; 5,447,922; 6,596,735; 6,586,461; 6,586,447; 6,579,887; 6,576,639; 6,545,020; 6,539,309; 6,535,820; 6,528,523; 6,511,800; 6,500,841; 6,495,564; 6,492,381; 6,458,935; 6,451,812; 6,441,017; 6,440,989; 6,440,974; 6,432,959; 6,426,352; 6,410,541; 6,403,581; 6,399,615; 6,387,948; 6,387,905; 6,387,903; 6,376,496; 6,372,747; 6,362,188; 6,358,968; 6,329,376; 6,316,462; 6,294,552; 6,277,854; 6,268,394; 6,265,382; 6,262,110; 6,258,824; 6,248,756; 6,242,458; 6,239,140; 6,228,865; 6,228,856; 6,225,322; 6,218,401; 6,214,828; 6,214,827; 6,211,193; 6,194,438, which are specifically incorporated herein by reference in their entirety.

A "farnesyl protein transferase inhibitor" or "FPT inhibitor" or "FTI" is defined herein as a compound which: (i) potently inhibits FPT (but generally not geranylgeranyl protein transferase I) and (ii) blocks intracellular farnesylation of ras. FPT catalyzes the addition of an isoprenyl lipid moiety onto a cysteine residue present near the carboxy-terminus of the Ras protein. This is the first step in a post-translational processing pathway that is essential for both Ras membrane-association and Ras-induced oncogenic transformation. A number of FPT inhibitors have been reported, including a variety of peptidomimetic inhibitors as well as other small molecule inhibitors.

Farnesyl transferase inhibitors generally fall into two classes: analogs of farnesyl diphosphate; and protein substrates for farnesyl transferase. Farnesyl transferase inhibitors have been described in U.S. Pat. No. 5,756,528, U.S. Pat. No. 5,141,851, U.S. Pat. No. 5,817,678, U.S. Pat. No. 5,830,868, U.S. Pat. No. 5,834,434, and U.S. Pat. No. 5,773,455, all of which are incorporated herein by reference in their entirety. Among the farnesyl transferase inhibitors shown to be effective for inhibiting the transfer of the farnesyl moiety to Ras-related proteins are L-739,749 (a peptidomimetic analog of the C-A-A-X sequence), L-744,832 (a peptidomimetic analog of the C-A-A-X sequence), SCH 44342 (1-(4-pyridylacetyl)-4-(8-chloro-5,6dihydro-IIH benzo[5,6]cyclohepta [1,2-b]pyridin-11-yhdene)piperidine), BZA-5B (a benzodiazepine peptidomimetic), FTI-276 (a C-A-A-X peptidomimetic), and B1086 (a C-A-A-X peptidomimetic). Administration of farnesyl transferase inhibitors (FTIs) is accomplished by standard methods known to those of skill in the art, most preferably by administration of tablets containing the FTI, and is expected to fall approximately within a range of about 0.1 mg/kg of body to weight to about 20 mg/kg of body weight per day.

In another embodiment, the additional agent comprises one or more inhibitor of geranylgeranyl-protein transferase (GGT) as have been described in U.S. Pat. No. 5,470,832 (Gibbs & Graham), which is incorporated herein by reference in its entirety. These compounds can be administered to an individual in dosage amounts of between 0.5 mg/kg of body weight to about 20 mg/kg of body weight. Alternatively, one or more inhibitors of isoprenylation, including farnesyl transferase (FT) inhibitors and/or geranylgeranyl transferase inhibitors (GGT) are administered to a patient.

In another embodiment, the additional agent comprises one or more toxins such as toxins A and B from *C. difficile* and *C. sordellii* lethal toxin (LT). In addition, Rac 1 and Rac2 can be inhibited when Rho is specifically ADP ribosylated by C3 enzyme, which is one of the botulinum toxins, and Staphylococcal toxin EDIN (Narumiya, S. and Morii, S., *Cell Signal*, 5, 9-19, 1993; Sekine, A. et al., *J. Biol. Chem.*, 264, 8602-8605, 1989, all of which are incorporated herein by reference in their entirety).

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the preferred embodiments. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses can be determined using the assays described herein. When one or more of these small molecules is to be administered to an animal (e.g., a human) in order to modulate expression or activity of a polypeptide or nucleic acid of the preferred embodiments, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The examples disclosed below illustrated preferred embodiments and are not intended to limit the scope. It is evident to those skilled in the art that modifications or variations can be made to the preferred embodiments described herein without departing from the teachings of the present invention.

EXAMPLES

Recombinant protein production. Recombinant Trio (residues 1225-1537) containing the N-terminal DH/PH module, Rac1, Cdc42 and the p21-binding domain (PBD) of PAK1 (residues 51-135) are expressed in *E. coli* BL21 (DE3) strain as N-terminal $His_6$-tagged fusion proteins by using the pET expression system (Novagen). Rac1, Cdc42, Intersectin, PAK1 (PBD) and WASP (PBD) are expressed in *E. coli* DH5α strain as GST fusions by using the pGEX-KG vector. The N-terminal tagged GST or $His_6$ fusion proteins are purified by glutathione- or $Ni^{2+}$-agarose affinity chromatography. GST-Rho GTPases on glutathione beads are eluted off bound guanine nucleotides or $Mg^{2+}$ by washing with a buffer containing 50 mM Trio-HCl, PH 7.6, 100 mM NaCl, 1 mM EDTA, and 1 mM DTT.

In vitro complex formation assay. About 0.5 µg of $His_6$-tagged Trio is incubated with 0.5 µg, EDTA-treated, GST-fused Cdc42 or Rac1 in a binding buffer containing 20 mM Tris-HCl, pH 7.6, 100 mM NaCl, 1 mM DTT, 1% bovine serum albumin, 1% Triton X-100, 1 mM MgCl$_2$ and 10 μl suspended glutathione-agarose beads. ~0.75 μg of GST-tagged Intersectin is incubated with nucleotide-free, His$_6$-tagged Cdc42 or Rac1 (0.25 μg) in the binding buffer with 10 μl suspended glutathione-agarose beads. After incubation at 4° C. for 30 min under constant agitation, the glutathione beads are washed twice with the binding buffer. The amount of His$_6$-tagged protein co-precipitated with the GST-fusion bound beads is detected by anti-His Western blotting.

In vitro guanine nucleotide exchange assay. For these, 200 nM Rac1 loaded with mant-GDP is incubated at 25° C. in an exchange buffer containing 100 mM NaCl, 5 mM MgCl$_2$, 50 mM Tris-HCl (pH 7.6), and 0.5 mM GTP in the absence or presence of 200 nM Trio. The mant-GDP fluorescence changes in the course of the exchange reactions are monitored with an excitation wavelength at 360 nm and the emission wavelength at 440 nm by a Cary Ellipse fluorescence spectrometer (Varian, Inc.).

Cell culture. NIH 3T3 fibroblasts are grown in Dulbecco's modified Dagle's medium supplemented with 10% calf serum. RWPE-1 cells are obtained from the American Type culture collection (ATCC) and are grown in keratinocyte-Serum Free medium (GIBCO-BRL) supplemented with 5 ng/ml EGF and 0.05 mg/ml bovine pituitary extract. PC-3 cells are cultured in RPM1 1640 medium (Cellgro) supplemented with 10% FBS.

Endogenous Rho GTPase activity assay. GST- or His$_6$-PAK1 (PBD) and GST-WASP (PBD) are expressed in Escherichia coli and purified by glutathione- or Ni$^{2+}$-agarose affinity chromatography. Cells are grown in log phase in a 10 cm dish, and are starved in 0.5% serum medium or indicated otherwise for 24 hrs prior to lysis in a buffer containing 20 mM Tris-HCl (pH 7.6), 100 mM NaCl, 10 mM MgCl$_2$, 1% NP-40, 10% glycerol, and 1× proteases inhibitor cocktail (Roch). Lysates are clarified and the protein concentrations are normalized. The cell lysates containing equal amount of proteins are incubated with 10 μg GST- or His$_6$-fusion probes for 40 min at 4° C. under constant rotation. The beads are washed twice with the lysis buffer, and the bound-Rho GTPases are detected by anti-Rac1 (Upstate), or anti-Cdc42 (BD Transduction Laboratories) Western blotting. Quantification of the Western blots is carried out using a LAS-1000 luminescent image analyzer (Fujifilm medical system, USA, Inc.).

Immunofluorescence. After overnight serum starvation in the presence or absence of 100 μM 23766, NIH 3T3 cells grown on cover glasses are treated with 10 nM PDGF for zero, five or ten minutes. The cells are fixed with 3.7% formaldehyde in PBS for 15 min, and permeabilized with 0.1% Trion X-100 for 20 min. The cellular actin is stained with TRITC-labeled phalloidin (Sigma) at 10 μg/ml in PBS for 40 min at room temperature. The actin and cell morphological changes are visualized by fluorescence microscopy.

Cell growth assay. Wild type and RacL61- or various GEF-transfected NIH 3T3 cells are grown in 5% calf serum. The cells are split in duplicate in 6-well plates at 5×10$^4$ cells per well and are counted daily with a hemocytometer for 4 days. The growth rate of the prostate PC-3 cells is measured by the CellTiter 96 AQueous assay (Promega). 1,500 cells/well in 200 μl of 5% FBS medium are plated in 96-well plates and are grown under normal conditions. Cultures are assayed in 0, 1, 2, 3, 4, or 5 days by the addition of 20 μl of the combined MTS/PMS solution followed by incubation for one hour at 37° C. Absorbency is measured at a wavelength of 490 nm on an automated microplate reader.

Anchorage independent growth. The prostate epithelia RWPE and PC-3 cells (1.25×10$^3$ per well) are grown in 0.3% agarose in the absence or presence of different doses of compound 23766 following a published protocol (Qiu et al., 1997, which is incorporated herein by reference in its entirety). The number of colonies formed in soft agar is counted after ten days.

Cell invasion assays. The cell invasion assays are performed using 6.4-mm Biocoat Matrigel invasion chambers with 8.0-micron pore size PET membrane (Becton-Dickinson) according to the manufactory instructions. Briefly, 5×10$^4$ cells are resuspended in 0.5 ml of serum free culture medium and added to the upper chamber. 10% fetal bovine serum in the culture medium is used as a chemo-attractant in the lower chamber. After the cells are incubated for overnight, the number of cell passed through the Matrigel is counted.

Results

Virtual Screening for Rac1-specific inhibitors. In the three-dimensional (3D) structure of Rac1-Tiam1 complex, Trp$^{56}$ of Rac1 is buried in a pocket formed by residues His$^{1178}$, Ser1$^{184}$, Glu$^{1183}$ and Ile$^{1197}$ of Tiam1 and Lys$^5$, Val$^7$, Thr$^{58}$, and Ser$^{71}$ of Rac1 (Worthylake et al., 2000, which is incorporated herein by reference in its entirety). To identify Rac1-specific inhibitors based on the structural features surrounding Trp$^{56}$, a potential inhibitor-binding pocket is created with residues of Rac1 within 6.5 angstroms of Trp$^{56}$ in the Rac1-Tiam1 monomer, including Lys$^5$, Val$^7$, Trp$^{56}$, and Ser$^{71}$. A 3D database search is performed to identify compounds whose conformations would fit the binding pocket. In order to take the flexibility of the compounds into consideration during the screening process, the program UNITY, whose Directed Tweak algorithm allows a rapid, conformationally flexible 3D search (Hurst, 1994, which is incorporated herein by reference in its entirety), is applied.

The small molecule hits yielded by the UNITY program are next docked into the predicted binding pocket of Rac1 containing Trp$^{56}$ by using the program FlexX, an energy minimization modeling software that can quickly and flexibly dock ligand to protein binding site (Rarey et al., 1996, which is incorporated herein by reference in its entirety). Following the docking procedures, the compounds are ranked based on their predicted ability to bind the binding pocket using the program Cscore. Cscore generates a relative, consensus score based on how well the individual scoring functions of the protein-ligand complex perform (Clark et al., 2002, which is incorporated herein by reference in its entirety).

Compound NCI 23766 specifically inhibits Rac1-GEF interaction. Compounds from the virtual screening, including Compound NCI 23766, were obtained from the National Cancer Institute—Research Samples and Services from Developmental Therapeutics Program (Bethesda, Md.). Also, Compound NCI 23766 can be synthesized as set forth herein.

Synthetic Scheme 1

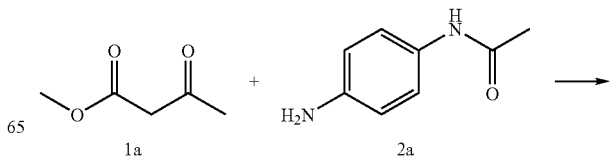

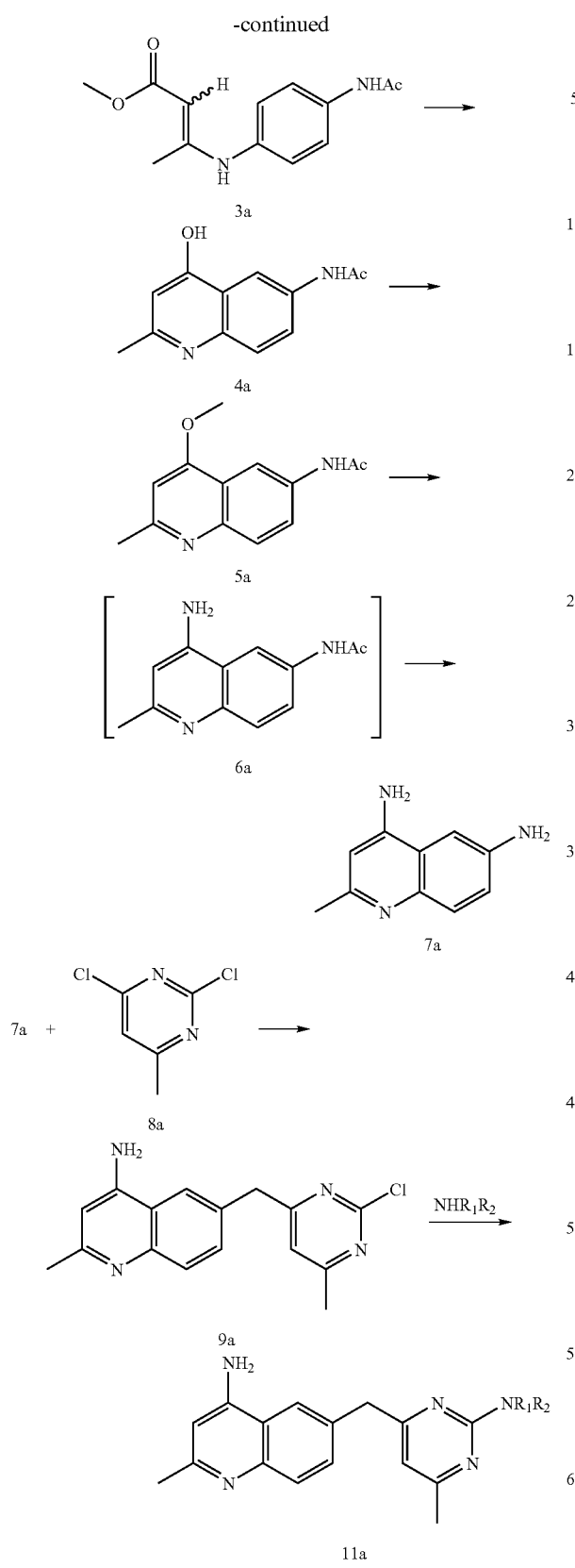
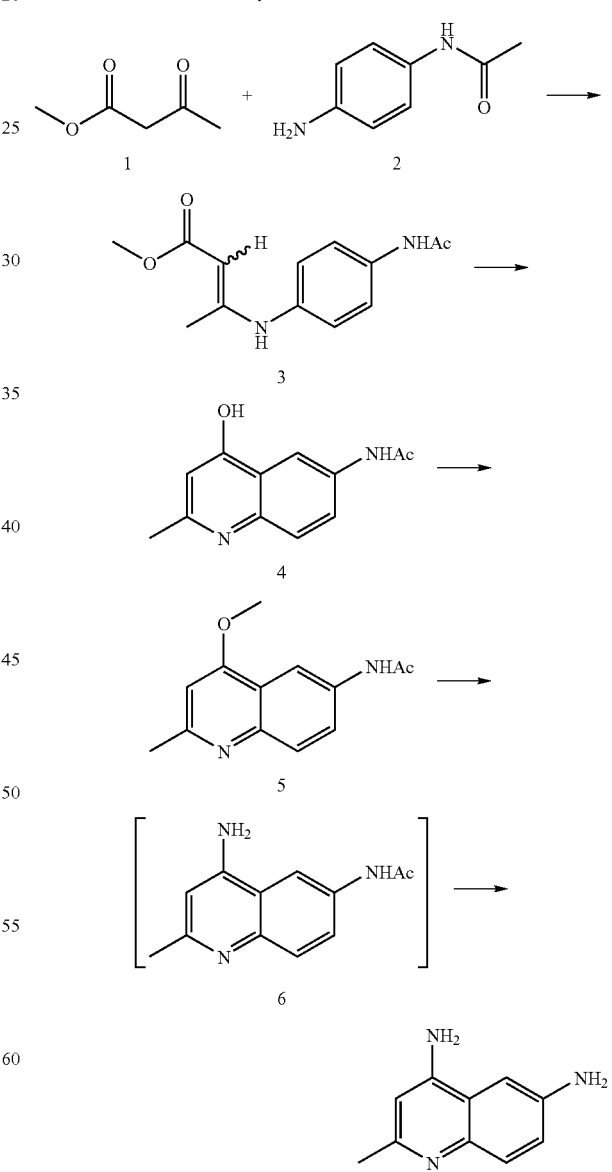

compound 10. $NHR_1R_2$ can be varied to be included within the preferred embodiments. $NHR_1R_2$ can be commercially available or synthesized using standard chemical methodologies. The reaction between $NHR_1R_2$ and Compound 9 or 9a is a standard amination reaction onto a haloaromatic ring.

The synthetic scheme described herein can be carried out using standard chemical methodologies described and referenced in standard textbooks. One may substitute other reagents known in the art which are known to be equivalent or perform a similar function. Starting material are commercially available reagents and reactions are preferably carried out in standard laboratory glassware under reaction conditions of standard temperature and pressure, except where otherwise indicated.

Synthetic Scheme 1 follows closely the reaction conditions of Synthetic Scheme 2. In Synthetic Scheme 2, $NHR_1R_2$ is

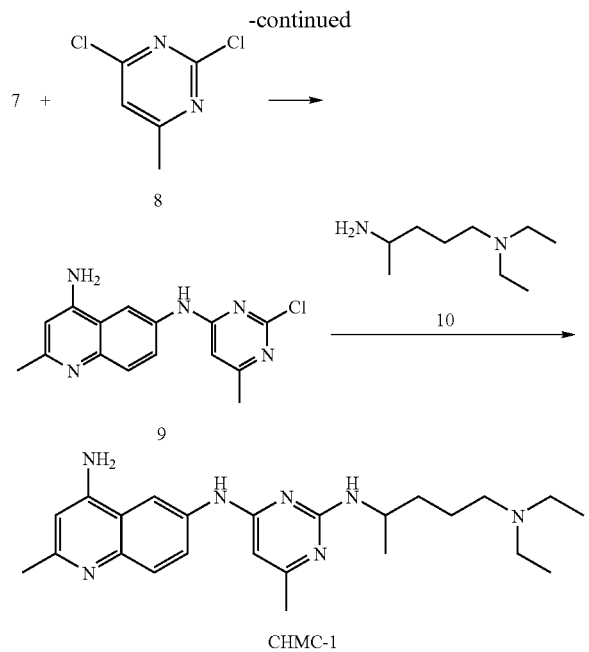

CHMC-1

EXPERIMENTAL

General:

Raw materials were purchased from Aldrich, Acros, Fisher or Matrix Scientific. All solvents were ACS grade or better. Reactions were run under an atmosphere of dry nitrogen as necessary. Removal of solvents "in vacuo" refers to rotary evaporation using a Buchi apparatus at 25-50° C. and 45 Torr. Vacuum drying was done under high vacuum. All NMR spectra were recorded using a Varian-Gemini 300 spectrometer at 300 MHz for $^1$H NMR using CHCl$_3$ (7.26 ppm) or DMSO (2.5 ppm) as a reference and at 75 MHz for $^{13}$C NMR using CDCl$_3$ (77.0 ppm) or DMSO (39.43) as a reference.

Methyl 3-{[4-(acetylamino)phenyl]amino}but-2-enoate (3): A suspension of 4-aminoacetanilide (2) (253 g, 1.68 mol) and methyl acetoacetate (215 g, 1.85 mol) in MeOH (0.75 L) was heated to reflux. The resulting solution was held at reflux for 16 h and then cooled to 5° C. The resulting off-white precipitate was filtered and washed with MTBE (3×200 mL) to give butenoate 3 (195 g, 47% yield). The mother liquor was concentrated in vacuo and filtered to give a second crop of 3 as pale pink solids (141 g, 34% yield, 81% overall yield). $^1$H NMR (DMSO) δ 10.22 (s, 1H), 9.97 (s, 1H), 7.57 (d, 2H), 7.11 (d, 2H), 4.65 (s, 1H), 3.56 (s, 3H), 2.04 (s, 3H), 1.94 (s, 3H); $^{13}$C NMR (DMSO) δ 169.64, 168.07, 159.33, 136.48, 133.55, 124.52, 119.44, 84.47, 49.77, 23.81, 19.68.

N-(4-Hydroxy-2-methylquinolin-6-yl)acetamide (4): Phenyl ether (1 L) was heated to 255° C. Butenoate 3 (334 g, 1.35 mol) was carefully added portionwise while maintaining temperature 245-260° C. After the addition was complete, the yellow-orange suspension was held at 255° C. for an additional 15 min. The mixture was slowly cooled to 40° C., the solids were collected by filtration and washed with EtOAc (3×500 mL) followed by MeOH (3×500 mL) to give hydroxy quinoline 4 as yellow-orange solid (256 g, 88% yield); $^1$H NMR (DMSO) δ 11.52 (br, s, 1H), 10.07 (s, 1H), 8.24 (s, 1H), 7.82 (d, 1H), 7.42 (d, 1H), 5.84 (s, 1H), 2.31 (s, 3H), 2.05 (s, 1H).

N-(4-Methoxy-2-methylquinolin-6-yl)acetamide (5): Dimethyl sulfate (294 g, 2.33 mol) was charged to a suspension of hydroxyquinoline 4 (287 g, 1.33 mol) in toluene (1.5 L) and the mixture was refluxed for 6 h. After cooling to ambient temperature, the resulting dark yellow solids were collected by filtration and washed with toluene. The dry solid was dissolved in water (2.5 L) and the pH adjusted to 14 using 35% aqueous NaOH (290 g). The resulting tan precipitate was collected by filtration, washed with copious amounts of water and dried in vacuo at 60° C. to give methoxyquinoline 5 as light tan solid (259 g, 85% yield); $^1$H NMR (DMSO) δ 10.18 (s, 1H), 8.46 (s, 1H), 7.76 (m, 2H), 6.84 (s, 1H), 3.99 (s, 3H), 2.55 (s, 3H), 2.09 (s, 3H); $^{13}$C NMR (DMSO) δ 168.36, 160.99, 158.07, 144.86, 135.87, 128.27, 122.78, 119.26, 108.80, 101.20, 55.69, 25.08, 23.97.

2-Methylquinoline-4,6-diamine (7): Ammonium acetate (1.3 kg) was melted and methoxyquinoline 5 (256 g, 1.11 mol) was added. The dark solution was refluxed at 135 for 4 h. After LC/MS indicated conversion of 5 (M+1=231) to intermediate 6 (M+1=216), the reaction mixture was poured into 37% HCl (2.1 L) and water (800 mL). The mixture was refluxed for 10 h and then cooled to ambient temperature for overnight. LC/MS indicated conversion of all intermediate 6 to diaminoquinoline 7 (M+1=174). The mixture was cooled to 5° C. and the resulting dihydrochloride salt was collected by filtration. The salt was dissolved in water (1.5 L) at 75° C. Charcoal (13 g, Darco G-60, −100 mesh) was charged to the dark solution, the mixture was refluxed for 45 minutes and was filtered through Celite. The yellow filtrate was cooled and the pH adjusted to 14 using 35% aqueous NaOH (1 kg). The resulting precipitate was collected by filtration, washed with copious amounts of water and dried in vacuo at 60° C. to give diaminoquinoline 7 as off-white solid (136 g, 71% yield); $^1$H NMR (DMSO) δ 7.41 (m, 1H), 6.95 (m, 2H), 6.30 (s, 1H), 6.03 (br, s, 2H), 5.05 (br, s, 2H), 2.32 (s, 3H); $^{13}$C NMR (DMSO) δ 153.42, 149.46, 144.28, 142.09, 128.84, 120.59, 118.60, 102.15, 101.11, 24.42.

N~6~-(2-chloro-6-methylpyrimidin-4-yl)-2-methylquinoline-4,6-diamine (9): Diaminoquinoline 7 (72.0 g, 0.416 mol) and 2,4-dichloro-6-methylpyrimidine (8) (67.8 g, 0.416 mol) were suspended in ethylene glycol (1 L). Addition of 37% HCl (35 mL, 0.43 mol) resulted in a yellow solution which was heated to and held at 50° C. for 4.5 h. The mixture was diluted with chilled water (1 L) which resulted in a thick white paste-like precipitate and the mixture was filtered through Celite. The Celite and solid containing the product and bis-substituted by-product was slurried in water (4 L) and the Celite and insoluble by-product were removed by filtration. The filtrate pH was adjusted to 14 using 1N aqueous NaOH (1 L) resulting in precipitation of product which was removed by filtration. The damp product was transferred to a rotovap flask and dried in vacuo by azeotropic water removal with toluene (3×1.5 L). Product 9 was obtained as an off-white solid (33.4 g, 27% yield; Notebook reference A134-137). Another batch of 9 (7.4 g, 17% yield; Notebook reference A 134-134) was similarly obtained by reaction of 7 (25.0 g, 0.144 mol) and recovery as above; MS [M+1]=300, 302; $^{13}$C NMR (DMSO) δ 167.51, 162.58, 159.22, 157.61, 151.05, 145.99, 133.17, 128.96, 125.39, 117.38, 114.23, 102.45, 102.26, 24.68, 23.19.

CHMC-1: A suspension of intermediate 9 (32.7 g, 0.109 mol) and diisopropylethylamine (20.0 mL, 0.115 mol) in ethylene glycol (500 mL) was heated to 90° C. to give a golden solution. 2-Amino-5-diethylaminopentane (32.0 mL, 0.165 mol) was added and the mixture was heated to and held at 110° C. for 5.5 h. The mixture was cooled to room temperature and EtOAc (750 mL) and 1N aqueous NaOH (500 mL) were added resulting in a thick white paste-like precipitate. The solid was removed by filtration through Celite and the filtrate layers were separated. The aqueous layer was twice basified using 1N NaOH (300 mL) and back-extracted using EtOAc (750 mL). The combined organic layers were washed with brine (3×750 mL), filtered through Celite and solvent removed in vacuo to give a brown oil (44 g). Heptane was added to the oil and allowed to sit for several days before decanting the solvent. The oil along with 12 g of crude oil from another batch were purified by silica gel (1.5 kg) flash column chromatography using EtOAc/MeOH/NEt$_3$ (7:3:0.5).

Chemical compounds are examined for their ability to inhibit the Rac1 binding interaction with GEF in a complex formation assay.

FIG. 1. shows identification of NSC23766 as an inhibitor of Rac1-Trio interaction. In the upper panel of FIG. 1, the inhibitory effect of a panel of compounds predicted by Virtual Screening on Rac1 interaction with TrioN was tested in a complex formation assay. 0.5 µg of (His)$_6$-tagged TrioN was incubated with GST alone or nucleotide-free GST-Rac1 (2 µg) in the presence or absence of 1 mM indicated NCI compound and 10 µl suspended glutathione-agarose beads. After an incubation at 4° C. for minutes, the beads associated (His)$_6$-TrioN were detected by anti-His Western blotting. In the lower panel of FIG. 1, the effect of the compounds on Cdc42 binding to Intersectin was determined similarly. ~1 µg of GST or GST-tagged Intersectin was incubated with the nucleotide-free, (His)$_6$-tagged Cdc42 (0.25 µg) under similar conditions. Data are representative of the results from four independent experiments.

For this purpose, Trio and Tiam-1, which specifically activate Rac1 but not Cdc42 (Gao et al., 2001, which is incorporated herein by reference in its entirety) and Intersectin, a Cdc42-specific GEF (Karnoub et al., 2001, which is incorporated herein by reference in its entirety), are used to assay the binding activity to their respective substrates in the presence of 1 mM of each individual compound. Trio and Tiam-1 co-precipitate with GST-Rac1, but not GST or GST-Cdc42. The inhibitory effect of compound 23766 appears to be specific towards the interaction between Rac1 and its GEFs since it does not interfere with the Cdc42 binding to Intersectin nor RhoA binding to PDZ-RhoGEF (FIG. 1). Further, the inhibitory effect of compound 23766 on Rac1 is dose dependent (FIG. 2).

Figure 2:
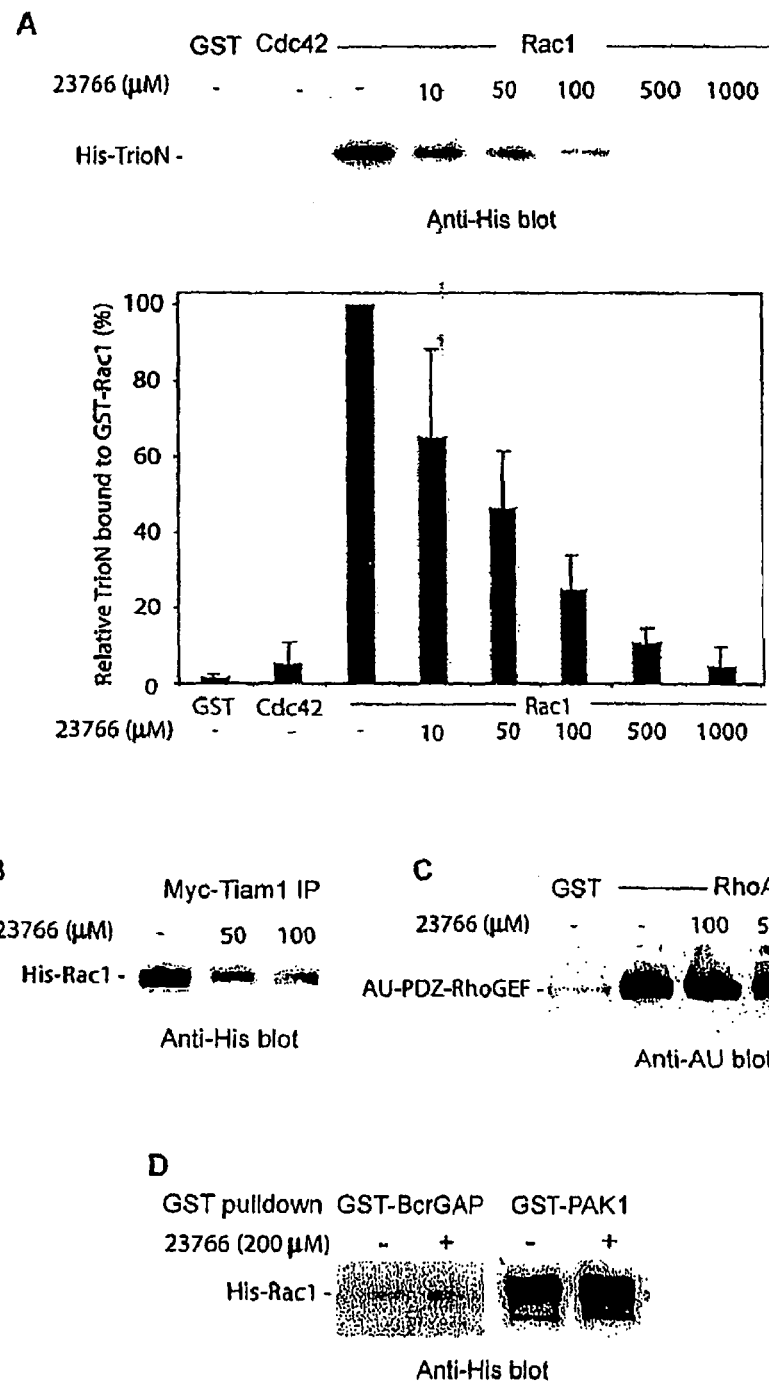
FIG. 2. shows dose dependent specific inhibition of GEF interaction with Rac1 by NSC23766.

FIG. 2. shows dose dependent specific inhibition of GEF interaction with Rac1 by NSC23766. In FIG. 2A, 0.5 µg of (His)$_6$-tagged TrioN was incubated with GST alone or nucleotide-free, GST-fused Cdc42 or Rac1 (2 µg) in the binding buffer containing different concentrations of NSC23766 and 10 µl suspended glutathione-agarose. After an incubation at 4° C. for 30 minutes, the beads associated (His)$_6$-TrioN were detected by anti-His Western blotting. The blots were quantified by densitometry analysis. The results are representative of three measurements. In FIG. 2B, myc-tagged Tiam1 expressed in Cos-7 cell lysates were incubated with (His)$_6$-Rac1 in the presence of increasing concentrations of NSC23766. The association of Rac1 with Tiam1 was examined by anti-His blot after anti-myc immunoprecipitation. In FIG. 2C, the AU-tagged PDZ-RhoGEF was expressed in Cos-7 lysates and incubated with GST or GST-RhoA in the presence of varying concentrations of NSC23766. The RhoA associated PDZ-RhoGEF was probed with anti-AU antibody after affinity precipitation by glutathione agarose beads. In FIG. 2D, (His)$_6$-Rac1 loaded with GTP γ S was incubated with GST-BcrGAP or GST-PAK1 (PBD) in the presence or absence of 200 µM NSC23766 and the interaction with GST-BcrGAP or GST-PAK1 was probed by anti-His blot after affinity precipitation by glutathione agarose beads.

Figure 3:
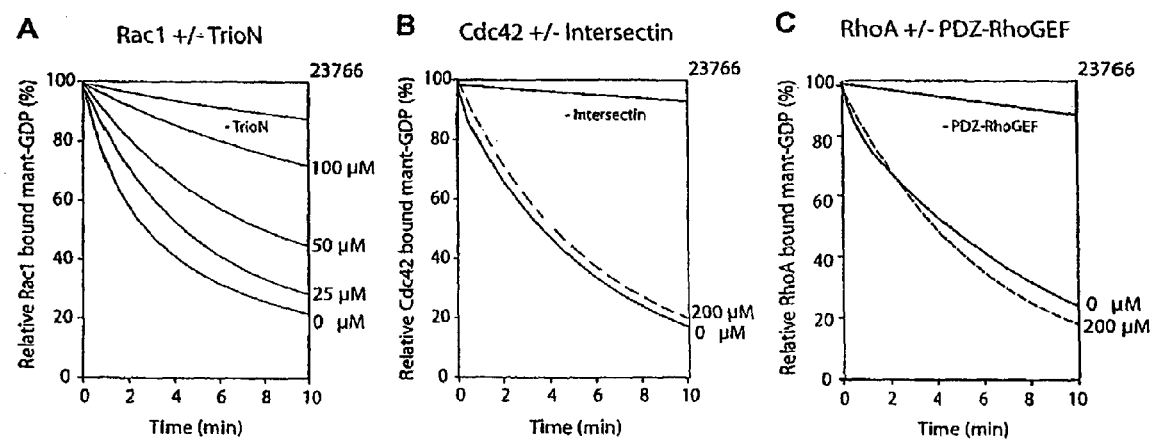
FIG. 3 shows that NSC23766 was effective in specifically inhibiting Rac1 GDP/GTP exchange stimulated by GEF.

To determine if compound 23766 is capable of inhibiting the GEF-stimulates nucleotide exchange of Rac1, the mant-GDP dissociation assays of Rac1 are carried out in the presence of increasing doses of compound 23766. In FIG. 3. NSC23766 was effective in specifically inhibiting Rac1 GDP/GTP exchange stimulated by GEF. In FIG. 3A, NSC23766 inhibited TrioN catalyzed GDP/GTP exchange of Rac1 in a dose dependent manner. 200 nM Rac1 loaded with mant-GDP was incubated at 25° C. in an exchange buffer containing 100 mM NaCl, 5 mM MgCl$_2$, 50 mM Tris-HCl (PH 7.6), and 0.5 mM GTP in the absence (top line) or presence of 100 nM TrioN. Increasing concentrations of NSC23766 were included in the exchange buffer as indicated. In FIG. 3B, NSC23766 had no effect on the Intersectin-stimulated GDP/GTP exchange of Cdc42. 200 nM Cdc42 loaded with mant-GDP was incubated in the exchange buffer in the absence (top line) or presence of 100 nM Intersectin with or without 200 µM NSC23766. In FIG. 3C, the exchange reaction of RhoA catalyzed by PDZ-RhoGEF was carried out similarly in the presence or absence of 200 µM NSC23766.

As shown in FIG. 3A, at increasing concentrations compound 23766 is able to block the mantGDP/GTP exchange catalyzed by Trio in a dose-dependent manner. On the other hand, compound 23766 has little impact on the Intersectin-stimulated mantGDP/GTP exchange of Cdc42 at similar doses (FIG. 3B), nor on the PDZ-RhoGEF-stimulated mant-GDP/GTP exchange of RhoA. These results demonstrate that in vitro compounds, e.g., 23766, are able to specifically inhibit the interaction and activation of Rac1 by its GEFs.

Figure 4:
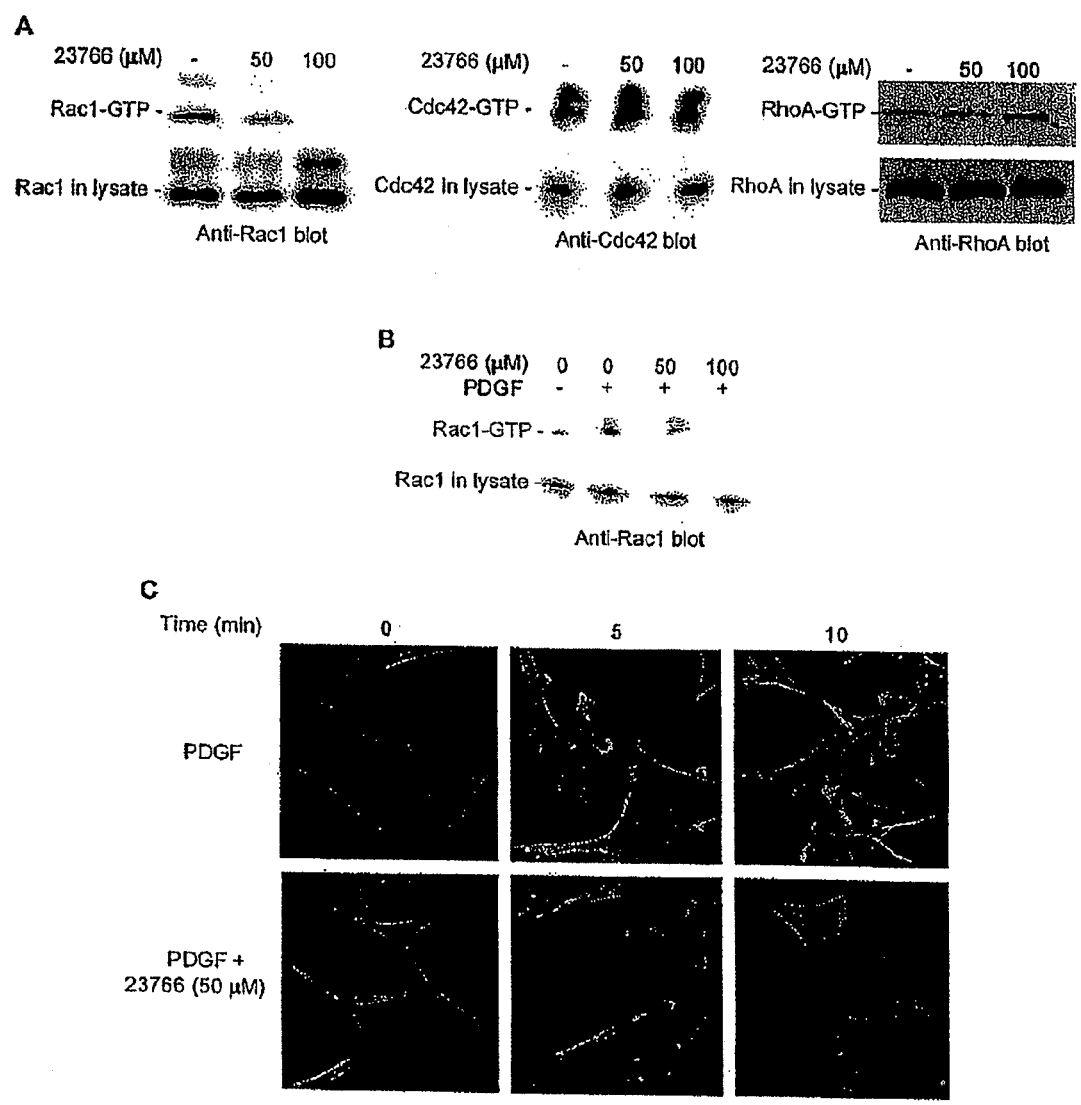
FIG. 4. shows that NSC23766 was effective in specifically inhibiting Rac1 activation in cells.

Inhibitory effect of compound 23766 on Rac1 activity in vivo. In fibroblasts, Rac is activated by diverse stimuli including serum and PDGF (Hawkins et al., 1995, which is incorporated herein by reference in its entirety). Rac activation in these situations is expected to be mediated by one or more Rac-specific GEFs such as Tiam1. To evaluate how compound 23766 can affect Rac activity in vivo, NIH 3T3 cells grown in 10% calf serum are treated with compound 23766 in different concentrations overnight, and the activation state of endogenous Rac1 in cells is detected by using the probe, GST-PAK (PBD) domain, that can specifically complex with Rac1-GTP. FIG. 4. shows that NSC23766 was effective in specifically inhibiting Rac1 activation in cells. In FIG. 4A, the activation states of endogenous Rac1, Cdc42 and RhoA in NIH3T3 cells with or without NSC23766 treatment were detected by the effector pull-down assays. At 80% confluency in the presence of 10% serum, NIH 3T3 cells in 100 mm dishes were treated with the indicated dosages of NSC23766 for 12 hours. Cell lysates containing similar amount of Rac1, Cdc42 or RhoA were incubated with the agarose immobilized GST-PAK1, GST-WASP or GST-Rhotekin, and the co-precipitates were subjected to anti-Rac1, Cdc42 or RhoA Western blot analysis to reveal the amount of GTP-Bound Rho proteins. In FIG. 4B, the inhibitory effect of NSC23766 on the PDGF-stimulated Rac1 activation was determined by the GST-PAK1 pull-down assay. Serum starved NIH 3T3 cells in the DMEM medium with different dosages of NSC23766 were treated with 10 nM PDGF for 2 minutes. In FIG. 4C, NSC23766 inhibited PDGF-stimulated lamellipodia formation. After overnight serum starvation in the presence or absence of 50 µM NSC23766, Swiss 3T3 cells were treated with 10 nM PDGF for the indicated time. The cells were fixed and stained with Rhodamine-labeled phalloidin.

As shown in FIG. 4A, compound 23766 strongly inhibits Rac1 activation induced by serum. Densitometric analysis reveals that the IC$_{50}$ of compound 23766 is about 40 µM under these conditions. Meanwhile, the inhibitory effect of compound 23766 appears to be specific toward Rac among Rho GTPases, since the activation state of Cdc42 in these cells under serum-stimulation is unaffected by the presence of compound 23766. Interestingly, treatment with this reagent leads to a slightly increased level of RhoA-GTP in cells, consistent with previous reports suggesting that Rac1 can counter-react with RhoA activity. To examine if compound 23766 can affect Rac1 activation by PDGF stimulation, serum starved NIH 3T3 cells in the presence or absence of the compound are challenged with 10 nM PDGF for 2 minutes, and the cell lysates are assayed for the active Rac1-GTP species. Comparing with the PDGF-stimulated Rac activity in the absence of compound 23766, the cells treated with 50 µM 23766 display a significant reduction of GTP-bound Rac (FIG. 4B), and the presence of 100 µM 23766 leads to lower than basal level of Rac1-GTP in the cells. Thus, consistent with the in vitro Rac1-GEF interaction results, compound 23766 is able to specifically inhibit Rac1 activity in vivo.

PDGF activates Rac and induces Rac-mediated membrane ruffles and lamellipodia in fibroblasts (Hawkins et al., 1995; Ridley et al., 1992, which are incorporated herein by reference in their entirety). To evaluate the ability of compound 23766 to inhibit Rac1-mediated morphological changes, the actin cytoskeleton structures, induced by PDGF in the absence or presence of compound 23766, was examined. As shown in FIG. 4C, 10 nM PDGF potently stimulates membrane ruffling and lamellipodial formation in Swiss3T3 cells. However, in the presence of 100 µM 23766, PDGF is only marginally effective in inducing lamellipodia at the cell edges at 5 min and completely ineffective at 10 min when the control cells that are not treated with compound 23766 displays significant lamellipodia structures. These results suggest that compound 23766 is effective in inhibiting Rac-mediated actin reorganization.

Compound 23766 specifically inhibits serum- or Trio-induced cell growth. Rho GTPase activities are important in cell growth regulation. Overexpression of dominant-negative Rac slows cell growth (Zheng et al., 1995b, which is incorporated herein by reference in its entirety). Conversely, constitutively active Rac increases growth rate of fibroblasts (Khosravi-Far et al., 1995, which is incorporated herein by reference in its entirety). Since compound 23766 is able to decrease Rac activity in NIH 3T3 cells, its effect on the growth properties of normal NIH 3T3 cells and the NIH 3T3 cells expressing constitutively active Rac1, L61Rac1 was examine.

Figure 5:
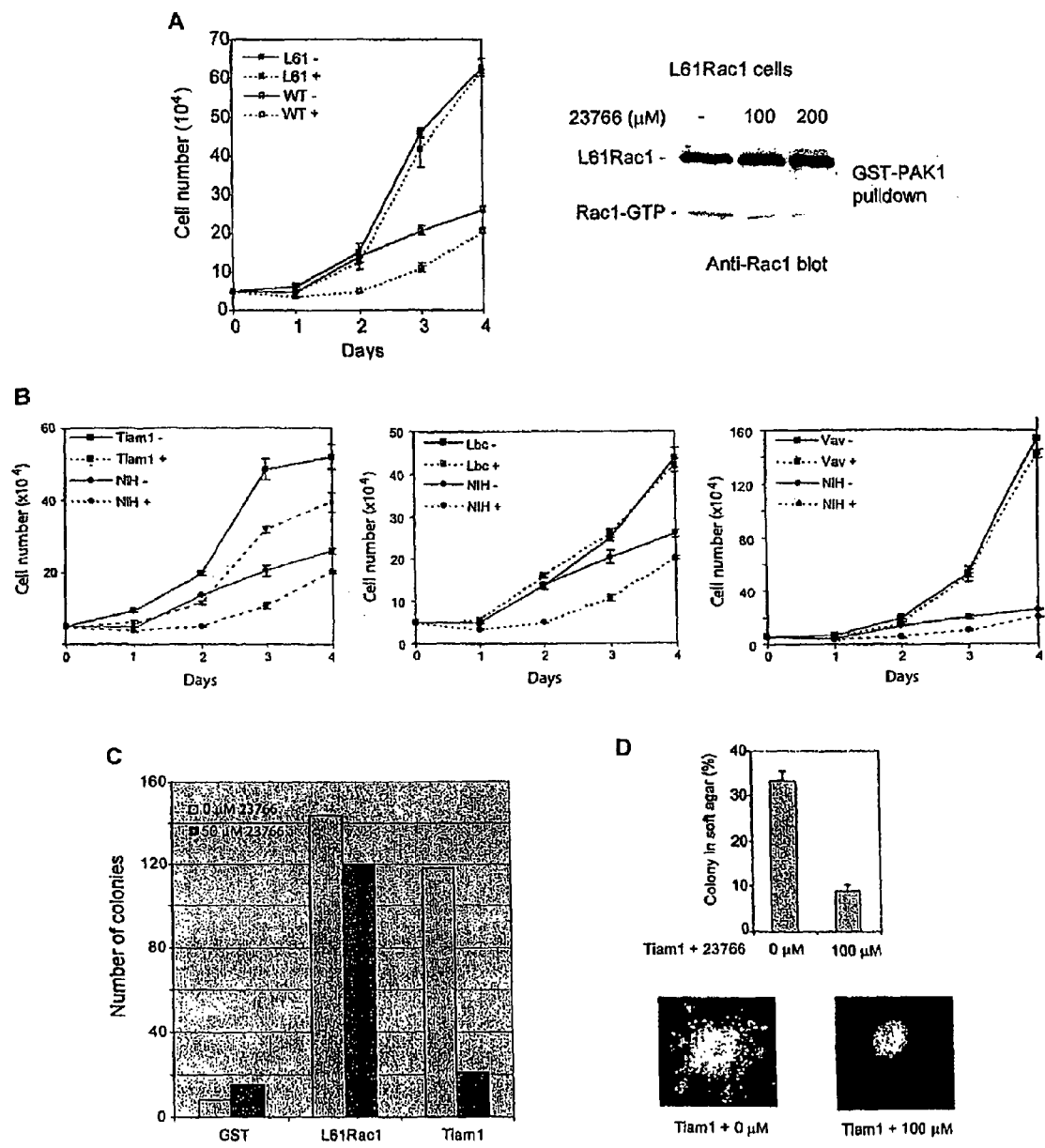
FIG. 5. shows that NSC23766 specifically inhibited Rac GEF stimulated cell growth and transformation.

FIG. 5. shows that NSC23766 specifically inhibited Rac GEF stimulated cell growth and transformation. In FIG. 5A, wild type (WT) or L61Rac1 expressing NIH 3T3 cells were grown in 5% serum in the presence (- - -) or absence (-) of 100 µM NSC23766. The cells were split in triplicate in 6-well plates at a density of $5 \times 10_4$ cells per well. The GTP-bound L61Rac1 and endogenous Rac1 of the L61Rac1-expressing cells were probed by GST-PAK1 pull-down after 12 hour treatment with increasing concentrations of NSC23766. In FIG. 5B, WT or the GEF (Tiam1, Lbc or Vav) expressing NIH 3T3 cells were grown in 5% serum in the presence (- - -) or absence (-) of 100 µM NSC23766, and the cell numbers were determined by daily cell counting. In FIG. 5C, GST, L61Rac1, or Tiam1 transfected cells were treated with 50 µM NSC23766 every two days. The foci numbers of the respective cells were quantified 14 days after transfection. In FIG. 5D, a stable transfectant of Tiam1-expressing NIH 3T3 cells was cultured in 0.3% soft-agar medium for 14 days in the presence or absence of 100 µM NSC23766. The number and the morphology of the colonies were examined under a microscope.

Comparison of the growth rates of the cells in the absence or presence of compound 23766 shows that compound 23766 slow the growth of wild type NIH 3T3 cells while having no effect on the growth rate of Rac1L61 expressing cells (FIG. 5A). The level of GTP-bound GST-Rac1L61 remains unchanged with or without the compound treatment, whereas the endogenous Rac activity is deceased significantly by the presence of compound 23766 (data not shown). These results suggest that the inhibitory effect of compound 23766 on cell growth correlates with its ability to inhibit cellular Rac activity.

Due to their ability to directly activate Rho GTPases, Dbl family GEFs are potent stimulators of cell proliferation. Compound 23766 is capable of inhibiting the cell growth induced by the Rac specific GEF Trio, but not that stimulated by the Rho-specific GEF Lbc, the Cdc42-specific GEF Intersectin, or the multiple Rho protein-activating GEF Vav (FIG. 5B). Thus compound 23766 is effective in specifically inhibiting cell growth caused by GEF-induced Rac activation.

Reversal of the PC-3 tumor cell phenotypes by compound 23766. Elevation of Rac1 activity is associated with cancer cell hyperproliferative and invasive properties. Next the effect of compound 23766 is tested on the growth and invasion capabilities of a prostate cancer cell line, PC-3. PC-3 cells are malignant prostate adenocarcinoma cells derived from the bone metastases of a patient with prostate cancer (Kaighn et al., 1979, which is incorporated herein by reference in its entirety). They are transforming and highly invasive (Lang et al., 2002, which is incorporated herein by reference in its entirety). The mRNA of the PTEN tumor suppressor is undetectable in these cells (Bastola et al., 2002, which is incorporated herein by reference in its entirety), and loss of PTEN has previously been correlated with Rac1 hyperactivation due to the significant increase of $PIP_3$ level (Liliental et al., 2000, which is incorporated herein by reference in its entirety). When the activity of endogenous Rac1 in PC-3 cells is examined by probing with GST-PAK (PBD), a ~100% higher level of GTP-bound Rac than that of the normal prostate epithelial RWPE-1 cells is observed (FIG. 5A). Consistent with the results obtained from fibroblasts, compound 23766 is able to inhibit Rac1 activity in PC-3 cells (FIG. 6A). Correlating with the decreased Rac1 activity, the proliferation rates of the compound 23766 treated PC-3 cells are inhibited by compound 23766 in a dose dependent manner (FIG. 6A). These results suggest that compound 23766 can effectively inhibit PC-3 tumor cell growth through down-regulation of Rac1 activity.

Figure 6:
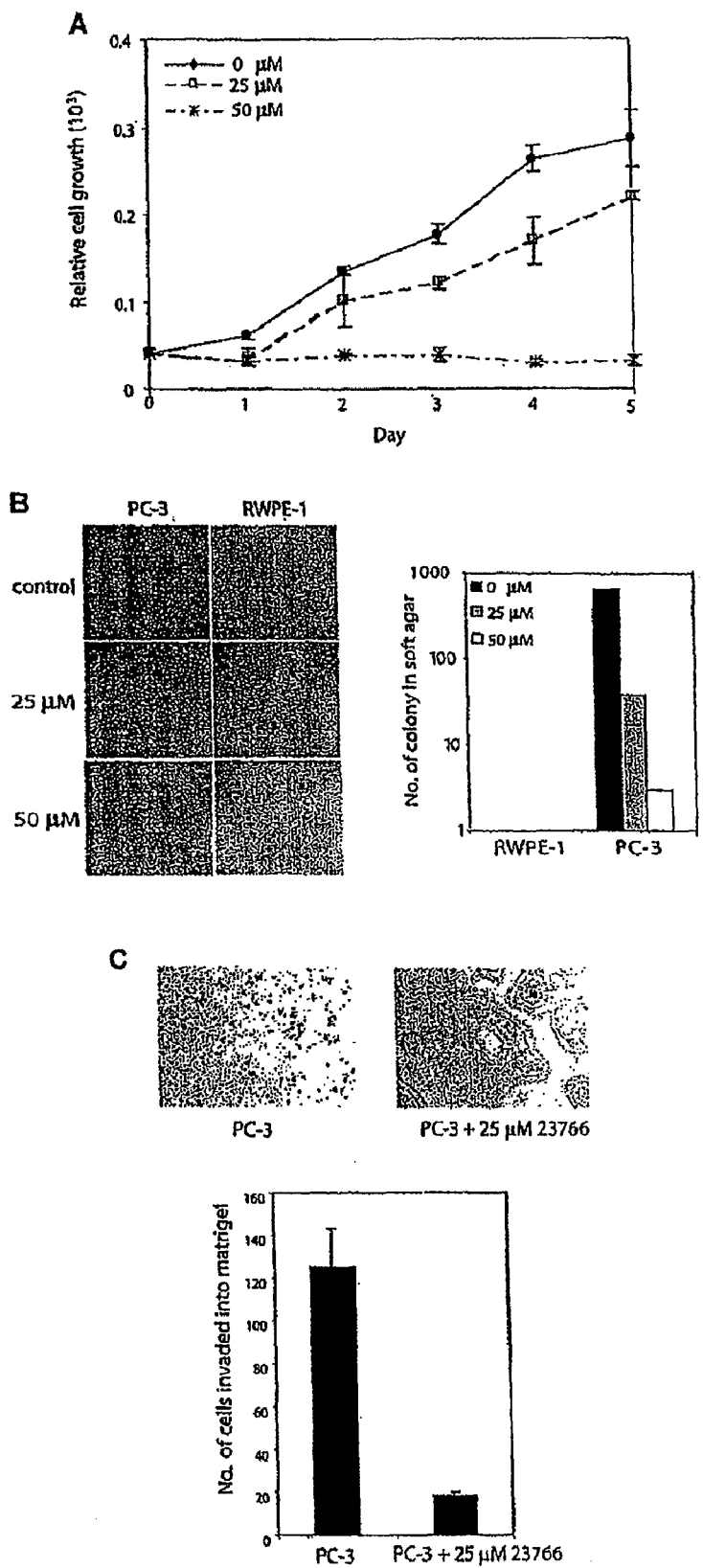
FIG. 6. shows that NSC23766 inhibited the proliferation, anchorage independent growth and invasion of PC-3 prostate cancer cells.

FIG. 6. shows that NSC23766 inhibited the proliferation, anchorage independent growth and invasion of PC-3 prostate cancer cells. In FIG. 6A, PC-3 cells were grown in 5% calf serum supplemented with the indicated concentrations of NSC23766. The cells were split in triplicate in 96-wells at $1.5 \times 10_3$ cells per well. Cell numbers were assayed by using CellTiter 96 AQueous cell proliferation assay kit in different days. In FIG. 6B, PC-3 and RWPE-1 prostate epithelial cells ($1.25 \times 10_3$ per well) were grown in 0.3% agarose in different doses of NSC23766, and the number of colonies formed in soft agar was quantified 12 days after plating. In FIG. 6C, PC-3 cells were placed in an invasion chamber for 24 hrs at 37° C. in the absence or presence of 25 µM NSC23766. Cells invaded through Matrigel matrix were visualized with Giemasa staining.

Given that PC-3 cells contain hyperactive Rac1 activity, the ability of PC-3 cells to grow on soft agar and the effect of compound 23766 on its anchorage independent growth property can be tested. FIG. 6B shows that PC-3 cells readily form colonies ten days after being placed on soft agar, under conditions in which the normal prostate epithelia RWPE-1 cells are unable to grow. Compound 23766 efficiently blocks the colony forming activity of PC-3 cells. Approximately 10% and 1% colony-forming activities remain after treatment of the cells with 25 μM and 50 μM compound 23766, respectively. Moreover, the size of colonies of the treated cells appears much smaller than those of the untreated ones (FIG. 6B). PC-3 cells are reported to possess highly invasive activity (Lang et al., 2002, which is incorporated herein by reference in its entirety), which is evident in a Matri-gel invasion assay. Under similar conditions, RWPE-1 cells are non-invasive. At a dose of 25 μM, compound 23766 significantly inhibits PC-3 cell invasion (FIG. 6C).

Taken together, these results show that the active agent is able to downregulate Rac1 activity of PC-3 tumor cells which likely results in the reversal of the proliferation, anchorage independent growth and invasion phenotypes.

Crystal Structure of Rac-1 GTPase Complexed with NCI 23766

Methods

Protein Purification: *Escherichia coli* BL21 Codon Plus (Stratagene) cells expressing $His_6$-tagged Rac-1 domain (residues 1 to 185 of SEQ ID NO:1) were grown at 37° C. in Luria-Bertani medium to an optical Density at 600 nm of 0.8-1.0 and induced for 3 hours with 0.5 mM IPTG. The harvested cells were lysed in 20 mM Tris, pH 8.0, 500 mM NaCl, 5 mM $MgCl_2$ by French pressure cell. The lysate was clarified by centrifugation for 20 minutes at 16,000 rpm in a 16.250 rotor (Beckman). Clarified lysate was passed over a Ni-NTA column (Qiagen) pre-equilibrated with 5 mM Imidazole in Buffer A (20 mM Tris-HCl, pH 8.0, 500 mM NaCl). The column was washed with 20 mM Imidazole in Buffer A. After reaching baseline, the $His_6$-tagged Rac1 was eluted from the column with 250 mM Imidazole in Buffer A and dialyzed against 20 mM Tris-HCl, pH 8.0, 5 mM $MgCl_2$, 5 mM β-Mercaptoethanol and digested with thrombin (Sigma) overnight. The digested protein was passed over a Source-15Q (Sigma) equilibrated with 20 mM Tris-HCl, pH 8.0, 5 mM $MgCl_2$, 5 mM β-Mercaptoethanol. Rac-1 domain polypeptide comprising residues 1 through 185 of SEQ ID NO:1 was collected in the flowthrough. The flowthrough was then passed over a Superdex 200 (Amersham Biosciences) size exclusion column equilibrated with 10 mM HEPES, pH 7.5, 2 mM $MgCl_2$, 150 mM NaCl. The peak corresponding to Rac-1 was pooled, concentrated to 22.5 mg/mL and used in crystallization trials.

Crystallization: Crystals of Rac1•GDP were grown in 20% PEG 8000, 5% Ethylene Glycol, 15% DMSO, 0.1 M HEPES, pH 7.0, 10 mM DTT, and 1 mM NSC23766 at 20° C. using the hanging drop method. Crystals of the complex appeared overnight and reached their maximum size after 2-3 days. Crystals were transferred to a drop containing 18% PEG 8000, 3.5% Ethylene Glycol, 10.7% DMSO, 0.1 M HEPES, pH 7.0, 10 mM DTT, 14.3 mM NSC23766 and allowed to equilibrate over a reservoir containing 25% PEG 8000, 5% Ethylene Glycol, 15% DMSO 0.1M HEPES, pH 7.0, 10 mM DTT. After 22 hrs of equilibration, the crystals were mounted and flash frozen in liquid nitrogen.

X-ray Data Collection and Structure Solution: A complete and redundant diffraction data set to 1.35 Å resolution was collected at the National Synchrotron Light Source (Brookhaven, Upton, N.Y.) beamline X26C on an ADSC Quantum 4 CCD detector at a temperature of 100 K, integrated, and scaled with the HKL2000 suite (Otwinowski 1997 & 2003). The Rac/NSC23766 crystals belong to space group $P2_1$ with one complex per asymmetric unit and unit cell dimensions of a=41.8 Å, b=40.0 Å, c=52.1 Å γ=105.83°. The Rac/NSC23766 structure was solved by molecular replacement using the coordinates of Rac•GDP (K. Skowronek & N. Nassar, unpublished observations) as the search model in the program MOLREP (Vagin & Teplyakov 1997). The actual model is refined using TLS groups (Winn 2003) in REFMAC (Murshudov 1997) against 1.35 Å resolution data. During refinement, an extra density in a hydrophobic pocket formed by Ile36, Trp56, Tyr64, Arg68, and Pro73 was apparent in the electron density. This extra density is not part of Rac and does not correspond to a metal ion or a water molecule. Subsequently, an NSC23766 molecule was modeled in this density and is being refined against the experimental data.

Table 1 depicts atomic coordinates of the Rac/NSC23766 structure as solved as described above and partially refined, where the amino acid sequence for Rac-1 is provided in SEQ ID NO:1. Table 2 depicts further refined to 1.50 Å resolution, with crystallographic residuals R/Rfree of 15.1/20.5 and good stereochemistry, where the amino acid sequence for Rac-1 is provided in SEQ ID NO:1.

It should be noted that the side chains of some residues are poorly resolved in the electron density. These are typically truncated to alanines in the listing of atomic coordinates (e.g., Table 1 or Table 2), however, this does not alter the amino acid sequence for Rac-1, which is provided in SEQ ID NO:1.

In addition, information regarding procedural or other details supplementary to those set forth herein, are described in cited references specifically incorporated herein by reference.

It is be evident to those skilled in the art that modifications or variations can be made to the preferred embodiment described herein without departing from the novel teachings of the present invention. All such modifications and variations are intended to be incorporated herein and within the scope of the claims.

TABLE 1

| REMARK | Written by O version 9.0.7 | | | | | | | | |
|---|---|---|---|---|---|---|---|---|---|
| CRYST1 | 41.792 | 40.008 | 52.071 | 90.00 | 105.83 | 90.00 | | | |
| ORIGX1 | 1.000000 | 0.000000 | 0.000000 | | | 0.00000 | | | |
| ORIGX2 | 0.000000 | 1.000000 | 0.000000 | | | 0.00000 | | | |
| ORIGX3 | 0.000000 | 0.000000 | 1.000000 | | | 0.00000 | | | |
| SCALE1 | 0.023928 | −0.000001 | 0.006784 | | | 0.00000 | | | |
| SCALE2 | 0.000000 | 0.024995 | −0.000001 | | | 0.00000 | | | |
| SCALE3 | 0.000000 | 0.000000 | 0.019961 | | | 0.00000 | | | |
| ATOM | 1 | N | ALA | A | 1 | 15.756 | 6.560 | −10.373 | 1.00 | 30.78 |
| ATOM | 2 | CA | ALA | A | 1 | 16.093 | 6.323 | −8.944 | 1.00 | 29.95 |
| ATOM | 3 | CB | ALA | A | 1 | 15.708 | 7.535 | −8.107 | 1.00 | 30.54 |
| ATOM | 4 | C | ALA | A | 1 | 15.397 | 5.066 | −8.426 | 1.00 | 29.34 |
| ATOM | 5 | O | ALA | A | 1 | 14.165 | 4.991 | −8.415 | 1.00 | 29.88 |
| ATOM | 6 | N | ALA | A | 2 | 16.190 | 4.079 | −8.013 | 1.00 | 28.31 |

TABLE 1-continued

| | | | | | | | | | |
|---|---|---|---|---|---|---|---|---|---|
| ATOM | 7 | CA | ALA | A | 2 | 15.653 | 2.839 | −7.447 | 1.00 | 26.70 |
| ATOM | 8 | CB | ALA | A | 2 | 16.739 | 1.776 | −7.330 | 1.00 | 27.15 |
| ATOM | 9 | C | ALA | A | 2 | 15.066 | 3.147 | −6.080 | 1.00 | 25.29 |
| ATOM | 10 | O | ALA | A | 2 | 15.671 | 3.887 | −5.294 | 1.00 | 25.34 |
| ATOM | 11 | N | ALA | A | 3 | 13.888 | 2.584 | −5.813 | 1.00 | 23.09 |
| ATOM | 12 | CA | ALA | A | 3 | 13.185 | 2.797 | −4.545 | 1.00 | 21.06 |
| ATOM | 13 | CB | ALA | A | 3 | 11.794 | 2.144 | −4.577 | 1.00 | 21.37 |
| ATOM | 14 | C | ALA | A | 3 | 13.992 | 2.272 | −3.360 | 1.00 | 19.51 |
| ATOM | 15 | O | ALA | A | 3 | 14.532 | 1.151 | −3.409 | 1.00 | 21.10 |
| ATOM | 16 | N | ILE | A | 4 | 14.103 | 3.097 | −2.322 | 1.00 | 16.92 |
| ATOM | 17 | CA | ILE | A | 4 | 14.495 | 2.610 | −1.001 | 1.00 | 15.02 |
| ATOM | 18 | CB | ILE | A | 4 | 14.648 | 3.775 | −0.026 | 1.00 | 14.41 |
| ATOM | 19 | CG1 | ILE | A | 4 | 15.895 | 4.579 | −0.429 | 1.00 | 16.51 |
| ATOM | 20 | CD1 | ILE | A | 4 | 16.154 | 5.841 | 0.397 | 1.00 | 16.77 |
| ATOM | 21 | CG2 | ILE | A | 4 | 14.740 | 3.274 | 1.433 | 1.00 | 15.96 |
| ATOM | 22 | C | ILE | A | 4 | 13.388 | 1.675 | −0.542 | 1.00 | 14.20 |
| ATOM | 23 | O | ILE | A | 4 | 12.232 | 2.101 | −0.406 | 1.00 | 15.07 |
| ATOM | 24 | N | LYS | A | 5 | 13.726 | 0.408 | −0.273 | 1.00 | 12.22 |
| ATOM | 25 | CA | LYS | A | 5 | 12.723 | −0.574 | 0.144 | 1.00 | 11.59 |
| ATOM | 26 | CB | LYS | A | 5 | 13.060 | −1.966 | −0.389 | 1.00 | 11.41 |
| ATOM | 27 | CG | LYS | A | 5 | 12.127 | −3.072 | 0.138 | 1.00 | 11.13 |
| ATOM | 28 | CD | LYS | A | 5 | 12.354 | −4.367 | −0.588 | 1.00 | 12.02 |
| ATOM | 29 | CE | LYS | A | 5 | 11.520 | −5.470 | 0.029 | 1.00 | 13.44 |
| ATOM | 30 | NZ | LYS | A | 5 | 11.555 | −6.719 | −0.805 | 1.00 | 14.02 |
| ATOM | 31 | C | LYS | A | 5 | 12.599 | −0.604 | 1.665 | 1.00 | 11.00 |
| ATOM | 32 | O | LYS | A | 5 | 13.549 | −0.951 | 2.376 | 1.00 | 11.63 |
| ATOM | 33 | N | CYS | A | 6 | 11.416 | −0.249 | 2.160 | 1.00 | 10.99 |
| ATOM | 34 | CA | CYS | A | 6 | 11.150 | −0.184 | 3.592 | 1.00 | 10.47 |
| ATOM | 35 | CB | CYS | A | 6 | 10.616 | 1.202 | 3.918 | 1.00 | 11.97 |
| ATOM | 36 | SG | CYS | A | 6 | 10.107 | 1.479 | 5.616 | 1.00 | 12.97 |
| ATOM | 37 | C | CYS | A | 6 | 10.108 | −1.234 | 3.915 | 1.00 | 10.18 |
| ATOM | 38 | O | CYS | A | 6 | 8.997 | −1.192 | 3.382 | 1.00 | 10.84 |
| ATOM | 39 | N | VAL | A | 7 | 10.453 | −2.173 | 4.789 | 1.00 | 10.01 |
| ATOM | 40 | CA | VAL | A | 7 | 9.549 | −3.260 | 5.155 | 1.00 | 9.99 |
| ATOM | 41 | CB | VAL | A | 7 | 10.261 | −4.622 | 5.022 | 1.00 | 11.17 |
| ATOM | 42 | CG1 | VAL | A | 7 | 9.362 | −5.747 | 5.495 | 1.00 | 12.37 |
| ATOM | 43 | CG2 | VAL | A | 7 | 10.680 | −4.873 | 3.596 | 1.00 | 12.17 |
| ATOM | 44 | C | VAL | A | 7 | 9.052 | −3.010 | 6.579 | 1.00 | 10.17 |
| ATOM | 45 | O | VAL | A | 7 | 9.833 | −2.691 | 7.463 | 1.00 | 10.48 |
| ATOM | 46 | N | VAL | A | 8 | 7.758 | −3.159 | 6.798 | 1.00 | 10.12 |
| ATOM | 47 | CA | VAL | A | 8 | 7.114 | −2.817 | 8.057 | 1.00 | 10.09 |
| ATOM | 48 | CB | VAL | A | 8 | 5.893 | −1.924 | 7.771 | 1.00 | 10.08 |
| ATOM | 49 | CG1 | VAL | A | 8 | 5.184 | −1.529 | 9.081 | 1.00 | 10.78 |
| ATOM | 50 | CG2 | VAL | A | 8 | 6.324 | −0.697 | 6.939 | 1.00 | 11.24 |
| ATOM | 51 | C | VAL | A | 8 | 6.658 | −4.129 | 8.684 | 1.00 | 9.54 |
| ATOM | 52 | O | VAL | A | 8 | 5.908 | −4.894 | 8.046 | 1.00 | 9.78 |
| ATOM | 53 | N | VAL | A | 9 | 7.144 | −4.421 | 9.887 | 1.00 | 9.18 |
| ATOM | 54 | CA | VAL | A | 9 | 6.827 | −5.669 | 10.590 | 1.00 | 9.67 |
| ATOM | 55 | CB | VAL | A | 9 | 8.027 | −6.665 | 10.597 | 1.00 | 9.51 |
| ATOM | 56 | CG1 | VAL | A | 9 | 8.500 | −6.952 | 9.170 | 1.00 | 11.60 |
| ATOM | 57 | CG2 | VAL | A | 9 | 9.183 | −6.171 | 11.474 | 1.00 | 11.98 |
| ATOM | 58 | C | VAL | A | 9 | 6.399 | −5.370 | 12.019 | 1.00 | 9.36 |
| ATOM | 59 | O | VAL | A | 9 | 6.596 | −4.276 | 12.541 | 1.00 | 9.87 |
| ATOM | 60 | N | GLY | A | 10 | 5.812 | −6.369 | 12.648 | 1.00 | 9.30 |
| ATOM | 61 | CA | GLY | A | 10 | 5.346 | −6.288 | 14.024 | 1.00 | 10.14 |
| ATOM | 62 | C | GLY | A | 10 | 4.095 | −7.136 | 14.205 | 1.00 | 9.38 |
| ATOM | 63 | O | GLY | A | 10 | 3.500 | −7.647 | 13.243 | 1.00 | 9.61 |
| ATOM | 64 | N | ASP | A | 11 | 3.702 | −7.283 | 15.466 | 1.00 | 9.39 |
| ATOM | 65 | CA | ASP | A | 11 | 2.596 | −8.170 | 15.822 | 1.00 | 10.45 |
| ATOM | 66 | CB | ASP | A | 11 | 2.329 | −8.105 | 17.323 | 1.00 | 10.06 |
| ATOM | 67 | CG | ASP | A | 11 | 3.288 | −8.959 | 18.135 | 1.00 | 12.02 |
| ATOM | 68 | OD1 | ASP | A | 11 | 4.248 | −9.545 | 17.584 | 1.00 | 12.12 |
| ATOM | 69 | OD2 | ASP | A | 11 | 3.029 | −9.044 | 19.354 | 1.00 | 13.04 |
| ATOM | 70 | C | ASP | A | 11 | 1.324 | −7.788 | 15.111 | 1.00 | 9.85 |
| ATOM | 71 | O | ASP | A | 11 | 1.101 | −6.621 | 14.774 | 1.00 | 9.42 |
| ATOM | 72 | N | GLY | A | 12 | 0.433 | −8.753 | 14.932 | 1.00 | 10.76 |
| ATOM | 73 | CA | GLY | A | 12 | −0.908 | −8.453 | 14.437 | 1.00 | 10.53 |
| ATOM | 74 | C | GLY | A | 12 | −1.572 | −7.408 | 15.312 | 1.00 | 10.68 |
| ATOM | 75 | O | GLY | A | 12 | −1.433 | −7.428 | 16.541 | 1.00 | 11.67 |
| ATOM | 76 | N | ALA | A | 13 | −2.290 | −6.488 | 14.674 | 1.00 | 10.27 |
| ATOM | 77 | CA | ALA | A | 13 | −3.124 | −5.478 | 15.320 | 1.00 | 10.10 |
| ATOM | 78 | CB | ALA | A | 13 | −4.081 | −6.090 | 16.347 | 1.00 | 11.47 |
| ATOM | 79 | C | ALA | A | 13 | −2.372 | −4.292 | 15.913 | 1.00 | 10.23 |
| ATOM | 80 | O | ALA | A | 13 | −2.991 | −3.454 | 16.586 | 1.00 | 11.32 |
| ATOM | 81 | N | VAL | A | 14 | −1.073 | −4.187 | 15.662 | 1.00 | 10.56 |
| ATOM | 82 | CA | VAL | A | 14 | −0.355 | −2.999 | 16.193 | 1.00 | 10.35 |
| ATOM | 83 | CB | VAL | A | 14 | 1.161 | −3.227 | 16.365 | 1.00 | 10.51 |
| ATOM | 84 | CG1 | VAL | A | 14 | 1.444 | −4.399 | 17.307 | 1.00 | 11.36 |
| ATOM | 85 | CG2 | VAL | A | 14 | 1.861 | −3.405 | 15.042 | 1.00 | 11.73 |

TABLE 1-continued

| | | | | | | | | | |
|---|---|---|---|---|---|---|---|---|---|
| ATOM | 86 | C | VAL | A | 14 | −0.617 | −1.727 | 15.403 | 1.00 | 10.69 |
| ATOM | 87 | O | VAL | A | 14 | −0.410 | −0.624 | 15.917 | 1.00 | 11.18 |
| ATOM | 88 | N | GLY | A | 15 | −1.108 | −1.859 | 14.176 | 1.00 | 9.47 |
| ATOM | 89 | CA | GLY | A | 15 | −1.432 | −0.721 | 13.333 | 1.00 | 10.07 |
| ATOM | 90 | C | GLY | A | 15 | −0.547 | −0.518 | 12.119 | 1.00 | 9.10 |
| ATOM | 91 | O | GLY | A | 15 | −0.502 | 0.581 | 11.585 | 1.00 | 9.75 |
| ATOM | 92 | N | LYS | A | 16 | 0.079 | −1.580 | 11.616 | 1.00 | 8.57 |
| ATOM | 93 | CA | LYS | A | 16 | 0.976 | −1.451 | 10.467 | 1.00 | 8.65 |
| ATOM | 94 | CB | LYS | A | 16 | 1.674 | −2.782 | 10.183 | 1.00 | 8.61 |
| ATOM | 95 | CG | LYS | A | 16 | 2.485 | −3.314 | 11.373 | 1.00 | 9.93 |
| ATOM | 96 | CD | LYS | A | 16 | 3.194 | −4.658 | 11.106 | 1.00 | 10.00 |
| ATOM | 97 | CE | LYS | A | 16 | 2.275 | −5.817 | 10.819 | 1.00 | 10.39 |
| ATOM | 98 | NZ | LYS | A | 16 | 1.366 | −6.104 | 11.952 | 1.00 | 9.45 |
| ATOM | 99 | C | LYS | A | 16 | 0.227 | −0.996 | 9.228 | 1.00 | 8.25 |
| ATOM | 100 | O | LYS | A | 16 | 0.641 | −0.060 | 8.535 | 1.00 | 8.46 |
| ATOM | 101 | N | THR | A | 17 | −0.875 | −1.672 | 8.912 | 1.00 | 8.80 |
| ATOM | 102 | CA | THR | A | 17 | −1.615 | −1.343 | 7.710 | 1.00 | 9.41 |
| ATOM | 103 | CB | THR | A | 17 | −2.689 | −2.400 | 7.503 | 1.00 | 8.99 |
| ATOM | 104 | OG1 | THR | A | 17 | −2.020 | −3.677 | 7.367 | 1.00 | 9.21 |
| ATOM | 105 | CG2 | THR | A | 17 | −3.503 | −2.155 | 6.248 | 1.00 | 10.06 |
| ATOM | 106 | C | THR | A | 17 | −2.204 | 0.070 | 7.800 | 1.00 | 8.93 |
| ATOM | 107 | O | THR | A | 17 | −2.136 | 0.834 | 6.828 | 1.00 | 9.41 |
| ATOM | 108 | N | CYS | A | 18 | −2.784 | 0.423 | 8.943 | 1.00 | 9.42 |
| ATOM | 109 | CA | CYS | A | 18 | −3.355 | 1.741 | 9.077 | 1.00 | 10.25 |
| ATOM | 110 | CB | CYS | A | 18 | −4.075 | 1.897 | 10.396 | 1.00 | 10.15 |
| ATOM | 111 | SG | CYS | A | 18 | −5.693 | 1.128 | 10.433 | 1.00 | 11.45 |
| ATOM | 112 | C | CYS | A | 18 | −2.296 | 2.805 | 8.984 | 1.00 | 10.14 |
| ATOM | 113 | O | CYS | A | 18 | −2.576 | 3.871 | 8.414 | 1.00 | 11.24 |
| ATOM | 114 | N | LEU | A | 19 | −1.114 | 2.611 | 9.549 | 1.00 | 10.34 |
| ATOM | 115 | CA | LEU | A | 19 | −0.175 | 3.719 | 9.443 | 1.00 | 11.62 |
| ATOM | 116 | C | LEU | A | 19 | 0.273 | 3.893 | 8.004 | 1.00 | 11.02 |
| ATOM | 117 | O | LEU | A | 19 | 0.512 | 5.022 | 7.575 | 1.00 | 11.14 |
| ATOM | 118 | CB | LEU | A | 19 | 1.025 | 3.494 | 10.365 | 1.00 | 12.92 |
| ATOM | 119 | CG | LEU | A | 19 | 1.988 | 2.375 | 9.965 | 1.00 | 20.00 |
| ATOM | 120 | CD1 | LEU | A | 19 | 3.014 | 2.881 | 8.963 | 1.00 | 15.00 |
| ATOM | 121 | CD2 | LEU | A | 19 | 2.677 | 1.795 | 11.190 | 1.00 | 20.00 |
| ATOM | 122 | N | LEU | A | 20 | 0.350 | 2.817 | 7.229 | 1.00 | 10.17 |
| ATOM | 123 | CA | LEU | A | 20 | 0.685 | 2.943 | 5.809 | 1.00 | 10.15 |
| ATOM | 124 | CB | LEU | A | 20 | 1.019 | 1.577 | 5.203 | 1.00 | 10.06 |
| ATOM | 125 | CG | LEU | A | 20 | 2.331 | 0.991 | 5.722 | 1.00 | 9.84 |
| ATOM | 126 | CD1 | LEU | A | 20 | 2.432 | −0.485 | 5.309 | 1.00 | 12.20 |
| ATOM | 127 | CD2 | LEU | A | 20 | 3.522 | 1.778 | 5.244 | 1.00 | 13.56 |
| ATOM | 128 | C | LEU | A | 20 | −0.421 | 3.631 | 5.007 | 1.00 | 10.29 |
| ATOM | 129 | O | LEU | A | 20 | −0.132 | 4.471 | 4.153 | 1.00 | 10.44 |
| ATOM | 130 | N | ILE | A | 21 | −1.669 | 3.293 | 5.279 | 1.00 | 10.12 |
| ATOM | 131 | CA | ILE | A | 21 | −2.789 | 3.912 | 4.590 | 1.00 | 10.14 |
| ATOM | 132 | CB | ILE | A | 21 | −4.093 | 3.182 | 4.880 | 1.00 | 10.76 |
| ATOM | 133 | CG1 | ILE | A | 21 | −4.044 | 1.818 | 4.193 | 1.00 | 11.42 |
| ATOM | 134 | CD1 | ILE | A | 21 | −5.125 | 0.806 | 4.611 | 1.00 | 13.68 |
| ATOM | 135 | CG2 | ILE | A | 21 | −5.300 | 3.964 | 4.352 | 1.00 | 12.21 |
| ATOM | 136 | C | ILE | A | 21 | −2.883 | 5.381 | 4.987 | 1.00 | 9.92 |
| ATOM | 137 | O | ILE | A | 21 | −3.078 | 6.234 | 4.112 | 1.00 | 10.89 |
| ATOM | 138 | N | SER | A | 22 | −2.730 | 5.697 | 6.259 | 0.50 | 6.37 |
| ATOM | 139 | CA | SER | A | 22 | −2.774 | 7.094 | 6.668 | 0.50 | 6.91 |
| ATOM | 140 | CB | SER | A | 22 | −2.711 | 7.193 | 8.182 | 0.50 | 6.73 |
| ATOM | 141 | OG | ASER | A | 22 | −3.945 | 6.769 | 8.703 | 0.50 | 12.30 |
| ATOM | 141 | OG | BSER | A | 22 | −2.826 | 8.535 | 8.599 | 0.50 | 11.36 |
| ATOM | 142 | C | SER | A | 22 | −1.642 | 7.893 | 6.019 | 0.50 | 6.92 |
| ATOM | 143 | O | SER | A | 22 | −1.841 | 9.031 | 5.573 | 0.50 | 5.72 |
| ATOM | 144 | N | TYR | A | 23 | −0.449 | 7.310 | 5.949 | 1.00 | 10.57 |
| ATOM | 145 | CA | TYR | A | 23 | 0.681 | 8.011 | 5.355 | 1.00 | 11.21 |
| ATOM | 146 | CB | TYR | A | 23 | 1.963 | 7.202 | 5.563 | 1.00 | 11.78 |
| ATOM | 147 | CG | TYR | A | 23 | 3.203 | 7.835 | 4.958 | 1.00 | 11.21 |
| ATOM | 148 | CD1 | TYR | A | 23 | 3.655 | 9.080 | 5.389 | 1.00 | 11.88 |
| ATOM | 149 | CE1 | TYR | A | 23 | 4.790 | 9.656 | 4.842 | 1.00 | 11.58 |
| ATOM | 150 | CZ | TYR | A | 23 | 5.513 | 8.958 | 3.884 | 1.00 | 11.24 |
| ATOM | 151 | OH | TYR | A | 23 | 6.654 | 9.496 | 3.318 | 1.00 | 12.92 |
| ATOM | 152 | CE2 | TYR | A | 23 | 5.091 | 7.730 | 3.446 | 1.00 | 11.94 |
| ATOM | 153 | CD2 | TYR | A | 23 | 3.953 | 7.167 | 3.992 | 1.00 | 11.19 |
| ATOM | 154 | C | TYR | A | 23 | 0.479 | 8.286 | 3.869 | 1.00 | 12.23 |
| ATOM | 155 | O | TYR | A | 23 | 0.855 | 9.356 | 3.343 | 1.00 | 13.13 |
| ATOM | 156 | N | THR | A | 24 | −0.100 | 7.321 | 3.172 | 1.00 | 12.75 |
| ATOM | 157 | CA | THR | A | 24 | −0.174 | 7.422 | 1.715 | 1.00 | 13.41 |
| ATOM | 158 | CB | THR | A | 24 | −0.089 | 6.044 | 1.027 | 1.00 | 13.28 |
| ATOM | 159 | OG1 | THR | A | 24 | −1.141 | 5.191 | 1.515 | 1.00 | 12.91 |
| ATOM | 160 | CG2 | THR | A | 24 | 1.259 | 5.394 | 1.283 | 1.00 | 13.69 |
| ATOM | 161 | C | THR | A | 24 | −1.406 | 8.160 | 1.230 | 1.00 | 14.93 |
| ATOM | 162 | O | THR | A | 24 | −1.369 | 8.734 | 0.143 | 1.00 | 15.84 |
| ATOM | 163 | N | THR | A | 25 | −2.477 | 8.181 | 2.022 | 1.00 | 14.62 |

TABLE 1-continued

| | | | | | | | | | |
|---|---|---|---|---|---|---|---|---|---|
| ATOM | 164 | CA | THR | A | 25 | −3.754 | 8.759 | 1.589 | 1.00 | 15.96 |
| ATOM | 165 | CB | THR | A | 25 | −4.890 | 7.711 | 1.573 | 1.00 | 15.67 |
| ATOM | 166 | OG1 | THR | A | 25 | −5.267 | 7.374 | 2.925 | 1.00 | 16.40 |
| ATOM | 167 | CG2 | THR | A | 25 | −4.498 | 6.474 | 0.785 | 1.00 | 15.73 |
| ATOM | 168 | C | THR | A | 25 | −4.234 | 9.918 | 2.459 | 1.00 | 17.13 |
| ATOM | 169 | O | THR | A | 25 | −5.197 | 10.593 | 2.089 | 1.00 | 17.10 |
| ATOM | 170 | N | ASN | A | 26 | −3.626 | 10.103 | 3.626 | 1.00 | 18.51 |
| ATOM | 171 | CA | ASN | A | 26 | −4.079 | 11.125 | 4.599 | 1.00 | 20.28 |
| ATOM | 172 | CB | ASN | A | 26 | −3.885 | 12.548 | 4.040 | 1.00 | 21.61 |
| ATOM | 173 | CG | ASN | A | 26 | −2.437 | 12.847 | 3.726 | 1.00 | 23.49 |
| ATOM | 174 | OD1 | ASN | A | 26 | −2.108 | 13.367 | 2.650 | 1.00 | 27.93 |
| ATOM | 175 | ND2 | ASN | A | 26 | −1.546 | 12.502 | 4.657 | 1.00 | 25.36 |
| ATOM | 176 | C | ASN | A | 26 | −5.496 | 10.915 | 5.133 | 1.00 | 21.61 |
| ATOM | 177 | O | ASN | A | 26 | −6.133 | 11.858 | 5.625 | 1.00 | 22.35 |
| ATOM | 178 | N | ALA | A | 27 | −5.999 | 9.690 | 5.041 | 1.00 | 21.20 |
| ATOM | 179 | CA | ALA | A | 27 | −7.270 | 9.364 | 5.665 | 1.00 | 21.90 |
| ATOM | 180 | CB | ALA | A | 27 | −8.324 | 9.074 | 4.626 | 1.00 | 22.79 |
| ATOM | 181 | C | ALA | A | 27 | −7.036 | 8.154 | 6.561 | 1.00 | 21.66 |
| ATOM | 182 | O | ALA | A | 27 | −6.462 | 7.172 | 6.115 | 1.00 | 22.33 |
| ATOM | 183 | N | PHE | A | 28 | −7.410 | 8.257 | 7.830 | 1.00 | 19.80 |
| ATOM | 184 | CA | PHE | A | 28 | −7.389 | 7.090 | 8.715 | 1.00 | 17.99 |
| ATOM | 185 | CB | PHE | A | 28 | −7.504 | 7.524 | 10.165 | 1.00 | 17.74 |
| ATOM | 186 | CG | PHE | A | 28 | −7.569 | 6.380 | 11.124 | 1.00 | 16.32 |
| ATOM | 187 | CD1 | PHE | A | 28 | −6.452 | 5.574 | 11.360 | 1.00 | 16.38 |
| ATOM | 188 | CE1 | PHE | A | 28 | −6.516 | 4.504 | 12.268 | 1.00 | 14.61 |
| ATOM | 189 | CZ | PHE | A | 28 | −7.713 | 4.235 | 12.930 | 1.00 | 16.53 |
| ATOM | 190 | CE2 | PHE | A | 28 | −8.840 | 5.025 | 12.686 | 1.00 | 16.63 |
| ATOM | 191 | CD2 | PHE | A | 28 | −8.759 | 6.095 | 11.783 | 1.00 | 15.57 |
| ATOM | 192 | C | PHE | A | 28 | −8.544 | 6.155 | 8.342 | 1.00 | 17.65 |
| ATOM | 193 | O | PHE | A | 28 | −9.707 | 6.563 | 8.334 | 1.00 | 17.89 |
| ATOM | 194 | N | PRO | A | 29 | −8.237 | 4.897 | 7.982 | 1.00 | 16.19 |
| ATOM | 195 | CA | PRO | A | 29 | −9.275 | 4.005 | 7.446 | 1.00 | 15.78 |
| ATOM | 196 | CB | PRO | A | 29 | −8.457 | 3.021 | 6.603 | 1.00 | 14.96 |
| ATOM | 197 | CG | PRO | A | 29 | −7.162 | 2.881 | 7.423 | 1.00 | 15.06 |
| ATOM | 198 | CD | PRO | A | 29 | −6.889 | 4.281 | 7.933 | 1.00 | 15.67 |
| ATOM | 199 | C | PRO | A | 29 | −10.111 | 3.225 | 8.456 | 1.00 | 16.17 |
| ATOM | 200 | O | PRO | A | 29 | −11.017 | 2.496 | 8.064 | 1.00 | 16.59 |
| ATOM | 201 | N | GLY | A | 30 | −9.816 | 3.343 | 9.741 | 1.00 | 16.47 |
| ATOM | 202 | CA | GLY | A | 30 | −10.613 | 2.622 | 10.746 | 1.00 | 16.48 |
| ATOM | 203 | C | GLY | A | 30 | −10.533 | 1.107 | 10.589 | 1.00 | 16.58 |
| ATOM | 204 | O | GLY | A | 30 | −9.443 | 0.543 | 10.592 | 1.00 | 16.49 |
| ATOM | 205 | N | GLU | A | 31 | −11.681 | 0.457 | 10.447 | 1.00 | 16.20 |
| ATOM | 206 | CA | GLU | A | 31 | −11.752 | −0.994 | 10.256 | 1.00 | 16.97 |
| ATOM | 207 | CB | GLU | A | 31 | −12.970 | −1.573 | 10.986 | 1.00 | 18.18 |
| ATOM | 208 | CG | GLU | A | 31 | −13.022 | −1.270 | 12.463 | 1.00 | 22.26 |
| ATOM | 209 | CD | GLU | A | 31 | −11.703 | −1.558 | 13.161 | 1.00 | 26.99 |
| ATOM | 210 | OE1 | GLU | A | 31 | −11.201 | −2.698 | 13.072 | 1.00 | 30.47 |
| ATOM | 211 | OE2 | GLU | A | 31 | −11.164 | −0.635 | 13.796 | 1.00 | 31.76 |
| ATOM | 212 | C | GLU | A | 31 | −11.802 | −1.400 | 8.780 | 1.00 | 15.98 |
| ATOM | 213 | O | GLU | A | 31 | −11.844 | −2.590 | 8.449 | 1.00 | 16.42 |
| ATOM | 214 | N | TYR | A | 32 | −11.785 | −0.410 | 7.900 | 1.00 | 16.12 |
| ATOM | 215 | CA | TYR | A | 32 | −11.922 | −0.686 | 6.468 | 1.00 | 17.14 |
| ATOM | 216 | CB | TYR | A | 32 | −12.725 | 0.415 | 5.782 | 1.00 | 18.87 |
| ATOM | 217 | CG | TYR | A | 32 | −14.165 | 0.415 | 6.240 | 1.00 | 20.99 |
| ATOM | 218 | CD1 | TYR | A | 32 | −15.095 | −0.446 | 5.667 | 1.00 | 23.72 |
| ATOM | 219 | CE1 | TYR | A | 32 | −16.417 | −0.460 | 6.093 | 1.00 | 26.05 |
| ATOM | 220 | CZ | TYR | A | 32 | −16.819 | 0.403 | 7.097 | 1.00 | 24.58 |
| ATOM | 221 | OH | TYR | A | 32 | −18.130 | 0.394 | 7.507 | 1.00 | 25.90 |
| ATOM | 222 | CE2 | TYR | A | 32 | −15.913 | 1.267 | 7.697 | 1.00 | 23.82 |
| ATOM | 223 | CD2 | TYR | A | 32 | −14.590 | 1.270 | 7.261 | 1.00 | 22.07 |
| ATOM | 224 | C | TYR | A | 32 | −10.556 | −0.856 | 5.848 | 1.00 | 15.47 |
| ATOM | 225 | O | TYR | A | 32 | −10.058 | −0.007 | 5.111 | 1.00 | 15.10 |
| ATOM | 226 | N | ILE | A | 33 | −9.935 | −1.979 | 6.210 | 1.00 | 14.88 |
| ATOM | 227 | CA | ILE | A | 33 | −8.540 | −2.215 | 5.873 | 1.00 | 14.90 |
| ATOM | 228 | CB | ILE | A | 33 | −7.635 | −1.892 | 7.090 | 1.00 | 15.46 |
| ATOM | 229 | CG1 | ILE | A | 33 | −8.141 | −2.656 | 8.343 | 1.00 | 17.42 |
| ATOM | 230 | CD1 | ILE | A | 33 | −7.582 | −2.237 | 9.684 | 1.00 | 17.18 |
| ATOM | 231 | CG2 | ILE | A | 33 | −7.558 | −0.378 | 7.332 | 1.00 | 14.83 |
| ATOM | 232 | C | ILE | A | 33 | −8.325 | −3.670 | 5.511 | 1.00 | 13.45 |
| ATOM | 233 | O | ILE | A | 33 | −9.015 | −4.544 | 6.032 | 1.00 | 14.07 |
| ATOM | 234 | N | PRO | A | 34 | −7.348 | −3.942 | 4.636 | 1.00 | 11.93 |
| ATOM | 235 | CA | PRO | A | 34 | −6.936 | −5.310 | 4.369 | 1.00 | 11.72 |
| ATOM | 236 | CB | PRO | A | 34 | −6.181 | −5.179 | 3.043 | 1.00 | 11.45 |
| ATOM | 237 | CG | PRO | A | 34 | −5.535 | −3.809 | 3.161 | 1.00 | 12.24 |
| ATOM | 238 | CD | PRO | A | 34 | −6.560 | −2.968 | 3.857 | 1.00 | 11.49 |
| ATOM | 239 | C | PRO | A | 34 | −5.994 | −5.804 | 5.481 | 1.00 | 11.22 |
| ATOM | 240 | O | PRO | A | 34 | −5.495 | −4.999 | 6.281 | 1.00 | 10.92 |
| ATOM | 241 | N | THR | A | 35 | −5.698 | −7.102 | 5.504 | 1.00 | 10.66 |
| ATOM | 242 | CA | THR | A | 35 | −4.644 | −7.603 | 6.366 | 1.00 | 10.28 |

TABLE 1-continued

| | | | | | | | | | |
|---|---|---|---|---|---|---|---|---|---|
| ATOM | 243 | CB | THR | A | 35 | −4.530 | −9.132 | 6.220 | 1.00 | 10.32 |
| ATOM | 244 | OG1 | THR | A | 35 | −5.787 | −9.740 | 6.564 | 1.00 | 10.83 |
| ATOM | 245 | CG2 | THR | A | 35 | −3.440 | −9.719 | 7.103 | 1.00 | 10.76 |
| ATOM | 246 | C | THR | A | 35 | −3.317 | −6.954 | 5.972 | 1.00 | 9.92 |
| ATOM | 247 | O | THR | A | 35 | −2.573 | −6.502 | 6.855 | 1.00 | 9.20 |
| ATOM | 248 | N | VAL | A | 36 | −3.026 | −6.915 | 4.676 | 1.00 | 9.92 |
| ATOM | 249 | CA | VAL | A | 36 | −1.765 | −6.390 | 4.189 | 1.00 | 11.66 |
| ATOM | 250 | CB | VAL | A | 36 | −0.911 | −7.532 | 3.564 | 1.00 | 12.55 |
| ATOM | 251 | CG1 | VAL | A | 36 | 0.435 | −7.006 | 3.135 | 1.00 | 14.75 |
| ATOM | 252 | CG2 | VAL | A | 36 | −0.764 | −8.749 | 4.538 | 1.00 | 13.86 |
| ATOM | 253 | C | VAL | A | 36 | −2.045 | −5.353 | 3.100 | 1.00 | 11.71 |
| ATOM | 254 | O | VAL | A | 36 | −2.736 | −5.644 | 2.124 | 1.00 | 12.92 |
| ATOM | 255 | N | PHE | A | 37 | −1.555 | −4.136 | 3.293 | 1.00 | 11.91 |
| ATOM | 256 | CA | PHE | A | 37 | −1.630 | −3.073 | 2.301 | 1.00 | 12.80 |
| ATOM | 257 | CB | PHE | A | 37 | −0.957 | −1.854 | 2.933 | 1.00 | 13.56 |
| ATOM | 258 | CG | PHE | A | 37 | −1.143 | −0.571 | 2.182 | 1.00 | 16.30 |
| ATOM | 259 | CD1 | PHE | A | 37 | −2.405 | −0.166 | 1.753 | 1.00 | 19.42 |
| ATOM | 260 | CE1 | PHE | A | 37 | −2.578 | 1.058 | 1.071 | 1.00 | 20.61 |
| ATOM | 261 | CZ | PHE | A | 37 | −1.475 | 1.871 | 0.845 | 1.00 | 17.13 |
| ATOM | 262 | CE2 | PHE | A | 37 | −0.211 | 1.483 | 1.264 | 1.00 | 17.41 |
| ATOM | 263 | CD2 | PHE | A | 37 | −0.050 | 0.250 | 1.948 | 1.00 | 18.70 |
| ATOM | 264 | C | PHE | A | 37 | −0.893 | −3.459 | 1.039 | 1.00 | 14.08 |
| ATOM | 265 | O | PHE | A | 37 | 0.169 | −4.074 | 1.120 | 1.00 | 14.02 |
| ATOM | 266 | N | ASP | A | 38 | −1.434 | −3.055 | −0.110 | 1.00 | 15.41 |
| ATOM | 267 | CA | ASP | A | 38 | −0.772 | −3.259 | −1.404 | 1.00 | 17.12 |
| ATOM | 268 | CB | ASP | A | 38 | −1.618 | −2.627 | −2.533 | 1.00 | 18.72 |
| ATOM | 269 | CG | ASP | A | 38 | −2.911 | −3.389 | −2.846 | 1.00 | 23.03 |
| ATOM | 270 | OD1 | ASP | A | 38 | −3.085 | −4.547 | −2.409 | 1.00 | 26.95 |
| ATOM | 271 | OD2 | ASP | A | 38 | −3.757 | −2.798 | −3.563 | 1.00 | 28.04 |
| ATOM | 272 | C | ASP | A | 38 | 0.616 | −2.577 | −1.389 | 1.00 | 16.38 |
| ATOM | 273 | O | ASP | A | 38 | 0.804 | −1.560 | −0.735 | 1.00 | 16.07 |
| ATOM | 274 | N | ASN | A | 39 | 1.584 | −3.135 | −2.099 | 1.00 | 16.55 |
| ATOM | 275 | CA | ASN | A | 39 | 2.857 | −2.436 | −2.288 | 1.00 | 17.38 |
| ATOM | 276 | CB | ASN | A | 39 | 3.694 | −3.191 | −3.309 | 1.00 | 18.41 |
| ATOM | 277 | CG | ASN | A | 39 | 5.083 | −2.657 | −3.403 | 1.00 | 22.02 |
| ATOM | 278 | OD1 | ASN | A | 39 | 5.471 | −2.085 | −4.423 | 1.00 | 26.34 |
| ATOM | 279 | ND2 | ASN | A | 39 | 5.844 | −2.809 | −2.327 | 1.00 | 27.14 |
| ATOM | 280 | C | ASN | A | 39 | 2.648 | −1.011 | −2.788 | 1.00 | 16.04 |
| ATOM | 281 | O | ASN | A | 39 | 1.772 | −0.761 | −3.622 | 1.00 | 16.15 |
| ATOM | 282 | N | TYR | A | 40 | 3.440 | −0.068 | −2.280 | 1.00 | 14.53 |
| ATOM | 283 | CA | TYR | A | 40 | 3.306 | 1.337 | −2.665 | 1.00 | 14.34 |
| ATOM | 284 | CB | TYR | A | 40 | 2.592 | 2.105 | −1.544 | 1.00 | 14.12 |
| ATOM | 285 | CG | TYR | A | 40 | 2.419 | 3.582 | −1.815 | 1.00 | 14.39 |
| ATOM | 286 | CD1 | TYR | A | 40 | 1.294 | 4.049 | −2.490 | 1.00 | 14.96 |
| ATOM | 287 | CE1 | TYR | A | 40 | 1.125 | 5.409 | −2.749 | 1.00 | 14.64 |
| ATOM | 288 | CZ | TYR | A | 40 | 2.090 | 6.291 | −2.330 | 1.00 | 15.18 |
| ATOM | 289 | OH | TYR | A | 40 | 1.898 | 7.628 | −2.607 | 1.00 | 16.39 |
| ATOM | 290 | CE2 | TYR | A | 40 | 3.220 | 5.859 | −1.665 | 1.00 | 14.84 |
| ATOM | 291 | CD2 | TYR | A | 40 | 3.385 | 4.500 | −1.414 | 1.00 | 14.38 |
| ATOM | 292 | C | TYR | A | 40 | 4.683 | 1.934 | −2.873 | 1.00 | 13.60 |
| ATOM | 293 | O | TYR | A | 40 | 5.580 | 1.718 | −2.064 | 1.00 | 14.93 |
| ATOM | 294 | N | SER | A | 41 | 4.875 | 2.685 | −3.951 | 1.00 | 12.48 |
| ATOM | 295 | CA | SER | A | 41 | 6.077 | 3.495 | −4.068 | 1.00 | 13.53 |
| ATOM | 296 | CB | SER | A | 41 | 7.158 | 2.872 | −4.960 | 1.00 | 14.96 |
| ATOM | 297 | OG | SER | A | 41 | 6.766 | 2.869 | −6.306 | 1.00 | 19.82 |
| ATOM | 298 | C | SER | A | 41 | 5.706 | 4.876 | −4.559 | 1.00 | 12.45 |
| ATOM | 299 | O | SER | A | 41 | 4.742 | 5.037 | −5.308 | 1.00 | 13.38 |
| ATOM | 300 | N | ALA | A | 42 | 6.485 | 5.856 | −4.136 | 1.00 | 11.65 |
| ATOM | 301 | CA | ALA | A | 42 | 6.322 | 7.235 | −4.575 | 1.00 | 11.45 |
| ATOM | 302 | CB | ALA | A | 42 | 5.093 | 7.881 | −3.900 | 1.00 | 12.12 |
| ATOM | 303 | C | ALA | A | 42 | 7.555 | 8.004 | −4.206 | 1.00 | 11.86 |
| ATOM | 304 | O | ALA | A | 42 | 8.337 | 7.574 | −3.341 | 1.00 | 11.97 |
| ATOM | 305 | N | ASN | A | 43 | 7.743 | 9.139 | −4.864 | 1.00 | 11.38 |
| ATOM | 306 | CA | ASN | A | 43 | 8.759 | 10.096 | −4.456 | 1.00 | 11.29 |
| ATOM | 307 | CB | ASN | A | 43 | 9.150 | 11.013 | −5.625 | 1.00 | 12.66 |
| ATOM | 308 | CG | ASN | A | 43 | 9.986 | 10.313 | −6.670 | 1.00 | 14.01 |
| ATOM | 309 | OD1 | ASN | A | 43 | 10.362 | 9.142 | −6.535 | 1.00 | 15.75 |
| ATOM | 310 | ND2 | ASN | A | 43 | 10.287 | 11.034 | −7.742 | 1.00 | 16.59 |
| ATOM | 311 | C | ASN | A | 43 | 8.258 | 10.943 | −3.315 | 1.00 | 11.75 |
| ATOM | 312 | O | ASN | A | 43 | 7.171 | 11.525 | −3.378 | 1.00 | 11.94 |
| ATOM | 313 | N | VAL | A | 44 | 9.056 | 11.010 | −2.257 | 1.00 | 11.62 |
| ATOM | 314 | CA | VAL | A | 44 | 8.733 | 11.826 | −1.097 | 1.00 | 13.22 |
| ATOM | 315 | CB | VAL | A | 44 | 8.432 | 10.946 | 0.147 | 1.00 | 14.92 |
| ATOM | 316 | CG1 | VAL | A | 44 | 7.320 | 9.959 | −0.145 | 1.00 | 16.55 |
| ATOM | 317 | CG2 | VAL | A | 44 | 9.626 | 10.198 | 0.556 | 1.00 | 15.99 |
| ATOM | 318 | C | VAL | A | 44 | 9.872 | 12.807 | −0.849 | 1.00 | 13.51 |
| ATOM | 319 | O | VAL | A | 44 | 11.029 | 12.488 | −1.103 | 1.00 | 13.42 |
| ATOM | 320 | N | MET | A | 45 | 9.541 | 13.990 | −0.353 | 1.00 | 14.85 |
| ATOM | 321 | CA | MET | A | 45 | 10.532 | 15.017 | −0.131 | 1.00 | 15.75 |

TABLE 1-continued

| | | | | | | | | | |
|---|---|---|---|---|---|---|---|---|---|
| ATOM | 322 | CB | MET | A | 45 | 9.877 | 16.407 | −0.141 | 1.00 | 16.60 |
| ATOM | 323 | CG | MET | A | 45 | 9.275 | 16.835 | −1.464 | 1.00 | 18.19 |
| ATOM | 324 | SD | MET | A | 45 | 10.418 | 16.742 | −2.826 | 1.00 | 21.74 |
| ATOM | 325 | CE | MET | A | 45 | 11.537 | 18.088 | −2.504 | 1.00 | 21.52 |
| ATOM | 326 | C | MET | A | 45 | 11.184 | 14.817 | 1.223 | 1.00 | 16.61 |
| ATOM | 327 | O | MET | A | 45 | 10.500 | 14.803 | 2.243 | 1.00 | 16.90 |
| ATOM | 328 | N | VAL | A | 46 | 12.506 | 14.689 | 1.220 | 1.00 | 16.86 |
| ATOM | 329 | CA | VAL | A | 46 | 13.286 | 14.637 | 2.455 | 1.00 | 18.05 |
| ATOM | 330 | CB | VAL | A | 46 | 13.720 | 13.181 | 2.816 | 1.00 | 18.32 |
| ATOM | 331 | CG1 | VAL | A | 46 | 14.477 | 13.146 | 4.150 | 1.00 | 19.56 |
| ATOM | 332 | CG2 | VAL | A | 46 | 12.501 | 12.288 | 2.910 | 1.00 | 18.50 |
| ATOM | 333 | C | VAL | A | 46 | 14.496 | 15.537 | 2.257 | 1.00 | 18.60 |
| ATOM | 334 | O | VAL | A | 46 | 15.222 | 15.388 | 1.288 | 1.00 | 18.55 |
| ATOM | 335 | N | ASP | A | 47 | 14.688 | 16.473 | 3.182 | 1.00 | 20.72 |
| ATOM | 336 | CA | ASP | A | 47 | 15.862 | 17.352 | 3.181 | 1.00 | 22.66 |
| ATOM | 337 | CB | ASP | A | 47 | 17.130 | 16.577 | 3.610 | 1.00 | 23.69 |
| ATOM | 338 | CG | ASP | A | 47 | 16.997 | 15.961 | 5.012 | 1.00 | 25.31 |
| ATOM | 339 | OD1 | ASP | A | 47 | 16.347 | 16.575 | 5.881 | 1.00 | 28.40 |
| ATOM | 340 | OD2 | ASP | A | 47 | 17.535 | 14.861 | 5.241 | 1.00 | 27.71 |
| ATOM | 341 | C | ASP | A | 47 | 16.010 | 18.073 | 1.832 | 1.00 | 23.13 |
| ATOM | 342 | O | ASP | A | 47 | 17.114 | 18.237 | 1.308 | 1.00 | 24.89 |
| ATOM | 343 | N | GLY | A | 48 | 14.866 | 18.474 | 1.274 | 1.00 | 23.26 |
| ATOM | 344 | CA | GLY | A | 48 | 14.804 | 19.254 | 0.030 | 1.00 | 23.23 |
| ATOM | 345 | C | GLY | A | 48 | 14.817 | 18.500 | −1.290 | 1.00 | 22.89 |
| ATOM | 346 | O | GLY | A | 48 | 14.720 | 19.114 | −2.359 | 1.00 | 23.43 |
| ATOM | 347 | N | LYS | A | 49 | 14.931 | 17.174 | −1.225 | 1.00 | 21.63 |
| ATOM | 348 | CA | LYS | A | 49 | 15.128 | 16.356 | −2.417 | 1.00 | 20.77 |
| ATOM | 349 | CB | LYS | A | 49 | 16.524 | 15.704 | −2.387 | 1.00 | 21.96 |
| ATOM | 350 | CG | LYS | A | 49 | 17.693 | 16.691 | −2.355 | 1.00 | 25.00 |
| ATOM | 351 | CD | LYS | A | 49 | 17.878 | 17.387 | −3.687 | 1.00 | 28.52 |
| ATOM | 352 | CE | LYS | A | 49 | 18.984 | 18.427 | −3.611 | 1.00 | 31.72 |
| ATOM | 353 | NZ | LYS | A | 49 | 19.420 | 18.893 | −4.957 | 1.00 | 32.72 |
| ATOM | 354 | C | LYS | A | 49 | 14.071 | 15.257 | −2.519 | 1.00 | 18.40 |
| ATOM | 355 | O | LYS | A | 49 | 13.704 | 14.664 | −1.506 | 1.00 | 18.26 |
| ATOM | 356 | N | PRO | A | 50 | 13.598 | 14.964 | −3.737 | 1.00 | 16.50 |
| ATOM | 357 | CA | PRO | A | 50 | 12.664 | 13.852 | −3.850 | 1.00 | 16.28 |
| ATOM | 358 | CB | PRO | A | 50 | 12.025 | 14.056 | −5.224 | 1.00 | 16.17 |
| ATOM | 359 | CG | PRO | A | 50 | 13.039 | 14.829 | −6.022 | 1.00 | 16.50 |
| ATOM | 360 | CD | PRO | A | 50 | 13.882 | 15.601 | −5.043 | 1.00 | 17.02 |
| ATOM | 361 | C | PRO | A | 50 | 13.405 | 12.521 | −3.781 | 1.00 | 15.94 |
| ATOM | 362 | O | PRO | A | 50 | 14.446 | 12.339 | −4.434 | 1.00 | 18.03 |
| ATOM | 363 | N | VAL | A | 51 | 12.881 | 11.601 | −2.980 | 1.00 | 14.23 |
| ATOM | 364 | CA | VAL | A | 51 | 13.484 | 10.289 | −2.796 | 1.00 | 13.32 |
| ATOM | 365 | CB | VAL | A | 51 | 14.018 | 10.128 | −1.347 | 1.00 | 14.06 |
| ATOM | 366 | CG1 | VAL | A | 51 | 14.630 | 8.741 | −1.116 | 1.00 | 14.65 |
| ATOM | 367 | CG2 | VAL | A | 51 | 15.039 | 11.224 | −1.013 | 1.00 | 16.35 |
| ATOM | 368 | C | VAL | A | 51 | 12.425 | 9.243 | −3.075 | 1.00 | 12.07 |
| ATOM | 369 | O | VAL | A | 51 | 11.325 | 9.309 | −2.516 | 1.00 | 12.14 |
| ATOM | 370 | N | ASN | A | 52 | 12.744 | 8.285 | −3.932 | 1.00 | 12.03 |
| ATOM | 371 | CA | ASN | A | 52 | 11.818 | 7.204 | −4.242 | 1.00 | 12.95 |
| ATOM | 372 | CB | ASN | A | 52 | 12.243 | 6.548 | −5.546 | 1.00 | 14.19 |
| ATOM | 373 | CG | ASN | A | 52 | 11.205 | 5.577 | −6.094 | 1.00 | 17.09 |
| ATOM | 374 | OD1 | ASN | A | 52 | 10.051 | 5.567 | −5.665 | 1.00 | 22.79 |
| ATOM | 375 | ND2 | ASN | A | 52 | 11.606 | 4.783 | −7.073 | 1.00 | 21.92 |
| ATOM | 376 | C | ASN | A | 52 | 11.778 | 6.192 | −3.087 | 1.00 | 12.56 |
| ATOM | 377 | O | ASN | A | 52 | 12.827 | 5.616 | −2.720 | 1.00 | 13.33 |
| ATOM | 378 | N | LEU | A | 53 | 10.601 | 6.057 | −2.484 | 1.00 | 11.75 |
| ATOM | 379 | CA | LEU | A | 53 | 10.391 | 5.213 | −1.318 | 1.00 | 11.92 |
| ATOM | 380 | CB | LEU | A | 53 | 9.909 | 6.087 | −0.151 | 1.00 | 12.50 |
| ATOM | 381 | CG | LEU | A | 53 | 9.552 | 5.350 | 1.135 | 1.00 | 11.65 |
| ATOM | 382 | CD1 | LEU | A | 53 | 10.788 | 4.694 | 1.770 | 1.00 | 13.65 |
| ATOM | 383 | CD2 | LEU | A | 53 | 8.882 | 6.340 | 2.104 | 1.00 | 14.03 |
| ATOM | 384 | C | LEU | A | 53 | 9.375 | 4.114 | −1.622 | 1.00 | 11.73 |
| ATOM | 385 | O | LEU | A | 53 | 8.270 | 4.411 | −2.109 | 1.00 | 12.99 |
| ATOM | 386 | N | GLY | A | 54 | 9.734 | 2.860 | −1.350 | 1.00 | 11.07 |
| ATOM | 387 | CA | GLY | A | 54 | 8.833 | 1.725 | −1.562 | 1.00 | 11.07 |
| ATOM | 388 | C | GLY | A | 54 | 8.436 | 1.156 | −0.207 | 1.00 | 10.64 |
| ATOM | 389 | O | GLY | A | 54 | 9.300 | 0.945 | 0.648 | 1.00 | 11.82 |
| ATOM | 390 | N | LEU | A | 55 | 7.151 | 0.919 | 0.002 | 1.00 | 10.59 |
| ATOM | 391 | CA | LEU | A | 55 | 6.614 | 0.486 | 1.282 | 1.00 | 10.70 |
| ATOM | 392 | CB | LEU | A | 55 | 5.548 | 1.462 | 1.760 | 1.00 | 11.17 |
| ATOM | 393 | CG | LEU | A | 55 | 5.995 | 2.920 | 1.882 | 1.00 | 12.50 |
| ATOM | 394 | CD1 | LEU | A | 55 | 4.789 | 3.784 | 2.201 | 1.00 | 14.81 |
| ATOM | 395 | CD2 | LEU | A | 55 | 7.030 | 3.045 | 2.943 | 1.00 | 14.06 |
| ATOM | 396 | C | LEU | A | 55 | 6.001 | −0.904 | 1.150 | 1.00 | 9.88 |
| ATOM | 397 | O | LEU | A | 55 | 5.134 | −1.143 | 0.306 | 1.00 | 10.58 |
| ATOM | 398 | N | TRP | A | 56 | 6.446 | −1.790 | 2.037 | 1.00 | 10.18 |
| ATOM | 399 | CA | TRP | A | 56 | 6.061 | −3.200 | 2.047 | 1.00 | 10.73 |
| ATOM | 400 | CB | TRP | A | 56 | 7.266 | −4.100 | 1.740 | 1.00 | 12.68 |

TABLE 1-continued

| | | | | | | | | | |
|---|---|---|---|---|---|---|---|---|---|
| ATOM | 401 | CG | TRP | A | 56 | 7.846 | −3.871 | 0.371 | 1.00 | 13.71 |
| ATOM | 402 | CD1 | TRP | A | 56 | 8.413 | −2.719 | −0.105 | 1.00 | 15.24 |
| ATOM | 403 | NE1 | TRP | A | 56 | 8.836 | −2.897 | −1.391 | 1.00 | 17.10 |
| ATOM | 404 | CE2 | TRP | A | 56 | 8.578 | −4.193 | −1.757 | 1.00 | 16.99 |
| ATOM | 405 | CD2 | TRP | A | 56 | 7.961 | −4.831 | −0.658 | 1.00 | 19.16 |
| ATOM | 406 | CE3 | TRP | A | 56 | 7.604 | −6.180 | −0.763 | 1.00 | 20.14 |
| ATOM | 407 | CZ3 | TRP | A | 56 | 7.868 | −6.852 | −1.949 | 1.00 | 19.43 |
| ATOM | 408 | CH2 | TRP | A | 56 | 8.489 | −6.193 | −3.031 | 1.00 | 18.67 |
| ATOM | 409 | CZ2 | TRP | A | 56 | 8.853 | −4.868 | −2.955 | 1.00 | 18.68 |
| ATOM | 410 | C | TRP | A | 56 | 5.470 | −3.549 | 3.410 | 1.00 | 10.65 |
| ATOM | 411 | O | TRP | A | 56 | 6.201 | −3.684 | 4.391 | 1.00 | 11.81 |
| ATOM | 412 | N | ASP | A | 57 | 4.172 | −3.756 | 3.441 | 1.00 | 10.06 |
| ATOM | 413 | CA | ASP | A | 57 | 3.465 | −4.187 | 4.637 | 1.00 | 9.81 |
| ATOM | 414 | CB | ASP | A | 57 | 1.994 | −3.820 | 4.461 | 1.00 | 10.02 |
| ATOM | 415 | CG | ASP | A | 57 | 1.179 | −3.832 | 5.749 | 1.00 | 9.84 |
| ATOM | 416 | OD1 | ASP | A | 57 | 1.699 | −4.104 | 6.842 | 1.00 | 10.07 |
| ATOM | 417 | OD2 | ASP | A | 57 | −0.047 | −3.614 | 5.611 | 1.00 | 10.00 |
| ATOM | 418 | C | ASP | A | 57 | 3.632 | −5.700 | 4.751 | 1.00 | 10.58 |
| ATOM | 419 | O | ASP | A | 57 | 3.901 | −6.383 | 3.766 | 1.00 | 11.80 |
| ATOM | 420 | N | THR | A | 58 | 3.486 | −6.225 | 5.960 | 1.00 | 10.01 |
| ATOM | 421 | CA | THR | A | 58 | 3.585 | −7.664 | 6.173 | 1.00 | 10.87 |
| ATOM | 422 | CB | THR | A | 58 | 4.964 | −8.090 | 6.735 | 1.00 | 11.02 |
| ATOM | 423 | OG1 | THR | A | 58 | 5.164 | −7.536 | 8.053 | 1.00 | 11.24 |
| ATOM | 424 | CG2 | THR | A | 58 | 6.097 | −7.729 | 5.792 | 1.00 | 11.90 |
| ATOM | 425 | C | THR | A | 58 | 2.514 | −8.075 | 7.151 | 1.00 | 10.83 |
| ATOM | 426 | O | THR | A | 58 | 1.956 | −7.241 | 7.867 | 1.00 | 11.29 |
| ATOM | 427 | N | ALA | A | 59 | 2.239 | −9.372 | 7.212 | 1.00 | 11.35 |
| ATOM | 428 | CA | ALA | A | 59 | 1.329 | −9.920 | 8.199 | 1.00 | 11.95 |
| ATOM | 429 | CB | ALA | A | 59 | 0.386 | −10.932 | 7.536 | 1.00 | 13.29 |
| ATOM | 430 | C | ALA | A | 59 | 2.173 | −10.583 | 9.284 | 1.00 | 11.57 |
| ATOM | 431 | O | ALA | A | 59 | 2.974 | −11.495 | 8.974 | 1.00 | 11.96 |
| ATOM | 432 | N | GLY | A | 60 | 2.009 | −10.130 | 10.526 | 1.00 | 11.72 |
| ATOM | 433 | CA | GLY | A | 60 | 2.897 | −10.527 | 11.600 | 1.00 | 12.73 |
| ATOM | 434 | C | GLY | A | 60 | 2.489 | −11.759 | 12.381 | 1.00 | 12.85 |
| ATOM | 435 | O | GLY | A | 60 | 3.301 | −12.278 | 13.147 | 1.00 | 13.80 |
| ATOM | 436 | N | GLN | A | 61 | 1.257 | −12.232 | 12.199 | 1.00 | 12.05 |
| ATOM | 437 | CA | GLN | A | 61 | 0.766 | −13.397 | 12.944 | 1.00 | 12.75 |
| ATOM | 438 | CB | GLN | A | 61 | −0.732 | −13.624 | 12.653 | 1.00 | 13.14 |
| ATOM | 439 | CG | GLN | A | 61 | −1.633 | −12.484 | 13.173 | 1.00 | 13.68 |
| ATOM | 440 | CD | GLN | A | 61 | −1.918 | −11.417 | 12.128 | 1.00 | 14.04 |
| ATOM | 441 | OE1 | GLN | A | 61 | −1.040 | −11.004 | 11.360 | 1.00 | 14.06 |
| ATOM | 442 | NE2 | GLN | A | 61 | −3.146 | −10.938 | 12.116 | 1.00 | 15.06 |
| ATOM | 443 | C | GLN | A | 61 | 1.556 | −14.631 | 12.593 | 1.00 | 14.06 |
| ATOM | 444 | O | GLN | A | 61 | 2.109 | −14.764 | 11.501 | 1.00 | 13.88 |
| ATOM | 445 | N | GLU | A | 62 | 1.565 | −15.564 | 13.546 | 1.00 | 14.98 |
| ATOM | 446 | CA | GLU | A | 62 | 2.299 | −16.825 | 13.410 | 1.00 | 17.27 |
| ATOM | 447 | CB | GLU | A | 62 | 2.075 | −17.709 | 14.636 | 1.00 | 17.00 |
| ATOM | 448 | CG | GLU | A | 62 | 2.893 | −18.988 | 14.598 | 1.00 | 21.33 |
| ATOM | 449 | CD | GLU | A | 62 | 2.667 | −19.900 | 15.785 | 1.00 | 21.12 |
| ATOM | 450 | OE1 | GLU | A | 62 | 1.627 | −19.786 | 16.462 | 1.00 | 25.59 |
| ATOM | 451 | OE2 | GLU | A | 62 | 3.548 | −20.752 | 16.008 | 1.00 | 25.60 |
| ATOM | 452 | C | GLU | A | 62 | 1.953 | −17.592 | 12.147 | 1.00 | 16.12 |
| ATOM | 453 | O | GLU | A | 62 | 2.821 | −18.207 | 11.536 | 1.00 | 15.90 |
| ATOM | 454 | N | ASP | A | 63 | 0.686 | −17.548 | 11.740 | 1.00 | 16.37 |
| ATOM | 455 | CA | ASP | A | 63 | 0.260 | −18.221 | 10.511 | 1.00 | 17.61 |
| ATOM | 456 | CB | ASP | A | 63 | −1.216 | −17.943 | 10.232 | 1.00 | 19.31 |
| ATOM | 457 | CG | ASP | A | 63 | −2.141 | −18.963 | 10.861 | 1.00 | 24.06 |
| ATOM | 458 | OD1 | ASP | A | 63 | −1.672 | −20.032 | 11.306 | 1.00 | 28.11 |
| ATOM | 459 | OD2 | ASP | A | 63 | −3.357 | −18.680 | 10.879 | 1.00 | 29.29 |
| ATOM | 460 | C | ASP | A | 63 | 1.048 | −17.822 | 9.269 | 1.00 | 15.86 |
| ATOM | 461 | O | ASP | A | 63 | 1.110 | −18.562 | 8.302 | 1.00 | 16.35 |
| ATOM | 462 | N | TYR | A | 64 | 1.621 | −16.614 | 9.283 | 1.00 | 14.65 |
| ATOM | 463 | CA | TYR | A | 64 | 2.334 | −16.086 | 8.127 | 1.00 | 13.33 |
| ATOM | 464 | CB | TYR | A | 64 | 1.964 | −14.616 | 7.880 | 1.00 | 12.64 |
| ATOM | 465 | CG | TYR | A | 64 | 0.479 | −14.387 | 7.710 | 1.00 | 12.50 |
| ATOM | 466 | CD1 | TYR | A | 64 | −0.148 | −14.596 | 6.492 | 1.00 | 12.77 |
| ATOM | 467 | CE1 | TYR | A | 64 | −1.531 | −14.375 | 6.350 | 1.00 | 14.98 |
| ATOM | 468 | CZ | TYR | A | 64 | −2.258 | −13.947 | 7.443 | 1.00 | 13.61 |
| ATOM | 469 | OH | TYR | A | 64 | −3.606 | −13.709 | 7.330 | 1.00 | 15.56 |
| ATOM | 470 | CE2 | TYR | A | 64 | −1.629 | −13.728 | 8.649 | 1.00 | 13.71 |
| ATOM | 471 | CD2 | TYR | A | 64 | −0.285 | −13.953 | 8.774 | 1.00 | 12.14 |
| ATOM | 472 | C | TYR | A | 64 | 3.837 | −16.189 | 8.260 | 1.00 | 13.33 |
| ATOM | 473 | O | TYR | A | 64 | 4.563 | −15.686 | 7.415 | 1.00 | 13.05 |
| ATOM | 474 | N | ASP | A | 65 | 4.306 | −16.880 | 9.300 | 1.00 | 13.58 |
| ATOM | 475 | CA | ASP | A | 65 | 5.748 | −16.919 | 9.584 | 1.00 | 14.85 |
| ATOM | 476 | CB | ASP | A | 65 | 6.018 | −17.727 | 10.861 | 1.00 | 15.32 |
| ATOM | 477 | CG | ASP | A | 65 | 5.757 | −16.951 | 12.136 | 1.00 | 16.90 |
| ATOM | 478 | OD1 | ASP | A | 65 | 5.384 | −15.753 | 12.094 | 1.00 | 16.97 |
| ATOM | 479 | OD2 | ASP | A | 65 | 5.906 | −17.558 | 13.226 | 1.00 | 20.20 |

TABLE 1-continued

| ATOM | 480 | C | ASP | A | 65 | 6.570 | −17.534 | 8.450 | 1.00 | 15.24 |
|------|-----|------|------|---|----|--------|---------|--------|------|-------|
| ATOM | 481 | O | ASP | A | 65 | 7.710 | −17.143 | 8.218 | 1.00 | 15.20 |
| ATOM | 482 | N | ARG | A | 66 | 6.003 | −18.507 | 7.739 | 1.00 | 15.03 |
| ATOM | 483 | CA | ARG | A | 66 | 6.718 | −19.130 | 6.623 | 1.00 | 15.74 |
| ATOM | 484 | CB | ARG | A | 66 | 6.162 | −20.530 | 6.348 | 1.00 | 16.44 |
| ATOM | 485 | CG | ARG | A | 66 | 6.338 | −21.464 | 7.517 | 1.00 | 17.39 |
| ATOM | 486 | CD | ARG | A | 66 | 5.662 | −22.807 | 7.250 | 1.00 | 20.96 |
| ATOM | 487 | NE | ARG | A | 66 | 6.389 | −23.591 | 6.258 | 1.00 | 22.46 |
| ATOM | 488 | CZ | ARG | A | 66 | 7.469 | −24.325 | 6.534 | 1.00 | 23.29 |
| ATOM | 489 | NH1 | ARG | A | 66 | 7.945 | −24.376 | 7.776 | 1.00 | 23.36 |
| ATOM | 490 | NH2 | ARG | A | 66 | 8.070 | −25.000 | 5.568 | 1.00 | 26.82 |
| ATOM | 491 | C | ARG | A | 66 | 6.700 | −18.302 | 5.335 | 1.00 | 16.07 |
| ATOM | 492 | O | ARG | A | 66 | 7.597 | −18.415 | 4.503 | 1.00 | 17.45 |
| ATOM | 493 | N | LEU | A | 67 | 5.698 | −17.570 | 5.190 | 1.00 | 15.40 |
| ATOM | 494 | CA | LEU | A | 67 | 5.552 | −16.810 | 3.945 | 1.00 | 15.49 |
| ATOM | 495 | CB | LEU | A | 67 | 4.078 | −16.706 | 3.580 | 1.00 | 15.84 |
| ATOM | 496 | CG | LEU | A | 67 | 3.702 | −15.969 | 2.291 | 1.00 | 17.97 |
| ATOM | 497 | CD1 | LEU | A | 67 | 4.246 | −16.739 | 1.095 | 1.00 | 17.77 |
| ATOM | 498 | CD2 | LEU | A | 67 | 2.207 | −15.856 | 2.216 | 1.00 | 18.43 |
| ATOM | 499 | C | LEU | A | 67 | 6.174 | −15.422 | 4.023 | 1.00 | 15.73 |
| ATOM | 500 | O | LEU | A | 67 | 6.766 | −14.940 | 3.057 | 1.00 | 15.69 |
| ATOM | 501 | N | ARG | A | 68 | 6.056 | −14.807 | 5.202 | 1.00 | 16.73 |
| ATOM | 502 | CA | ARG | A | 68 | 6.505 | −13.442 | 5.402 | 1.00 | 17.12 |
| ATOM | 503 | CB | ARG | A | 68 | 6.233 | −13.038 | 6.851 | 1.00 | 17.50 |
| ATOM | 504 | CG | ARG | A | 68 | 6.684 | −11.644 | 7.216 | 1.00 | 14.25 |
| ATOM | 505 | CD | ARG | A | 68 | 6.307 | −11.334 | 8.660 | 1.00 | 14.22 |
| ATOM | 506 | NE | ARG | A | 68 | 6.888 | −12.277 | 9.614 | 1.00 | 15.63 |
| ATOM | 507 | CZ | ARG | A | 68 | 6.225 | −13.190 | 10.317 | 1.00 | 13.45 |
| ATOM | 508 | NH1 | ARG | A | 68 | 4.893 | −13.350 | 10.240 | 1.00 | 12.81 |
| ATOM | 509 | NH2 | ARG | A | 68 | 6.923 | −13.947 | 11.139 | 1.00 | 15.55 |
| ATOM | 510 | C | ARG | A | 68 | 7.959 | −13.205 | 4.964 | 1.00 | 17.61 |
| ATOM | 511 | O | ARG | A | 68 | 8.256 | −12.166 | 4.383 | 1.00 | 17.22 |
| ATOM | 512 | N | PRO | A | 69 | 8.877 | −14.153 | 5.209 | 1.00 | 17.60 |
| ATOM | 513 | CA | PRO | A | 69 | 10.254 | −13.896 | 4.771 | 1.00 | 18.02 |
| ATOM | 514 | CB | PRO | A | 69 | 11.036 | −15.080 | 5.357 | 1.00 | 18.83 |
| ATOM | 515 | CG | PRO | A | 69 | 10.180 | −15.514 | 6.539 | 1.00 | 19.69 |
| ATOM | 516 | CD | PRO | A | 69 | 8.793 | −15.412 | 5.977 | 1.00 | 18.13 |
| ATOM | 517 | C | PRO | A | 69 | 10.481 | −13.723 | 3.251 | 1.00 | 17.20 |
| ATOM | 518 | O | PRO | A | 69 | 11.544 | −13.234 | 2.850 | 1.00 | 17.02 |
| ATOM | 519 | N | LEU | A | 70 | 9.503 | −14.098 | 2.414 | 1.00 | 16.34 |
| ATOM | 520 | CA | LEU | A | 70 | 9.606 | −13.778 | 0.985 | 1.00 | 15.96 |
| ATOM | 521 | CB | LEU | A | 70 | 8.468 | −14.410 | 0.185 | 1.00 | 16.34 |
| ATOM | 522 | CG | LEU | A | 70 | 8.755 | −15.829 | −0.321 | 1.00 | 19.86 |
| ATOM | 523 | CD1 | LEU | A | 70 | 8.815 | −16.809 | 0.828 | 1.00 | 22.48 |
| ATOM | 524 | CD2 | LEU | A | 70 | 7.669 | −16.218 | −1.308 | 1.00 | 21.49 |
| ATOM | 525 | C | LEU | A | 70 | 9.608 | −12.276 | 0.731 | 1.00 | 14.54 |
| ATOM | 526 | O | LEU | A | 70 | 9.965 | −11.853 | −0.361 | 1.00 | 15.20 |
| ATOM | 527 | N | SER | A | 71 | 9.188 | −11.487 | 1.722 | 1.00 | 13.51 |
| ATOM | 528 | CA | SER | A | 71 | 9.200 | −10.014 | 1.624 | 1.00 | 14.79 |
| ATOM | 529 | CB | SER | A | 71 | 8.211 | −9.408 | 2.624 | 1.00 | 14.76 |
| ATOM | 530 | OG | SER | A | 71 | 6.920 | −9.946 | 2.432 | 1.00 | 19.09 |
| ATOM | 531 | C | SER | A | 71 | 10.550 | −9.367 | 1.891 | 1.00 | 13.58 |
| ATOM | 532 | O | SER | A | 71 | 10.753 | −8.216 | 1.533 | 1.00 | 13.44 |
| ATOM | 533 | N | TYR | A | 72 | 11.469 | −10.086 | 2.540 | 1.00 | 13.81 |
| ATOM | 534 | CA | TYR | A | 72 | 12.729 | −9.472 | 2.994 | 1.00 | 13.60 |
| ATOM | 535 | CB | TYR | A | 72 | 13.329 | −10.252 | 4.171 | 1.00 | 14.71 |
| ATOM | 536 | CG | TYR | A | 72 | 12.553 | −10.168 | 5.464 | 1.00 | 12.94 |
| ATOM | 537 | CD1 | TYR | A | 72 | 12.266 | −8.937 | 6.064 | 1.00 | 13.82 |
| ATOM | 538 | CE1 | TYR | A | 72 | 11.587 | −8.877 | 7.270 | 1.00 | 13.38 |
| ATOM | 539 | CZ | TYR | A | 72 | 11.183 | −10.045 | 7.884 | 1.00 | 12.61 |
| ATOM | 540 | OH | TYR | A | 72 | 10.514 | −9.929 | 9.067 | 1.00 | 15.65 |
| ATOM | 541 | CE2 | TYR | A | 72 | 11.462 | −11.272 | 7.320 | 1.00 | 13.90 |
| ATOM | 542 | CD2 | TYR | A | 72 | 12.163 | −11.316 | 6.122 | 1.00 | 12.90 |
| ATOM | 543 | C | TYR | A | 72 | 13.852 | −9.223 | 1.969 | 1.00 | 14.07 |
| ATOM | 544 | O | TYR | A | 72 | 14.681 | −8.359 | 2.209 | 1.00 | 14.07 |
| ATOM | 545 | N | PRO | A | 73 | 13.950 | −10.022 | 0.885 | 1.00 | 15.01 |
| ATOM | 546 | CA | PRO | A | 73 | 15.057 | −9.728 | −0.024 | 1.00 | 15.59 |
| ATOM | 547 | CB | PRO | A | 73 | 14.766 | −10.640 | −1.217 | 1.00 | 15.64 |
| ATOM | 548 | CG | PRO | A | 73 | 14.149 | −11.831 | −0.575 | 1.00 | 17.21 |
| ATOM | 549 | CD | PRO | A | 73 | 13.205 | −11.212 | 0.435 | 1.00 | 16.17 |
| ATOM | 550 | C | PRO | A | 73 | 15.148 | −8.278 | −0.458 | 1.00 | 15.42 |
| ATOM | 551 | O | PRO | A | 73 | 14.136 | −7.634 | −0.763 | 1.00 | 15.01 |
| ATOM | 552 | N | GLN | A | 74 | 16.376 | −7.776 | −0.484 | 1.00 | 14.91 |
| ATOM | 553 | CA | GLN | A | 74 | 16.687 | −6.420 | −0.946 | 1.00 | 15.51 |
| ATOM | 554 | CB | GLN | A | 74 | 16.264 | −6.223 | −2.408 | 1.00 | 16.44 |
| ATOM | 555 | CG | GLN | A | 74 | 16.882 | −7.245 | −3.386 | 1.00 | 19.27 |
| ATOM | 556 | CD | GLN | A | 74 | 15.910 | −8.340 | −3.803 | 1.00 | 24.79 |
| ATOM | 557 | OE1 | GLN | A | 74 | 14.722 | −8.088 | −4.031 | 1.00 | 27.77 |
| ATOM | 558 | NE2 | GLN | A | 74 | 16.414 | −9.564 | −3.926 | 1.00 | 26.38 |

TABLE 1-continued

| | | | | | | | | | |
|---|---|---|---|---|---|---|---|---|---|
| ATOM | 559 | C | GLN | A | 74 | 16.139 | −5.310 | −0.045 | 1.00 | 14.57 |
| ATOM | 560 | O | GLN | A | 74 | 16.047 | −4.151 | −0.436 | 1.00 | 15.13 |
| ATOM | 561 | N | THR | A | 75 | 15.809 | −5.655 | 1.186 | 1.00 | 13.90 |
| ATOM | 562 | CA | THR | A | 75 | 15.355 | −4.625 | 2.129 | 1.00 | 13.47 |
| ATOM | 563 | CB | THR | A | 75 | 14.808 | −5.261 | 3.430 | 1.00 | 13.21 |
| ATOM | 564 | OG1 | THR | A | 75 | 13.662 | −6.056 | 3.114 | 1.00 | 13.74 |
| ATOM | 565 | CG2 | THR | A | 75 | 14.403 | −4.203 | 4.454 | 1.00 | 13.03 |
| ATOM | 566 | C | THR | A | 75 | 16.460 | −3.634 | 2.453 | 1.00 | 13.15 |
| ATOM | 567 | O | THR | A | 75 | 17.611 | −4.037 | 2.727 | 1.00 | 14.79 |
| ATOM | 568 | N | ASP | A | 76 | 16.123 | −2.347 | 2.456 | 1.00 | 11.58 |
| ATOM | 569 | CA | ASP | A | 76 | 17.074 | −1.281 | 2.806 | 1.00 | 11.85 |
| ATOM | 570 | CB | ASP | A | 76 | 16.955 | −0.108 | 1.828 | 1.00 | 11.89 |
| ATOM | 571 | CG | ASP | A | 76 | 17.315 | −0.498 | 0.424 | 1.00 | 14.34 |
| ATOM | 572 | OD1 | ASP | A | 76 | 18.452 | −0.984 | 0.219 | 1.00 | 17.00 |
| ATOM | 573 | OD2 | ASP | A | 76 | 16.471 | −0.378 | −0.493 | 1.00 | 13.48 |
| ATOM | 574 | C | ASP | A | 76 | 16.887 | −0.771 | 4.228 | 1.00 | 12.51 |
| ATOM | 575 | O | ASP | A | 76 | 17.849 | −0.324 | 4.846 | 1.00 | 13.24 |
| ATOM | 576 | N | VAL | A | 77 | 15.639 | −0.758 | 4.737 | 1.00 | 11.39 |
| ATOM | 577 | CA | VAL | A | 77 | 15.361 | −0.284 | 6.085 | 1.00 | 11.27 |
| ATOM | 578 | CB | VAL | A | 77 | 15.200 | 1.263 | 6.135 | 1.00 | 10.92 |
| ATOM | 579 | CG1 | VAL | A | 77 | 14.118 | 1.771 | 5.187 | 1.00 | 12.49 |
| ATOM | 580 | CG2 | VAL | A | 77 | 14.955 | 1.766 | 7.562 | 1.00 | 12.84 |
| ATOM | 581 | C | VAL | A | 77 | 14.122 | −1.007 | 6.562 | 1.00 | 11.19 |
| ATOM | 582 | O | VAL | A | 77 | 13.236 | −1.321 | 5.747 | 1.00 | 10.58 |
| ATOM | 583 | N | SER | A | 78 | 14.079 | −1.311 | 7.848 | 0.50 | 11.65 |
| ATOM | 584 | CA | SER | A | 78 | 12.903 | −1.976 | 8.404 | 0.50 | 12.31 |
| ATOM | 585 | CB | SER | A | 78 | 13.223 | −3.368 | 8.931 | 0.50 | 13.27 |
| ATOM | 586 | OG | ASER | A | 78 | 12.034 | −4.011 | 9.347 | 0.50 | 14.27 |
| ATOM | 586 | OG | BSER | A | 78 | 13.799 | −4.229 | 7.961 | 0.50 | 14.62 |
| ATOM | 587 | C | SER | A | 78 | 12.326 | −1.155 | 9.534 | 0.50 | 12.86 |
| ATOM | 588 | O | SER | A | 78 | 13.053 | −0.618 | 10.368 | 0.50 | 12.62 |
| ATOM | 589 | N | LEU | A | 79 | 11.006 | −1.103 | 9.591 | 1.00 | 11.00 |
| ATOM | 590 | CA | LEU | A | 79 | 10.301 | −0.542 | 10.721 | 1.00 | 11.67 |
| ATOM | 591 | CB | LEU | A | 79 | 9.103 | 0.295 | 10.283 | 1.00 | 11.27 |
| ATOM | 592 | CG | LEU | A | 79 | 9.342 | 1.390 | 9.249 | 1.00 | 13.99 |
| ATOM | 593 | CD1 | LEU | A | 79 | 8.087 | 2.201 | 9.048 | 1.00 | 15.38 |
| ATOM | 594 | CD2 | LEU | A | 79 | 10.467 | 2.331 | 9.646 | 1.00 | 15.86 |
| ATOM | 595 | C | LEU | A | 79 | 9.782 | −1.691 | 11.543 | 1.00 | 10.67 |
| ATOM | 596 | O | LEU | A | 79 | 8.967 | −2.466 | 11.060 | 1.00 | 12.30 |
| ATOM | 597 | N | ILE | A | 80 | 10.265 | −1.817 | 12.772 | 1.00 | 11.03 |
| ATOM | 598 | CA | ILE | A | 80 | 9.671 | −2.773 | 13.715 | 1.00 | 10.63 |
| ATOM | 599 | CB | ILE | A | 80 | 10.707 | −3.483 | 14.588 | 1.00 | 10.95 |
| ATOM | 600 | CG1 | ILE | A | 80 | 11.647 | −4.331 | 13.716 | 1.00 | 11.97 |
| ATOM | 601 | CD1 | ILE | A | 80 | 12.768 | −5.045 | 14.503 | 1.00 | 12.36 |
| ATOM | 602 | CG2 | ILE | A | 80 | 9.982 | −4.373 | 15.630 | 1.00 | 11.76 |
| ATOM | 603 | C | ILE | A | 80 | 8.685 | −2.013 | 14.569 | 1.00 | 10.30 |
| ATOM | 604 | O | ILE | A | 80 | 9.041 | −1.054 | 15.245 | 1.00 | 10.00 |
| ATOM | 605 | N | CYS | A | 81 | 7.416 | −2.406 | 14.484 | 1.00 | 9.99 |
| ATOM | 606 | CA | CYS | A | 81 | 6.332 | −1.674 | 15.116 | 1.00 | 10.50 |
| ATOM | 607 | CB | CYS | A | 81 | 5.191 | −1.489 | 14.115 | 1.00 | 10.19 |
| ATOM | 608 | SG | CYS | A | 81 | 5.666 | −0.559 | 12.649 | 1.00 | 11.71 |
| ATOM | 609 | C | CYS | A | 81 | 5.777 | −2.453 | 16.303 | 1.00 | 10.21 |
| ATOM | 610 | O | CYS | A | 81 | 5.626 | −3.683 | 16.239 | 1.00 | 9.95 |
| ATOM | 611 | N | PHE | A | 82 | 5.382 | −1.727 | 17.344 | 1.00 | 9.79 |
| ATOM | 612 | CA | PHE | A | 82 | 4.606 | −2.301 | 18.446 | 1.00 | 10.00 |
| ATOM | 613 | CB | PHE | A | 82 | 5.527 | −2.694 | 19.607 | 1.00 | 10.97 |
| ATOM | 614 | CG | PHE | A | 82 | 6.103 | −1.504 | 20.336 | 1.00 | 10.42 |
| ATOM | 615 | CD1 | PHE | A | 82 | 5.450 | −0.961 | 21.425 | 1.00 | 10.28 |
| ATOM | 616 | CE1 | PHE | A | 82 | 5.961 | 0.171 | 22.084 | 1.00 | 11.10 |
| ATOM | 617 | CZ | PHE | A | 82 | 7.121 | 0.775 | 21.612 | 1.00 | 11.17 |
| ATOM | 618 | CE2 | PHE | A | 82 | 7.776 | 0.258 | 20.518 | 1.00 | 11.35 |
| ATOM | 619 | CD2 | PHE | A | 82 | 7.267 | −0.869 | 19.868 | 1.00 | 11.50 |
| ATOM | 620 | C | PHE | A | 82 | 3.620 | −1.232 | 18.880 | 1.00 | 10.12 |
| ATOM | 621 | O | PHE | A | 82 | 3.858 | −0.030 | 18.717 | 1.00 | 10.63 |
| ATOM | 622 | N | SER | A | 83 | 2.498 | −1.656 | 19.437 | 1.00 | 10.02 |
| ATOM | 623 | CA | SER | A | 83 | 1.511 | −0.707 | 19.921 | 1.00 | 10.02 |
| ATOM | 624 | CB | SER | A | 83 | 0.147 | −1.362 | 19.964 | 1.00 | 10.25 |
| ATOM | 625 | OG | SER | A | 83 | −0.717 | −0.549 | 20.740 | 1.00 | 11.09 |
| ATOM | 626 | C | SER | A | 83 | 1.883 | −0.201 | 21.306 | 1.00 | 10.65 |
| ATOM | 627 | O | SER | A | 83 | 2.181 | −1.004 | 22.203 | 1.00 | 10.75 |
| ATOM | 628 | N | LEU | A | 84 | 1.821 | 1.118 | 21.476 | 1.00 | 10.96 |
| ATOM | 629 | CA | LEU | A | 84 | 2.132 | 1.734 | 22.768 | 1.00 | 11.88 |
| ATOM | 630 | CB | LEU | A | 84 | 2.192 | 3.255 | 22.657 | 1.00 | 13.00 |
| ATOM | 631 | CG | LEU | A | 84 | 3.389 | 3.776 | 21.852 | 1.00 | 12.58 |
| ATOM | 632 | CD1 | LEU | A | 84 | 3.174 | 5.194 | 21.409 | 1.00 | 14.70 |
| ATOM | 633 | CD2 | LEU | A | 84 | 4.675 | 3.653 | 22.610 | 1.00 | 12.21 |
| ATOM | 634 | C | LEU | A | 84 | 1.163 | 1.294 | 23.853 | 1.00 | 11.76 |
| ATOM | 635 | O | LEU | A | 84 | 1.446 | 1.479 | 25.047 | 1.00 | 13.30 |
| ATOM | 636 | N | VAL | A | 85 | 0.034 | 0.708 | 23.458 | 1.00 | 11.66 |

TABLE 1-continued

| | | | | | | | | | |
|---|---|---|---|---|---|---|---|---|---|
| ATOM | 637 | CA | VAL | A | 85 | −0.939 | 0.222 | 24.448 | 1.00 12.51 |
| ATOM | 638 | CB | VAL | A | 85 | −2.310 | 0.951 | 24.330 | 1.00 12.44 |
| ATOM | 639 | CG1 | VAL | A | 85 | −2.134 | 2.448 | 24.624 | 1.00 14.58 |
| ATOM | 640 | CG2 | VAL | A | 85 | −2.968 | 0.733 | 22.987 | 1.00 13.59 |
| ATOM | 641 | C | VAL | A | 85 | −1.073 | −1.298 | 24.433 | 1.00 12.30 |
| ATOM | 642 | O | VAL | A | 85 | −2.069 | −1.842 | 24.915 | 1.00 13.43 |
| ATOM | 643 | N | SER | A | 86 | −0.040 | −1.981 | 23.926 | 1.00 12.15 |
| ATOM | 644 | CA | SER | A | 86 | 0.044 | −3.431 | 24.003 | 1.00 12.42 |
| ATOM | 645 | CB | SER | A | 86 | −0.314 | −4.125 | 22.683 | 1.00 12.04 |
| ATOM | 646 | OG | SER | A | 86 | −0.086 | −5.522 | 22.842 | 1.00 15.41 |
| ATOM | 647 | C | SER | A | 86 | 1.433 | −3.844 | 24.475 | 1.00 12.50 |
| ATOM | 648 | O | SER | A | 86 | 2.351 | −4.063 | 23.678 | 1.00 12.54 |
| ATOM | 649 | N | PRO | A | 87 | 1.598 | −4.002 | 25.787 | 1.00 12.95 |
| ATOM | 650 | CA | PRO | A | 87 | 2.869 | −4.514 | 26.290 | 1.00 13.29 |
| ATOM | 651 | CB | PRO | A | 87 | 2.627 | −4.615 | 27.808 | 1.00 14.21 |
| ATOM | 652 | CG | PRO | A | 87 | 1.645 | −3.503 | 28.077 | 1.00 13.86 |
| ATOM | 653 | CD | PRO | A | 87 | 0.686 | −3.627 | 26.891 | 1.00 13.43 |
| ATOM | 654 | C | PRO | A | 87 | 3.327 | −5.837 | 25.679 | 1.00 13.26 |
| ATOM | 655 | O | PRO | A | 87 | 4.533 | −6.031 | 25.474 | 1.00 13.67 |
| ATOM | 656 | N | ALA | A | 88 | 2.391 | −6.731 | 25.355 | 1.00 13.08 |
| ATOM | 657 | CA | ALA | A | 88 | 2.770 | −7.984 | 24.699 | 1.00 13.15 |
| ATOM | 658 | CB | ALA | A | 88 | 1.537 | −8.871 | 24.492 | 1.00 14.24 |
| ATOM | 659 | C | ALA | A | 88 | 3.470 | −7.721 | 23.363 | 1.00 12.54 |
| ATOM | 660 | O | ALA | A | 88 | 4.464 | −8.363 | 23.019 | 1.00 13.00 |
| ATOM | 661 | N | SER | A | 89 | 2.945 | −6.767 | 22.595 | 1.00 12.21 |
| ATOM | 662 | CA | SER | A | 89 | 3.536 | −6.455 | 21.290 | 1.00 12.15 |
| ATOM | 663 | CB | SER | A | 89 | 2.611 | −5.546 | 20.457 | 1.00 12.88 |
| ATOM | 664 | OG | SER | A | 89 | 2.641 | −4.174 | 20.869 | 1.00 11.46 |
| ATOM | 665 | C | SER | A | 89 | 4.922 | −5.853 | 21.448 | 1.00 11.97 |
| ATOM | 666 | O | SER | A | 89 | 5.808 | −6.046 | 20.615 | 1.00 11.89 |
| ATOM | 667 | N | PHE | A | 90 | 5.106 | −5.126 | 22.540 | 1.00 11.56 |
| ATOM | 668 | CA | PHE | A | 90 | 6.397 | −4.531 | 22.869 | 1.00 11.82 |
| ATOM | 669 | CB | PHE | A | 90 | 6.201 | −3.565 | 24.049 | 1.00 12.37 |
| ATOM | 670 | CG | PHE | A | 90 | 7.438 | −2.830 | 24.475 | 1.00 13.30 |
| ATOM | 671 | CD1 | PHE | A | 90 | 8.122 | −2.022 | 23.586 | 1.00 14.79 |
| ATOM | 672 | CE1 | PHE | A | 90 | 9.243 | −1.296 | 24.008 | 1.00 15.32 |
| ATOM | 673 | CZ | PHE | A | 90 | 9.664 | −1.355 | 25.330 | 1.00 15.13 |
| ATOM | 674 | CE2 | PHE | A | 90 | 8.993 | −2.147 | 26.230 | 1.00 15.63 |
| ATOM | 675 | CD2 | PHE | A | 90 | 7.865 | −2.883 | 25.807 | 1.00 15.19 |
| ATOM | 676 | C | PHE | A | 90 | 7.422 | −5.613 | 23.178 | 1.00 12.20 |
| ATOM | 677 | O | PHE | A | 90 | 8.534 | −5.599 | 22.672 | 1.00 12.96 |
| ATOM | 678 | N | GLU | A | 91 | 7.033 | −6.572 | 24.006 | 1.00 13.27 |
| ATOM | 679 | CA | GLU | A | 91 | 7.960 | −7.637 | 24.327 | 1.00 14.67 |
| ATOM | 680 | CB | GLU | A | 91 | 7.403 | −8.530 | 25.432 | 1.00 15.80 |
| ATOM | 681 | CG | GLU | A | 91 | 7.325 | −7.839 | 26.801 | 1.00 21.18 |
| ATOM | 682 | CD | GLU | A | 91 | 8.683 | −7.312 | 27.296 | 1.00 26.68 |
| ATOM | 683 | OE1 | GLU | A | 91 | 8.728 | −6.172 | 27.812 | 1.00 31.58 |
| ATOM | 684 | OE2 | GLU | A | 91 | 9.705 | −8.023 | 27.166 | 1.00 29.55 |
| ATOM | 685 | C | GLU | A | 91 | 8.341 | −8.442 | 23.087 | 1.00 13.24 |
| ATOM | 686 | O | GLU | A | 91 | 9.480 | −8.870 | 22.961 | 1.00 14.31 |
| ATOM | 687 | N | ASN | A | 92 | 7.402 | −8.613 | 22.151 | 1.00 11.84 |
| ATOM | 688 | CA | ASN | A | 92 | 7.744 | −9.293 | 20.909 | 1.00 12.41 |
| ATOM | 689 | CB | ASN | A | 92 | 6.493 | −9.684 | 20.145 | 1.00 13.20 |
| ATOM | 690 | CG | ASN | A | 92 | 5.894 | −10.946 | 20.686 | 1.00 15.85 |
| ATOM | 691 | OD1 | ASN | A | 92 | 6.617 | −11.853 | 21.123 | 1.00 17.38 |
| ATOM | 692 | ND2 | ASN | A | 92 | 4.571 | −11.029 | 20.675 | 1.00 17.83 |
| ATOM | 693 | C | ASN | A | 92 | 8.718 | −8.579 | 19.986 | 1.00 11.68 |
| ATOM | 694 | O | ASN | A | 92 | 9.267 | −9.213 | 19.093 | 1.00 12.11 |
| ATOM | 695 | N | VAL | A | 93 | 8.950 | −7.282 | 20.203 | 1.00 12.44 |
| ATOM | 696 | CA | VAL | A | 93 | 9.993 | −6.580 | 19.454 | 1.00 13.31 |
| ATOM | 697 | CB | VAL | A | 93 | 10.151 | −5.140 | 19.954 | 1.00 13.15 |
| ATOM | 698 | CG1 | VAL | A | 93 | 11.439 | −4.514 | 19.419 | 1.00 13.98 |
| ATOM | 699 | CG2 | VAL | A | 93 | 8.918 | −4.329 | 19.575 | 1.00 13.99 |
| ATOM | 700 | C | VAL | A | 93 | 11.312 | −7.329 | 19.630 | 1.00 14.01 |
| ATOM | 701 | O | VAL | A | 93 | 12.030 | −7.582 | 18.672 | 1.00 15.10 |
| ATOM | 702 | N | ARG | A | 94 | 11.611 | −7.711 | 20.867 | 1.00 15.11 |
| ATOM | 703 | CA | ARG | A | 94 | 12.873 | −8.371 | 21.160 | 1.00 16.16 |
| ATOM | 704 | CB | ARG | A | 94 | 13.326 | −7.993 | 22.575 | 1.00 17.62 |
| ATOM | 705 | CG | ARG | A | 94 | 14.632 | −8.627 | 22.959 | 1.00 21.98 |
| ATOM | 706 | CD | ARG | A | 94 | 15.816 | −7.740 | 22.632 | 1.00 28.79 |
| ATOM | 707 | NE | ARG | A | 94 | 16.859 | −8.516 | 21.966 | 1.00 34.14 |
| ATOM | 708 | CZ | ARG | A | 94 | 18.164 | −8.362 | 22.164 | 1.00 35.82 |
| ATOM | 709 | NH1 | ARG | A | 94 | 18.611 | −7.460 | 23.024 | 1.00 37.30 |
| ATOM | 710 | NH2 | ARG | A | 94 | 19.025 | −9.129 | 21.504 | 1.00 38.38 |
| ATOM | 711 | C | ARG | A | 94 | 12.741 | −9.883 | 20.991 | 1.00 15.53 |
| ATOM | 712 | O | ARG | A | 94 | 13.679 | −10.550 | 20.556 | 1.00 16.61 |
| ATOM | 713 | N | ALA | A | 95 | 11.579 | −10.433 | 21.331 | 1.00 13.61 |
| ATOM | 714 | CA | ALA | A | 95 | 11.399 | −11.878 | 21.304 | 1.00 13.39 |
| ATOM | 715 | CB | ALA | A | 95 | 10.156 | −12.269 | 22.125 | 1.00 13.49 |

TABLE 1-continued

| | | | | | | | | | |
|---|---|---|---|---|---|---|---|---|---|
| ATOM | 716 | C | ALA | A | 95 | 11.315 | −12.453 | 19.892 | 1.00 | 13.50 |
| ATOM | 717 | O | ALA | A | 95 | 11.737 | −13.575 | 19.626 | 1.00 | 14.22 |
| ATOM | 718 | N | LYS | A | 96 | 10.747 | −11.661 | 18.982 | 1.00 | 13.38 |
| ATOM | 719 | CA | LYS | A | 96 | 10.404 | −12.148 | 17.652 | 1.00 | 12.97 |
| ATOM | 720 | CB | LYS | A | 96 | 8.876 | −12.266 | 17.478 | 1.00 | 13.16 |
| ATOM | 721 | CG | LYS | A | 96 | 8.473 | −12.789 | 16.104 | 1.00 | 14.36 |
| ATOM | 722 | CD | LYS | A | 96 | 6.995 | −13.121 | 16.024 | 1.00 | 15.01 |
| ATOM | 723 | CE | LYS | A | 96 | 6.677 | −13.705 | 14.652 | 1.00 | 18.16 |
| ATOM | 724 | NZ | LYS | A | 96 | 5.205 | −13.960 | 14.468 | 1.00 | 18.60 |
| ATOM | 725 | C | LYS | A | 96 | 10.973 | −11.275 | 16.541 | 1.00 | 12.23 |
| ATOM | 726 | O | LYS | A | 96 | 11.650 | −11.780 | 15.618 | 1.00 | 12.58 |
| ATOM | 727 | N | TRP | A | 97 | 10.686 | −9.974 | 16.591 | 1.00 | 11.57 |
| ATOM | 728 | CA | TRP | A | 97 | 10.922 | −9.147 | 15.394 | 1.00 | 11.61 |
| ATOM | 729 | CB | TRP | A | 97 | 10.047 | −7.883 | 15.409 | 1.00 | 10.66 |
| ATOM | 730 | CG | TRP | A | 97 | 8.634 | −8.324 | 15.386 | 1.00 | 10.77 |
| ATOM | 731 | CD1 | TRP | A | 97 | 7.712 | −8.217 | 16.400 | 1.00 | 10.78 |
| ATOM | 732 | NE1 | TRP | A | 97 | 6.550 | −8.851 | 16.035 | 1.00 | 11.23 |
| ATOM | 733 | CE2 | TRP | A | 97 | 6.711 | −9.401 | 14.788 | 1.00 | 10.82 |
| ATOM | 734 | CD2 | TRP | A | 97 | 8.019 | −9.110 | 14.357 | 1.00 | 10.00 |
| ATOM | 735 | CE3 | TRP | A | 97 | 8.445 | −9.577 | 13.101 | 1.00 | 10.71 |
| ATOM | 736 | CZ3 | TRP | A | 97 | 7.569 | −10.294 | 12.328 | 1.00 | 11.15 |
| ATOM | 737 | CH2 | TRP | A | 97 | 6.282 | −10.600 | 12.796 | 1.00 | 11.59 |
| ATOM | 738 | CZ2 | TRP | A | 97 | 5.830 | −10.161 | 14.011 | 1.00 | 11.63 |
| ATOM | 739 | C | TRP | A | 97 | 12.370 | −8.859 | 15.123 | 1.00 | 12.18 |
| ATOM | 740 | O | TRP | A | 97 | 12.834 | −9.005 | 13.987 | 1.00 | 11.96 |
| ATOM | 741 | N | TYR | A | 98 | 13.096 | −8.446 | 16.161 | 1.00 | 12.70 |
| ATOM | 742 | CA | TYR | A | 98 | 14.528 | −8.222 | 16.017 | 1.00 | 14.03 |
| ATOM | 743 | CB | TYR | A | 98 | 15.122 | −7.749 | 17.346 | 1.00 | 16.61 |
| ATOM | 744 | CG | TYR | A | 98 | 16.633 | −7.603 | 17.329 | 1.00 | 20.30 |
| ATOM | 745 | CD1 | TYR | A | 98 | 17.274 | −6.824 | 16.355 | 1.00 | 22.77 |
| ATOM | 746 | CE1 | TYR | A | 98 | 18.662 | −6.703 | 16.330 | 1.00 | 24.51 |
| ATOM | 747 | CZ | TYR | A | 98 | 19.411 | −7.347 | 17.290 | 1.00 | 23.70 |
| ATOM | 748 | OH | TYR | A | 98 | 20.789 | −7.224 | 17.270 | 1.00 | 25.67 |
| ATOM | 749 | CE2 | TYR | A | 98 | 18.809 | −8.115 | 18.270 | 1.00 | 24.56 |
| ATOM | 750 | CD2 | TYR | A | 98 | 17.413 | −8.242 | 18.284 | 1.00 | 25.03 |
| ATOM | 751 | C | TYR | A | 98 | 15.272 | −9.443 | 15.467 | 1.00 | 13.19 |
| ATOM | 752 | O | TYR | A | 98 | 15.981 | −9.316 | 14.483 | 1.00 | 12.70 |
| ATOM | 753 | N | PRO | A | 99 | 15.129 | −10.619 | 16.100 | 1.00 | 13.11 |
| ATOM | 754 | CA | PRO | A | 99 | 15.862 | −11.748 | 15.514 | 1.00 | 13.92 |
| ATOM | 755 | CB | PRO | A | 99 | 15.605 | −12.915 | 16.491 | 1.00 | 14.48 |
| ATOM | 756 | CG | PRO | A | 99 | 14.426 | −12.507 | 17.292 | 1.00 | 14.24 |
| ATOM | 757 | CD | PRO | A | 99 | 14.448 | −10.992 | 17.356 | 1.00 | 13.23 |
| ATOM | 758 | C | PRO | A | 99 | 15.431 | −12.083 | 14.087 | 1.00 | 13.28 |
| ATOM | 759 | O | PRO | A | 99 | 16.284 | −12.423 | 13.259 | 1.00 | 14.28 |
| ATOM | 760 | N | GLU | A | 100 | 14.141 | −11.995 | 13.765 | 1.00 | 13.11 |
| ATOM | 761 | CA | GLU | A | 100 | 13.722 | −12.301 | 12.402 | 1.00 | 12.73 |
| ATOM | 762 | CB | GLU | A | 100 | 12.195 | −12.290 | 12.296 | 1.00 | 13.10 |
| ATOM | 763 | CG | GLU | A | 100 | 11.737 | −12.685 | 10.893 | 1.00 | 13.83 |
| ATOM | 764 | CD | GLU | A | 100 | 10.257 | −12.894 | 10.778 | 1.00 | 15.02 |
| ATOM | 765 | OE1 | GLU | A | 100 | 9.716 | −13.813 | 11.423 | 1.00 | 16.97 |
| ATOM | 766 | OE2 | GLU | A | 100 | 9.637 | −12.123 | 10.023 | 1.00 | 14.34 |
| ATOM | 767 | C | GLU | A | 100 | 14.306 | −11.318 | 11.377 | 1.00 | 12.68 |
| ATOM | 768 | O | GLU | A | 100 | 14.843 | −11.720 | 10.320 | 1.00 | 12.94 |
| ATOM | 769 | N | VAL | A | 101 | 14.219 | −10.040 | 11.684 | 1.00 | 12.96 |
| ATOM | 770 | CA | VAL | A | 101 | 14.710 | −9.022 | 10.761 | 1.00 | 13.65 |
| ATOM | 771 | CB | VAL | A | 101 | 14.283 | −7.602 | 11.213 | 1.00 | 13.29 |
| ATOM | 772 | CG1 | VAL | A | 101 | 14.986 | −6.503 | 10.385 | 1.00 | 16.16 |
| ATOM | 773 | CG2 | VAL | A | 101 | 12.773 | −7.457 | 11.127 | 1.00 | 13.75 |
| ATOM | 774 | C | VAL | A | 101 | 16.220 | −9.148 | 10.611 | 1.00 | 14.67 |
| ATOM | 775 | O | VAL | A | 101 | 16.722 | −9.083 | 9.509 | 1.00 | 15.13 |
| ATOM | 776 | N | ARG | A | 102 | 16.932 | −9.347 | 11.713 | 1.00 | 15.37 |
| ATOM | 777 | CA | ARG | A | 102 | 18.398 | −9.427 | 11.659 | 1.00 | 16.75 |
| ATOM | 778 | CB | ARG | A | 102 | 18.965 | −9.395 | 13.087 | 1.00 | 17.79 |
| ATOM | 779 | CG | ARG | A | 102 | 20.399 | −8.843 | 13.205 | 1.00 | 21.62 |
| ATOM | 780 | CD | ARG | A | 102 | 20.645 | −7.684 | 12.236 | 1.00 | 23.24 |
| ATOM | 781 | NE | ARG | A | 102 | 20.443 | −6.323 | 12.755 | 1.00 | 23.20 |
| ATOM | 782 | CZ | ARG | A | 102 | 19.984 | −5.315 | 12.006 | 1.00 | 23.24 |
| ATOM | 783 | NH1 | ARG | A | 102 | 19.599 | −5.551 | 10.751 | 1.00 | 23.30 |
| ATOM | 784 | NH2 | ARG | A | 102 | 19.860 | −4.088 | 12.512 | 1.00 | 23.94 |
| ATOM | 785 | C | ARG | A | 102 | 18.835 | −10.683 | 10.907 | 1.00 | 16.87 |
| ATOM | 786 | O | ARG | A | 102 | 19.842 | −10.671 | 10.199 | 1.00 | 18.30 |
| ATOM | 787 | N | HIS | A | 103 | 18.058 | −11.758 | 11.009 | 1.00 | 16.43 |
| ATOM | 788 | CA | HIS | A | 103 | 18.377 | −12.966 | 10.286 | 1.00 | 17.48 |
| ATOM | 789 | CB | HIS | A | 103 | 17.492 | −14.125 | 10.723 | 1.00 | 17.59 |
| ATOM | 790 | CG | HIS | A | 103 | 17.809 | −15.400 | 10.004 | 1.00 | 21.53 |
| ATOM | 791 | ND1 | HIS | A | 103 | 16.983 | −15.945 | 9.049 | 1.00 | 24.85 |
| ATOM | 792 | CE1 | HIS | A | 103 | 17.538 | −17.042 | 8.559 | 1.00 | 26.32 |
| ATOM | 793 | NE2 | HIS | A | 103 | 18.706 | −17.213 | 9.148 | 1.00 | 26.17 |
| ATOM | 794 | CD2 | HIS | A | 103 | 18.906 | −16.193 | 10.047 | 1.00 | 23.34 |

TABLE 1-continued

| | | | | | | | | | |
|---|---|---|---|---|---|---|---|---|---|
| ATOM | 795 | C | HIS | A | 103 | 18.249 | −12.767 | 8.783 | 1.00 | 16.88 |
| ATOM | 796 | O | HIS | A | 103 | 19.135 | −13.160 | 8.025 | 1.00 | 17.24 |
| ATOM | 797 | N | HIS | A | 104 | 17.139 | −12.181 | 8.345 | 1.00 | 16.36 |
| ATOM | 798 | CA | HIS | A | 104 | 16.870 | −12.052 | 6.925 | 1.00 | 16.24 |
| ATOM | 799 | CB | HIS | A | 104 | 15.363 | −12.094 | 6.675 | 1.00 | 16.12 |
| ATOM | 800 | CG | HIS | A | 104 | 14.758 | −13.433 | 6.940 | 1.00 | 15.16 |
| ATOM | 801 | ND1 | HIS | A | 104 | 14.797 | −14.464 | 6.024 | 1.00 | 17.29 |
| ATOM | 802 | CE1 | HIS | A | 104 | 14.187 | −15.518 | 6.534 | 1.00 | 16.02 |
| ATOM | 803 | NE2 | HIS | A | 104 | 13.770 | −15.213 | 7.751 | 1.00 | 16.75 |
| ATOM | 804 | CD2 | HIS | A | 104 | 14.099 | −13.909 | 8.021 | 1.00 | 16.36 |
| ATOM | 805 | C | HIS | A | 104 | 17.466 | −10.812 | 6.294 | 1.00 | 16.71 |
| ATOM | 806 | O | HIS | A | 104 | 17.629 | −10.759 | 5.066 | 1.00 | 17.06 |
| ATOM | 807 | N | CYS | A | 105 | 17.770 | −9.821 | 7.128 | 1.00 | 16.06 |
| ATOM | 808 | CA | CYS | A | 105 | 18.278 | −8.524 | 6.690 | 1.00 | 16.59 |
| ATOM | 809 | CB | CYS | A | 105 | 17.197 | −7.448 | 6.805 | 1.00 | 15.75 |
| ATOM | 810 | SG | CYS | A | 105 | 15.584 | −7.864 | 6.090 | 1.00 | 17.37 |
| ATOM | 811 | C | CYS | A | 105 | 19.456 | −8.140 | 7.573 | 1.00 | 18.00 |
| ATOM | 812 | O | CYS | A | 105 | 19.388 | −7.172 | 8.319 | 1.00 | 17.69 |
| ATOM | 813 | N | PRO | A | 106 | 20.554 | −8.899 | 7.482 | 1.00 | 18.97 |
| ATOM | 814 | CA | PRO | A | 106 | 21.656 | −8.676 | 8.409 | 1.00 | 20.28 |
| ATOM | 815 | CB | PRO | A | 106 | 22.677 | −9.754 | 8.005 | 1.00 | 20.67 |
| ATOM | 816 | CG | PRO | A | 106 | 22.345 | −10.089 | 6.604 | 1.00 | 19.73 |
| ATOM | 817 | CD | PRO | A | 106 | 20.853 | −9.998 | 6.545 | 1.00 | 19.37 |
| ATOM | 818 | C | PRO | A | 106 | 22.299 | −7.282 | 8.418 | 1.00 | 22.24 |
| ATOM | 819 | O | PRO | A | 106 | 22.809 | −6.871 | 9.462 | 1.00 | 24.24 |
| ATOM | 820 | N | ASN | A | 107 | 22.276 | −6.559 | 7.304 | 1.00 | 23.21 |
| ATOM | 821 | CA | ASN | A | 107 | 23.015 | −5.292 | 7.241 | 1.00 | 24.66 |
| ATOM | 822 | CB | ASN | A | 107 | 23.979 | −5.303 | 6.062 | 1.00 | 26.10 |
| ATOM | 823 | CG | ASN | A | 107 | 25.043 | −6.324 | 6.207 | 1.00 | 27.68 |
| ATOM | 824 | OD1 | ASN | A | 107 | 25.261 | −7.119 | 5.296 | 1.00 | 29.64 |
| ATOM | 825 | ND2 | ASN | A | 107 | 25.713 | −6.338 | 7.362 | 1.00 | 29.00 |
| ATOM | 826 | C | ASN | A | 107 | 22.139 | −4.056 | 7.158 | 1.00 | 24.72 |
| ATOM | 827 | O | ASN | A | 107 | 22.586 | −2.999 | 6.709 | 1.00 | 26.29 |
| ATOM | 828 | N | THR | A | 108 | 20.910 | −4.195 | 7.632 | 1.00 | 23.11 |
| ATOM | 829 | CA | THR | A | 108 | 19.828 | −3.246 | 7.386 | 1.00 | 22.12 |
| ATOM | 830 | CB | THR | A | 108 | 18.561 | −4.066 | 7.011 | 1.00 | 22.14 |
| ATOM | 831 | OG1 | THR | A | 108 | 18.807 | −4.802 | 5.813 | 1.00 | 25.06 |
| ATOM | 832 | CG2 | THR | A | 108 | 17.318 | −3.190 | 6.815 | 1.00 | 24.17 |
| ATOM | 833 | C | THR | A | 108 | 19.525 | −2.445 | 8.644 | 1.00 | 19.74 |
| ATOM | 834 | O | THR | A | 108 | 19.311 | −3.049 | 9.695 | 1.00 | 19.19 |
| ATOM | 835 | N | PRO | A | 109 | 19.470 | −1.102 | 8.550 | 1.00 | 16.40 |
| ATOM | 836 | CA | PRO | A | 109 | 19.031 | −0.347 | 9.722 | 1.00 | 15.60 |
| ATOM | 837 | CB | PRO | A | 109 | 19.143 | 1.114 | 9.282 | 1.00 | 15.76 |
| ATOM | 838 | CG | PRO | A | 109 | 19.124 | 1.064 | 7.757 | 1.00 | 16.60 |
| ATOM | 839 | CD | PRO | A | 109 | 19.824 | −0.211 | 7.423 | 1.00 | 15.88 |
| ATOM | 840 | C | PRO | A | 109 | 17.592 | −0.663 | 10.112 | 1.00 | 15.49 |
| ATOM | 841 | O | PRO | A | 109 | 16.750 | −0.973 | 9.252 | 1.00 | 14.97 |
| ATOM | 842 | N | ILE | A | 110 | 17.340 | −0.577 | 11.416 | 1.00 | 14.61 |
| ATOM | 843 | CA | ILE | A | 110 | 16.030 | −0.790 | 11.999 | 1.00 | 14.49 |
| ATOM | 844 | CB | ILE | A | 110 | 16.068 | −1.905 | 13.054 | 1.00 | 15.01 |
| ATOM | 845 | CG1 | ILE | A | 110 | 16.364 | −3.245 | 12.393 | 1.00 | 15.73 |
| ATOM | 846 | CD1 | ILE | A | 110 | 16.593 | −4.392 | 13.368 | 1.00 | 19.39 |
| ATOM | 847 | CG2 | ILE | A | 110 | 14.742 | −1.941 | 13.870 | 1.00 | 15.94 |
| ATOM | 848 | C | ILE | A | 110 | 15.584 | 0.466 | 12.677 | 1.00 | 13.80 |
| ATOM | 849 | O | ILE | A | 110 | 16.362 | 1.088 | 13.417 | 1.00 | 14.50 |
| ATOM | 850 | N | ILE | A | 111 | 14.346 | 0.869 | 12.420 | 1.00 | 13.72 |
| ATOM | 851 | CA | ILE | A | 111 | 13.734 | 1.920 | 13.209 | 1.00 | 13.09 |
| ATOM | 852 | CB | ILE | A | 111 | 13.175 | 3.006 | 12.318 | 1.00 | 13.97 |
| ATOM | 853 | CG1 | ILE | A | 111 | 14.392 | 3.647 | 11.608 | 1.00 | 18.10 |
| ATOM | 854 | CD1 | ILE | A | 111 | 14.161 | 4.925 | 10.924 | 1.00 | 22.57 |
| ATOM | 855 | CG2 | ILE | A | 111 | 12.345 | 4.022 | 13.119 | 1.00 | 14.53 |
| ATOM | 856 | C | ILE | A | 111 | 12.653 | 1.279 | 14.075 | 1.00 | 12.70 |
| ATOM | 857 | O | ILE | A | 111 | 11.822 | 0.520 | 13.559 | 1.00 | 12.11 |
| ATOM | 858 | N | LEU | A | 112 | 12.674 | 1.558 | 15.377 | 1.00 | 12.35 |
| ATOM | 859 | CA | LEU | A | 112 | 11.647 | 1.028 | 16.283 | 1.00 | 11.30 |
| ATOM | 860 | CB | LEU | A | 112 | 12.251 | 0.756 | 17.660 | 1.00 | 12.08 |
| ATOM | 861 | CG | LEU | A | 112 | 11.241 | 0.181 | 18.651 | 1.00 | 11.67 |
| ATOM | 862 | CD1 | LEU | A | 112 | 10.703 | −1.171 | 18.185 | 1.00 | 13.05 |
| ATOM | 863 | CD2 | LEU | A | 112 | 11.879 | 0.073 | 20.040 | 1.00 | 13.53 |
| ATOM | 864 | C | LEU | A | 112 | 10.535 | 2.043 | 16.383 | 1.00 | 11.41 |
| ATOM | 865 | O | LEU | A | 112 | 10.776 | 3.209 | 16.709 | 1.00 | 11.83 |
| ATOM | 866 | N | VAL | A | 113 | 9.301 | 1.612 | 16.081 | 1.00 | 11.11 |
| ATOM | 867 | CA | VAL | A | 113 | 8.166 | 2.517 | 15.997 | 1.00 | 11.25 |
| ATOM | 868 | CB | VAL | A | 113 | 7.568 | 2.562 | 14.555 | 1.00 | 11.45 |
| ATOM | 869 | CG1 | VAL | A | 113 | 6.389 | 3.544 | 14.464 | 1.00 | 12.35 |
| ATOM | 870 | CG2 | VAL | A | 113 | 8.653 | 2.966 | 13.533 | 1.00 | 11.84 |
| ATOM | 871 | C | VAL | A | 113 | 7.081 | 2.122 | 16.997 | 1.00 | 10.54 |
| ATOM | 872 | O | VAL | A | 113 | 6.545 | 1.010 | 16.912 | 1.00 | 10.85 |
| ATOM | 873 | N | GLY | A | 114 | 6.795 | 3.003 | 17.953 | 1.00 | 10.72 |

TABLE 1-continued

| | | | | | | | | | |
|---|---|---|---|---|---|---|---|---|---|
| ATOM | 874 | CA | GLY | A | 114 | 5.626 | 2.834 | 18.831 | 1.00 | 10.62 |
| ATOM | 875 | C | GLY | A | 114 | 4.412 | 3.434 | 18.152 | 1.00 | 11.24 |
| ATOM | 876 | O | GLY | A | 114 | 4.420 | 4.609 | 17.765 | 1.00 | 12.45 |
| ATOM | 877 | N | THR | A | 115 | 3.365 | 2.633 | 17.972 | 1.00 | 10.04 |
| ATOM | 878 | CA | THR | A | 115 | 2.156 | 3.038 | 17.267 | 1.00 | 10.46 |
| ATOM | 879 | CB | THR | A | 115 | 1.711 | 1.939 | 16.291 | 1.00 | 10.43 |
| ATOM | 880 | OG1 | THR | A | 115 | 1.467 | 0.771 | 17.063 | 1.00 | 11.87 |
| ATOM | 881 | CG2 | THR | A | 115 | 2.800 | 1.638 | 15.237 | 1.00 | 11.11 |
| ATOM | 882 | C | THR | A | 115 | 1.012 | 3.319 | 18.250 | 1.00 | 10.45 |
| ATOM | 883 | O | THR | A | 115 | 1.107 | 2.999 | 19.452 | 1.00 | 11.66 |
| ATOM | 884 | N | LYS | A | 116 | −0.075 | 3.847 | 17.703 | 1.00 | 10.99 |
| ATOM | 885 | CA | LYS | A | 116 | −1.291 | 4.184 | 18.452 | 1.00 | 11.62 |
| ATOM | 886 | CB | LYS | A | 116 | −1.996 | 2.939 | 18.986 | 1.00 | 11.39 |
| ATOM | 887 | CG | LYS | A | 116 | −2.250 | 1.895 | 17.905 | 1.00 | 10.85 |
| ATOM | 888 | CD | LYS | A | 116 | −3.303 | 0.882 | 18.343 | 1.00 | 11.77 |
| ATOM | 889 | CE | LYS | A | 116 | −3.395 | −0.273 | 17.383 | 1.00 | 12.92 |
| ATOM | 890 | NZ | LYS | A | 116 | −4.345 | −1.319 | 17.904 | 1.00 | 11.97 |
| ATOM | 891 | C | LYS | A | 116 | −0.999 | 5.163 | 19.574 | 1.00 | 12.31 |
| ATOM | 892 | O | LYS | A | 116 | −1.557 | 5.062 | 20.670 | 1.00 | 12.60 |
| ATOM | 893 | N | LEU | A | 117 | −0.160 | 6.147 | 19.268 | 1.00 | 12.97 |
| ATOM | 894 | CA | LEU | A | 117 | 0.210 | 7.158 | 20.249 | 1.00 | 14.06 |
| ATOM | 895 | CB | LEU | A | 117 | 1.129 | 8.182 | 19.571 | 1.00 | 13.64 |
| ATOM | 896 | CG | LEU | A | 117 | 1.521 | 9.443 | 20.352 | 1.00 | 14.58 |
| ATOM | 897 | CD1 | LEU | A | 117 | 2.293 | 9.043 | 21.565 | 1.00 | 16.08 |
| ATOM | 898 | CD2 | LEU | A | 117 | 2.368 | 10.351 | 19.496 | 1.00 | 16.13 |
| ATOM | 899 | C | LEU | A | 117 | −1.014 | 7.851 | 20.851 | 1.00 | 13.77 |
| ATOM | 900 | O | LEU | A | 117 | −0.992 | 8.227 | 22.041 | 1.00 | 15.02 |
| ATOM | 901 | N | ASP | A | 118 | −2.055 | 8.024 | 20.047 | 1.00 | 13.75 |
| ATOM | 902 | CA | ASP | A | 118 | −3.300 | 8.677 | 20.499 | 1.00 | 14.43 |
| ATOM | 903 | CB | ASP | A | 118 | −4.271 | 8.865 | 19.330 | 1.00 | 14.70 |
| ATOM | 904 | CG | ASP | A | 118 | −4.687 | 7.553 | 18.704 | 1.00 | 13.72 |
| ATOM | 905 | OD1 | ASP | A | 118 | −3.846 | 6.912 | 18.028 | 1.00 | 14.20 |
| ATOM | 906 | OD2 | ASP | A | 118 | −5.845 | 7.166 | 18.880 | 1.00 | 14.91 |
| ATOM | 907 | C | ASP | A | 118 | −3.968 | 7.927 | 21.662 | 1.00 | 15.41 |
| ATOM | 908 | O | ASP | A | 118 | −4.742 | 8.523 | 22.417 | 1.00 | 16.15 |
| ATOM | 909 | N | LEU | A | 119 | −3.656 | 6.645 | 21.832 | 1.00 | 14.12 |
| ATOM | 910 | CA | LEU | A | 119 | −4.297 | 5.853 | 22.873 | 1.00 | 14.41 |
| ATOM | 911 | CB | LEU | A | 119 | −4.555 | 4.414 | 22.387 | 1.00 | 14.30 |
| ATOM | 912 | CG | LEU | A | 119 | −5.555 | 4.218 | 21.247 | 1.00 | 14.14 |
| ATOM | 913 | CD1 | LEU | A | 119 | −5.721 | 2.728 | 20.924 | 1.00 | 14.99 |
| ATOM | 914 | CD2 | LEU | A | 119 | −6.917 | 4.854 | 21.569 | 1.00 | 14.15 |
| ATOM | 915 | C | LEU | A | 119 | −3.542 | 5.866 | 24.191 | 1.00 | 15.31 |
| ATOM | 916 | O | LEU | A | 119 | −4.098 | 5.437 | 25.213 | 1.00 | 15.58 |
| ATOM | 917 | N | ARG | A | 120 | −2.294 | 6.333 | 24.191 | 1.00 | 15.71 |
| ATOM | 918 | CA | ARG | A | 120 | −1.474 | 6.250 | 25.399 | 1.00 | 17.33 |
| ATOM | 919 | CB | ARG | A | 120 | −0.005 | 6.632 | 25.178 | 1.00 | 16.86 |
| ATOM | 920 | CG | ARG | A | 120 | 0.811 | 6.546 | 26.491 | 1.00 | 16.99 |
| ATOM | 921 | CD | ARG | A | 120 | 2.296 | 6.428 | 26.273 | 1.00 | 16.57 |
| ATOM | 922 | NE | ARG | A | 120 | 2.819 | 7.584 | 25.564 | 1.00 | 17.42 |
| ATOM | 923 | CZ | ARG | A | 120 | 3.981 | 7.595 | 24.933 | 1.00 | 15.40 |
| ATOM | 924 | NH1 | ARG | A | 120 | 4.746 | 6.503 | 24.897 | 1.00 | 15.17 |
| ATOM | 925 | NH2 | ARG | A | 120 | 4.357 | 8.708 | 24.306 | 1.00 | 16.70 |
| ATOM | 926 | C | ARG | A | 120 | −2.083 | 7.071 | 26.534 | 1.00 | 19.03 |
| ATOM | 927 | O | ARG | A | 120 | −2.005 | 6.669 | 27.705 | 1.00 | 19.26 |
| ATOM | 928 | N | ASP | A | 121 | −2.728 | 8.177 | 26.184 | 1.00 | 21.08 |
| ATOM | 929 | CA | ASP | A | 121 | −3.414 | 8.964 | 27.211 | 1.00 | 23.85 |
| ATOM | 930 | CB | ASP | A | 121 | −2.857 | 10.401 | 27.262 | 1.00 | 24.79 |
| ATOM | 931 | CG | ASP | A | 121 | −3.016 | 11.149 | 25.950 | 1.00 | 28.79 |
| ATOM | 932 | OD1 | ASP | A | 121 | −2.641 | 12.344 | 25.899 | 1.00 | 33.35 |
| ATOM | 933 | OD2 | ASP | A | 121 | −3.514 | 10.559 | 24.974 | 1.00 | 32.10 |
| ATOM | 934 | C | ASP | A | 121 | −4.953 | 8.886 | 27.147 | 1.00 | 24.43 |
| ATOM | 935 | O | ASP | A | 121 | −5.637 | 9.704 | 27.777 | 1.00 | 26.11 |
| ATOM | 936 | N | ASP | A | 122 | −5.477 | 7.881 | 26.427 | 1.00 | 23.95 |
| ATOM | 937 | CA | ASP | A | 122 | −6.928 | 7.600 | 26.266 | 1.00 | 24.46 |
| ATOM | 938 | CB | ASP | A | 122 | −7.177 | 6.663 | 25.068 | 1.00 | 24.33 |
| ATOM | 939 | CG | ASP | A | 122 | −8.673 | 6.326 | 24.848 | 1.00 | 24.95 |
| ATOM | 940 | OD1 | ASP | A | 122 | −9.439 | 7.225 | 24.431 | 1.00 | 27.49 |
| ATOM | 941 | OD2 | ASP | A | 122 | −9.080 | 5.158 | 25.043 | 1.00 | 24.18 |
| ATOM | 942 | C | ASP | A | 122 | −7.456 | 6.928 | 27.521 | 1.00 | 24.87 |
| ATOM | 943 | O | ASP | A | 122 | −6.878 | 5.948 | 27.999 | 1.00 | 25.09 |
| ATOM | 944 | N | LYS | A | 123 | −8.581 | 7.436 | 28.026 | 1.00 | 25.34 |
| ATOM | 945 | CA | LYS | A | 123 | −9.105 | 7.041 | 29.328 | 1.00 | 25.83 |
| ATOM | 946 | CB | LYS | A | 123 | −10.261 | 7.968 | 29.731 | 1.00 | 26.11 |
| ATOM | 947 | CG | LYS | A | 123 | −9.831 | 9.405 | 30.013 | 1.00 | 28.80 |
| ATOM | 948 | CD | LYS | A | 123 | −8.859 | 9.464 | 31.181 | 1.00 | 31.10 |
| ATOM | 949 | CE | LYS | A | 123 | −8.804 | 10.839 | 31.826 | 1.00 | 33.04 |
| ATOM | 950 | NZ | LYS | A | 123 | −8.546 | 10.688 | 33.283 | 1.00 | 33.17 |
| ATOM | 951 | C | LYS | A | 123 | −9.525 | 5.585 | 29.406 | 1.00 | 25.13 |
| ATOM | 952 | O | LYS | A | 123 | −9.068 | 4.857 | 30.289 | 1.00 | 25.32 |

TABLE 1-continued

| | | | | | | | | | |
|---|---|---|---|---|---|---|---|---|---|
| ATOM | 953 | N | ASP | A | 124 | −10.366 | 5.152 | 28.467 | 1.00 | 25.18 |
| ATOM | 954 | CA | ASP | A | 124 | −10.836 | 3.769 | 28.418 | 1.00 | 25.02 |
| ATOM | 955 | CB | ASP | A | 124 | −11.861 | 3.580 | 27.302 | 1.00 | 25.90 |
| ATOM | 956 | CG | ASP | A | 124 | −12.532 | 2.215 | 27.337 | 1.00 | 29.21 |
| ATOM | 957 | OD1 | ASP | A | 124 | −13.297 | 1.943 | 28.292 | 1.00 | 32.53 |
| ATOM | 958 | OD2 | ASP | A | 124 | −12.321 | 1.416 | 26.397 | 1.00 | 33.80 |
| ATOM | 959 | C | ASP | A | 124 | −9.685 | 2.798 | 28.231 | 1.00 | 23.79 |
| ATOM | 960 | O | ASP | A | 124 | −9.663 | 1.747 | 28.861 | 1.00 | 23.80 |
| ATOM | 961 | N | THR | A | 125 | −8.723 | 3.160 | 27.374 | 1.00 | 22.32 |
| ATOM | 962 | CA | THR | A | 125 | −7.581 | 2.290 | 27.125 | 1.00 | 20.76 |
| ATOM | 963 | CB | THR | A | 125 | −6.716 | 2.824 | 25.974 | 1.00 | 20.70 |
| ATOM | 964 | OG1 | THR | A | 125 | −7.526 | 2.972 | 24.801 | 1.00 | 22.33 |
| ATOM | 965 | CG2 | THR | A | 125 | −5.602 | 1.832 | 25.674 | 1.00 | 19.54 |
| ATOM | 966 | C | THR | A | 125 | −6.724 | 2.110 | 28.380 | 1.00 | 20.07 |
| ATOM | 967 | O | THR | A | 125 | −6.333 | 0.993 | 28.712 | 1.00 | 18.81 |
| ATOM | 968 | N | ILE | A | 126 | −6.459 | 3.207 | 29.085 | 1.00 | 19.39 |
| ATOM | 969 | CA | ILE | A | 126 | −5.681 | 3.144 | 30.321 | 1.00 | 19.62 |
| ATOM | 970 | CB | ILE | A | 126 | −5.364 | 4.532 | 30.887 | 1.00 | 19.40 |
| ATOM | 971 | CG1 | ILE | A | 126 | −4.396 | 5.268 | 29.960 | 1.00 | 19.35 |
| ATOM | 972 | CD1 | ILE | A | 126 | −4.362 | 6.779 | 30.214 | 1.00 | 22.93 |
| ATOM | 973 | CG2 | ILE | A | 126 | −4.727 | 4.420 | 32.273 | 1.00 | 21.54 |
| ATOM | 974 | C | ILE | A | 126 | −6.419 | 2.285 | 31.363 | 1.00 | 19.93 |
| ATOM | 975 | O | ILE | A | 126 | −5.806 | 1.451 | 32.015 | 1.00 | 19.00 |
| ATOM | 976 | N | GLU | A | 127 | −7.738 | 2.483 | 31.467 | 1.00 | 21.26 |
| ATOM | 977 | CA | GLU | A | 127 | −8.583 | 1.729 | 32.397 | 1.00 | 23.21 |
| ATOM | 978 | CB | GLU | A | 127 | −10.031 | 2.206 | 32.318 | 1.00 | 23.25 |
| ATOM | 979 | CG | GLU | A | 127 | −10.360 | 3.475 | 33.104 | 1.00 | 25.80 |
| ATOM | 980 | CD | GLU | A | 127 | −11.848 | 3.834 | 33.054 | 1.00 | 26.81 |
| ATOM | 981 | OE1 | GLU | A | 127 | −12.633 | 3.114 | 32.387 | 1.00 | 32.68 |
| ATOM | 982 | OE2 | GLU | A | 127 | −12.233 | 4.835 | 33.697 | 1.00 | 31.64 |
| ATOM | 983 | C | GLU | A | 127 | −8.542 | 0.238 | 32.083 | 1.00 | 22.25 |
| ATOM | 984 | O | GLU | A | 127 | −8.324 | −0.593 | 32.988 | 1.00 | 22.51 |
| ATOM | 985 | N | LYS | A | 128 | −8.732 | −0.099 | 30.801 | 1.00 | 22.02 |
| ATOM | 986 | CA | LYS | A | 128 | −8.708 | −1.499 | 30.345 | 1.00 | 23.13 |
| ATOM | 987 | CB | LYS | A | 128 | −9.106 | −1.614 | 28.864 | 1.00 | 23.41 |
| ATOM | 988 | CG | LYS | A | 128 | −10.556 | −1.981 | 28.639 | 1.00 | 26.63 |
| ATOM | 989 | CD | LYS | A | 128 | −10.900 | −2.054 | 27.154 | 1.00 | 27.10 |
| ATOM | 990 | CE | LYS | A | 128 | −12.342 | −2.503 | 26.951 | 1.00 | 32.09 |
| ATOM | 991 | NZ | LYS | A | 128 | −12.819 | −2.188 | 25.566 | 1.00 | 34.87 |
| ATOM | 992 | C | LYS | A | 128 | −7.382 | −2.201 | 30.607 | 1.00 | 21.64 |
| ATOM | 993 | O | LYS | A | 128 | −7.351 | −3.373 | 30.992 | 1.00 | 21.72 |
| ATOM | 994 | N | LEU | A | 129 | −6.274 | −1.492 | 30.390 | 1.00 | 19.65 |
| ATOM | 995 | CA | LEU | A | 129 | −4.970 | −2.031 | 30.719 | 1.00 | 18.39 |
| ATOM | 996 | CB | LEU | A | 129 | −3.826 | −1.147 | 30.159 | 1.00 | 17.50 |
| ATOM | 997 | CG | LEU | A | 129 | −3.624 | −1.209 | 28.638 | 1.00 | 17.68 |
| ATOM | 998 | CD1 | LEU | A | 129 | −2.705 | −0.084 | 28.182 | 1.00 | 17.69 |
| ATOM | 999 | CD2 | LEU | A | 129 | −3.061 | −2.566 | 28.208 | 1.00 | 19.43 |
| ATOM | 1000 | C | LEU | A | 129 | −4.818 | −2.218 | 32.220 | 1.00 | 18.22 |
| ATOM | 1001 | O | LEU | A | 129 | −4.308 | −3.243 | 32.668 | 1.00 | 17.93 |
| ATOM | 1002 | N | LYS | A | 130 | −5.281 | −1.239 | 32.999 | 1.00 | 18.30 |
| ATOM | 1003 | CA | LYS | A | 130 | −5.138 | −1.281 | 34.448 | 1.00 | 19.99 |
| ATOM | 1004 | CB | LYS | A | 130 | −5.657 | 0.019 | 35.077 | 1.00 | 19.61 |
| ATOM | 1005 | CG | LYS | A | 130 | −5.327 | 0.161 | 36.563 | 1.00 | 22.48 |
| ATOM | 1006 | CD | LYS | A | 130 | −5.971 | 1.394 | 37.175 | 1.00 | 23.21 |
| ATOM | 1007 | CE | LYS | A | 130 | −5.621 | 1.505 | 38.650 | 1.00 | 28.22 |
| ATOM | 1008 | NZ | LYS | A | 130 | −6.438 | 2.560 | 39.305 | 1.00 | 31.69 |
| ATOM | 1009 | C | LYS | A | 130 | −5.835 | −2.500 | 35.066 | 1.00 | 19.55 |
| ATOM | 1010 | O | LYS | A | 130 | −5.298 | −3.110 | 35.978 | 1.00 | 20.66 |
| ATOM | 1011 | N | GLU | A | 131 | −7.002 | −2.844 | 34.534 | 1.00 | 19.98 |
| ATOM | 1012 | CA | GLU | A | 131 | −7.762 | −4.027 | 34.993 | 1.00 | 21.82 |
| ATOM | 1013 | CB | GLU | A | 131 | −8.989 | −4.225 | 34.127 | 1.00 | 22.37 |
| ATOM | 1014 | CG | GLU | A | 131 | −10.065 | −3.208 | 34.295 | 1.00 | 25.39 |
| ATOM | 1015 | CD | GLU | A | 131 | −11.267 | −3.528 | 33.423 | 1.00 | 27.20 |
| ATOM | 1016 | OE1 | GLU | A | 131 | −11.173 | −4.443 | 32.570 | 1.00 | 28.48 |
| ATOM | 1017 | OE2 | GLU | A | 131 | −12.305 | −2.868 | 33.584 | 1.00 | 32.18 |
| ATOM | 1018 | C | GLU | A | 131 | −6.935 | −5.302 | 34.910 | 1.00 | 22.56 |
| ATOM | 1019 | O | GLU | A | 131 | −7.151 | −6.244 | 35.678 | 1.00 | 22.48 |
| ATOM | 1020 | N | LYS | A | 132 | −6.014 | −5.334 | 33.944 | 1.00 | 23.05 |
| ATOM | 1021 | CA | LYS | A | 132 | −5.088 | −6.449 | 33.722 | 1.00 | 23.56 |
| ATOM | 1022 | CB | LYS | A | 132 | −4.911 | −6.675 | 32.218 | 1.00 | 23.83 |
| ATOM | 1023 | CG | LYS | A | 132 | −6.192 | −6.985 | 31.466 | 1.00 | 24.91 |
| ATOM | 1024 | CD | LYS | A | 132 | −5.929 | −7.130 | 29.978 | 1.00 | 27.51 |
| ATOM | 1025 | CE | LYS | A | 132 | −7.172 | −7.624 | 29.260 | 1.00 | 28.92 |
| ATOM | 1026 | NZ | LYS | A | 132 | −6.986 | −7.606 | 27.778 | 1.00 | 31.70 |
| ATOM | 1027 | C | LYS | A | 132 | −3.712 | −6.226 | 34.363 | 1.00 | 23.22 |
| ATOM | 1028 | O | LYS | A | 132 | −2.764 | −7.003 | 34.114 | 1.00 | 23.85 |
| ATOM | 1029 | N | LYS | A | 133 | −3.600 | −5.181 | 35.185 | 1.00 | 23.67 |
| ATOM | 1030 | CA | LYS | A | 133 | −2.353 | −4.822 | 35.870 | 1.00 | 23.68 |
| ATOM | 1031 | CB | LYS | A | 133 | −1.865 | −5.956 | 36.793 | 1.00 | 24.89 |

TABLE 1-continued

| | | | | | | | | | |
|---|---|---|---|---|---|---|---|---|---|
| ATOM | 1032 | CG | LYS | A | 133 | −2.776 | −6.265 | 37.989 | 1.00 | 26.71 |
| ATOM | 1033 | CD | LYS | A | 133 | −1.990 | −6.993 | 39.082 | 1.00 | 30.39 |
| ATOM | 1034 | CE | LYS | A | 133 | −2.797 | −7.142 | 40.374 | 1.00 | 32.61 |
| ATOM | 1035 | NZ | LYS | A | 133 | −1.962 | −7.691 | 41.489 | 1.00 | 34.46 |
| ATOM | 1036 | C | LYS | A | 133 | −1.263 | −4.440 | 34.857 | 1.00 | 23.39 |
| ATOM | 1037 | O | LYS | A | 133 | −0.074 | −4.726 | 35.058 | 1.00 | 23.85 |
| ATOM | 1038 | N | LEU | A | 134 | −1.691 | −3.794 | 33.774 | 1.00 | 21.93 |
| ATOM | 1039 | CA | LEU | A | 134 | −0.784 | −3.320 | 32.721 | 1.00 | 20.83 |
| ATOM | 1040 | CB | LEU | A | 134 | −1.149 | −3.965 | 31.395 | 1.00 | 20.76 |
| ATOM | 1041 | CG | LEU | A | 134 | −1.077 | −5.492 | 31.338 | 1.00 | 22.55 |
| ATOM | 1042 | CD1 | LEU | A | 134 | −1.670 | −5.959 | 30.040 | 1.00 | 22.21 |
| ATOM | 1043 | CD2 | LEU | A | 134 | 0.361 | −5.965 | 31.506 | 1.00 | 23.61 |
| ATOM | 1044 | C | LEU | A | 134 | −0.889 | −1.817 | 32.584 | 1.00 | 20.05 |
| ATOM | 1045 | O | LEU | A | 134 | −1.841 | −1.208 | 33.051 | 1.00 | 19.28 |
| ATOM | 1046 | N | ILE | A | 135 | 0.086 | −1.233 | 31.891 | 1.00 | 18.39 |
| ATOM | 1047 | CA | ILE | A | 135 | 0.162 | 0.198 | 31.682 | 1.00 | 18.18 |
| ATOM | 1048 | CB | ILE | A | 135 | 1.028 | 0.856 | 32.786 | 1.00 | 19.88 |
| ATOM | 1049 | CG1 | ILE | A | 135 | 0.682 | 2.322 | 32.955 | 1.00 | 22.25 |
| ATOM | 1050 | CD1 | ILE | A | 135 | 0.371 | 2.670 | 34.398 | 1.00 | 26.92 |
| ATOM | 1051 | CG2 | ILE | A | 135 | 2.501 | 0.581 | 32.588 | 1.00 | 20.81 |
| ATOM | 1052 | C | ILE | A | 135 | 0.731 | 0.409 | 30.281 | 1.00 | 16.57 |
| ATOM | 1053 | O | ILE | A | 135 | 1.407 | −0.483 | 29.770 | 1.00 | 16.98 |
| ATOM | 1054 | N | PRO | A | 136 | 0.401 | 1.539 | 29.638 | 1.00 | 15.39 |
| ATOM | 1055 | CA | PRO | A | 136 | 1.034 | 1.824 | 28.342 | 1.00 | 14.59 |
| ATOM | 1056 | CB | PRO | A | 136 | 0.468 | 3.184 | 27.968 | 1.00 | 14.59 |
| ATOM | 1057 | CG | PRO | A | 136 | −0.852 | 3.252 | 28.667 | 1.00 | 15.57 |
| ATOM | 1058 | CD | PRO | A | 136 | −0.598 | 2.568 | 29.986 | 1.00 | 15.78 |
| ATOM | 1059 | C | PRO | A | 136 | 2.550 | 1.891 | 28.388 | 1.00 | 15.06 |
| ATOM | 1060 | O | PRO | A | 136 | 3.148 | 2.161 | 29.436 | 1.00 | 15.72 |
| ATOM | 1061 | N | ILE | A | 137 | 3.165 | 1.615 | 27.245 | 1.00 | 13.89 |
| ATOM | 1062 | CA | ILE | A | 137 | 4.600 | 1.756 | 27.119 | 1.00 | 13.54 |
| ATOM | 1063 | CB | ILE | A | 137 | 5.107 | 1.026 | 25.857 | 1.00 | 13.19 |
| ATOM | 1064 | CG1 | ILE | A | 137 | 4.725 | −0.467 | 25.896 | 1.00 | 14.05 |
| ATOM | 1065 | CD1 | ILE | A | 137 | 5.097 | −1.217 | 27.175 | 1.00 | 16.84 |
| ATOM | 1066 | CG2 | ILE | A | 137 | 6.610 | 1.212 | 25.703 | 1.00 | 13.91 |
| ATOM | 1067 | C | ILE | A | 137 | 4.959 | 3.237 | 27.048 | 1.00 | 13.44 |
| ATOM | 1068 | O | ILE | A | 137 | 4.387 | 4.003 | 26.304 | 1.00 | 13.44 |
| ATOM | 1069 | N | THR | A | 138 | 5.933 | 3.618 | 27.867 | 1.00 | 13.55 |
| ATOM | 1070 | CA | THR | A | 138 | 6.369 | 5.011 | 27.973 | 1.00 | 13.78 |
| ATOM | 1071 | CB | THR | A | 138 | 6.930 | 5.314 | 29.379 | 1.00 | 14.14 |
| ATOM | 1072 | OG1 | THR | A | 138 | 8.163 | 4.631 | 29.537 | 1.00 | 15.81 |
| ATOM | 1073 | CG2 | THR | A | 138 | 5.955 | 4.861 | 30.469 | 1.00 | 15.66 |
| ATOM | 1074 | C | THR | A | 138 | 7.490 | 5.285 | 26.980 | 1.00 | 13.92 |
| ATOM | 1075 | O | THR | A | 138 | 8.163 | 4.354 | 26.514 | 1.00 | 14.34 |
| ATOM | 1076 | N | TYR | A | 139 | 7.703 | 6.555 | 26.654 | 1.00 | 15.03 |
| ATOM | 1077 | CA | TYR | A | 139 | 8.784 | 6.909 | 25.761 | 1.00 | 15.03 |
| ATOM | 1078 | CB | TYR | A | 139 | 8.822 | 8.424 | 25.553 | 1.00 | 16.21 |
| ATOM | 1079 | CG | TYR | A | 139 | 9.806 | 8.858 | 24.507 | 1.00 | 17.32 |
| ATOM | 1080 | CD1 | TYR | A | 139 | 9.384 | 9.113 | 23.206 | 1.00 | 18.21 |
| ATOM | 1081 | CE1 | TYR | A | 139 | 10.287 | 9.508 | 22.221 | 1.00 | 18.42 |
| ATOM | 1082 | CZ | TYR | A | 139 | 11.623 | 9.663 | 22.535 | 1.00 | 19.94 |
| ATOM | 1083 | OH | TYR | A | 139 | 12.503 | 10.051 | 21.534 | 1.00 | 21.13 |
| ATOM | 1084 | CE2 | TYR | A | 139 | 12.079 | 9.414 | 23.821 | 1.00 | 19.28 |
| ATOM | 1085 | CD2 | TYR | A | 139 | 11.159 | 9.015 | 24.815 | 1.00 | 18.75 |
| ATOM | 1086 | C | TYR | A | 139 | 10.168 | 6.360 | 26.207 | 1.00 | 15.12 |
| ATOM | 1087 | O | TYR | A | 139 | 10.919 | 5.797 | 25.404 | 1.00 | 14.95 |
| ATOM | 1088 | N | PRO | A | 140 | 10.540 | 6.530 | 27.497 | 1.00 | 14.94 |
| ATOM | 1089 | CA | PRO | A | 140 | 11.825 | 5.963 | 27.923 | 1.00 | 15.05 |
| ATOM | 1090 | CB | PRO | A | 140 | 11.962 | 6.437 | 29.391 | 1.00 | 15.31 |
| ATOM | 1091 | CG | PRO | A | 140 | 11.130 | 7.672 | 29.439 | 1.00 | 16.93 |
| ATOM | 1092 | CD | PRO | A | 140 | 9.921 | 7.297 | 28.591 | 1.00 | 15.16 |
| ATOM | 1093 | C | PRO | A | 140 | 11.934 | 4.454 | 27.796 | 1.00 | 14.68 |
| ATOM | 1094 | O | PRO | A | 140 | 13.010 | 3.925 | 27.532 | 1.00 | 14.99 |
| ATOM | 1095 | N | GLN | A | 141 | 10.821 | 3.755 | 27.992 | 1.00 | 14.91 |
| ATOM | 1096 | CA | GLN | A | 141 | 10.831 | 2.321 | 27.795 | 1.00 | 15.32 |
| ATOM | 1097 | CB | GLN | A | 141 | 9.504 | 1.709 | 28.260 | 1.00 | 15.84 |
| ATOM | 1098 | CG | GLN | A | 141 | 9.408 | 1.695 | 29.805 | 1.00 | 17.42 |
| ATOM | 1099 | CD | GLN | A | 141 | 8.033 | 1.372 | 30.337 | 1.00 | 21.38 |
| ATOM | 1100 | OE1 | GLN | A | 141 | 7.048 | 1.409 | 29.613 | 1.00 | 19.25 |
| ATOM | 1101 | NE2 | GLN | A | 141 | 7.959 | 1.069 | 31.638 | 1.00 | 24.15 |
| ATOM | 1102 | C | GLN | A | 141 | 11.100 | 1.970 | 26.329 | 1.00 | 14.71 |
| ATOM | 1103 | O | GLN | A | 141 | 11.888 | 1.070 | 26.028 | 1.00 | 14.43 |
| ATOM | 1104 | N | GLY | A | 142 | 10.450 | 2.704 | 25.432 | 1.00 | 14.86 |
| ATOM | 1105 | CA | GLY | A | 142 | 10.638 | 2.471 | 23.988 | 1.00 | 14.98 |
| ATOM | 1106 | C | GLY | A | 142 | 12.078 | 2.752 | 23.598 | 1.00 | 15.62 |
| ATOM | 1107 | O | GLY | A | 142 | 12.702 | 1.979 | 22.871 | 1.00 | 15.98 |
| ATOM | 1108 | N | LEU | A | 143 | 12.633 | 3.843 | 24.124 | 1.00 | 15.83 |
| ATOM | 1109 | CA | LEU | A | 143 | 14.029 | 4.179 | 23.832 | 1.00 | 16.50 |
| ATOM | 1110 | CB | LEU | A | 143 | 14.401 | 5.527 | 24.425 | 1.00 | 17.32 |

TABLE 1-continued

| ATOM | 1111 | CG  | LEU | A | 143 | 15.810 | 6.009  | 24.080 | 1.00 | 19.47 |
|------|------|-----|-----|---|-----|--------|--------|--------|------|-------|
| ATOM | 1112 | CD1 | LEU | A | 143 | 16.041 | 6.135  | 22.575 | 1.00 | 21.78 |
| ATOM | 1113 | CD2 | LEU | A | 143 | 15.999 | 7.332  | 24.763 | 1.00 | 20.72 |
| ATOM | 1114 | C   | LEU | A | 143 | 14.988 | 3.100  | 24.327 | 1.00 | 15.76 |
| ATOM | 1115 | O   | LEU | A | 143 | 15.939 | 2.738  | 23.623 | 1.00 | 15.95 |
| ATOM | 1116 | N   | ALA | A | 144 | 14.747 | 2.576  | 25.529 | 1.00 | 15.60 |
| ATOM | 1117 | CA  | ALA | A | 144 | 15.579 | 1.489  | 26.048 | 1.00 | 15.89 |
| ATOM | 1118 | CB  | ALA | A | 144 | 15.176 | 1.128  | 27.474 | 1.00 | 16.77 |
| ATOM | 1119 | C   | ALA | A | 144 | 15.525 | 0.242  | 25.171 | 1.00 | 15.42 |
| ATOM | 1120 | O   | ALA | A | 144 | 16.529 | −0.409 | 24.935 | 1.00 | 15.80 |
| ATOM | 1121 | N   | MET | A | 145 | 14.329 | −0.085 | 24.695 | 1.00 | 15.04 |
| ATOM | 1122 | CA  | MET | A | 145 | 14.169 | −1.232 | 23.817 | 1.00 | 15.55 |
| ATOM | 1123 | CB  | MET | A | 145 | 12.690 | −1.461 | 23.547 | 1.00 | 15.20 |
| ATOM | 1124 | CG  | MET | A | 145 | 12.399 | −2.650 | 22.624 | 1.00 | 17.01 |
| ATOM | 1125 | SD  | MET | A | 145 | 12.861 | −4.261 | 23.305 | 1.00 | 18.66 |
| ATOM | 1126 | CE  | MET | A | 145 | 11.458 | −4.668 | 24.331 | 1.00 | 19.29 |
| ATOM | 1127 | C   | MET | A | 145 | 14.920 | −1.014 | 22.503 | 1.00 | 15.46 |
| ATOM | 1128 | O   | MET | A | 145 | 15.556 | −1.943 | 21.992 | 1.00 | 15.89 |
| ATOM | 1129 | N   | ALA | A | 146 | 14.853 | 0.203  | 21.971 | 1.00 | 15.90 |
| ATOM | 1130 | CA  | ALA | A | 146 | 15.560 | 0.543  | 20.729 | 1.00 | 16.14 |
| ATOM | 1131 | CB  | ALA | A | 146 | 15.283 | 1.978  | 20.323 | 1.00 | 16.29 |
| ATOM | 1132 | C   | ALA | A | 146 | 17.057 | 0.303  | 20.887 | 1.00 | 17.01 |
| ATOM | 1133 | O   | ALA | A | 146 | 17.708 | −0.245 | 19.997 | 1.00 | 16.87 |
| ATOM | 1134 | N   | LYS | A | 147 | 17.605 | 0.702  | 22.028 | 1.00 | 18.16 |
| ATOM | 1135 | CA  | LYS | A | 147 | 19.021 | 0.439  | 22.286 | 1.00 | 19.48 |
| ATOM | 1136 | CB  | LYS | A | 147 | 19.467 | 1.115  | 23.577 | 1.00 | 19.86 |
| ATOM | 1137 | CG  | LYS | A | 147 | 19.450 | 2.619  | 23.513 | 1.00 | 22.38 |
| ATOM | 1138 | CD  | LYS | A | 147 | 19.918 | 3.218  | 24.835 | 1.00 | 25.84 |
| ATOM | 1139 | CE  | LYS | A | 147 | 19.857 | 4.739  | 24.809 | 1.00 | 27.13 |
| ATOM | 1140 | NZ  | LYS | A | 147 | 20.013 | 5.289  | 26.179 | 1.00 | 29.52 |
| ATOM | 1141 | C   | LYS | A | 147 | 19.341 | −1.050 | 22.364 | 1.00 | 20.06 |
| ATOM | 1142 | O   | LYS | A | 147 | 20.356 | −1.501 | 21.828 | 1.00 | 19.99 |
| ATOM | 1143 | N   | GLU | A | 148 | 18.486 | −1.812 | 23.035 | 1.00 | 20.59 |
| ATOM | 1144 | CA  | GLU | A | 148 | 18.694 | −3.269 | 23.159 | 1.00 | 22.17 |
| ATOM | 1145 | CB  | GLU | A | 148 | 17.576 | −3.927 | 23.965 | 1.00 | 22.06 |
| ATOM | 1146 | CG  | GLU | A | 148 | 17.501 | −3.578 | 25.446 | 1.00 | 24.20 |
| ATOM | 1147 | CD  | GLU | A | 148 | 16.383 | −4.326 | 26.153 | 1.00 | 25.70 |
| ATOM | 1148 | OE1 | GLU | A | 148 | 16.031 | −5.439 | 25.711 | 1.00 | 31.32 |
| ATOM | 1149 | OE2 | GLU | A | 148 | 15.838 | −3.800 | 27.146 | 1.00 | 31.68 |
| ATOM | 1150 | C   | GLU | A | 148 | 18.773 | −3.977 | 21.809 | 1.00 | 21.83 |
| ATOM | 1151 | O   | GLU | A | 148 | 19.475 | −4.985 | 21.659 | 1.00 | 23.00 |
| ATOM | 1152 | N   | ILE | A | 149 | 18.024 | −3.473 | 20.833 | 1.00 | 20.08 |
| ATOM | 1153 | CA  | ILE | A | 149 | 17.978 | −4.121 | 19.519 | 1.00 | 19.47 |
| ATOM | 1154 | CB  | ILE | A | 149 | 16.519 | −4.318 | 18.997 | 1.00 | 18.75 |
| ATOM | 1155 | CG1 | ILE | A | 149 | 15.837 | −2.982 | 18.655 | 1.00 | 18.13 |
| ATOM | 1156 | CD1 | ILE | A | 149 | 14.511 | −3.149 | 17.895 | 1.00 | 18.17 |
| ATOM | 1157 | CG2 | ILE | A | 149 | 15.700 | −5.096 | 20.019 | 1.00 | 19.10 |
| ATOM | 1158 | C   | ILE | A | 149 | 18.834 | −3.408 | 18.492 | 1.00 | 19.23 |
| ATOM | 1159 | O   | ILE | A | 149 | 18.845 | −3.791 | 17.323 | 1.00 | 20.25 |
| ATOM | 1160 | N   | GLY | A | 150 | 19.558 | −2.381 | 18.927 | 1.00 | 18.35 |
| ATOM | 1161 | CA  | GLY | A | 150 | 20.482 | −1.680 | 18.039 | 1.00 | 17.82 |
| ATOM | 1162 | C   | GLY | A | 150 | 19.745 | −0.943 | 16.930 | 1.00 | 18.01 |
| ATOM | 1163 | O   | GLY | A | 150 | 20.273 | −0.782 | 15.825 | 1.00 | 18.92 |
| ATOM | 1164 | N   | ALA | A | 151 | 18.530 | −0.494 | 17.230 | 1.00 | 16.81 |
| ATOM | 1165 | CA  | ALA | A | 151 | 17.785 | 0.386  | 16.309 | 1.00 | 16.58 |
| ATOM | 1166 | CB  | ALA | A | 151 | 16.365 | 0.610  | 16.814 | 1.00 | 15.51 |
| ATOM | 1167 | C   | ALA | A | 151 | 18.502 | 1.727  | 16.150 | 1.00 | 17.00 |
| ATOM | 1168 | O   | ALA | A | 151 | 19.131 | 2.215  | 17.105 | 1.00 | 18.28 |
| ATOM | 1169 | N   | VAL | A | 152 | 18.430 | 2.329  | 14.964 | 1.00 | 16.92 |
| ATOM | 1170 | CA  | VAL | A | 152 | 19.067 | 3.619  | 14.731 | 1.00 | 17.25 |
| ATOM | 1171 | CB  | VAL | A | 152 | 19.465 | 3.825  | 13.238 | 1.00 | 17.70 |
| ATOM | 1172 | CG1 | VAL | A | 152 | 20.419 | 2.722  | 12.762 | 1.00 | 20.29 |
| ATOM | 1173 | CG2 | VAL | A | 152 | 18.251 | 3.882  | 12.357 | 1.00 | 17.61 |
| ATOM | 1174 | C   | VAL | A | 152 | 18.223 | 4.782  | 15.266 | 1.00 | 17.04 |
| ATOM | 1175 | O   | VAL | A | 152 | 18.718 | 5.881  | 15.513 | 1.00 | 17.43 |
| ATOM | 1176 | N   | LYS | A | 153 | 16.919 | 4.549  | 15.427 | 1.00 | 16.32 |
| ATOM | 1177 | CA  | LYS | A | 153 | 16.014 | 5.561  | 15.943 | 1.00 | 15.90 |
| ATOM | 1178 | CB  | LYS | A | 153 | 15.424 | 6.391  | 14.792 | 1.00 | 17.62 |
| ATOM | 1179 | CG  | LYS | A | 153 | 16.374 | 7.355  | 14.069 | 1.00 | 21.36 |
| ATOM | 1180 | CD  | LYS | A | 153 | 16.886 | 8.472  | 14.985 | 1.00 | 26.36 |
| ATOM | 1181 | CE  | LYS | A | 153 | 15.779 | 9.375  | 15.496 | 1.00 | 29.00 |
| ATOM | 1182 | NZ  | LYS | A | 153 | 16.295 | 10.500 | 16.351 | 1.00 | 31.93 |
| ATOM | 1183 | C   | LYS | A | 153 | 14.867 | 4.871  | 16.657 | 1.00 | 14.89 |
| ATOM | 1184 | O   | LYS | A | 153 | 14.495 | 3.745  | 16.280 | 1.00 | 14.72 |
| ATOM | 1185 | N   | TYR | A | 154 | 14.316 | 5.562  | 17.655 | 1.00 | 14.38 |
| ATOM | 1186 | CA  | TYR | A | 154 | 13.031 | 5.224  | 18.255 | 1.00 | 13.82 |
| ATOM | 1187 | CB  | TYR | A | 154 | 13.164 | 5.052  | 19.779 | 1.00 | 14.86 |
| ATOM | 1188 | CG  | TYR | A | 154 | 11.808 | 4.874  | 20.433 | 1.00 | 14.08 |
| ATOM | 1189 | CD1 | TYR | A | 154 | 11.018 | 3.754  | 20.142 | 1.00 | 15.57 |

TABLE 1-continued

| | | | | | | | | | |
|---|---|---|---|---|---|---|---|---|---|
| ATOM | 1190 | CE1 | TYR | A | 154 | 9.763 | 3.594 | 20.695 | 1.00 | 15.86 |
| ATOM | 1191 | CZ | TYR | A | 154 | 9.267 | 4.569 | 21.547 | 1.00 | 15.10 |
| ATOM | 1192 | OH | TYR | A | 154 | 8.019 | 4.379 | 22.110 | 1.00 | 15.01 |
| ATOM | 1193 | CE2 | TYR | A | 154 | 10.016 | 5.700 | 21.845 | 1.00 | 15.83 |
| ATOM | 1194 | CD2 | TYR | A | 154 | 11.279 | 5.852 | 21.272 | 1.00 | 14.37 |
| ATOM | 1195 | C | TYR | A | 154 | 12.087 | 6.372 | 17.980 | 1.00 | 13.73 |
| ATOM | 1196 | O | TYR | A | 154 | 12.419 | 7.544 | 18.252 | 1.00 | 14.62 |
| ATOM | 1197 | N | LEU | A | 155 | 10.917 | 6.062 | 17.427 | 1.00 | 12.95 |
| ATOM | 1198 | CA | LEU | A | 155 | 9.902 | 7.055 | 17.068 | 1.00 | 13.09 |
| ATOM | 1199 | CB | LEU | A | 155 | 9.914 | 7.303 | 15.564 | 1.00 | 13.61 |
| ATOM | 1200 | CG | LEU | A | 155 | 11.217 | 7.832 | 14.961 | 1.00 | 15.78 |
| ATOM | 1201 | CD1 | LEU | A | 155 | 11.156 | 7.731 | 13.448 | 1.00 | 16.92 |
| ATOM | 1202 | CD2 | LEU | A | 155 | 11.464 | 9.258 | 15.437 | 1.00 | 16.38 |
| ATOM | 1203 | C | LEU | A | 155 | 8.512 | 6.596 | 17.458 | 1.00 | 13.31 |
| ATOM | 1204 | O | LEU | A | 155 | 8.231 | 5.400 | 17.429 | 1.00 | 13.15 |
| ATOM | 1205 | N | GLU | A | 156 | 7.647 | 7.540 | 17.819 | 1.00 | 12.73 |
| ATOM | 1206 | CA | GLU | A | 156 | 6.245 | 7.258 | 18.145 | 1.00 | 13.69 |
| ATOM | 1207 | CB | GLU | A | 156 | 5.935 | 7.716 | 19.575 | 1.00 | 13.99 |
| ATOM | 1208 | CG | GLU | A | 156 | 6.791 | 6.988 | 20.607 | 1.00 | 14.44 |
| ATOM | 1209 | CD | GLU | A | 156 | 6.538 | 7.410 | 22.041 | 1.00 | 15.10 |
| ATOM | 1210 | OE1 | GLU | A | 156 | 6.088 | 8.555 | 22.252 | 1.00 | 17.29 |
| ATOM | 1211 | OE2 | GLU | A | 156 | 6.845 | 6.584 | 22.916 | 1.00 | 16.33 |
| ATOM | 1212 | C | GLU | A | 156 | 5.315 | 7.948 | 17.162 | 1.00 | 13.28 |
| ATOM | 1213 | O | GLU | A | 156 | 5.608 | 9.056 | 16.667 | 1.00 | 14.15 |
| ATOM | 1214 | N | CYS | A | 157 | 4.173 | 7.332 | 16.869 | 1.00 | 12.48 |
| ATOM | 1215 | CA | CYS | A | 157 | 3.248 | 7.946 | 15.935 | 1.00 | 12.25 |
| ATOM | 1216 | CB | CYS | A | 157 | 3.685 | 7.653 | 14.491 | 1.00 | 12.28 |
| ATOM | 1217 | SG | CYS | A | 157 | 3.426 | 5.920 | 13.944 | 1.00 | 13.16 |
| ATOM | 1218 | C | CYS | A | 157 | 1.832 | 7.442 | 16.176 | 1.00 | 11.07 |
| ATOM | 1219 | O | CYS | A | 157 | 1.635 | 6.467 | 16.913 | 1.00 | 11.61 |
| ATOM | 1220 | N | SER | A | 158 | 0.883 | 8.110 | 15.530 | 1.00 | 11.86 |
| ATOM | 1221 | CA | SER | A | 158 | −0.529 | 7.714 | 15.475 | 1.00 | 11.57 |
| ATOM | 1222 | CB | SER | A | 158 | −1.400 | 8.639 | 16.344 | 1.00 | 11.46 |
| ATOM | 1223 | OG | SER | A | 158 | −2.777 | 8.454 | 16.067 | 1.00 | 12.84 |
| ATOM | 1224 | C | SER | A | 158 | −1.030 | 7.770 | 14.043 | 1.00 | 12.35 |
| ATOM | 1225 | O | SER | A | 158 | −0.912 | 8.817 | 13.399 | 1.00 | 13.35 |
| ATOM | 1226 | N | ALA | A | 159 | −1.565 | 6.671 | 13.515 | 1.00 | 12.23 |
| ATOM | 1227 | CA | ALA | A | 159 | −2.230 | 6.704 | 12.210 | 1.00 | 12.91 |
| ATOM | 1228 | CB | ALA | A | 159 | −2.548 | 5.283 | 11.741 | 1.00 | 12.63 |
| ATOM | 1229 | C | ALA | A | 159 | −3.520 | 7.513 | 12.248 | 1.00 | 13.19 |
| ATOM | 1230 | O | ALA | A | 159 | −3.945 | 8.058 | 11.223 | 1.00 | 13.32 |
| ATOM | 1231 | N | LEU | A | 160 | −4.156 | 7.563 | 13.414 | 1.00 | 13.73 |
| ATOM | 1232 | CA | LEU | A | 160 | −5.424 | 8.250 | 13.580 | 1.00 | 14.94 |
| ATOM | 1233 | CB | LEU | A | 160 | −6.096 | 7.781 | 14.872 | 1.00 | 15.57 |
| ATOM | 1234 | CG | LEU | A | 160 | −7.542 | 8.210 | 15.145 | 1.00 | 17.88 |
| ATOM | 1235 | CD1 | LEU | A | 160 | −8.273 | 7.116 | 15.948 | 1.00 | 19.48 |
| ATOM | 1236 | CD2 | LEU | A | 160 | −7.551 | 9.552 | 15.882 | 1.00 | 19.96 |
| ATOM | 1237 | C | LEU | A | 160 | −5.253 | 9.781 | 13.525 | 1.00 | 14.74 |
| ATOM | 1238 | O | LEU | A | 160 | −5.977 | 10.445 | 12.763 | 1.00 | 16.73 |
| ATOM | 1239 | N | THR | A | 161 | −4.291 | 10.314 | 14.271 | 1.00 | 14.73 |
| ATOM | 1240 | CA | THR | A | 161 | −4.076 | 11.779 | 14.312 | 1.00 | 15.61 |
| ATOM | 1241 | CB | THR | A | 161 | −3.653 | 12.248 | 15.708 | 1.00 | 15.82 |
| ATOM | 1242 | OG1 | THR | A | 161 | −2.357 | 11.718 | 16.027 | 1.00 | 15.63 |
| ATOM | 1243 | CG2 | THR | A | 161 | −4.667 | 11.818 | 16.780 | 1.00 | 16.36 |
| ATOM | 1244 | C | THR | A | 161 | −2.985 | 12.248 | 13.357 | 1.00 | 16.70 |
| ATOM | 1245 | O | THR | A | 161 | −2.850 | 13.446 | 13.091 | 1.00 | 17.02 |
| ATOM | 1246 | N | GLN | A | 162 | −2.203 | 11.288 | 12.859 | 1.00 | 15.83 |
| ATOM | 1247 | CA | GLN | A | 162 | −0.997 | 11.511 | 12.035 | 1.00 | 16.95 |
| ATOM | 1248 | CB | GLN | A | 162 | −1.294 | 12.308 | 10.764 | 1.00 | 17.58 |
| ATOM | 1249 | CG | GLN | A | 162 | −2.244 | 11.634 | 9.840 | 1.00 | 20.45 |
| ATOM | 1250 | CD | GLN | A | 162 | −2.105 | 12.156 | 8.438 | 1.00 | 24.07 |
| ATOM | 1251 | OE1 | GLN | A | 162 | −2.089 | 11.398 | 7.477 | 1.00 | 25.85 |
| ATOM | 1252 | NE2 | GLN | A | 162 | −1.965 | 13.465 | 8.314 | 1.00 | 23.76 |
| ATOM | 1253 | C | GLN | A | 162 | 0.189 | 12.105 | 12.785 | 1.00 | 16.79 |
| ATOM | 1254 | O | GLN | A | 162 | 1.225 | 12.404 | 12.176 | 1.00 | 16.94 |
| ATOM | 1255 | N | ARG | A | 163 | 0.055 | 12.309 | 14.093 | 1.00 | 15.75 |
| ATOM | 1256 | CA | ARG | A | 163 | 1.174 | 12.792 | 14.891 | 1.00 | 15.88 |
| ATOM | 1257 | CB | ARG | A | 163 | 0.751 | 12.960 | 16.356 | 1.00 | 17.08 |
| ATOM | 1258 | CG | ARG | A | 163 | 1.879 | 13.133 | 17.357 | 1.00 | 20.93 |
| ATOM | 1259 | CD | ARG | A | 163 | 2.435 | 14.511 | 17.436 | 1.00 | 26.06 |
| ATOM | 1260 | NE | ARG | A | 163 | 1.382 | 15.517 | 17.404 | 0.75 | 27.25 |
| ATOM | 1261 | CZ | ARG | A | 163 | 1.616 | 16.822 | 17.415 | 1.00 | 28.54 |
| ATOM | 1262 | NH1 | ARG | A | 163 | 2.865 | 17.266 | 17.462 | 1.00 | 29.24 |
| ATOM | 1263 | NH2 | ARG | A | 163 | 0.602 | 17.670 | 17.354 | 1.00 | 27.89 |
| ATOM | 1264 | C | ARG | A | 163 | 2.378 | 11.859 | 14.749 | 1.00 | 15.55 |
| ATOM | 1265 | O | ARG | A | 163 | 2.258 | 10.640 | 14.947 | 0.50 | 12.27 |
| ATOM | 1266 | N | GLY | A | 164 | 3.525 | 12.425 | 14.373 | 1.00 | 14.69 |
| ATOM | 1267 | CA | GLY | A | 164 | 4.763 | 11.665 | 14.200 | 1.00 | 14.63 |
| ATOM | 1268 | C | GLY | A | 164 | 4.863 | 10.804 | 12.950 | 1.00 | 13.55 |

TABLE 1-continued

| | | | | | | | | | |
|---|---|---|---|---|---|---|---|---|---|
| ATOM | 1269 | O | GLY | A | 164 | 5.899 | 10.197 | 12.702 | 1.00 | 14.55 |
| ATOM | 1270 | N | LEU | A | 165 | 3.797 | 10.762 | 12.162 | 1.00 | 13.31 |
| ATOM | 1271 | CA | LEU | A | 165 | 3.707 | 9.782 | 11.084 | 1.00 | 13.13 |
| ATOM | 1272 | CB | LEU | A | 165 | 2.261 | 9.658 | 10.595 | 1.00 | 13.76 |
| ATOM | 1273 | CG | LEU | A | 165 | 1.980 | 8.553 | 9.573 | 1.00 | 14.86 |
| ATOM | 1274 | CD1 | LEU | A | 165 | 2.309 | 7.157 | 10.106 | 1.00 | 16.12 |
| ATOM | 1275 | CD2 | LEU | A | 165 | 0.535 | 8.633 | 9.149 | 1.00 | 14.31 |
| ATOM | 1276 | C | LEU | A | 165 | 4.664 | 10.070 | 9.935 | 1.00 | 13.35 |
| ATOM | 1277 | O | LEU | A | 165 | 5.419 | 9.185 | 9.497 | 1.00 | 13.32 |
| ATOM | 1278 | N | LYS | A | 166 | 4.666 | 11.299 | 9.425 | 1.00 | 13.52 |
| ATOM | 1279 | CA | LYS | A | 166 | 5.577 | 11.628 | 8.331 | 1.00 | 13.76 |
| ATOM | 1280 | CB | LYS | A | 166 | 5.261 | 13.010 | 7.784 | 1.00 | 14.69 |
| ATOM | 1281 | CG | LYS | A | 166 | 3.905 | 13.080 | 7.142 | 1.00 | 15.92 |
| ATOM | 1282 | CD | LYS | A | 166 | 3.602 | 14.524 | 6.741 | 1.00 | 19.54 |
| ATOM | 1283 | CE | LYS | A | 166 | 2.328 | 14.673 | 5.953 | 1.00 | 23.03 |
| ATOM | 1284 | NZ | LYS | A | 166 | 1.129 | 14.415 | 6.801 | 1.00 | 27.33 |
| ATOM | 1285 | C | LYS | A | 166 | 7.035 | 11.520 | 8.779 | 1.00 | 13.49 |
| ATOM | 1286 | O | LYS | A | 166 | 7.892 | 11.110 | 7.995 | 1.00 | 14.34 |
| ATOM | 1287 | N | THR | A | 167 | 7.327 | 11.841 | 10.038 | 1.00 | 13.55 |
| ATOM | 1288 | CA | THR | A | 167 | 8.671 | 11.722 | 10.581 | 1.00 | 13.77 |
| ATOM | 1289 | CB | THR | A | 167 | 8.710 | 12.319 | 11.997 | 1.00 | 14.09 |
| ATOM | 1290 | OG1 | THR | A | 167 | 8.464 | 13.729 | 11.886 | 1.00 | 18.21 |
| ATOM | 1291 | CG2 | THR | A | 167 | 10.041 | 12.057 | 12.697 | 1.00 | 15.51 |
| ATOM | 1292 | C | THR | A | 167 | 9.211 | 10.297 | 10.528 | 1.00 | 13.82 |
| ATOM | 1293 | O | THR | A | 167 | 10.397 | 10.080 | 10.290 | 1.00 | 13.73 |
| ATOM | 1294 | N | VAL | A | 168 | 8.341 | 9.311 | 10.743 | 1.00 | 12.93 |
| ATOM | 1295 | CA | VAL | A | 168 | 8.782 | 7.928 | 10.666 | 1.00 | 13.09 |
| ATOM | 1296 | CB | VAL | A | 168 | 7.585 | 6.971 | 10.881 | 1.00 | 12.82 |
| ATOM | 1297 | CG1 | VAL | A | 168 | 7.969 | 5.525 | 10.510 | 1.00 | 13.06 |
| ATOM | 1298 | CG2 | VAL | A | 168 | 7.118 | 7.023 | 12.336 | 1.00 | 13.99 |
| ATOM | 1299 | C | VAL | A | 168 | 9.458 | 7.652 | 9.316 | 1.00 | 12.52 |
| ATOM | 1300 | O | VAL | A | 168 | 10.544 | 7.070 | 9.260 | 1.00 | 12.69 |
| ATOM | 1301 | N | PHE | A | 169 | 8.807 | 8.071 | 8.244 | 1.00 | 12.32 |
| ATOM | 1302 | CA | PHE | A | 169 | 9.301 | 7.796 | 6.904 | 1.00 | 12.53 |
| ATOM | 1303 | CB | PHE | A | 169 | 8.129 | 7.771 | 5.926 | 1.00 | 12.31 |
| ATOM | 1304 | CG | PHE | A | 169 | 7.176 | 6.663 | 6.252 | 1.00 | 12.91 |
| ATOM | 1305 | CD1 | PHE | A | 169 | 7.521 | 5.355 | 5.938 | 1.00 | 12.66 |
| ATOM | 1306 | CE1 | PHE | A | 169 | 6.701 | 4.291 | 6.307 | 1.00 | 14.90 |
| ATOM | 1307 | CZ | PHE | A | 169 | 5.530 | 4.540 | 6.973 | 1.00 | 14.20 |
| ATOM | 1308 | CE2 | PHE | A | 169 | 5.187 | 5.847 | 7.321 | 1.00 | 12.87 |
| ATOM | 1309 | CD2 | PHE | A | 169 | 6.002 | 6.901 | 6.949 | 1.00 | 13.39 |
| ATOM | 1310 | C | PHE | A | 169 | 10.469 | 8.680 | 6.503 | 1.00 | 13.15 |
| ATOM | 1311 | O | PHE | A | 169 | 11.369 | 8.225 | 5.805 | 1.00 | 13.31 |
| ATOM | 1312 | N | ASP | A | 170 | 10.488 | 9.913 | 7.016 | 1.00 | 13.64 |
| ATOM | 1313 | CA | ASP | A | 170 | 11.672 | 10.784 | 6.859 | 1.00 | 14.87 |
| ATOM | 1314 | CB | ASP | A | 170 | 11.524 | 12.080 | 7.651 | 1.00 | 16.28 |
| ATOM | 1315 | CG | ASP | A | 170 | 10.543 | 13.048 | 7.058 | 1.00 | 19.88 |
| ATOM | 1316 | OD1 | ASP | A | 170 | 10.119 | 12.892 | 5.896 | 1.00 | 21.00 |
| ATOM | 1317 | OD2 | ASP | A | 170 | 10.202 | 14.002 | 7.798 | 1.00 | 23.66 |
| ATOM | 1318 | C | ASP | A | 170 | 12.890 | 10.077 | 7.440 | 1.00 | 14.49 |
| ATOM | 1319 | O | ASP | A | 170 | 13.957 | 10.021 | 6.826 | 1.00 | 14.33 |
| ATOM | 1320 | N | GLU | A | 171 | 12.728 | 9.529 | 8.642 | 1.00 | 13.56 |
| ATOM | 1321 | CA | GLU | A | 171 | 13.831 | 8.893 | 9.342 | 1.00 | 13.86 |
| ATOM | 1322 | CB | GLU | A | 171 | 13.515 | 8.776 | 10.840 | 1.00 | 14.47 |
| ATOM | 1323 | CG | GLU | A | 171 | 13.513 | 10.133 | 11.541 | 1.00 | 16.70 |
| ATOM | 1324 | CD | GLU | A | 171 | 14.864 | 10.844 | 11.544 | 1.00 | 22.34 |
| ATOM | 1325 | OE1 | GLU | A | 171 | 15.913 | 10.175 | 11.616 | 1.00 | 25.74 |
| ATOM | 1326 | OE2 | GLU | A | 171 | 14.863 | 12.085 | 11.477 | 1.00 | 26.06 |
| ATOM | 1327 | C | GLU | A | 171 | 14.221 | 7.564 | 8.716 | 1.00 | 13.90 |
| ATOM | 1328 | O | GLU | A | 171 | 15.403 | 7.200 | 8.709 | 1.00 | 14.62 |
| ATOM | 1329 | N | ALA | A | 172 | 13.246 | 6.838 | 8.180 | 1.00 | 13.38 |
| ATOM | 1330 | CA | ALA | A | 172 | 13.546 | 5.622 | 7.432 | 1.00 | 13.23 |
| ATOM | 1331 | CB | ALA | A | 172 | 12.252 | 5.014 | 6.897 | 1.00 | 14.03 |
| ATOM | 1332 | C | ALA | A | 172 | 14.495 | 5.956 | 6.286 | 1.00 | 13.28 |
| ATOM | 1333 | O | ALA | A | 172 | 15.493 | 5.250 | 6.050 | 1.00 | 14.11 |
| ATOM | 1334 | N | ILE | A | 173 | 14.178 | 7.033 | 5.573 | 1.00 | 12.65 |
| ATOM | 1335 | CA | ILE | A | 173 | 14.992 | 7.458 | 4.434 | 1.00 | 13.19 |
| ATOM | 1336 | CB | ILE | A | 173 | 14.250 | 8.516 | 3.612 | 1.00 | 12.40 |
| ATOM | 1337 | CG1 | ILE | A | 173 | 13.103 | 7.828 | 2.857 | 1.00 | 14.78 |
| ATOM | 1338 | CD1 | ILE | A | 173 | 12.081 | 8.785 | 2.302 | 1.00 | 13.37 |
| ATOM | 1339 | CG2 | ILE | A | 173 | 15.229 | 9.228 | 2.643 | 1.00 | 13.54 |
| ATOM | 1340 | C | ILE | A | 173 | 16.370 | 7.940 | 4.916 | 1.00 | 13.03 |
| ATOM | 1341 | O | ILE | A | 173 | 17.402 | 7.545 | 4.344 | 1.00 | 13.20 |
| ATOM | 1342 | N | ARG | A | 174 | 16.382 | 8.744 | 5.977 | 1.00 | 13.62 |
| ATOM | 1343 | CA | ARG | A | 174 | 17.674 | 9.196 | 6.521 | 1.00 | 14.74 |
| ATOM | 1344 | CB | ARG | A | 174 | 17.494 | 10.195 | 7.646 | 1.00 | 15.41 |
| ATOM | 1345 | CG | ARG | A | 174 | 16.882 | 11.488 | 7.168 | 1.00 | 15.94 |
| ATOM | 1346 | CD | ARG | A | 174 | 16.629 | 12.458 | 8.320 | 1.00 | 20.70 |
| ATOM | 1347 | NE | ARG | A | 174 | 16.118 | 13.738 | 7.823 | 1.00 | 22.87 |

TABLE 1-continued

| | | | | | | | | | |
|---|---|---|---|---|---|---|---|---|---|
| ATOM | 1348 | CZ | ARG | A | 174 | 15.001 | 14.333 | 8.237 | 1.00 | 26.43 |
| ATOM | 1349 | NH1 | ARG | A | 174 | 14.252 | 13.806 | 9.205 | 1.00 | 29.29 |
| ATOM | 1350 | NH2 | ARG | A | 174 | 14.640 | 15.486 | 7.689 | 1.00 | 29.09 |
| ATOM | 1351 | C | ARG | A | 174 | 18.557 | 8.055 | 6.972 | 1.00 | 15.31 |
| ATOM | 1352 | O | ARG | A | 174 | 19.786 | 8.137 | 6.874 | 1.00 | 16.11 |
| ATOM | 1353 | N | ALA | A | 175 | 17.955 | 6.974 | 7.463 | 1.00 | 15.52 |
| ATOM | 1354 | CA | ALA | A | 175 | 18.750 | 5.836 | 7.925 | 1.00 | 16.05 |
| ATOM | 1355 | CB | ALA | A | 175 | 17.848 | 4.791 | 8.567 | 1.00 | 16.64 |
| ATOM | 1356 | C | ALA | A | 175 | 19.527 | 5.214 | 6.784 | 1.00 | 16.94 |
| ATOM | 1357 | O | ALA | A | 175 | 20.554 | 4.546 | 6.996 | 1.00 | 17.87 |
| ATOM | 1358 | N | VAL | A | 176 | 19.023 | 5.398 | 5.570 | 1.00 | 16.33 |
| ATOM | 1359 | CA | VAL | A | 176 | 19.637 | 4.805 | 4.402 | 1.00 | 16.94 |
| ATOM | 1360 | CB | VAL | A | 176 | 18.558 | 4.324 | 3.380 | 1.00 | 16.82 |
| ATOM | 1361 | CG1 | VAL | A | 176 | 19.199 | 3.795 | 2.097 | 1.00 | 17.60 |
| ATOM | 1362 | CG2 | VAL | A | 176 | 17.671 | 3.260 | 4.012 | 1.00 | 17.37 |
| ATOM | 1363 | C | VAL | A | 176 | 20.608 | 5.811 | 3.770 | 1.00 | 18.02 |
| ATOM | 1364 | O | VAL | A | 176 | 21.728 | 5.427 | 3.375 | 1.00 | 19.01 |
| ATOM | 1365 | N | LEU | A | 177 | 20.209 | 7.085 | 3.716 | 1.00 | 18.56 |
| ATOM | 1366 | CA | LEU | A | 177 | 20.959 | 8.112 | 2.960 | 1.00 | 19.99 |
| ATOM | 1367 | CB | LEU | A | 177 | 19.995 | 9.076 | 2.262 | 1.00 | 19.32 |
| ATOM | 1368 | CG | LEU | A | 177 | 19.084 | 8.466 | 1.202 | 1.00 | 19.69 |
| ATOM | 1369 | CD1 | LEU | A | 177 | 18.245 | 9.570 | 0.570 | 1.00 | 21.53 |
| ATOM | 1370 | CD2 | LEU | A | 177 | 19.869 | 7.693 | 0.137 | 1.00 | 20.62 |
| ATOM | 1371 | C | LEU | A | 177 | 21.971 | 8.922 | 3.771 | 1.00 | 21.89 |
| ATOM | 1372 | O | LEU | A | 177 | 22.858 | 9.576 | 3.198 | 1.00 | 22.03 |
| ATOM | 1373 | N | CYS | A | 178 | 21.826 | 8.919 | 5.089 | 1.00 | 22.74 |
| ATOM | 1374 | CA | CYS | A | 178 | 22.743 | 9.643 | 5.961 | 1.00 | 25.08 |
| ATOM | 1375 | CB | CYS | A | 178 | 21.984 | 10.500 | 6.977 | 1.00 | 25.34 |
| ATOM | 1376 | SG | CYS | A | 178 | 20.806 | 11.678 | 6.228 | 0.75 | 28.16 |
| ATOM | 1377 | C | CYS | A | 178 | 23.648 | 8.648 | 6.661 | 1.00 | 26.11 |
| ATOM | 1378 | O | CYS | A | 178 | 23.186 | 7.875 | 7.499 | 1.00 | 27.77 |
| ATOM | 1379 | O6 | GDP | A | 191 | −3.009 | 5.022 | 15.369 | 1.00 | 12.24 |
| ATOM | 1380 | C6 | GDP | A | 191 | −4.015 | 4.359 | 15.678 | 1.00 | 12.17 |
| ATOM | 1381 | N1 | GDP | A | 191 | −4.860 | 4.763 | 16.631 | 1.00 | 11.86 |
| ATOM | 1382 | C2 | GDP | A | 191 | −5.946 | 4.059 | 17.010 | 1.00 | 13.33 |
| ATOM | 1383 | N3 | GDP | A | 191 | −6.335 | 2.908 | 16.446 | 1.00 | 12.94 |
| ATOM | 1384 | C4 | GDP | A | 191 | −5.563 | 2.390 | 15.462 | 1.00 | 12.01 |
| ATOM | 1385 | N2 | GDP | A | 191 | −6.728 | 4.592 | 17.968 | 1.00 | 14.08 |
| ATOM | 1386 | C5 | GDP | A | 191 | −4.355 | 3.101 | 15.012 | 1.00 | 11.72 |
| ATOM | 1387 | N7 | GDP | A | 191 | −3.778 | 2.354 | 14.043 | 1.00 | 11.60 |
| ATOM | 1388 | C8 | GDP | A | 191 | −4.554 | 1.260 | 13.880 | 1.00 | 11.74 |
| ATOM | 1389 | N9 | GDP | A | 191 | −5.622 | 1.293 | 14.713 | 1.00 | 11.13 |
| ATOM | 1390 | C1* | GDP | A | 191 | −6.641 | 0.245 | 14.813 | 1.00 | 12.04 |
| ATOM | 1391 | C2* | GDP | A | 191 | −7.274 | −0.146 | 13.495 | 1.00 | 13.49 |
| ATOM | 1392 | O2* | GDP | A | 191 | −8.363 | 0.720 | 13.221 | 1.00 | 15.11 |
| ATOM | 1393 | C3* | GDP | A | 191 | −7.655 | −1.573 | 13.776 | 1.00 | 13.18 |
| ATOM | 1394 | O3* | GDP | A | 191 | −8.833 | −1.618 | 14.593 | 1.00 | 14.69 |
| ATOM | 1395 | O4* | GDP | A | 191 | −5.970 | −0.930 | 15.291 | 1.00 | 11.20 |
| ATOM | 1396 | C4* | GDP | A | 191 | −6.533 | −2.077 | 14.643 | 1.00 | 12.56 |
| ATOM | 1397 | C5* | GDP | A | 191 | −5.462 | −2.819 | 13.842 | 1.00 | 10.91 |
| ATOM | 1398 | O5* | GDP | A | 191 | −4.919 | −1.976 | 12.814 | 1.00 | 9.53 |
| ATOM | 1399 | PA | GDP | A | 191 | −4.141 | −2.627 | 11.586 | 1.00 | 9.51 |
| ATOM | 1400 | O1A | GDP | A | 191 | −3.619 | −1.488 | 10.785 | 1.00 | 9.65 |
| ATOM | 1401 | O2A | GDP | A | 191 | −4.994 | −3.603 | 10.878 | 1.00 | 10.36 |
| ATOM | 1402 | O3A | GDP | A | 191 | −2.961 | −3.377 | 12.352 | 1.00 | 9.19 |
| ATOM | 1403 | PB | GDP | A | 191 | −1.946 | −4.469 | 11.696 | 1.00 | 8.75 |
| ATOM | 1404 | O1B | GDP | A | 191 | −0.668 | −4.238 | 12.435 | 1.00 | 8.01 |
| ATOM | 1405 | O3B | GDP | A | 191 | −2.522 | −5.850 | 12.023 | 1.00 | 9.28 |
| ATOM | 1406 | O2B | GDP | A | 191 | −1.858 | −4.210 | 10.209 | 1.00 | 9.68 |
| ATOM | 1407 | MG | MG | A | 192 | −2.167 | −5.353 | 8.526 | 1.00 | 8.83 |
| ATOM | 1408 | CBD | DRG | A | 193 | 0.681 | −13.450 | 2.776 | 1.00 | 20.00 |
| ATOM | 1409 | CBB | DRG | A | 193 | 2.267 | −11.782 | 3.301 | 1.00 | 20.00 |
| ATOM | 1410 | NBA | DRG | A | 193 | 3.593 | −11.504 | 3.903 | 1.00 | 20.00 |
| ATOM | 1411 | CBC | DRG | A | 193 | 3.584 | −11.334 | 5.380 | 1.00 | 20.00 |
| ATOM | 1412 | CBE | DRG | A | 193 | 2.285 | −10.824 | 6.039 | 1.00 | 20.00 |
| ATOM | 1413 | CAZ | DRG | A | 193 | 4.146 | −10.330 | 3.193 | 1.00 | 20.00 |
| ATOM | 1414 | CAY | DRG | A | 193 | 3.104 | −9.261 | 2.850 | 1.00 | 20.00 |
| ATOM | 1415 | CAW | DRG | A | 193 | 3.698 | −7.876 | 3.101 | 1.00 | 20.00 |
| ATOM | 1416 | CAV | DRG | A | 193 | 4.865 | −7.544 | 2.157 | 1.00 | 20.00 |
| ATOM | 1417 | CAX | DRG | A | 193 | 4.462 | −6.384 | 1.241 | 1.00 | 20.00 |
| ATOM | 1418 | NAT | DRG | A | 193 | 5.218 | −8.724 | 1.338 | 1.00 | 20.00 |
| ATOM | 1419 | C2 | DRG | A | 193 | 5.884 | −8.629 | 0.171 | 1.00 | 20.00 |
| ATOM | 1420 | N1 | DRG | A | 193 | 7.077 | −9.259 | −0.012 | 1.00 | 20.00 |
| ATOM | 1421 | N3 | DRG | A | 193 | 5.379 | −7.889 | −0.848 | 1.00 | 20.00 |
| ATOM | 1422 | C4 | DRG | A | 193 | 6.016 | −7.768 | −2.033 | 1.00 | 20.00 |
| ATOM | 1423 | CAU | DRG | A | 193 | 5.400 | −6.926 | −3.158 | 1.00 | 20.00 |
| ATOM | 1424 | C5 | DRG | A | 193 | 7.453 | −8.603 | −2.141 | 1.00 | 20.00 |
| ATOM | 1425 | C6 | DRG | A | 193 | 7.779 | −9.175 | −1.178 | 1.00 | 20.00 |
| ATOM | 1426 | NAM | DRG | A | 193 | 8.934 | −9.860 | −1.330 | 1.00 | 20.00 |

TABLE 1-continued

| | | | | | | | | | |
|---|---|---|---|---|---|---|---|---|---|
| ATOM | 1427 | CAJ | DRG | A | 193 | 9.976 | −9.460 | −2.102 | 1.00 20.00 |
| ATOM | 1428 | CAF | DRG | A | 193 | 10.753 | −10.423 | −2.779 | 1.00 20.00 |
| ATOM | 1429 | CAB | DRG | A | 193 | 11.751 | −9.996 | −3.687 | 1.00 20.00 |
| ATOM | 1430 | CAA | DRG | A | 193 | 12.544 | −10.894 | −4.439 | 1.00 20.00 |
| ATOM | 1431 | NAD | DRG | A | 193 | 12.440 | −12.222 | −4.327 | 1.00 20.00 |
| ATOM | 1432 | CAC | DRG | A | 193 | 13.496 | −10.415 | −5.348 | 1.00 20.00 |
| ATOM | 1433 | CAG | DRG | A | 193 | 13.635 | −9.025 | −5.501 | 1.00 20.00 |
| ATOM | 1434 | CAK | DRG | A | 193 | 14.657 | −8.464 | −6.495 | 1.00 20.00 |
| ATOM | 1435 | NAH | DRG | A | 193 | 12.880 | −8.183 | −4.767 | 1.00 20.00 |
| ATOM | 1436 | CAE | DRG | A | 193 | 11.950 | −8.599 | −3.881 | 1.00 20.00 |
| ATOM | 1437 | CAI | DRG | A | 193 | 11.197 | −7.636 | −3.199 | 1.00 20.00 |
| ATOM | 1438 | CAL | DRG | A | 193 | 10.205 | −8.083 | −2.316 | 1.00 20.00 |
| ATOM | 1439 | O | HOH | Z | 1 | −0.134 | −5.584 | 8.242 | 1.00 8.96 |
| ATOM | 1440 | O | HOH | Z | 2 | −4.232 | −5.015 | 8.711 | 1.00 9.58 |
| ATOM | 1441 | O | HOH | Z | 3 | −2.275 | −7.057 | 9.673 | 1.00 10.94 |
| ATOM | 1442 | O | HOH | Z | 4 | 10.477 | −1.304 | −3.031 | 1.00 26.08 |
| ATOM | 1443 | O | HOH | Z | 5 | 16.317 | −2.369 | −2.524 | 1.00 29.42 |
| ATOM | 1444 | O | HOH | Z | 6 | 5.047 | −8.484 | 10.591 | 1.00 12.91 |
| ATOM | 1445 | O | HOH | Z | 7 | 5.124 | −6.010 | 17.744 | 1.00 11.06 |
| ATOM | 1446 | O | HOH | Z | 8 | 0.567 | −9.158 | 20.354 | 1.00 21.09 |
| ATOM | 1447 | O | HOH | Z | 9 | 0.703 | −11.544 | 16.131 | 1.00 12.46 |
| ATOM | 1448 | O | HOH | Z | 10 | 3.703 | −12.071 | 16.597 | 1.00 22.55 |
| ATOM | 1449 | O | HOH | Z | 11 | −0.182 | −8.384 | 10.983 | 1.00 11.20 |
| ATOM | 1450 | O | HOH | Z | 12 | −4.333 | −8.769 | 10.467 | 1.00 14.76 |
| ATOM | 1451 | O | HOH | Z | 13 | −4.936 | −6.912 | 12.473 | 1.00 14.22 |
| ATOM | 1452 | O | HOH | Z | 14 | −8.445 | 11.206 | 35.892 | 1.00 27.24 |
| ATOM | 1453 | O | HOH | Z | 15 | −3.210 | −2.135 | 20.575 | 1.00 12.27 |
| ATOM | 1454 | O | HOH | Z | 16 | −1.032 | 2.706 | 13.325 | 1.00 11.23 |
| ATOM | 1455 | O | HOH | Z | 17 | 0.215 | 4.566 | 14.883 | 1.00 12.32 |
| ATOM | 1456 | O | HOH | Z | 18 | 1.314 | 11.622 | 4.713 | 1.00 23.82 |
| ATOM | 1457 | O | HOH | Z | 19 | 0.615 | 11.501 | 7.265 | 1.00 29.69 |
| ATOM | 1458 | O | HOH | Z | 20 | −14.149 | 1.973 | 10.917 | 1.00 22.67 |
| ATOM | 1459 | O | HOH | Z | 21 | −11.299 | −4.865 | 9.719 | 1.00 22.28 |
| ATOM | 1460 | O | HOH | Z | 22 | −9.705 | −6.203 | 8.035 | 1.00 17.69 |
| ATOM | 1461 | O | HOH | Z | 23 | 7.468 | 13.145 | −9.245 | 1.00 28.76 |
| ATOM | 1462 | O | HOH | Z | 24 | −6.991 | −5.346 | 11.452 | 1.00 15.83 |
| ATOM | 1463 | O | HOH | Z | 25 | 4.514 | 11.481 | −2.718 | 1.00 12.76 |
| ATOM | 1464 | O | HOH | Z | 26 | 6.818 | 14.498 | 0.538 | 1.00 22.98 |
| ATOM | 1465 | O | HOH | Z | 27 | −6.619 | −9.355 | 9.099 | 1.00 17.44 |
| ATOM | 1466 | O | HOH | Z | 28 | 15.357 | 6.087 | −3.675 | 1.00 27.71 |
| ATOM | 1467 | O | HOH | Z | 29 | 15.754 | 8.383 | −5.057 | 1.00 25.97 |
| ATOM | 1468 | O | HOH | Z | 30 | −1.307 | −5.728 | 19.093 | 1.00 27.63 |
| ATOM | 1469 | O | HOH | Z | 31 | −0.946 | −7.181 | 21.049 | 1.00 23.44 |
| ATOM | 1470 | O | HOH | Z | 32 | −3.074 | −4.762 | 20.234 | 1.00 31.01 |
| ATOM | 1471 | O | HOH | Z | 33 | 2.733 | 9.521 | 0.192 | 1.00 13.56 |
| ATOM | 1472 | O | HOH | Z | 34 | 3.360 | 9.455 | −1.336 | 1.00 18.57 |
| ATOM | 1473 | O | HOH | Z | 36 | 11.041 | −13.275 | −2.389 | 1.00 29.42 |
| ATOM | 1474 | O | HOH | Z | 37 | −6.223 | 11.555 | 10.296 | 1.00 32.37 |
| ATOM | 1475 | O | HOH | Z | 38 | −9.612 | −4.467 | 12.063 | 1.00 31.51 |
| ATOM | 1476 | O | HOH | Z | 44 | 4.098 | −4.948 | −0.736 | 1.00 26.48 |
| ATOM | 1477 | O | HOH | Z | 45 | 2.704 | −3.500 | 0.992 | 1.00 25.13 |
| ATOM | 1478 | O | HOH | Z | 46 | 2.826 | −1.554 | 1.772 | 1.00 32.13 |
| ATOM | 1479 | O | HOH | Z | 47 | −5.682 | 11.211 | −0.359 | 1.00 25.76 |
| ATOM | 1480 | O | HOH | Z | 48 | −4.127 | −5.680 | −0.140 | 1.00 32.87 |
| ATOM | 1481 | O | HOH | Z | 49 | 0.270 | −2.172 | −5.395 | 1.00 28.65 |
| ATOM | 1482 | O | HOH | Z | 50 | −2.450 | −1.603 | −5.615 | 1.00 31.17 |
| ATOM | 1483 | O | HOH | Z | 51 | 3.268 | −18.749 | 6.483 | 1.00 21.70 |
| ATOM | 1484 | O | HOH | Z | 52 | 2.161 | −21.956 | 8.428 | 1.00 31.44 |
| ATOM | 1485 | O | HOH | Z | 53 | −1.571 | −18.172 | 6.694 | 1.00 17.34 |
| ATOM | 1486 | O | HOH | Z | 54 | −0.249 | −18.135 | 5.433 | 1.00 29.65 |
| ATOM | 1487 | O | HOH | Z | 55 | 2.971 | 2.171 | −6.016 | 1.00 23.51 |
| ATOM | 1488 | O | HOH | Z | 56 | 7.729 | 11.463 | 5.016 | 1.00 17.76 |
| ATOM | 1489 | O | HOH | Z | 57 | 12.155 | 18.376 | 1.959 | 1.00 26.19 |
| ATOM | 1490 | O | HOH | Z | 58 | 12.594 | 17.158 | 5.114 | 1.00 31.33 |
| ATOM | 1491 | O | HOH | Z | 59 | −1.569 | 11.596 | 18.927 | 1.00 16.57 |
| ATOM | 1492 | O | HOH | Z | 60 | 7.579 | 9.928 | 14.909 | 1.00 15.76 |
| ATOM | 1493 | O | HOH | Z | 61 | 19.744 | −0.867 | 13.120 | 1.00 18.17 |
| ATOM | 1494 | O | HOH | Z | 62 | 8.707 | 10.237 | 18.525 | 1.00 17.38 |
| ATOM | 1495 | O | HOH | Z | 63 | 21.457 | 20.231 | −3.910 | 1.00 19.88 |
| ATOM | 1496 | O | HOH | Z | 64 | 11.940 | −14.538 | 15.403 | 1.00 19.32 |
| ATOM | 1497 | O | HOH | Z | 65 | −3.012 | 1.332 | 32.662 | 1.00 17.87 |
| ATOM | 1498 | O | HOH | Z | 66 | 2.933 | 13.528 | 10.444 | 1.00 18.09 |
| ATOM | 1499 | O | HOH | Z | 67 | 5.511 | 13.684 | 11.621 | 1.00 18.83 |
| ATOM | 1500 | O | HOH | Z | 68 | −0.341 | −6.697 | 26.164 | 1.00 22.76 |
| ATOM | 1501 | O | HOH | Z | 69 | 15.508 | 4.752 | 28.264 | 1.00 19.65 |
| ATOM | 1502 | O | HOH | Z | 70 | 9.568 | −16.322 | 9.992 | 1.00 22.23 |
| ATOM | 1503 | O | HOH | Z | 71 | 15.958 | 7.636 | 18.742 | 1.00 23.87 |
| ATOM | 1504 | O | HOH | Z | 72 | −6.783 | 0.200 | 18.310 | 1.00 21.13 |
| ATOM | 1505 | O | HOH | Z | 73 | 11.447 | 9.949 | 19.027 | 1.00 19.55 |

TABLE 1-continued

| | | | | | | | | | |
|---|---|---|---|---|---|---|---|---|---|
| ATOM | 1506 | O | HOH | Z | 74 | 23.144 | 10.431 | 0.689 | 1.00 23.34 |
| ATOM | 1507 | O | HOH | Z | 75 | −7.996 | 8.406 | 20.020 | 1.00 25.41 |
| ATOM | 1508 | O | HOH | Z | 76 | 2.608 | 3.969 | 31.316 | 1.00 26.88 |
| ATOM | 1509 | O | HOH | Z | 77 | 2.425 | −3.227 | 31.617 | 1.00 27.72 |
| ATOM | 1510 | O | HOH | Z | 78 | 17.254 | −8.666 | 3.011 | 1.00 25.39 |
| ATOM | 1511 | O | HOH | Z | 79 | 12.918 | −15.190 | −0.608 | 1.00 34.94 |
| ATOM | 1512 | O | HOH | Z | 80 | 12.067 | −17.714 | −1.315 | 1.00 32.30 |
| ATOM | 1513 | O | HOH | Z | 81 | −10.581 | 2.386 | 3.590 | 1.00 25.93 |
| ATOM | 1514 | O | HOH | Z | 82 | 9.735 | −14.832 | −4.003 | 1.00 32.53 |
| ATOM | 1515 | O | HOH | Z | 83 | 11.835 | −6.311 | −3.598 | 1.00 32.48 |
| ATOM | 1516 | O | HOH | Z | 84 | 8.689 | 11.909 | 16.333 | 1.00 23.24 |
| ATOM | 1517 | O | HOH | Z | 85 | −6.601 | −3.539 | 17.808 | 1.00 23.91 |
| ATOM | 1518 | O | HOH | Z | 86 | 17.879 | 3.999 | 27.428 | 1.00 28.73 |
| ATOM | 1519 | O | HOH | Z | 87 | 12.222 | −16.863 | 9.403 | 1.00 23.77 |
| ATOM | 1520 | O | HOH | Z | 88 | 5.867 | 8.517 | 27.830 | 1.00 26.11 |
| ATOM | 1521 | O | HOH | Z | 89 | 17.094 | 7.930 | 10.841 | 1.00 29.44 |
| ATOM | 1522 | O | HOH | Z | 90 | −8.791 | −1.299 | 17.296 | 1.00 26.69 |
| ATOM | 1523 | O | HOH | Z | 91 | 4.804 | 0.800 | 30.972 | 1.00 28.06 |
| ATOM | 1524 | O | HOH | Z | 92 | 3.461 | 15.172 | 13.591 | 1.00 26.08 |
| ATOM | 1525 | O | HOH | Z | 93 | −14.826 | 5.257 | 33.876 | 1.00 28.68 |
| ATOM | 1526 | O | HOH | Z | 94 | 10.358 | −15.459 | 13.503 | 1.00 27.42 |
| ATOM | 1527 | O | HOH | Z | 95 | 21.417 | 4.120 | 9.561 | 1.00 25.75 |
| ATOM | 1528 | O | HOH | Z | 96 | −1.574 | −17.006 | 13.344 | 1.00 27.33 |
| ATOM | 1529 | O | HOH | Z | 97 | 3.802 | −20.213 | 9.738 | 1.00 26.02 |
| ATOM | 1530 | O | HOH | Z | 98 | 4.687 | −10.827 | 24.294 | 1.00 27.00 |
| ATOM | 1531 | O | HOH | Z | 99 | 18.579 | −0.462 | 26.775 | 1.00 28.17 |
| ATOM | 1532 | O | HOH | Z | 100 | 9.226 | 4.998 | 32.035 | 1.00 26.92 |
| ATOM | 1533 | O | HOH | Z | 101 | −0.655 | 6.897 | 29.980 | 1.00 28.47 |
| ATOM | 1534 | O | HOH | Z | 102 | 6.947 | 10.853 | 20.750 | 1.00 25.28 |
| ATOM | 1535 | O | HOH | Z | 103 | 18.739 | −13.365 | 14.310 | 1.00 28.79 |
| ATOM | 1536 | O | HOH | Z | 104 | 1.875 | 6.190 | 29.907 | 1.00 28.27 |
| ATOM | 1537 | O | HOH | Z | 105 | 11.693 | 3.613 | 32.212 | 1.00 34.50 |
| ATOM | 1538 | O | HOH | Z | 106 | −10.191 | 6.741 | 34.392 | 1.00 29.28 |
| ATOM | 1539 | O | HOH | Z | 107 | −6.667 | 8.319 | 32.568 | 1.00 35.78 |
| ATOM | 1540 | O | HOH | Z | 108 | 22.107 | −0.247 | 11.857 | 1.00 35.64 |
| ATOM | 1541 | O | HOH | Z | 109 | 5.419 | 11.752 | 18.009 | 1.00 33.54 |
| ATOM | 1542 | O | HOH | Z | 110 | 18.317 | 4.725 | 18.913 | 1.00 28.26 |
| ATOM | 1543 | O | HOH | Z | 111 | −19.579 | 1.950 | 5.342 | 1.00 33.46 |
| ATOM | 1544 | O | HOH | Z | 112 | −0.971 | −9.842 | 17.992 | 1.00 26.85 |
| ATOM | 1545 | O | HOH | Z | 113 | 18.991 | 1.782 | 28.143 | 1.00 32.15 |
| ATOM | 1546 | O | HOH | Z | 114 | −8.447 | 10.667 | 8.833 | 1.00 31.09 |
| ATOM | 1547 | O | HOH | Z | 115 | −7.957 | −5.784 | 38.341 | 1.00 33.78 |
| ATOM | 1548 | O | HOH | Z | 116 | 23.481 | 8.252 | −0.900 | 1.00 31.21 |
| ATOM | 1549 | O | HOH | Z | 117 | 16.296 | −11.718 | 2.686 | 1.00 25.55 |
| ATOM | 1550 | O | HOH | Z | 118 | −8.089 | 6.124 | 32.836 | 1.00 33.27 |
| ATOM | 1551 | O | HOH | Z | 119 | −18.899 | 1.773 | 9.908 | 1.00 28.82 |
| ATOM | 1552 | O | HOH | Z | 120 | −4.891 | 11.134 | 22.878 | 1.00 34.04 |
| ATOM | 1553 | O | HOH | Z | 121 | −3.879 | −6.962 | −3.653 | 1.00 25.64 |
| ATOM | 1554 | O | HOH | Z | 122 | 6.294 | −5.334 | 27.716 | 1.00 32.59 |
| ATOM | 1555 | O | HOH | Z | 123 | 19.061 | −12.417 | 17.639 | 1.00 35.78 |
| ATOM | 1556 | O | HOH | Z | 124 | 3.653 | 8.065 | 29.157 | 1.00 31.42 |
| ATOM | 1557 | O | HOH | Z | 125 | 20.626 | −6.832 | 4.898 | 1.00 30.71 |
| ATOM | 1558 | O | HOH | Z | 126 | −4.089 | 15.494 | 11.914 | 1.00 37.36 |
| ATOM | 1559 | O | HOH | Z | 127 | −5.505 | −1.483 | 22.141 | 1.00 33.40 |
| ATOM | 1560 | O | HOH | Z | 128 | 13.760 | −7.726 | 25.645 | 1.00 43.49 |
| ATOM | 1561 | O | HOH | Z | 129 | 11.225 | 13.014 | 16.204 | 1.00 31.87 |
| ATOM | 1562 | O | HOH | Z | 130 | −10.901 | 1.977 | 13.994 | 1.00 31.78 |
| ATOM | 1563 | O | HOH | Z | 131 | −1.232 | 15.529 | 13.872 | 1.00 31.18 |
| ATOM | 1564 | O | HOH | Z | 132 | −8.158 | 1.006 | 23.180 | 1.00 33.63 |
| ATOM | 1565 | O | HOH | Z | 133 | 3.948 | −1.576 | 30.415 | 1.00 43.32 |
| ATOM | 1566 | O | HOH | Z | 134 | −7.606 | 6.346 | 3.782 | 1.00 37.67 |
| ATOM | 1567 | O | HOH | Z | 135 | 20.292 | −7.467 | 0.209 | 1.00 31.70 |
| ATOM | 1568 | O | HOH | Z | 136 | 20.357 | 7.828 | 26.267 | 1.00 35.06 |
| ATOM | 1569 | O | HOH | Z | 137 | 20.649 | −0.024 | 1.228 | 1.00 31.80 |
| ATOM | 1570 | O | HOH | Z | 138 | −0.771 | 10.384 | 23.630 | 1.00 32.99 |
| ATOM | 1571 | O | HOH | Z | 139 | 17.801 | −7.406 | 25.546 | 1.00 33.06 |
| ATOM | 1572 | O | HOH | Z | 140 | −4.102 | −2.547 | −0.245 | 1.00 32.75 |
| ATOM | 1573 | O | HOH | Z | 141 | −9.581 | −5.177 | 30.449 | 1.00 32.14 |
| ATOM | 1574 | O | HOH | Z | 142 | 5.765 | −21.459 | 11.112 | 1.00 32.28 |
| ATOM | 1575 | O | HOH | Z | 143 | −7.145 | −10.843 | 13.347 | 1.00 38.51 |
| END | | | | | | | | | |

TABLE 2

REMARK Written by O version 9.0.7
CRYST1    41.792    40.008    52.071    90.00   105.83    90.00

TABLE 2-continued

| | | | | | | | | | |
|---|---|---|---|---|---|---|---|---|---|
| ORIGX1 | 1.000000 | 0.000000 | 0.000000 | 0.00000 | | | | | |
| ORIGX2 | 0.000000 | 1.000000 | 0.000000 | 0.00000 | | | | | |
| ORIGX3 | 0.000000 | 0.000000 | 1.000000 | 0.00000 | | | | | |
| SCALE1 | 0.023928 | −0.000001 | 0.006784 | 0.00000 | | | | | |
| SCALE2 | 0.000000 | 0.024995 | −0.000001 | 0.00000 | | | | | |
| SCALE3 | 0.000000 | 0.000000 | 0.019961 | 0.00000 | | | | | |
| ATOM | 1 | N | ALA | A | 1 | 15.756 | 6.560 | −10.373 | 1.00 30.78 N |
| ATOM | 2 | CA | ALA | A | 1 | 16.093 | 6.323 | −8.944 | 1.00 29.95 C |
| ATOM | 3 | CB | ALA | A | 1 | 15.708 | 7.535 | −8.107 | 1.00 30.54 C |
| ATOM | 4 | C | ALA | A | 1 | 15.397 | 5.066 | −8.426 | 1.00 29.34 C |
| ATOM | 5 | O | ALA | A | 1 | 14.165 | 4.991 | −8.415 | 1.00 29.88 O |
| ATOM | 6 | N | ALA | A | 2 | 16.190 | 4.079 | −8.013 | 1.00 28.31 N |
| ATOM | 7 | CA | ALA | A | 2 | 15.653 | 2.839 | −7.447 | 1.00 26.70 C |
| ATOM | 8 | CB | ALA | A | 2 | 16.739 | 1.776 | −7.330 | 1.00 27.15 C |
| ATOM | 9 | C | ALA | A | 2 | 15.066 | 3.147 | −6.080 | 1.00 25.29 C |
| ATOM | 10 | O | ALA | A | 2 | 15.671 | 3.887 | −5.294 | 1.00 25.34 O |
| ATOM | 11 | N | ALA | A | 3 | 13.888 | 2.584 | −5.813 | 1.00 23.09 N |
| ATOM | 12 | CA | ALA | A | 3 | 13.185 | 2.797 | −4.545 | 1.00 21.06 C |
| ATOM | 13 | CB | ALA | A | 3 | 11.794 | 2.144 | −4.577 | 1.00 21.37 C |
| ATOM | 14 | C | ALA | A | 3 | 13.992 | 2.272 | −3.360 | 1.00 19.51 C |
| ATOM | 15 | O | ALA | A | 3 | 14.532 | 1.151 | −3.409 | 1.00 21.10 O |
| ATOM | 16 | N | ILE | A | 4 | 14.103 | 3.097 | −2.322 | 1.00 16.92 N |
| ATOM | 17 | CA | ILE | A | 4 | 14.495 | 2.610 | −1.001 | 1.00 15.02 C |
| ATOM | 18 | CB | ILE | A | 4 | 14.648 | 3.775 | −0.026 | 1.00 14.41 C |
| ATOM | 19 | CG1 | ILE | A | 4 | 15.895 | 4.579 | −0.429 | 1.00 16.51 C |
| ATOM | 20 | CD1 | ILE | A | 4 | 16.154 | 5.841 | 0.397 | 1.00 16.77 C |
| ATOM | 21 | CG2 | ILE | A | 4 | 14.740 | 3.274 | 1.433 | 1.00 15.96 C |
| ATOM | 22 | C | ILE | A | 4 | 13.388 | 1.675 | −0.542 | 1.00 14.20 C |
| ATOM | 23 | O | ILE | A | 4 | 12.232 | 2.101 | −0.406 | 1.00 15.07 O |
| ATOM | 24 | N | LYS | A | 5 | 13.726 | 0.408 | −0.273 | 1.00 12.22 N |
| ATOM | 25 | CA | LYS | A | 5 | 12.723 | −0.574 | 0.144 | 1.00 11.59 C |
| ATOM | 26 | CB | LYS | A | 5 | 13.060 | −1.966 | −0.389 | 1.00 11.41 C |
| ATOM | 27 | CG | LYS | A | 5 | 12.127 | −3.072 | 0.138 | 1.00 11.13 C |
| ATOM | 28 | CD | LYS | A | 5 | 12.354 | −4.367 | −0.588 | 1.00 12.02 C |
| ATOM | 29 | CE | LYS | A | 5 | 11.520 | −5.470 | 0.029 | 1.00 13.44 C |
| ATOM | 30 | NZ | LYS | A | 5 | 11.555 | −6.719 | −0.805 | 1.00 14.02 N |
| ATOM | 31 | C | LYS | A | 5 | 12.599 | −0.604 | 1.665 | 1.00 11.00 C |
| ATOM | 32 | O | LYS | A | 5 | 13.549 | −0.951 | 2.376 | 1.00 11.63 O |
| ATOM | 33 | N | CYS | A | 6 | 11.416 | −0.249 | 2.160 | 1.00 10.99 N |
| ATOM | 34 | CA | CYS | A | 6 | 11.150 | −0.184 | 3.592 | 1.00 10.47 C |
| ATOM | 35 | CB | CYS | A | 6 | 10.616 | 1.202 | 3.918 | 1.00 11.97 C |
| ATOM | 36 | SG | CYS | A | 6 | 10.107 | 1.479 | 5.616 | 1.00 12.97 S |
| ATOM | 37 | C | CYS | A | 6 | 10.108 | −1.234 | 3.915 | 1.00 10.18 C |
| ATOM | 38 | O | CYS | A | 6 | 8.997 | −1.192 | 3.382 | 1.00 10.84 O |
| ATOM | 39 | N | VAL | A | 7 | 10.453 | −2.173 | 4.789 | 1.00 10.01 N |
| ATOM | 40 | CA | VAL | A | 7 | 9.549 | −3.260 | 5.155 | 1.00 9.99 C |
| ATOM | 41 | CB | VAL | A | 7 | 10.261 | −4.622 | 5.022 | 1.00 11.17 C |
| ATOM | 42 | CG1 | VAL | A | 7 | 9.362 | −5.747 | 5.495 | 1.00 12.37 C |
| ATOM | 43 | CG2 | VAL | A | 7 | 10.680 | −4.873 | 3.596 | 1.00 12.17 C |
| ATOM | 44 | C | VAL | A | 7 | 9.052 | −3.010 | 6.579 | 1.00 10.17 C |
| ATOM | 45 | O | VAL | A | 7 | 9.833 | −2.691 | 7.463 | 1.00 10.48 O |
| ATOM | 46 | N | VAL | A | 8 | 7.758 | −3.159 | 6.798 | 1.00 10.12 N |
| ATOM | 47 | CA | VAL | A | 8 | 7.114 | −2.817 | 8.057 | 1.00 10.09 C |
| ATOM | 48 | CB | VAL | A | 8 | 5.893 | −1.924 | 7.771 | 1.00 10.08 C |
| ATOM | 49 | CG1 | VAL | A | 8 | 5.184 | −1.529 | 9.081 | 1.00 10.78 C |
| ATOM | 50 | CG2 | VAL | A | 8 | 6.324 | −0.697 | 6.939 | 1.00 11.24 C |
| ATOM | 51 | C | VAL | A | 8 | 6.658 | −4.129 | 8.684 | 1.00 9.54 C |
| ATOM | 52 | O | VAL | A | 8 | 5.908 | −4.894 | 8.046 | 1.00 9.78 O |
| ATOM | 53 | N | VAL | A | 9 | 7.144 | −4.421 | 9.887 | 1.00 9.18 N |
| ATOM | 54 | CA | VAL | A | 9 | 6.827 | −5.669 | 10.590 | 1.00 9.67 C |
| ATOM | 55 | CB | VAL | A | 9 | 8.027 | −6.665 | 10.597 | 1.00 9.51 C |
| ATOM | 56 | CG1 | VAL | A | 9 | 8.500 | −6.952 | 9.170 | 1.00 11.60 C |
| ATOM | 57 | CG2 | VAL | A | 9 | 9.183 | −6.171 | 11.474 | 1.00 11.98 C |
| ATOM | 58 | C | VAL | A | 9 | 6.399 | −5.370 | 12.019 | 1.00 9.36 C |
| ATOM | 59 | O | VAL | A | 9 | 6.596 | −4.276 | 12.541 | 1.00 9.87 O |
| ATOM | 60 | N | GLY | A | 10 | 5.812 | −6.369 | 12.648 | 1.00 9.30 N |
| ATOM | 61 | CA | GLY | A | 10 | 5.346 | −6.288 | 14.024 | 1.00 10.14 C |
| ATOM | 62 | C | GLY | A | 10 | 4.095 | −7.136 | 14.205 | 1.00 9.38 C |
| ATOM | 63 | O | GLY | A | 10 | 3.500 | −7.647 | 13.243 | 1.00 9.61 O |
| ATOM | 64 | N | ASP | A | 11 | 3.702 | −7.283 | 15.466 | 1.00 9.39 N |
| ATOM | 65 | CA | ASP | A | 11 | 2.596 | −8.170 | 15.822 | 1.00 10.45 C |
| ATOM | 66 | CB | ASP | A | 11 | 2.329 | −8.105 | 17.323 | 1.00 10.06 C |
| ATOM | 67 | CG | ASP | A | 11 | 3.288 | −8.959 | 18.135 | 1.00 12.02 C |
| ATOM | 68 | OD1 | ASP | A | 11 | 4.248 | −9.545 | 17.584 | 1.00 12.12 O |
| ATOM | 69 | OD2 | ASP | A | 11 | 3.029 | −9.044 | 19.354 | 1.00 13.04 O |
| ATOM | 70 | C | ASP | A | 11 | 1.324 | −7.788 | 15.111 | 1.00 9.85 C |
| ATOM | 71 | O | ASP | A | 11 | 1.101 | −6.621 | 14.774 | 1.00 9.42 O |
| ATOM | 72 | N | GLY | A | 12 | 0.433 | −8.753 | 14.932 | 1.00 10.76 N |
| ATOM | 73 | CA | GLY | A | 12 | −0.908 | −8.453 | 14.437 | 1.00 10.53 C |

TABLE 2-continued

| ATOM | 74  | C   | GLY  | A | 12 | −1.572 | −7.408 | 15.312 | 1.00 | 10.68 | C |
|------|-----|-----|------|---|----|--------|--------|--------|------|-------|---|
| ATOM | 75  | O   | GLY  | A | 12 | −1.433 | −7.428 | 16.541 | 1.00 | 11.67 | O |
| ATOM | 76  | N   | ALA  | A | 13 | −2.290 | −6.488 | 14.674 | 1.00 | 10.27 | N |
| ATOM | 77  | CA  | ALA  | A | 13 | −3.124 | −5.478 | 15.320 | 1.00 | 10.10 | C |
| ATOM | 78  | CB  | ALA  | A | 13 | −4.081 | −6.090 | 16.347 | 1.00 | 11.47 | C |
| ATOM | 79  | C   | ALA  | A | 13 | −2.372 | −4.292 | 15.913 | 1.00 | 10.23 | C |
| ATOM | 80  | O   | ALA  | A | 13 | −2.991 | −3.454 | 16.586 | 1.00 | 11.32 | O |
| ATOM | 81  | N   | VAL  | A | 14 | −1.073 | −4.187 | 15.662 | 1.00 | 10.56 | N |
| ATOM | 82  | CA  | VAL  | A | 14 | −0.355 | −2.999 | 16.193 | 1.00 | 10.35 | C |
| ATOM | 83  | CB  | VAL  | A | 14 | 1.161  | −3.227 | 16.365 | 1.00 | 10.51 | C |
| ATOM | 84  | CG1 | VAL  | A | 14 | 1.444  | −4.399 | 17.307 | 1.00 | 11.36 | C |
| ATOM | 85  | CG2 | VAL  | A | 14 | 1.861  | −3.405 | 15.042 | 1.00 | 11.73 | C |
| ATOM | 86  | C   | VAL  | A | 14 | −0.617 | −1.727 | 15.403 | 1.00 | 10.69 | C |
| ATOM | 87  | O   | VAL  | A | 14 | −0.410 | −0.624 | 15.917 | 1.00 | 11.18 | O |
| ATOM | 88  | N   | GLY  | A | 15 | −1.108 | −1.859 | 14.176 | 1.00 | 9.47  | N |
| ATOM | 89  | CA  | GLY  | A | 15 | −1.432 | −0.721 | 13.333 | 1.00 | 10.07 | C |
| ATOM | 90  | C   | GLY  | A | 15 | −0.547 | −0.518 | 12.119 | 1.00 | 9.10  | C |
| ATOM | 91  | O   | GLY  | A | 15 | −0.502 | 0.581  | 11.585 | 1.00 | 9.75  | O |
| ATOM | 92  | N   | LYS  | A | 16 | 0.079  | −1.580 | 11.616 | 1.00 | 8.57  | N |
| ATOM | 93  | CA  | LYS  | A | 16 | 0.976  | −1.451 | 10.467 | 1.00 | 8.65  | C |
| ATOM | 94  | CB  | LYS  | A | 16 | 1.674  | −2.782 | 10.183 | 1.00 | 8.61  | C |
| ATOM | 95  | CG  | LYS  | A | 16 | 2.485  | −3.314 | 11.373 | 1.00 | 9.93  | C |
| ATOM | 96  | CD  | LYS  | A | 16 | 3.194  | −4.658 | 11.106 | 1.00 | 10.00 | C |
| ATOM | 97  | CE  | LYS  | A | 16 | 2.275  | −5.817 | 10.819 | 1.00 | 10.39 | C |
| ATOM | 98  | NZ  | LYS  | A | 16 | 1.366  | −6.104 | 11.952 | 1.00 | 9.45  | N |
| ATOM | 99  | C   | LYS  | A | 16 | 0.227  | −0.996 | 9.228  | 1.00 | 8.25  | C |
| ATOM | 100 | O   | LYS  | A | 16 | 0.641  | −0.060 | 8.535  | 1.00 | 8.46  | O |
| ATOM | 101 | N   | THR  | A | 17 | −0.875 | −1.672 | 8.912  | 1.00 | 8.80  | N |
| ATOM | 102 | CA  | THR  | A | 17 | −1.615 | −1.343 | 7.710  | 1.00 | 9.41  | C |
| ATOM | 103 | CB  | THR  | A | 17 | −2.689 | −2.400 | 7.503  | 1.00 | 8.99  | C |
| ATOM | 104 | OG1 | THR  | A | 17 | −2.020 | −3.677 | 7.367  | 1.00 | 9.21  | O |
| ATOM | 105 | CG2 | THR  | A | 17 | −3.503 | −2.155 | 6.248  | 1.00 | 10.06 | C |
| ATOM | 106 | C   | THR  | A | 17 | −2.204 | 0.070  | 7.800  | 1.00 | 8.93  | C |
| ATOM | 107 | O   | THR  | A | 17 | −2.136 | 0.834  | 6.828  | 1.00 | 9.41  | O |
| ATOM | 108 | N   | CYS  | A | 18 | −2.784 | 0.423  | 8.943  | 1.00 | 9.42  | N |
| ATOM | 109 | CA  | CYS  | A | 18 | −3.355 | 1.741  | 9.077  | 1.00 | 10.25 | C |
| ATOM | 110 | CB  | CYS  | A | 18 | −4.075 | 1.897  | 10.396 | 1.00 | 10.15 | C |
| ATOM | 111 | SG  | CYS  | A | 18 | −5.693 | 1.128  | 10.433 | 1.00 | 11.45 | S |
| ATOM | 112 | C   | CYS  | A | 18 | −2.296 | 2.805  | 8.984  | 1.00 | 10.14 | C |
| ATOM | 113 | O   | CYS  | A | 18 | −2.576 | 3.871  | 8.414  | 1.00 | 11.24 | O |
| ATOM | 114 | N   | LEU  | A | 19 | −1.114 | 2.611  | 9.549  | 1.00 | 10.34 | N |
| ATOM | 115 | CA  | LEU  | A | 19 | −0.175 | 3.719  | 9.443  | 1.00 | 11.62 | C |
| ATOM | 116 | C   | LEU  | A | 19 | 0.273  | 3.893  | 8.004  | 1.00 | 11.02 | C |
| ATOM | 117 | O   | LEU  | A | 19 | 0.512  | 5.022  | 7.575  | 1.00 | 11.14 | O |
| ATOM | 118 | CB  | LEU  | A | 19 | 1.025  | 3.494  | 10.365 | 1.00 | 12.92 | C |
| ATOM | 119 | CG  | LEU  | A | 19 | 1.988  | 2.375  | 9.965  | 1.00 | 20.00 | C |
| ATOM | 120 | CD1 | LEU  | A | 19 | 3.014  | 2.881  | 8.963  | 1.00 | 15.00 | C |
| ATOM | 121 | CD2 | LEU  | A | 19 | 2.677  | 1.795  | 11.190 | 1.00 | 20.00 | C |
| ATOM | 122 | N   | LEU  | A | 20 | 0.350  | 2.817  | 7.229  | 1.00 | 10.17 | N |
| ATOM | 123 | CA  | LEU  | A | 20 | 0.685  | 2.943  | 5.809  | 1.00 | 10.15 | C |
| ATOM | 124 | CB  | LEU  | A | 20 | 1.019  | 1.577  | 5.203  | 1.00 | 10.06 | C |
| ATOM | 125 | CG  | LEU  | A | 20 | 2.331  | 0.991  | 5.722  | 1.00 | 9.84  | C |
| ATOM | 126 | CD1 | LEU  | A | 20 | 2.432  | −0.485 | 5.309  | 1.00 | 12.20 | C |
| ATOM | 127 | CD2 | LEU  | A | 20 | 3.522  | 1.778  | 5.244  | 1.00 | 13.56 | C |
| ATOM | 128 | C   | LEU  | A | 20 | −0.421 | 3.631  | 5.007  | 1.00 | 10.29 | C |
| ATOM | 129 | O   | LEU  | A | 20 | −0.132 | 4.471  | 4.153  | 1.00 | 10.44 | O |
| ATOM | 130 | N   | ILE  | A | 21 | −1.669 | 3.293  | 5.279  | 1.00 | 10.12 | N |
| ATOM | 131 | CA  | ILE  | A | 21 | −2.789 | 3.912  | 4.590  | 1.00 | 10.14 | C |
| ATOM | 132 | CB  | ILE  | A | 21 | −4.093 | 3.182  | 4.880  | 1.00 | 10.76 | C |
| ATOM | 133 | CG1 | ILE  | A | 21 | −4.044 | 1.818  | 4.193  | 1.00 | 11.42 | C |
| ATOM | 134 | CD1 | ILE  | A | 21 | −5.125 | 0.806  | 4.611  | 1.00 | 13.68 | C |
| ATOM | 135 | CG2 | ILE  | A | 21 | −5.300 | 3.964  | 4.352  | 1.00 | 12.21 | C |
| ATOM | 136 | C   | ILE  | A | 21 | −2.883 | 5.381  | 4.987  | 1.00 | 9.92  | C |
| ATOM | 137 | O   | ILE  | A | 21 | −3.078 | 6.234  | 4.112  | 1.00 | 10.89 | O |
| ATOM | 138 | N   | SER  | A | 22 | −2.730 | 5.697  | 6.259  | 0.50 | 6.37  | N |
| ATOM | 139 | CA  | SER  | A | 22 | −2.774 | 7.094  | 6.668  | 0.50 | 6.91  | C |
| ATOM | 140 | CB  | SER  | A | 22 | −2.711 | 7.193  | 8.182  | 0.50 | 6.73  | C |
| ATOM | 141 | OG  | ASER | A | 22 | −3.945 | 6.769  | 8.703  | 0.50 | 12.30 | O |
| ATOM | 141 | OG  | BSER | A | 22 | −2.826 | 8.535  | 8.599  | 0.50 | 11.36 | O |
| ATOM | 142 | C   | SER  | A | 22 | −1.642 | 7.893  | 6.019  | 0.50 | 6.92  | C |
| ATOM | 143 | O   | SER  | A | 22 | −1.841 | 9.031  | 5.573  | 0.50 | 5.72  | O |
| ATOM | 144 | N   | TYR  | A | 23 | −0.449 | 7.310  | 5.949  | 1.00 | 10.57 | N |
| ATOM | 145 | CA  | TYR  | A | 23 | 0.681  | 8.011  | 5.355  | 1.00 | 11.21 | C |
| ATOM | 146 | CB  | TYR  | A | 23 | 1.963  | 7.202  | 5.563  | 1.00 | 11.78 | C |
| ATOM | 147 | CG  | TYR  | A | 23 | 3.203  | 7.835  | 4.958  | 1.00 | 11.21 | C |
| ATOM | 148 | CD1 | TYR  | A | 23 | 3.655  | 9.080  | 5.389  | 1.00 | 11.88 | C |
| ATOM | 149 | CE1 | TYR  | A | 23 | 4.790  | 9.656  | 4.842  | 1.00 | 11.58 | C |
| ATOM | 150 | CZ  | TYR  | A | 23 | 5.513  | 8.958  | 3.884  | 1.00 | 11.24 | C |
| ATOM | 151 | OH  | TYR  | A | 23 | 6.654  | 9.496  | 3.318  | 1.00 | 12.92 | O |

TABLE 2-continued

| | | | | | | | | | | |
|---|---|---|---|---|---|---|---|---|---|---|
| ATOM | 152 | CE2 | TYR | A | 23 | 5.091 | 7.730 | 3.446 | 1.00 | 11.94 C |
| ATOM | 153 | CD2 | TYR | A | 23 | 3.953 | 7.167 | 3.992 | 1.00 | 11.19 C |
| ATOM | 154 | C | TYR | A | 23 | 0.479 | 8.286 | 3.869 | 1.00 | 12.23 C |
| ATOM | 155 | O | TYR | A | 23 | 0.855 | 9.356 | 3.343 | 1.00 | 13.13 O |
| ATOM | 156 | N | THR | A | 24 | −0.100 | 7.321 | 3.172 | 1.00 | 12.75 N |
| ATOM | 157 | CA | THR | A | 24 | −0.174 | 7.422 | 1.715 | 1.00 | 13.41 C |
| ATOM | 158 | CB | THR | A | 24 | −0.089 | 6.044 | 1.027 | 1.00 | 13.28 C |
| ATOM | 159 | OG1 | THR | A | 24 | −1.141 | 5.191 | 1.515 | 1.00 | 12.91 O |
| ATOM | 160 | CG2 | THR | A | 24 | 1.259 | 5.394 | 1.283 | 1.00 | 13.69 C |
| ATOM | 161 | C | THR | A | 24 | −1.406 | 8.160 | 1.230 | 1.00 | 14.93 C |
| ATOM | 162 | O | THR | A | 24 | −1.369 | 8.734 | 0.143 | 1.00 | 15.84 O |
| ATOM | 163 | N | THR | A | 25 | −2.477 | 8.181 | 2.022 | 1.00 | 14.62 N |
| ATOM | 164 | CA | THR | A | 25 | −3.754 | 8.759 | 1.589 | 1.00 | 15.96 C |
| ATOM | 165 | CB | THR | A | 25 | −4.890 | 7.711 | 1.573 | 1.00 | 15.67 C |
| ATOM | 166 | OG1 | THR | A | 25 | −5.267 | 7.374 | 2.925 | 1.00 | 16.40 O |
| ATOM | 167 | CG2 | THR | A | 25 | −4.498 | 6.474 | 0.785 | 1.00 | 15.73 C |
| ATOM | 168 | C | THR | A | 25 | −4.234 | 9.918 | 2.459 | 1.00 | 17.13 C |
| ATOM | 169 | O | THR | A | 25 | −5.197 | 10.593 | 2.089 | 1.00 | 17.10 O |
| ATOM | 170 | N | ASN | A | 26 | −3.626 | 10.103 | 3.626 | 1.00 | 18.51 N |
| ATOM | 171 | CA | ASN | A | 26 | −4.079 | 11.125 | 4.599 | 1.00 | 20.28 C |
| ATOM | 172 | CB | ASN | A | 26 | −3.885 | 12.548 | 4.040 | 1.00 | 21.61 C |
| ATOM | 173 | CG | ASN | A | 26 | −2.437 | 12.847 | 3.726 | 1.00 | 23.49 C |
| ATOM | 174 | OD1 | ASN | A | 26 | −2.108 | 13.367 | 2.650 | 1.00 | 27.93 O |
| ATOM | 175 | ND2 | ASN | A | 26 | −1.546 | 12.502 | 4.657 | 1.00 | 25.36 N |
| ATOM | 176 | C | ASN | A | 26 | −5.496 | 10.915 | 5.133 | 1.00 | 21.61 C |
| ATOM | 177 | O | ASN | A | 26 | −6.133 | 11.858 | 5.625 | 1.00 | 22.35 O |
| ATOM | 178 | N | ALA | A | 27 | −5.999 | 9.690 | 5.041 | 1.00 | 21.20 N |
| ATOM | 179 | CA | ALA | A | 27 | −7.270 | 9.364 | 5.665 | 1.00 | 21.90 C |
| ATOM | 180 | CB | ALA | A | 27 | −8.324 | 9.074 | 4.626 | 1.00 | 22.79 C |
| ATOM | 181 | C | ALA | A | 27 | −7.036 | 8.154 | 6.561 | 1.00 | 21.66 C |
| ATOM | 182 | O | ALA | A | 27 | −6.462 | 7.172 | 6.115 | 1.00 | 22.33 O |
| ATOM | 183 | N | PHE | A | 28 | −7.410 | 8.257 | 7.830 | 1.00 | 19.80 N |
| ATOM | 184 | CA | PHE | A | 28 | −7.389 | 7.090 | 8.715 | 1.00 | 17.99 C |
| ATOM | 185 | CB | PHE | A | 28 | −7.504 | 7.524 | 10.165 | 1.00 | 17.74 C |
| ATOM | 186 | CG | PHE | A | 28 | −7.569 | 6.380 | 11.124 | 1.00 | 16.32 C |
| ATOM | 187 | CD1 | PHE | A | 28 | −6.452 | 5.574 | 11.360 | 1.00 | 16.38 C |
| ATOM | 188 | CE1 | PHE | A | 28 | −6.516 | 4.504 | 12.268 | 1.00 | 14.61 C |
| ATOM | 189 | CZ | PHE | A | 28 | −7.713 | 4.235 | 12.930 | 1.00 | 16.53 C |
| ATOM | 190 | CE2 | PHE | A | 28 | −8.840 | 5.025 | 12.686 | 1.00 | 16.63 C |
| ATOM | 191 | CD2 | PHE | A | 28 | −8.759 | 6.095 | 11.783 | 1.00 | 15.57 C |
| ATOM | 192 | C | PHE | A | 28 | −8.544 | 6.155 | 8.342 | 1.00 | 17.65 C |
| ATOM | 193 | O | PHE | A | 28 | −9.707 | 6.563 | 8.334 | 1.00 | 17.89 O |
| ATOM | 194 | N | PRO | A | 29 | −8.237 | 4.897 | 7.982 | 1.00 | 16.19 N |
| ATOM | 195 | CA | PRO | A | 29 | −9.275 | 4.005 | 7.446 | 1.00 | 15.78 C |
| ATOM | 196 | CB | PRO | A | 29 | −8.457 | 3.021 | 6.603 | 1.00 | 14.96 C |
| ATOM | 197 | CG | PRO | A | 29 | −7.162 | 2.881 | 7.423 | 1.00 | 15.06 C |
| ATOM | 198 | CD | PRO | A | 29 | −6.889 | 4.281 | 7.933 | 1.00 | 15.67 C |
| ATOM | 199 | C | PRO | A | 29 | −10.111 | 3.225 | 8.456 | 1.00 | 16.17 C |
| ATOM | 200 | O | PRO | A | 29 | −11.017 | 2.496 | 8.064 | 1.00 | 16.59 O |
| ATOM | 201 | N | GLY | A | 30 | −9.816 | 3.343 | 9.741 | 1.00 | 16.47 N |
| ATOM | 202 | CA | GLY | A | 30 | −10.613 | 2.622 | 10.746 | 1.00 | 16.48 C |
| ATOM | 203 | C | GLY | A | 30 | −10.533 | 1.107 | 10.589 | 1.00 | 16.58 C |
| ATOM | 204 | O | GLY | A | 30 | −9.443 | 0.543 | 10.592 | 1.00 | 16.49 O |
| ATOM | 205 | N | GLU | A | 31 | −11.681 | 0.457 | 10.447 | 1.00 | 16.20 N |
| ATOM | 206 | CA | GLU | A | 31 | −11.752 | −0.994 | 10.256 | 1.00 | 16.97 C |
| ATOM | 207 | CB | GLU | A | 31 | −12.970 | −1.573 | 10.986 | 1.00 | 18.18 C |
| ATOM | 208 | CG | GLU | A | 31 | −13.022 | −1.270 | 12.463 | 1.00 | 22.26 C |
| ATOM | 209 | CD | GLU | A | 31 | −11.703 | −1.558 | 13.161 | 1.00 | 26.99 C |
| ATOM | 210 | OE1 | GLU | A | 31 | −11.201 | −2.698 | 13.072 | 1.00 | 30.47 O |
| ATOM | 211 | OE2 | GLU | A | 31 | −11.164 | −0.635 | 13.796 | 1.00 | 31.76 O |
| ATOM | 212 | C | GLU | A | 31 | −11.802 | −1.400 | 8.780 | 1.00 | 15.98 C |
| ATOM | 213 | O | GLU | A | 31 | −11.844 | −2.590 | 8.449 | 1.00 | 16.42 O |
| ATOM | 214 | N | TYR | A | 32 | −11.785 | −0.410 | 7.900 | 1.00 | 16.12 N |
| ATOM | 215 | CA | TYR | A | 32 | −11.922 | −0.686 | 6.468 | 1.00 | 17.14 C |
| ATOM | 216 | CB | TYR | A | 32 | −12.725 | 0.415 | 5.782 | 1.00 | 18.87 C |
| ATOM | 217 | CG | TYR | A | 32 | −14.165 | 0.415 | 6.240 | 1.00 | 20.99 C |
| ATOM | 218 | CD1 | TYR | A | 32 | −15.095 | −0.446 | 5.667 | 1.00 | 23.72 C |
| ATOM | 219 | CE1 | TYR | A | 32 | −16.417 | −0.460 | 6.093 | 1.00 | 26.05 C |
| ATOM | 220 | CZ | TYR | A | 32 | −16.819 | 0.403 | 7.097 | 1.00 | 24.58 C |
| ATOM | 221 | OH | TYR | A | 32 | −18.130 | 0.394 | 7.507 | 1.00 | 25.90 O |
| ATOM | 222 | CE2 | TYR | A | 32 | −15.913 | 1.267 | 7.697 | 1.00 | 23.82 C |
| ATOM | 223 | CD2 | TYR | A | 32 | −14.590 | 1.270 | 7.261 | 1.00 | 22.07 C |
| ATOM | 224 | C | TYR | A | 32 | −10.556 | −0.856 | 5.848 | 1.00 | 15.47 C |
| ATOM | 225 | O | TYR | A | 32 | −10.058 | −0.007 | 5.111 | 1.00 | 15.10 O |
| ATOM | 226 | N | ILE | A | 33 | −9.935 | −1.979 | 6.210 | 1.00 | 14.88 N |
| ATOM | 227 | CA | ILE | A | 33 | −8.540 | −2.215 | 5.873 | 1.00 | 14.90 C |
| ATOM | 228 | CB | ILE | A | 33 | −7.635 | −1.892 | 7.090 | 1.00 | 15.46 C |
| ATOM | 229 | CG1 | ILE | A | 33 | −8.141 | −2.656 | 8.343 | 1.00 | 17.42 C |
| ATOM | 230 | CD1 | ILE | A | 33 | −7.582 | −2.237 | 9.684 | 1.00 | 17.18 C |

TABLE 2-continued

| | | | | | | | | | | |
|---|---|---|---|---|---|---|---|---|---|---|
| ATOM | 231 | CG2 | ILE | A | 33 | −7.558 | −0.378 | 7.332 | 1.00 | 14.83 C |
| ATOM | 232 | C | ILE | A | 33 | −8.325 | −3.670 | 5.511 | 1.00 | 13.45 C |
| ATOM | 233 | O | ILE | A | 33 | −9.015 | −4.544 | 6.032 | 1.00 | 14.07 O |
| ATOM | 234 | N | PRO | A | 34 | −7.348 | −3.942 | 4.636 | 1.00 | 11.93 N |
| ATOM | 235 | CA | PRO | A | 34 | −6.936 | −5.310 | 4.369 | 1.00 | 11.72 C |
| ATOM | 236 | CB | PRO | A | 34 | −6.181 | −5.179 | 3.043 | 1.00 | 11.45 C |
| ATOM | 237 | CG | PRO | A | 34 | −5.535 | −3.809 | 3.161 | 1.00 | 12.24 C |
| ATOM | 238 | CD | PRO | A | 34 | −6.560 | −2.968 | 3.857 | 1.00 | 11.49 C |
| ATOM | 239 | C | PRO | A | 34 | −5.994 | −5.804 | 5.481 | 1.00 | 11.22 C |
| ATOM | 240 | O | PRO | A | 34 | −5.495 | −4.999 | 6.281 | 1.00 | 10.92 O |
| ATOM | 241 | N | THR | A | 35 | −5.698 | −7.102 | 5.504 | 1.00 | 10.66 N |
| ATOM | 242 | CA | THR | A | 35 | −4.644 | −7.603 | 6.366 | 1.00 | 10.28 C |
| ATOM | 243 | CB | THR | A | 35 | −4.530 | −9.132 | 6.220 | 1.00 | 10.32 C |
| ATOM | 244 | OG1 | THR | A | 35 | −5.787 | −9.740 | 6.564 | 1.00 | 10.83 O |
| ATOM | 245 | CG2 | THR | A | 35 | −3.440 | −9.719 | 7.103 | 1.00 | 10.76 C |
| ATOM | 246 | C | THR | A | 35 | −3.317 | −6.954 | 5.972 | 1.00 | 9.92 C |
| ATOM | 247 | O | THR | A | 35 | −2.573 | −6.502 | 6.855 | 1.00 | 9.20 O |
| ATOM | 248 | N | VAL | A | 36 | −3.026 | −6.915 | 4.676 | 1.00 | 9.92 N |
| ATOM | 249 | CA | VAL | A | 36 | −1.765 | −6.390 | 4.189 | 1.00 | 11.66 C |
| ATOM | 250 | CB | VAL | A | 36 | −0.911 | −7.532 | 3.564 | 1.00 | 12.55 C |
| ATOM | 251 | CG1 | VAL | A | 36 | 0.435 | −7.006 | 3.135 | 1.00 | 14.75 C |
| ATOM | 252 | CG2 | VAL | A | 36 | −0.764 | −8.749 | 4.538 | 1.00 | 13.86 C |
| ATOM | 253 | C | VAL | A | 36 | −2.045 | −5.353 | 3.100 | 1.00 | 11.71 C |
| ATOM | 254 | O | VAL | A | 36 | −2.736 | −5.644 | 2.124 | 1.00 | 12.92 O |
| ATOM | 255 | N | PHE | A | 37 | −1.555 | −4.136 | 3.293 | 1.00 | 11.91 N |
| ATOM | 256 | CA | PHE | A | 37 | −1.630 | −3.073 | 2.301 | 1.00 | 12.80 C |
| ATOM | 257 | CB | PHE | A | 37 | −0.957 | −1.854 | 2.933 | 1.00 | 13.56 C |
| ATOM | 258 | CG | PHE | A | 37 | −1.143 | −0.571 | 2.182 | 1.00 | 16.30 C |
| ATOM | 259 | CD1 | PHE | A | 37 | −2.405 | −0.166 | 1.753 | 1.00 | 19.42 C |
| ATOM | 260 | CE1 | PHE | A | 37 | −2.578 | 1.058 | 1.071 | 1.00 | 20.61 C |
| ATOM | 261 | CZ | PHE | A | 37 | −1.475 | 1.871 | 0.845 | 1.00 | 17.13 C |
| ATOM | 262 | CE2 | PHE | A | 37 | −0.211 | 1.483 | 1.264 | 1.00 | 17.41 C |
| ATOM | 263 | CD2 | PHE | A | 37 | −0.050 | 0.250 | 1.948 | 1.00 | 18.70 C |
| ATOM | 264 | C | PHE | A | 37 | −0.893 | −3.459 | 1.039 | 1.00 | 14.08 C |
| ATOM | 265 | O | PHE | A | 37 | 0.169 | −4.074 | 1.120 | 1.00 | 14.02 O |
| ATOM | 266 | N | ASP | A | 38 | −1.434 | −3.055 | −0.110 | 1.00 | 15.41 N |
| ATOM | 267 | CA | ASP | A | 38 | −0.772 | −3.259 | −1.404 | 1.00 | 17.12 C |
| ATOM | 268 | CB | ASP | A | 38 | −1.618 | −2.627 | −2.533 | 1.00 | 18.72 C |
| ATOM | 269 | CG | ASP | A | 38 | −2.911 | −3.389 | −2.846 | 1.00 | 23.03 C |
| ATOM | 270 | OD1 | ASP | A | 38 | −3.085 | −4.547 | −2.409 | 1.00 | 26.95 O |
| ATOM | 271 | OD2 | ASP | A | 38 | −3.757 | −2.798 | −3.563 | 1.00 | 28.04 O |
| ATOM | 272 | C | ASP | A | 38 | 0.616 | −2.577 | −1.389 | 1.00 | 16.38 C |
| ATOM | 273 | O | ASP | A | 38 | 0.804 | −1.560 | −0.735 | 1.00 | 16.07 O |
| ATOM | 274 | N | ASN | A | 39 | 1.584 | −3.135 | −2.099 | 1.00 | 16.55 N |
| ATOM | 275 | CA | ASN | A | 39 | 2.857 | −2.436 | −2.288 | 1.00 | 17.38 C |
| ATOM | 276 | CB | ASN | A | 39 | 3.694 | −3.191 | −3.309 | 1.00 | 18.41 C |
| ATOM | 277 | CG | ASN | A | 39 | 5.083 | −2.657 | −3.403 | 1.00 | 22.02 C |
| ATOM | 278 | OD1 | ASN | A | 39 | 5.471 | −2.085 | −4.423 | 1.00 | 26.34 O |
| ATOM | 279 | ND2 | ASN | A | 39 | 5.844 | −2.809 | −2.327 | 1.00 | 27.14 N |
| ATOM | 280 | C | ASN | A | 39 | 2.648 | −1.011 | −2.788 | 1.00 | 16.04 C |
| ATOM | 281 | O | ASN | A | 39 | 1.772 | −0.761 | −3.622 | 1.00 | 16.15 O |
| ATOM | 282 | N | TYR | A | 40 | 3.440 | −0.068 | −2.280 | 1.00 | 14.53 N |
| ATOM | 283 | CA | TYR | A | 40 | 3.306 | 1.337 | −2.665 | 1.00 | 14.34 C |
| ATOM | 284 | CB | TYR | A | 40 | 2.592 | 2.105 | −1.544 | 1.00 | 14.12 C |
| ATOM | 285 | CG | TYR | A | 40 | 2.419 | 3.582 | −1.815 | 1.00 | 14.39 C |
| ATOM | 286 | CD1 | TYR | A | 40 | 1.294 | 4.049 | −2.490 | 1.00 | 14.96 C |
| ATOM | 287 | CE1 | TYR | A | 40 | 1.125 | 5.409 | −2.749 | 1.00 | 14.64 C |
| ATOM | 288 | CZ | TYR | A | 40 | 2.090 | 6.291 | −2.330 | 1.00 | 15.18 C |
| ATOM | 289 | OH | TYR | A | 40 | 1.898 | 7.628 | −2.607 | 1.00 | 16.39 O |
| ATOM | 290 | CE2 | TYR | A | 40 | 3.220 | 5.859 | −1.665 | 1.00 | 14.84 C |
| ATOM | 291 | CD2 | TYR | A | 40 | 3.385 | 4.500 | −1.414 | 1.00 | 14.38 C |
| ATOM | 292 | C | TYR | A | 40 | 4.683 | 1.934 | −2.873 | 1.00 | 13.60 C |
| ATOM | 293 | O | TYR | A | 40 | 5.580 | 1.718 | −2.064 | 1.00 | 14.93 O |
| ATOM | 294 | N | SER | A | 41 | 4.875 | 2.685 | −3.951 | 1.00 | 12.48 N |
| ATOM | 295 | CA | SER | A | 41 | 6.077 | 3.495 | −4.068 | 1.00 | 13.53 C |
| ATOM | 296 | CB | SER | A | 41 | 7.158 | 2.872 | −4.960 | 1.00 | 14.96 C |
| ATOM | 297 | OG | SER | A | 41 | 6.766 | 2.869 | −6.306 | 1.00 | 19.82 O |
| ATOM | 298 | C | SER | A | 41 | 5.706 | 4.876 | −4.559 | 1.00 | 12.45 C |
| ATOM | 299 | O | SER | A | 41 | 4.742 | 5.037 | −5.308 | 1.00 | 13.38 O |
| ATOM | 300 | N | ALA | A | 42 | 6.485 | 5.856 | −4.136 | 1.00 | 11.65 N |
| ATOM | 301 | CA | ALA | A | 42 | 6.322 | 7.235 | −4.575 | 1.00 | 11.45 C |
| ATOM | 302 | CB | ALA | A | 42 | 5.093 | 7.881 | −3.900 | 1.00 | 12.12 C |
| ATOM | 303 | C | ALA | A | 42 | 7.555 | 8.004 | −4.206 | 1.00 | 11.86 C |
| ATOM | 304 | O | ALA | A | 42 | 8.337 | 7.574 | −3.341 | 1.00 | 11.97 O |
| ATOM | 305 | N | ASN | A | 43 | 7.743 | 9.139 | −4.864 | 1.00 | 11.38 N |
| ATOM | 306 | CA | ASN | A | 43 | 8.759 | 10.096 | −4.456 | 1.00 | 11.29 C |
| ATOM | 307 | CB | ASN | A | 43 | 9.150 | 11.013 | −5.625 | 1.00 | 12.66 C |
| ATOM | 308 | CG | ASN | A | 43 | 9.986 | 10.313 | −6.670 | 1.00 | 14.01 C |
| ATOM | 309 | OD1 | ASN | A | 43 | 10.362 | 9.142 | −6.535 | 1.00 | 15.75 O |

TABLE 2-continued

| ATOM | 310 | ND2 | ASN | A | 43 | 10.287 | 11.034 | −7.742 | 1.00 | 16.59 | N |
| ATOM | 311 | C | ASN | A | 43 | 8.258 | 10.943 | −3.315 | 1.00 | 11.75 | C |
| ATOM | 312 | O | ASN | A | 43 | 7.171 | 11.525 | −3.378 | 1.00 | 11.94 | O |
| ATOM | 313 | N | VAL | A | 44 | 9.056 | 11.010 | −2.257 | 1.00 | 11.62 | N |
| ATOM | 314 | CA | VAL | A | 44 | 8.733 | 11.826 | −1.097 | 1.00 | 13.22 | C |
| ATOM | 315 | CB | VAL | A | 44 | 8.432 | 10.946 | 0.147 | 1.00 | 14.92 | C |
| ATOM | 316 | CG1 | VAL | A | 44 | 7.320 | 9.959 | −0.145 | 1.00 | 16.55 | C |
| ATOM | 317 | CG2 | VAL | A | 44 | 9.626 | 10.198 | 0.556 | 1.00 | 15.99 | C |
| ATOM | 318 | C | VAL | A | 44 | 9.872 | 12.807 | −0.849 | 1.00 | 13.51 | C |
| ATOM | 319 | O | VAL | A | 44 | 11.029 | 12.488 | −1.103 | 1.00 | 13.42 | O |
| ATOM | 320 | N | MET | A | 45 | 9.541 | 13.990 | −0.353 | 1.00 | 14.85 | N |
| ATOM | 321 | CA | MET | A | 45 | 10.532 | 15.017 | −0.131 | 1.00 | 15.75 | C |
| ATOM | 322 | CB | MET | A | 45 | 9.877 | 16.407 | −0.141 | 1.00 | 16.60 | C |
| ATOM | 323 | CG | MET | A | 45 | 9.275 | 16.835 | −1.464 | 1.00 | 18.19 | C |
| ATOM | 324 | SD | MET | A | 45 | 10.418 | 16.742 | −2.826 | 1.00 | 21.74 | S |
| ATOM | 325 | CE | MET | A | 45 | 11.537 | 18.088 | −2.504 | 1.00 | 21.52 | C |
| ATOM | 326 | C | MET | A | 45 | 11.184 | 14.817 | 1.223 | 1.00 | 16.61 | C |
| ATOM | 327 | O | MET | A | 45 | 10.500 | 14.803 | 2.243 | 1.00 | 16.90 | O |
| ATOM | 328 | N | VAL | A | 46 | 12.506 | 14.689 | 1.220 | 1.00 | 16.86 | N |
| ATOM | 329 | CA | VAL | A | 46 | 13.286 | 14.637 | 2.455 | 1.00 | 18.05 | C |
| ATOM | 330 | CB | VAL | A | 46 | 13.720 | 13.181 | 2.816 | 1.00 | 18.32 | C |
| ATOM | 331 | CG1 | VAL | A | 46 | 14.477 | 13.146 | 4.150 | 1.00 | 19.56 | C |
| ATOM | 332 | CG2 | VAL | A | 46 | 12.501 | 12.288 | 2.910 | 1.00 | 18.50 | C |
| ATOM | 333 | C | VAL | A | 46 | 14.496 | 15.537 | 2.257 | 1.00 | 18.60 | C |
| ATOM | 334 | O | VAL | A | 46 | 15.222 | 15.388 | 1.288 | 1.00 | 18.55 | O |
| ATOM | 335 | N | ASP | A | 47 | 14.688 | 16.473 | 3.182 | 1.00 | 20.72 | N |
| ATOM | 336 | CA | ASP | A | 47 | 15.862 | 17.352 | 3.181 | 1.00 | 22.66 | C |
| ATOM | 337 | CB | ASP | A | 47 | 17.130 | 16.577 | 3.610 | 1.00 | 23.69 | C |
| ATOM | 338 | CG | ASP | A | 47 | 16.997 | 15.961 | 5.012 | 1.00 | 25.31 | C |
| ATOM | 339 | OD1 | ASP | A | 47 | 16.347 | 16.575 | 5.881 | 1.00 | 28.40 | O |
| ATOM | 340 | OD2 | ASP | A | 47 | 17.535 | 14.861 | 5.241 | 1.00 | 27.71 | O |
| ATOM | 341 | C | ASP | A | 47 | 16.010 | 18.073 | 1.832 | 1.00 | 23.13 | C |
| ATOM | 342 | O | ASP | A | 47 | 17.114 | 18.237 | 1.308 | 1.00 | 24.89 | O |
| ATOM | 343 | N | GLY | A | 48 | 14.866 | 18.474 | 1.274 | 1.00 | 23.26 | N |
| ATOM | 344 | CA | GLY | A | 48 | 14.804 | 19.254 | 0.030 | 1.00 | 23.23 | C |
| ATOM | 345 | C | GLY | A | 48 | 14.817 | 18.500 | −1.290 | 1.00 | 22.89 | C |
| ATOM | 346 | O | GLY | A | 48 | 14.720 | 19.114 | −2.359 | 1.00 | 23.43 | O |
| ATOM | 347 | N | LYS | A | 49 | 14.931 | 17.174 | −1.225 | 1.00 | 21.63 | N |
| ATOM | 348 | CA | LYS | A | 49 | 15.128 | 16.356 | −2.417 | 1.00 | 20.77 | C |
| ATOM | 349 | CB | LYS | A | 49 | 16.524 | 15.704 | −2.387 | 1.00 | 21.96 | C |
| ATOM | 350 | CG | LYS | A | 49 | 17.693 | 16.691 | −2.355 | 1.00 | 25.00 | C |
| ATOM | 351 | CD | LYS | A | 49 | 17.878 | 17.387 | −3.687 | 1.00 | 28.52 | C |
| ATOM | 352 | CE | LYS | A | 49 | 18.984 | 18.427 | −3.611 | 1.00 | 31.72 | C |
| ATOM | 353 | NZ | LYS | A | 49 | 19.420 | 18.893 | −4.957 | 1.00 | 32.72 | N |
| ATOM | 354 | C | LYS | A | 49 | 14.071 | 15.257 | −2.519 | 1.00 | 18.40 | C |
| ATOM | 355 | O | LYS | A | 49 | 13.704 | 14.664 | −1.506 | 1.00 | 18.26 | O |
| ATOM | 356 | N | PRO | A | 50 | 13.598 | 14.964 | −3.737 | 1.00 | 16.50 | N |
| ATOM | 357 | CA | PRO | A | 50 | 12.664 | 13.852 | −3.850 | 1.00 | 16.28 | C |
| ATOM | 358 | CB | PRO | A | 50 | 12.025 | 14.056 | −5.224 | 1.00 | 16.17 | C |
| ATOM | 359 | CG | PRO | A | 50 | 13.039 | 14.829 | −6.022 | 1.00 | 16.50 | C |
| ATOM | 360 | CD | PRO | A | 50 | 13.882 | 15.601 | −5.043 | 1.00 | 17.02 | C |
| ATOM | 361 | C | PRO | A | 50 | 13.405 | 12.521 | −3.781 | 1.00 | 15.94 | C |
| ATOM | 362 | O | PRO | A | 50 | 14.446 | 12.339 | −4.434 | 1.00 | 18.03 | O |
| ATOM | 363 | N | VAL | A | 51 | 12.881 | 11.601 | −2.980 | 1.00 | 14.23 | N |
| ATOM | 364 | CA | VAL | A | 51 | 13.484 | 10.289 | −2.796 | 1.00 | 13.32 | C |
| ATOM | 365 | CB | VAL | A | 51 | 14.018 | 10.128 | −1.347 | 1.00 | 14.06 | C |
| ATOM | 366 | CG1 | VAL | A | 51 | 14.630 | 8.741 | −1.116 | 1.00 | 14.65 | C |
| ATOM | 367 | CG2 | VAL | A | 51 | 15.039 | 11.224 | −1.013 | 1.00 | 16.35 | C |
| ATOM | 368 | C | VAL | A | 51 | 12.425 | 9.243 | −3.075 | 1.00 | 12.07 | C |
| ATOM | 369 | O | VAL | A | 51 | 11.325 | 9.309 | −2.516 | 1.00 | 12.14 | O |
| ATOM | 370 | N | ASN | A | 52 | 12.744 | 8.285 | −3.932 | 1.00 | 12.03 | N |
| ATOM | 371 | CA | ASN | A | 52 | 11.818 | 7.204 | −4.242 | 1.00 | 12.95 | C |
| ATOM | 372 | CB | ASN | A | 52 | 12.243 | 6.548 | −5.546 | 1.00 | 14.19 | C |
| ATOM | 373 | CG | ASN | A | 52 | 11.205 | 5.577 | −6.094 | 1.00 | 17.09 | C |
| ATOM | 374 | OD1 | ASN | A | 52 | 10.051 | 5.567 | −5.665 | 1.00 | 22.79 | O |
| ATOM | 375 | ND2 | ASN | A | 52 | 11.606 | 4.783 | −7.073 | 1.00 | 21.92 | N |
| ATOM | 376 | C | ASN | A | 52 | 11.778 | 6.192 | −3.087 | 1.00 | 12.56 | C |
| ATOM | 377 | O | ASN | A | 52 | 12.827 | 5.616 | −2.720 | 1.00 | 13.33 | O |
| ATOM | 378 | N | LEU | A | 53 | 10.601 | 6.057 | −2.484 | 1.00 | 11.75 | N |
| ATOM | 379 | CA | LEU | A | 53 | 10.391 | 5.213 | −1.318 | 1.00 | 11.92 | C |
| ATOM | 380 | CB | LEU | A | 53 | 9.909 | 6.087 | −0.151 | 1.00 | 12.50 | C |
| ATOM | 381 | CG | LEU | A | 53 | 9.552 | 5.350 | 1.135 | 1.00 | 11.65 | C |
| ATOM | 382 | CD1 | LEU | A | 53 | 10.788 | 4.694 | 1.770 | 1.00 | 13.65 | C |
| ATOM | 383 | CD2 | LEU | A | 53 | 8.882 | 6.340 | 2.104 | 1.00 | 14.03 | C |
| ATOM | 384 | C | LEU | A | 53 | 9.375 | 4.114 | −1.622 | 1.00 | 11.73 | C |
| ATOM | 385 | O | LEU | A | 53 | 8.270 | 4.411 | −2.109 | 1.00 | 12.99 | O |
| ATOM | 386 | N | GLY | A | 54 | 9.734 | 2.860 | −1.350 | 1.00 | 11.07 | N |
| ATOM | 387 | CA | GLY | A | 54 | 8.833 | 1.725 | −1.562 | 1.00 | 11.07 | C |
| ATOM | 388 | C | GLY | A | 54 | 8.436 | 1.156 | −0.207 | 1.00 | 10.64 | C |

TABLE 2-continued

| ATOM | 389 | O | GLY | A | 54 | 9.300 | 0.945 | 0.648 | 1.00 | 11.82 | O |
|---|---|---|---|---|---|---|---|---|---|---|---|
| ATOM | 390 | N | LEU | A | 55 | 7.151 | 0.919 | 0.002 | 1.00 | 10.59 | N |
| ATOM | 391 | CA | LEU | A | 55 | 6.614 | 0.486 | 1.282 | 1.00 | 10.70 | C |
| ATOM | 392 | CB | LEU | A | 55 | 5.548 | 1.462 | 1.760 | 1.00 | 11.17 | C |
| ATOM | 393 | CG | LEU | A | 55 | 5.995 | 2.920 | 1.882 | 1.00 | 12.50 | C |
| ATOM | 394 | CD1 | LEU | A | 55 | 4.789 | 3.784 | 2.201 | 1.00 | 14.81 | C |
| ATOM | 395 | CD2 | LEU | A | 55 | 7.030 | 3.045 | 2.943 | 1.00 | 14.06 | C |
| ATOM | 396 | C | LEU | A | 55 | 6.001 | −0.904 | 1.150 | 1.00 | 9.88 | C |
| ATOM | 397 | O | LEU | A | 55 | 5.134 | −1.143 | 0.306 | 1.00 | 10.58 | O |
| ATOM | 398 | N | TRP | A | 56 | 6.446 | −1.790 | 2.037 | 1.00 | 10.18 | N |
| ATOM | 399 | CA | TRP | A | 56 | 6.061 | −3.200 | 2.047 | 1.00 | 10.73 | C |
| ATOM | 400 | CB | TRP | A | 56 | 7.266 | −4.100 | 1.740 | 1.00 | 12.68 | C |
| ATOM | 401 | CG | TRP | A | 56 | 7.846 | −3.871 | 0.371 | 1.00 | 13.71 | C |
| ATOM | 402 | CD1 | TRP | A | 56 | 8.413 | −2.719 | −0.105 | 1.00 | 15.24 | C |
| ATOM | 403 | NE1 | TRP | A | 56 | 8.836 | −2.897 | −1.391 | 1.00 | 17.10 | N |
| ATOM | 404 | CE2 | TRP | A | 56 | 8.578 | −4.193 | −1.757 | 1.00 | 16.99 | C |
| ATOM | 405 | CD2 | TRP | A | 56 | 7.961 | −4.831 | −0.658 | 1.00 | 19.16 | C |
| ATOM | 406 | CE3 | TRP | A | 56 | 7.604 | −6.180 | −0.763 | 1.00 | 20.14 | C |
| ATOM | 407 | CZ3 | TRP | A | 56 | 7.868 | −6.852 | −1.949 | 1.00 | 19.43 | C |
| ATOM | 408 | CH2 | TRP | A | 56 | 8.489 | −6.193 | −3.031 | 1.00 | 18.67 | C |
| ATOM | 409 | CZ2 | TRP | A | 56 | 8.853 | −4.868 | −2.955 | 1.00 | 18.68 | C |
| ATOM | 410 | C | TRP | A | 56 | 5.470 | −3.549 | 3.410 | 1.00 | 10.65 | C |
| ATOM | 411 | O | TRP | A | 56 | 6.201 | −3.684 | 4.391 | 1.00 | 11.81 | O |
| ATOM | 412 | N | ASP | A | 57 | 4.172 | −3.756 | 3.441 | 1.00 | 10.06 | N |
| ATOM | 413 | CA | ASP | A | 57 | 3.465 | −4.187 | 4.637 | 1.00 | 9.81 | C |
| ATOM | 414 | CB | ASP | A | 57 | 1.994 | −3.820 | 4.461 | 1.00 | 10.02 | C |
| ATOM | 415 | CG | ASP | A | 57 | 1.179 | −3.832 | 5.749 | 1.00 | 9.84 | C |
| ATOM | 416 | OD1 | ASP | A | 57 | 1.699 | −4.104 | 6.842 | 1.00 | 10.07 | O |
| ATOM | 417 | OD2 | ASP | A | 57 | −0.047 | −3.614 | 5.611 | 1.00 | 10.00 | O |
| ATOM | 418 | C | ASP | A | 57 | 3.632 | −5.700 | 4.751 | 1.00 | 10.58 | C |
| ATOM | 419 | O | ASP | A | 57 | 3.901 | −6.383 | 3.766 | 1.00 | 11.80 | O |
| ATOM | 420 | N | THR | A | 58 | 3.486 | −6.225 | 5.960 | 1.00 | 10.01 | N |
| ATOM | 421 | CA | THR | A | 58 | 3.585 | −7.664 | 6.173 | 1.00 | 10.87 | C |
| ATOM | 422 | CB | THR | A | 58 | 4.964 | −8.090 | 6.735 | 1.00 | 11.02 | C |
| ATOM | 423 | OG1 | THR | A | 58 | 5.164 | −7.536 | 8.053 | 1.00 | 11.24 | O |
| ATOM | 424 | CG2 | THR | A | 58 | 6.097 | −7.729 | 5.792 | 1.00 | 11.90 | C |
| ATOM | 425 | C | THR | A | 58 | 2.514 | −8.075 | 7.151 | 1.00 | 10.83 | C |
| ATOM | 426 | O | THR | A | 58 | 1.956 | −7.241 | 7.867 | 1.00 | 11.29 | O |
| ATOM | 427 | N | ALA | A | 59 | 2.239 | −9.372 | 7.212 | 1.00 | 11.35 | N |
| ATOM | 428 | CA | ALA | A | 59 | 1.329 | −9.920 | 8.199 | 1.00 | 11.95 | C |
| ATOM | 429 | CB | ALA | A | 59 | 0.386 | −10.932 | 7.536 | 1.00 | 13.29 | C |
| ATOM | 430 | C | ALA | A | 59 | 2.173 | −10.583 | 9.284 | 1.00 | 11.57 | C |
| ATOM | 431 | O | ALA | A | 59 | 2.974 | −11.495 | 8.974 | 1.00 | 11.96 | O |
| ATOM | 432 | N | GLY | A | 60 | 2.009 | −10.130 | 10.526 | 1.00 | 11.72 | N |
| ATOM | 433 | CA | GLY | A | 60 | 2.897 | −10.527 | 11.600 | 1.00 | 12.73 | C |
| ATOM | 434 | C | GLY | A | 60 | 2.489 | −11.759 | 12.381 | 1.00 | 12.85 | C |
| ATOM | 435 | O | GLY | A | 60 | 3.301 | −12.278 | 13.147 | 1.00 | 13.80 | O |
| ATOM | 436 | N | GLN | A | 61 | 1.257 | −12.232 | 12.199 | 1.00 | 12.05 | N |
| ATOM | 437 | CA | GLN | A | 61 | 0.766 | −13.397 | 12.944 | 1.00 | 12.75 | C |
| ATOM | 438 | CB | GLN | A | 61 | −0.732 | −13.624 | 12.653 | 1.00 | 13.14 | C |
| ATOM | 439 | CG | GLN | A | 61 | −1.633 | −12.484 | 13.173 | 1.00 | 13.68 | C |
| ATOM | 440 | CD | GLN | A | 61 | −1.918 | −11.417 | 12.128 | 1.00 | 14.04 | C |
| ATOM | 441 | OE1 | GLN | A | 61 | −1.040 | −11.004 | 11.360 | 1.00 | 14.06 | O |
| ATOM | 442 | NE2 | GLN | A | 61 | −3.146 | −10.938 | 12.116 | 1.00 | 15.06 | N |
| ATOM | 443 | C | GLN | A | 61 | 1.556 | −14.631 | 12.593 | 1.00 | 14.06 | C |
| ATOM | 444 | O | GLN | A | 61 | 2.109 | −14.764 | 11.501 | 1.00 | 13.88 | O |
| ATOM | 445 | N | GLU | A | 62 | 1.565 | −15.564 | 13.546 | 1.00 | 14.98 | N |
| ATOM | 446 | CA | GLU | A | 62 | 2.299 | −16.825 | 13.410 | 1.00 | 17.27 | C |
| ATOM | 447 | CB | GLU | A | 62 | 2.075 | −17.709 | 14.636 | 1.00 | 17.00 | C |
| ATOM | 448 | CG | GLU | A | 62 | 2.893 | −18.988 | 14.598 | 1.00 | 21.33 | C |
| ATOM | 449 | CD | GLU | A | 62 | 2.667 | −19.900 | 15.785 | 1.00 | 21.12 | C |
| ATOM | 450 | OE1 | GLU | A | 62 | 1.627 | −19.786 | 16.462 | 1.00 | 25.59 | O |
| ATOM | 451 | OE2 | GLU | A | 62 | 3.548 | −20.752 | 16.008 | 1.00 | 25.60 | O |
| ATOM | 452 | C | GLU | A | 62 | 1.953 | −17.592 | 12.147 | 1.00 | 16.12 | C |
| ATOM | 453 | O | GLU | A | 62 | 2.821 | −18.207 | 11.536 | 1.00 | 15.90 | O |
| ATOM | 454 | N | ASP | A | 63 | 0.686 | −17.548 | 11.740 | 1.00 | 16.37 | N |
| ATOM | 455 | CA | ASP | A | 63 | 0.260 | −18.221 | 10.511 | 1.00 | 17.61 | C |
| ATOM | 456 | CB | ASP | A | 63 | −1.216 | −17.943 | 10.232 | 1.00 | 19.31 | C |
| ATOM | 457 | CG | ASP | A | 63 | −2.141 | −18.963 | 10.861 | 1.00 | 24.06 | C |
| ATOM | 458 | OD1 | ASP | A | 63 | −1.672 | −20.032 | 11.306 | 1.00 | 28.11 | O |
| ATOM | 459 | OD2 | ASP | A | 63 | −3.357 | −18.680 | 10.879 | 1.00 | 29.29 | O |
| ATOM | 460 | C | ASP | A | 63 | 1.048 | −17.822 | 9.269 | 1.00 | 15.86 | C |
| ATOM | 461 | O | ASP | A | 63 | 1.110 | −18.562 | 8.302 | 1.00 | 16.35 | O |
| ATOM | 462 | N | TYR | A | 64 | 1.621 | −16.614 | 9.283 | 1.00 | 14.65 | N |
| ATOM | 463 | CA | TYR | A | 64 | 2.334 | −16.086 | 8.127 | 1.00 | 13.33 | C |
| ATOM | 464 | CB | TYR | A | 64 | 1.964 | −14.616 | 7.880 | 1.00 | 12.64 | C |
| ATOM | 465 | CG | TYR | A | 64 | 0.479 | −14.387 | 7.710 | 1.00 | 12.50 | C |
| ATOM | 466 | CD1 | TYR | A | 64 | −0.148 | −14.596 | 6.492 | 1.00 | 12.77 | C |
| ATOM | 467 | CE1 | TYR | A | 64 | −1.531 | −14.375 | 6.350 | 1.00 | 14.98 | C |

TABLE 2-continued

| ATOM | 468 | CZ | TYR | A | 64 | −2.258 | −13.947 | 7.443 | 1.00 | 13.61 | C |
| ATOM | 469 | OH | TYR | A | 64 | −3.606 | −13.709 | 7.330 | 1.00 | 15.56 | O |
| ATOM | 470 | CE2 | TYR | A | 64 | −1.629 | −13.728 | 8.649 | 1.00 | 13.71 | C |
| ATOM | 471 | CD2 | TYR | A | 64 | −0.285 | −13.953 | 8.774 | 1.00 | 12.14 | C |
| ATOM | 472 | C | TYR | A | 64 | 3.837 | −16.189 | 8.260 | 1.00 | 13.33 | C |
| ATOM | 473 | O | TYR | A | 64 | 4.563 | −15.686 | 7.415 | 1.00 | 13.05 | O |
| ATOM | 474 | N | ASP | A | 65 | 4.306 | −16.880 | 9.300 | 1.00 | 13.58 | N |
| ATOM | 475 | CA | ASP | A | 65 | 5.748 | −16.919 | 9.584 | 1.00 | 14.85 | C |
| ATOM | 476 | CB | ASP | A | 65 | 6.018 | −17.727 | 10.861 | 1.00 | 15.32 | C |
| ATOM | 477 | CG | ASP | A | 65 | 5.757 | −16.951 | 12.136 | 1.00 | 16.90 | C |
| ATOM | 478 | OD1 | ASP | A | 65 | 5.384 | −15.753 | 12.094 | 1.00 | 16.97 | O |
| ATOM | 479 | OD2 | ASP | A | 65 | 5.906 | −17.558 | 13.226 | 1.00 | 20.20 | O |
| ATOM | 480 | C | ASP | A | 65 | 6.570 | −17.534 | 8.450 | 1.00 | 15.24 | C |
| ATOM | 481 | O | ASP | A | 65 | 7.710 | −17.143 | 8.218 | 1.00 | 15.20 | O |
| ATOM | 482 | N | ARG | A | 66 | 6.003 | −18.507 | 7.739 | 1.00 | 15.03 | N |
| ATOM | 483 | CA | ARG | A | 66 | 6.718 | −19.130 | 6.623 | 1.00 | 15.74 | C |
| ATOM | 484 | CB | ARG | A | 66 | 6.162 | −20.530 | 6.348 | 1.00 | 16.44 | C |
| ATOM | 485 | CG | ARG | A | 66 | 6.338 | −21.464 | 7.517 | 1.00 | 17.39 | C |
| ATOM | 486 | CD | ARG | A | 66 | 5.662 | −22.807 | 7.250 | 1.00 | 20.96 | C |
| ATOM | 487 | NE | ARG | A | 66 | 6.389 | −23.591 | 6.258 | 1.00 | 22.46 | N |
| ATOM | 488 | CZ | ARG | A | 66 | 7.469 | −24.325 | 6.534 | 1.00 | 23.29 | C |
| ATOM | 489 | NH1 | ARG | A | 66 | 7.945 | −24.376 | 7.776 | 1.00 | 23.36 | N |
| ATOM | 490 | NH2 | ARG | A | 66 | 8.070 | −25.000 | 5.568 | 1.00 | 26.82 | N |
| ATOM | 491 | C | ARG | A | 66 | 6.700 | −18.302 | 5.335 | 1.00 | 16.07 | C |
| ATOM | 492 | O | ARG | A | 66 | 7.597 | −18.415 | 4.503 | 1.00 | 17.45 | O |
| ATOM | 493 | N | LEU | A | 67 | 5.698 | −17.570 | 5.190 | 1.00 | 15.40 | N |
| ATOM | 494 | CA | LEU | A | 67 | 5.552 | −16.810 | 3.945 | 1.00 | 15.49 | C |
| ATOM | 495 | CB | LEU | A | 67 | 4.078 | −16.706 | 3.580 | 1.00 | 15.84 | C |
| ATOM | 496 | CG | LEU | A | 67 | 3.702 | −15.969 | 2.291 | 1.00 | 17.97 | C |
| ATOM | 497 | CD1 | LEU | A | 67 | 4.246 | −16.739 | 1.095 | 1.00 | 17.77 | C |
| ATOM | 498 | CD2 | LEU | A | 67 | 2.207 | −15.856 | 2.216 | 1.00 | 18.43 | C |
| ATOM | 499 | C | LEU | A | 67 | 6.174 | −15.422 | 4.023 | 1.00 | 15.73 | C |
| ATOM | 500 | O | LEU | A | 67 | 6.766 | −14.940 | 3.057 | 1.00 | 15.69 | O |
| ATOM | 501 | N | ARG | A | 68 | 6.056 | −14.807 | 5.202 | 1.00 | 16.73 | N |
| ATOM | 502 | CA | ARG | A | 68 | 6.505 | −13.442 | 5.402 | 1.00 | 17.12 | C |
| ATOM | 503 | CB | ARG | A | 68 | 6.233 | −13.038 | 6.851 | 1.00 | 17.50 | C |
| ATOM | 504 | CG | ARG | A | 68 | 6.684 | −11.644 | 7.216 | 1.00 | 14.25 | C |
| ATOM | 505 | CD | ARG | A | 68 | 6.307 | −11.334 | 8.660 | 1.00 | 14.22 | C |
| ATOM | 506 | NE | ARG | A | 68 | 6.888 | −12.277 | 9.614 | 1.00 | 15.63 | N |
| ATOM | 507 | CZ | ARG | A | 68 | 6.225 | −13.190 | 10.317 | 1.00 | 13.45 | C |
| ATOM | 508 | NH1 | ARG | A | 68 | 4.893 | −13.350 | 10.240 | 1.00 | 12.81 | N |
| ATOM | 509 | NH2 | ARG | A | 68 | 6.923 | −13.947 | 11.139 | 1.00 | 15.55 | N |
| ATOM | 510 | C | ARG | A | 68 | 7.959 | −13.205 | 4.964 | 1.00 | 17.61 | C |
| ATOM | 511 | O | ARG | A | 68 | 8.256 | −12.166 | 4.383 | 1.00 | 17.22 | O |
| ATOM | 512 | N | PRO | A | 69 | 8.877 | −14.153 | 5.209 | 1.00 | 17.60 | N |
| ATOM | 513 | CA | PRO | A | 69 | 10.254 | −13.896 | 4.771 | 1.00 | 18.02 | C |
| ATOM | 514 | CB | PRO | A | 69 | 11.036 | −15.080 | 5.357 | 1.00 | 18.83 | C |
| ATOM | 515 | CG | PRO | A | 69 | 10.180 | −15.514 | 6.539 | 1.00 | 19.69 | C |
| ATOM | 516 | CD | PRO | A | 69 | 8.793 | −15.412 | 5.977 | 1.00 | 18.13 | C |
| ATOM | 517 | C | PRO | A | 69 | 10.481 | −13.723 | 3.251 | 1.00 | 17.20 | C |
| ATOM | 518 | O | PRO | A | 69 | 11.544 | −13.234 | 2.850 | 1.00 | 17.02 | O |
| ATOM | 519 | N | LEU | A | 70 | 9.503 | −14.098 | 2.414 | 1.00 | 16.34 | N |
| ATOM | 520 | CA | LEU | A | 70 | 9.606 | −13.778 | 0.985 | 1.00 | 15.96 | C |
| ATOM | 521 | CB | LEU | A | 70 | 8.468 | −14.410 | 0.185 | 1.00 | 16.34 | C |
| ATOM | 522 | CG | LEU | A | 70 | 8.755 | −15.829 | −0.321 | 1.00 | 19.86 | C |
| ATOM | 523 | CD1 | LEU | A | 70 | 8.815 | −16.809 | 0.828 | 1.00 | 22.48 | C |
| ATOM | 524 | CD2 | LEU | A | 70 | 7.669 | −16.218 | −1.308 | 1.00 | 21.49 | C |
| ATOM | 525 | C | LEU | A | 70 | 9.608 | −12.276 | 0.731 | 1.00 | 14.54 | C |
| ATOM | 526 | O | LEU | A | 70 | 9.965 | −11.853 | −0.361 | 1.00 | 15.20 | O |
| ATOM | 527 | N | SER | A | 71 | 9.188 | −11.487 | 1.722 | 1.00 | 13.51 | N |
| ATOM | 528 | CA | SER | A | 71 | 9.200 | −10.014 | 1.624 | 1.00 | 14.79 | C |
| ATOM | 529 | CB | SER | A | 71 | 8.211 | −9.408 | 2.624 | 1.00 | 14.76 | C |
| ATOM | 530 | OG | SER | A | 71 | 6.920 | −9.946 | 2.432 | 1.00 | 19.09 | O |
| ATOM | 531 | C | SER | A | 71 | 10.550 | −9.367 | 1.891 | 1.00 | 13.58 | C |
| ATOM | 532 | O | SER | A | 71 | 10.753 | −8.216 | 1.533 | 1.00 | 13.44 | O |
| ATOM | 533 | N | TYR | A | 72 | 11.469 | −10.086 | 2.540 | 1.00 | 13.81 | N |
| ATOM | 534 | CA | TYR | A | 72 | 12.729 | −9.472 | 2.994 | 1.00 | 13.60 | C |
| ATOM | 535 | CB | TYR | A | 72 | 13.329 | −10.252 | 4.171 | 1.00 | 14.71 | C |
| ATOM | 536 | CG | TYR | A | 72 | 12.553 | −10.168 | 5.464 | 1.00 | 12.94 | C |
| ATOM | 537 | CD1 | TYR | A | 72 | 12.266 | −8.937 | 6.064 | 1.00 | 13.82 | C |
| ATOM | 538 | CE1 | TYR | A | 72 | 11.587 | −8.877 | 7.270 | 1.00 | 13.38 | C |
| ATOM | 539 | CZ | TYR | A | 72 | 11.183 | −10.045 | 7.884 | 1.00 | 12.61 | C |
| ATOM | 540 | OH | TYR | A | 72 | 10.514 | −9.929 | 9.067 | 1.00 | 15.65 | O |
| ATOM | 541 | CE2 | TYR | A | 72 | 11.462 | −11.272 | 7.320 | 1.00 | 13.90 | C |
| ATOM | 542 | CD2 | TYR | A | 72 | 12.163 | −11.316 | 6.122 | 1.00 | 12.90 | C |
| ATOM | 543 | C | TYR | A | 72 | 13.852 | −9.223 | 1.969 | 1.00 | 14.07 | C |
| ATOM | 544 | O | TYR | A | 72 | 14.681 | −8.359 | 2.209 | 1.00 | 14.07 | O |
| ATOM | 545 | N | PRO | A | 73 | 13.950 | −10.022 | 0.885 | 1.00 | 15.01 | N |
| ATOM | 546 | CA | PRO | A | 73 | 15.057 | −9.728 | −0.024 | 1.00 | 15.59 | C |

TABLE 2-continued

| ATOM | 547 | CB | PRO | A | 73 | 14.766 | −10.640 | −1.217 | 1.00 | 15.64 | C |
|---|---|---|---|---|---|---|---|---|---|---|---|
| ATOM | 548 | CG | PRO | A | 73 | 14.149 | −11.831 | −0.575 | 1.00 | 17.21 | C |
| ATOM | 549 | CD | PRO | A | 73 | 13.205 | −11.212 | 0.435 | 1.00 | 16.17 | C |
| ATOM | 550 | C | PRO | A | 73 | 15.148 | −8.278 | −0.458 | 1.00 | 15.42 | C |
| ATOM | 551 | O | PRO | A | 73 | 14.136 | −7.634 | −0.763 | 1.00 | 15.01 | O |
| ATOM | 552 | N | GLN | A | 74 | 16.376 | −7.776 | −0.484 | 1.00 | 14.91 | N |
| ATOM | 553 | CA | GLN | A | 74 | 16.687 | −6.420 | −0.946 | 1.00 | 15.51 | C |
| ATOM | 554 | CB | GLN | A | 74 | 16.264 | −6.223 | −2.408 | 1.00 | 16.44 | C |
| ATOM | 555 | CG | GLN | A | 74 | 16.882 | −7.245 | −3.386 | 1.00 | 19.27 | C |
| ATOM | 556 | CD | GLN | A | 74 | 15.910 | −8.340 | −3.803 | 1.00 | 24.79 | C |
| ATOM | 557 | OE1 | GLN | A | 74 | 14.722 | −8.088 | −4.031 | 1.00 | 27.77 | O |
| ATOM | 558 | NE2 | GLN | A | 74 | 16.414 | −9.564 | −3.926 | 1.00 | 26.38 | N |
| ATOM | 559 | C | GLN | A | 74 | 16.139 | −5.310 | −0.045 | 1.00 | 14.57 | C |
| ATOM | 560 | O | GLN | A | 74 | 16.047 | −4.151 | −0.436 | 1.00 | 15.13 | O |
| ATOM | 561 | N | THR | A | 75 | 15.809 | −5.655 | 1.186 | 1.00 | 13.90 | N |
| ATOM | 562 | CA | THR | A | 75 | 15.355 | −4.625 | 2.129 | 1.00 | 13.47 | C |
| ATOM | 563 | CB | THR | A | 75 | 14.808 | −5.261 | 3.430 | 1.00 | 13.21 | C |
| ATOM | 564 | OG1 | THR | A | 75 | 13.662 | −6.056 | 3.114 | 1.00 | 13.74 | O |
| ATOM | 565 | CG2 | THR | A | 75 | 14.403 | −4.203 | 4.454 | 1.00 | 13.03 | C |
| ATOM | 566 | C | THR | A | 75 | 16.460 | −3.634 | 2.453 | 1.00 | 13.15 | C |
| ATOM | 567 | O | THR | A | 75 | 17.611 | −4.037 | 2.727 | 1.00 | 14.79 | O |
| ATOM | 568 | N | ASP | A | 76 | 16.123 | −2.347 | 2.456 | 1.00 | 11.58 | N |
| ATOM | 569 | CA | ASP | A | 76 | 17.074 | −1.281 | 2.806 | 1.00 | 11.85 | C |
| ATOM | 570 | CB | ASP | A | 76 | 16.955 | −0.108 | 1.828 | 1.00 | 11.89 | C |
| ATOM | 571 | CG | ASP | A | 76 | 17.315 | −0.498 | 0.424 | 1.00 | 14.34 | C |
| ATOM | 572 | OD1 | ASP | A | 76 | 18.452 | −0.984 | 0.219 | 1.00 | 17.00 | O |
| ATOM | 573 | OD2 | ASP | A | 76 | 16.471 | −0.378 | −0.493 | 1.00 | 13.48 | O |
| ATOM | 574 | C | ASP | A | 76 | 16.887 | −0.771 | 4.228 | 1.00 | 12.51 | C |
| ATOM | 575 | O | ASP | A | 76 | 17.849 | −0.324 | 4.846 | 1.00 | 13.24 | O |
| ATOM | 576 | N | VAL | A | 77 | 15.639 | −0.758 | 4.737 | 1.00 | 11.39 | N |
| ATOM | 577 | CA | VAL | A | 77 | 15.361 | −0.284 | 6.085 | 1.00 | 11.27 | C |
| ATOM | 578 | CB | VAL | A | 77 | 15.200 | 1.263 | 6.135 | 1.00 | 10.92 | C |
| ATOM | 579 | CG1 | VAL | A | 77 | 14.118 | 1.771 | 5.187 | 1.00 | 12.49 | C |
| ATOM | 580 | CG2 | VAL | A | 77 | 14.955 | 1.766 | 7.562 | 1.00 | 12.84 | C |
| ATOM | 581 | C | VAL | A | 77 | 14.122 | −1.007 | 6.562 | 1.00 | 11.19 | C |
| ATOM | 582 | O | VAL | A | 77 | 13.236 | −1.321 | 5.747 | 1.00 | 10.58 | O |
| ATOM | 583 | N | SER | A | 78 | 14.079 | −1.311 | 7.848 | 0.50 | 11.65 | N |
| ATOM | 584 | CA | SER | A | 78 | 12.903 | −1.976 | 8.404 | 0.50 | 12.31 | C |
| ATOM | 585 | CB | SER | A | 78 | 13.223 | −3.368 | 8.931 | 0.50 | 13.27 | C |
| ATOM | 586 | OG | ASER | A | 78 | 12.034 | −4.011 | 9.347 | 0.50 | 14.27 | O |
| ATOM | 586 | OG | BSER | A | 78 | 13.799 | −4.229 | 7.961 | 0.50 | 14.62 | O |
| ATOM | 587 | C | SER | A | 78 | 12.326 | −1.155 | 9.534 | 0.50 | 12.86 | C |
| ATOM | 588 | O | SER | A | 78 | 13.053 | −0.618 | 10.368 | 0.50 | 12.62 | O |
| ATOM | 589 | N | LEU | A | 79 | 11.006 | −1.103 | 9.591 | 1.00 | 11.00 | N |
| ATOM | 590 | CA | LEU | A | 79 | 10.301 | −0.542 | 10.721 | 1.00 | 11.67 | C |
| ATOM | 591 | CB | LEU | A | 79 | 9.103 | 0.295 | 10.283 | 1.00 | 11.27 | C |
| ATOM | 592 | CG | LEU | A | 79 | 9.342 | 1.390 | 9.249 | 1.00 | 13.99 | C |
| ATOM | 593 | CD1 | LEU | A | 79 | 8.087 | 2.201 | 9.048 | 1.00 | 15.38 | C |
| ATOM | 594 | CD2 | LEU | A | 79 | 10.467 | 2.331 | 9.646 | 1.00 | 15.86 | C |
| ATOM | 595 | C | LEU | A | 79 | 9.782 | −1.691 | 11.543 | 1.00 | 10.67 | C |
| ATOM | 596 | O | LEU | A | 79 | 8.967 | −2.466 | 11.060 | 1.00 | 12.30 | O |
| ATOM | 597 | N | ILE | A | 80 | 10.265 | −1.817 | 12.772 | 1.00 | 11.03 | N |
| ATOM | 598 | CA | ILE | A | 80 | 9.671 | −2.773 | 13.715 | 1.00 | 10.63 | C |
| ATOM | 599 | CB | ILE | A | 80 | 10.707 | −3.483 | 14.588 | 1.00 | 10.95 | C |
| ATOM | 600 | CG1 | ILE | A | 80 | 11.647 | −4.331 | 13.716 | 1.00 | 11.97 | C |
| ATOM | 601 | CD1 | ILE | A | 80 | 12.768 | −5.045 | 14.503 | 1.00 | 12.36 | C |
| ATOM | 602 | CG2 | ILE | A | 80 | 9.982 | −4.373 | 15.630 | 1.00 | 11.76 | C |
| ATOM | 603 | C | ILE | A | 80 | 8.685 | −2.013 | 14.569 | 1.00 | 10.30 | C |
| ATOM | 604 | O | ILE | A | 80 | 9.041 | −1.054 | 15.245 | 1.00 | 10.00 | O |
| ATOM | 605 | N | CYS | A | 81 | 7.416 | −2.406 | 14.484 | 1.00 | 9.99 | N |
| ATOM | 606 | CA | CYS | A | 81 | 6.332 | −1.674 | 15.116 | 1.00 | 10.50 | C |
| ATOM | 607 | CB | CYS | A | 81 | 5.191 | −1.489 | 14.115 | 1.00 | 10.19 | C |
| ATOM | 608 | SG | CYS | A | 81 | 5.666 | −0.559 | 12.649 | 1.00 | 11.71 | S |
| ATOM | 609 | C | CYS | A | 81 | 5.777 | −2.453 | 16.303 | 1.00 | 10.21 | C |
| ATOM | 610 | O | CYS | A | 81 | 5.626 | −3.683 | 16.239 | 1.00 | 9.95 | O |
| ATOM | 611 | N | PHE | A | 82 | 5.382 | −1.727 | 17.344 | 1.00 | 9.79 | N |
| ATOM | 612 | CA | PHE | A | 82 | 4.606 | −2.301 | 18.446 | 1.00 | 10.00 | C |
| ATOM | 613 | CB | PHE | A | 82 | 5.527 | −2.694 | 19.607 | 1.00 | 10.97 | C |
| ATOM | 614 | CG | PHE | A | 82 | 6.103 | −1.504 | 20.336 | 1.00 | 10.42 | C |
| ATOM | 615 | CD1 | PHE | A | 82 | 5.450 | −0.961 | 21.425 | 1.00 | 10.28 | C |
| ATOM | 616 | CE1 | PHE | A | 82 | 5.961 | 0.171 | 22.084 | 1.00 | 11.10 | C |
| ATOM | 617 | CZ | PHE | A | 82 | 7.121 | 0.775 | 21.612 | 1.00 | 11.17 | C |
| ATOM | 618 | CE2 | PHE | A | 82 | 7.776 | 0.258 | 20.518 | 1.00 | 11.35 | C |
| ATOM | 619 | CD2 | PHE | A | 82 | 7.267 | −0.869 | 19.868 | 1.00 | 11.50 | C |
| ATOM | 620 | C | PHE | A | 82 | 3.620 | −1.232 | 18.880 | 1.00 | 10.12 | C |
| ATOM | 621 | O | PHE | A | 82 | 3.858 | −0.030 | 18.717 | 1.00 | 10.63 | O |
| ATOM | 622 | N | SER | A | 83 | 2.498 | −1.656 | 19.437 | 1.00 | 10.02 | N |
| ATOM | 623 | CA | SER | A | 83 | 1.511 | −0.707 | 19.921 | 1.00 | 10.02 | C |
| ATOM | 624 | CB | SER | A | 83 | 0.147 | −1.362 | 19.964 | 1.00 | 10.25 | C |

TABLE 2-continued

| | | | | | | | | | | |
|---|---|---|---|---|---|---|---|---|---|---|
| ATOM | 625 | OG | SER | A | 83 | −0.717 | −0.549 | 20.740 | 1.00 | 11.09 O |
| ATOM | 626 | C | SER | A | 83 | 1.883 | −0.201 | 21.306 | 1.00 | 10.65 C |
| ATOM | 627 | O | SER | A | 83 | 2.181 | −1.004 | 22.203 | 1.00 | 10.75 O |
| ATOM | 628 | N | LEU | A | 84 | 1.821 | 1.118 | 21.476 | 1.00 | 10.96 N |
| ATOM | 629 | CA | LEU | A | 84 | 2.132 | 1.734 | 22.768 | 1.00 | 11.88 C |
| ATOM | 630 | CB | LEU | A | 84 | 2.192 | 3.255 | 22.657 | 1.00 | 13.00 C |
| ATOM | 631 | CG | LEU | A | 84 | 3.389 | 3.776 | 21.852 | 1.00 | 12.58 C |
| ATOM | 632 | CD1 | LEU | A | 84 | 3.174 | 5.194 | 21.409 | 1.00 | 14.70 C |
| ATOM | 633 | CD2 | LEU | A | 84 | 4.675 | 3.653 | 22.610 | 1.00 | 12.21 C |
| ATOM | 634 | C | LEU | A | 84 | 1.163 | 1.294 | 23.853 | 1.00 | 11.76 C |
| ATOM | 635 | O | LEU | A | 84 | 1.446 | 1.479 | 25.047 | 1.00 | 13.30 O |
| ATOM | 636 | N | VAL | A | 85 | 0.034 | 0.708 | 23.458 | 1.00 | 11.66 N |
| ATOM | 637 | CA | VAL | A | 85 | −0.939 | 0.222 | 24.448 | 1.00 | 12.51 C |
| ATOM | 638 | CB | VAL | A | 85 | −2.310 | 0.951 | 24.330 | 1.00 | 12.44 C |
| ATOM | 639 | CG1 | VAL | A | 85 | −2.134 | 2.448 | 24.624 | 1.00 | 14.58 C |
| ATOM | 640 | CG2 | VAL | A | 85 | −2.968 | 0.733 | 22.987 | 1.00 | 13.59 C |
| ATOM | 641 | C | VAL | A | 85 | −1.073 | −1.298 | 24.433 | 1.00 | 12.30 C |
| ATOM | 642 | O | VAL | A | 85 | −2.069 | −1.842 | 24.915 | 1.00 | 13.43 O |
| ATOM | 643 | N | SER | A | 86 | −0.040 | −1.981 | 23.926 | 1.00 | 12.15 N |
| ATOM | 644 | CA | SER | A | 86 | 0.044 | −3.431 | 24.003 | 1.00 | 12.42 C |
| ATOM | 645 | CB | SER | A | 86 | −0.314 | −4.125 | 22.683 | 1.00 | 12.04 C |
| ATOM | 646 | OG | SER | A | 86 | −0.086 | −5.522 | 22.842 | 1.00 | 15.41 O |
| ATOM | 647 | C | SER | A | 86 | 1.433 | −3.844 | 24.475 | 1.00 | 12.50 C |
| ATOM | 648 | O | SER | A | 86 | 2.351 | −4.063 | 23.678 | 1.00 | 12.54 O |
| ATOM | 649 | N | PRO | A | 87 | 1.598 | −4.002 | 25.787 | 1.00 | 12.95 N |
| ATOM | 650 | CA | PRO | A | 87 | 2.869 | −4.514 | 26.290 | 1.00 | 13.29 C |
| ATOM | 651 | CB | PRO | A | 87 | 2.627 | −4.615 | 27.808 | 1.00 | 14.21 C |
| ATOM | 652 | CG | PRO | A | 87 | 1.645 | −3.503 | 28.077 | 1.00 | 13.86 C |
| ATOM | 653 | CD | PRO | A | 87 | 0.686 | −3.627 | 26.891 | 1.00 | 13.43 C |
| ATOM | 654 | C | PRO | A | 87 | 3.327 | −5.837 | 25.679 | 1.00 | 13.26 C |
| ATOM | 655 | O | PRO | A | 87 | 4.533 | −6.031 | 25.474 | 1.00 | 13.67 O |
| ATOM | 656 | N | ALA | A | 88 | 2.391 | −6.731 | 25.355 | 1.00 | 13.08 N |
| ATOM | 657 | CA | ALA | A | 88 | 2.770 | −7.984 | 24.699 | 1.00 | 13.15 C |
| ATOM | 658 | CB | ALA | A | 88 | 1.537 | −8.871 | 24.492 | 1.00 | 14.24 C |
| ATOM | 659 | C | ALA | A | 88 | 3.470 | −7.721 | 23.363 | 1.00 | 12.54 C |
| ATOM | 660 | O | ALA | A | 88 | 4.464 | −8.363 | 23.019 | 1.00 | 13.00 O |
| ATOM | 661 | N | SER | A | 89 | 2.945 | −6.767 | 22.595 | 1.00 | 12.21 N |
| ATOM | 662 | CA | SER | A | 89 | 3.536 | −6.455 | 21.290 | 1.00 | 12.15 C |
| ATOM | 663 | CB | SER | A | 89 | 2.611 | −5.546 | 20.457 | 1.00 | 12.88 C |
| ATOM | 664 | OG | SER | A | 89 | 2.641 | −4.174 | 20.869 | 1.00 | 11.46 O |
| ATOM | 665 | C | SER | A | 89 | 4.922 | −5.853 | 21.448 | 1.00 | 11.97 C |
| ATOM | 666 | O | SER | A | 89 | 5.808 | −6.046 | 20.615 | 1.00 | 11.89 O |
| ATOM | 667 | N | PHE | A | 90 | 5.106 | −5.126 | 22.540 | 1.00 | 11.56 N |
| ATOM | 668 | CA | PHE | A | 90 | 6.397 | −4.531 | 22.869 | 1.00 | 11.82 C |
| ATOM | 669 | CB | PHE | A | 90 | 6.201 | −3.565 | 24.049 | 1.00 | 12.37 C |
| ATOM | 670 | CG | PHE | A | 90 | 7.438 | −2.830 | 24.475 | 1.00 | 13.30 C |
| ATOM | 671 | CD1 | PHE | A | 90 | 8.122 | −2.022 | 23.586 | 1.00 | 14.79 C |
| ATOM | 672 | CE1 | PHE | A | 90 | 9.243 | −1.296 | 24.008 | 1.00 | 15.32 C |
| ATOM | 673 | CZ | PHE | A | 90 | 9.664 | −1.355 | 25.330 | 1.00 | 15.13 C |
| ATOM | 674 | CE2 | PHE | A | 90 | 8.993 | −2.147 | 26.230 | 1.00 | 15.63 C |
| ATOM | 675 | CD2 | PHE | A | 90 | 7.865 | −2.883 | 25.807 | 1.00 | 15.19 C |
| ATOM | 676 | C | PHE | A | 90 | 7.422 | −5.613 | 23.178 | 1.00 | 12.20 C |
| ATOM | 677 | O | PHE | A | 90 | 8.534 | −5.599 | 22.672 | 1.00 | 12.96 O |
| ATOM | 678 | N | GLU | A | 91 | 7.033 | −6.572 | 24.006 | 1.00 | 13.27 N |
| ATOM | 679 | CA | GLU | A | 91 | 7.960 | −7.637 | 24.327 | 1.00 | 14.67 C |
| ATOM | 680 | CB | GLU | A | 91 | 7.403 | −8.530 | 25.432 | 1.00 | 15.80 C |
| ATOM | 681 | CG | GLU | A | 91 | 7.325 | −7.839 | 26.801 | 1.00 | 21.18 C |
| ATOM | 682 | CD | GLU | A | 91 | 8.683 | −7.312 | 27.296 | 1.00 | 26.68 C |
| ATOM | 683 | OE1 | GLU | A | 91 | 8.728 | −6.172 | 27.812 | 1.00 | 31.58 O |
| ATOM | 684 | OE2 | GLU | A | 91 | 9.705 | −8.023 | 27.166 | 1.00 | 29.55 O |
| ATOM | 685 | C | GLU | A | 91 | 8.341 | −8.442 | 23.087 | 1.00 | 13.24 C |
| ATOM | 686 | O | GLU | A | 91 | 9.480 | −8.870 | 22.961 | 1.00 | 14.31 O |
| ATOM | 687 | N | ASN | A | 92 | 7.402 | −8.613 | 22.151 | 1.00 | 11.84 N |
| ATOM | 688 | CA | ASN | A | 92 | 7.744 | −9.293 | 20.909 | 1.00 | 12.41 C |
| ATOM | 689 | CB | ASN | A | 92 | 6.493 | −9.684 | 20.145 | 1.00 | 13.20 C |
| ATOM | 690 | CG | ASN | A | 92 | 5.894 | −10.946 | 20.686 | 1.00 | 15.85 C |
| ATOM | 691 | OD1 | ASN | A | 92 | 6.617 | −11.853 | 21.123 | 1.00 | 17.38 O |
| ATOM | 692 | ND2 | ASN | A | 92 | 4.571 | −11.029 | 20.675 | 1.00 | 17.83 N |
| ATOM | 693 | C | ASN | A | 92 | 8.718 | −8.579 | 19.986 | 1.00 | 11.68 C |
| ATOM | 694 | O | ASN | A | 92 | 9.267 | −9.213 | 19.093 | 1.00 | 12.11 O |
| ATOM | 695 | N | VAL | A | 93 | 8.950 | −7.282 | 20.203 | 1.00 | 12.44 N |
| ATOM | 696 | CA | VAL | A | 93 | 9.993 | −6.580 | 19.454 | 1.00 | 13.31 C |
| ATOM | 697 | CB | VAL | A | 93 | 10.151 | −5.140 | 19.954 | 1.00 | 13.15 C |
| ATOM | 698 | CG1 | VAL | A | 93 | 11.439 | −4.514 | 19.419 | 1.00 | 13.98 C |
| ATOM | 699 | CG2 | VAL | A | 93 | 8.918 | −4.329 | 19.575 | 1.00 | 13.99 C |
| ATOM | 700 | C | VAL | A | 93 | 11.312 | −7.329 | 19.630 | 1.00 | 14.01 C |
| ATOM | 701 | O | VAL | A | 93 | 12.030 | −7.582 | 18.672 | 1.00 | 15.10 O |
| ATOM | 702 | N | ARG | A | 94 | 11.611 | −7.711 | 20.867 | 1.00 | 15.11 N |
| ATOM | 703 | CA | ARG | A | 94 | 12.873 | −8.371 | 21.160 | 1.00 | 16.16 C |

TABLE 2-continued

| | | | | | | | | | |
|---|---|---|---|---|---|---|---|---|---|
| ATOM | 704 | CB | ARG | A | 94 | 13.326 | −7.993 | 22.575 | 1.00 17.62 C |
| ATOM | 705 | CG | ARG | A | 94 | 14.632 | −8.627 | 22.959 | 1.00 21.98 C |
| ATOM | 706 | CD | ARG | A | 94 | 15.816 | −7.740 | 22.632 | 1.00 28.79 C |
| ATOM | 707 | NE | ARG | A | 94 | 16.859 | −8.516 | 21.966 | 1.00 34.14 N |
| ATOM | 708 | CZ | ARG | A | 94 | 18.164 | −8.362 | 22.164 | 1.00 35.82 C |
| ATOM | 709 | NH1 | ARG | A | 94 | 18.611 | −7.460 | 23.024 | 1.00 37.30 N |
| ATOM | 710 | NH2 | ARG | A | 94 | 19.025 | −9.129 | 21.504 | 1.00 38.38 N |
| ATOM | 711 | C | ARG | A | 94 | 12.741 | −9.883 | 20.991 | 1.00 15.53 C |
| ATOM | 712 | O | ARG | A | 94 | 13.679 | −10.550 | 20.556 | 1.00 16.61 O |
| ATOM | 713 | N | ALA | A | 95 | 11.579 | −10.433 | 21.331 | 1.00 13.61 N |
| ATOM | 714 | CA | ALA | A | 95 | 11.399 | −11.878 | 21.304 | 1.00 13.39 C |
| ATOM | 715 | CB | ALA | A | 95 | 10.156 | −12.269 | 22.125 | 1.00 13.49 C |
| ATOM | 716 | C | ALA | A | 95 | 11.315 | −12.453 | 19.892 | 1.00 13.50 C |
| ATOM | 717 | O | ALA | A | 95 | 11.737 | −13.575 | 19.626 | 1.00 14.22 O |
| ATOM | 718 | N | LYS | A | 96 | 10.747 | −11.661 | 18.982 | 1.00 13.38 N |
| ATOM | 719 | CA | LYS | A | 96 | 10.404 | −12.148 | 17.652 | 1.00 12.97 C |
| ATOM | 720 | CB | LYS | A | 96 | 8.876 | −12.266 | 17.478 | 1.00 13.16 C |
| ATOM | 721 | CG | LYS | A | 96 | 8.473 | −12.789 | 16.104 | 1.00 14.36 C |
| ATOM | 722 | CD | LYS | A | 96 | 6.995 | −13.121 | 16.024 | 1.00 15.01 C |
| ATOM | 723 | CE | LYS | A | 96 | 6.677 | −13.705 | 14.652 | 1.00 18.16 C |
| ATOM | 724 | NZ | LYS | A | 96 | 5.205 | −13.960 | 14.468 | 1.00 18.60 N |
| ATOM | 725 | C | LYS | A | 96 | 10.973 | −11.275 | 16.541 | 1.00 12.23 C |
| ATOM | 726 | O | LYS | A | 96 | 11.650 | −11.780 | 15.618 | 1.00 12.58 O |
| ATOM | 727 | N | TRP | A | 97 | 10.686 | −9.974 | 16.591 | 1.00 11.57 N |
| ATOM | 728 | CA | TRP | A | 97 | 10.922 | −9.147 | 15.394 | 1.00 11.61 C |
| ATOM | 729 | CB | TRP | A | 97 | 10.047 | −7.883 | 15.409 | 1.00 10.66 C |
| ATOM | 730 | CG | TRP | A | 97 | 8.634 | −8.324 | 15.386 | 1.00 10.77 C |
| ATOM | 731 | CD1 | TRP | A | 97 | 7.712 | −8.217 | 16.400 | 1.00 10.78 C |
| ATOM | 732 | NE1 | TRP | A | 97 | 6.550 | −8.851 | 16.035 | 1.00 11.23 N |
| ATOM | 733 | CE2 | TRP | A | 97 | 6.711 | −9.401 | 14.788 | 1.00 10.82 C |
| ATOM | 734 | CD2 | TRP | A | 97 | 8.019 | −9.110 | 14.357 | 1.00 10.00 C |
| ATOM | 735 | CE3 | TRP | A | 97 | 8.445 | −9.577 | 13.101 | 1.00 10.71 C |
| ATOM | 736 | CZ3 | TRP | A | 97 | 7.569 | −10.294 | 12.328 | 1.00 11.15 C |
| ATOM | 737 | CH2 | TRP | A | 97 | 6.282 | −10.600 | 12.796 | 1.00 11.59 C |
| ATOM | 738 | CZ2 | TRP | A | 97 | 5.830 | −10.161 | 14.011 | 1.00 11.63 C |
| ATOM | 739 | C | TRP | A | 97 | 12.370 | −8.859 | 15.123 | 1.00 12.18 C |
| ATOM | 740 | O | TRP | A | 97 | 12.834 | −9.005 | 13.987 | 1.00 11.96 O |
| ATOM | 741 | N | TYR | A | 98 | 13.096 | −8.446 | 16.161 | 1.00 12.70 N |
| ATOM | 742 | CA | TYR | A | 98 | 14.528 | −8.222 | 16.017 | 1.00 14.03 C |
| ATOM | 743 | CB | TYR | A | 98 | 15.122 | −7.749 | 17.346 | 1.00 16.61 C |
| ATOM | 744 | CG | TYR | A | 98 | 16.633 | −7.603 | 17.329 | 1.00 20.30 C |
| ATOM | 745 | CD1 | TYR | A | 98 | 17.274 | −6.824 | 16.355 | 1.00 22.77 C |
| ATOM | 746 | CE1 | TYR | A | 98 | 18.662 | −6.703 | 16.330 | 1.00 24.51 C |
| ATOM | 747 | CZ | TYR | A | 98 | 19.411 | −7.347 | 17.290 | 1.00 23.70 C |
| ATOM | 748 | OH | TYR | A | 98 | 20.789 | −7.224 | 17.270 | 1.00 25.67 O |
| ATOM | 749 | CE2 | TYR | A | 98 | 18.809 | −8.115 | 18.270 | 1.00 24.56 C |
| ATOM | 750 | CD2 | TYR | A | 98 | 17.413 | −8.242 | 18.284 | 1.00 25.03 C |
| ATOM | 751 | C | TYR | A | 98 | 15.272 | −9.443 | 15.467 | 1.00 13.19 C |
| ATOM | 752 | O | TYR | A | 98 | 15.981 | −9.316 | 14.483 | 1.00 12.70 O |
| ATOM | 753 | N | PRO | A | 99 | 15.129 | −10.619 | 16.100 | 1.00 13.11 N |
| ATOM | 754 | CA | PRO | A | 99 | 15.862 | −11.748 | 15.514 | 1.00 13.92 C |
| ATOM | 755 | CB | PRO | A | 99 | 15.605 | −12.915 | 16.491 | 1.00 14.48 C |
| ATOM | 756 | CG | PRO | A | 99 | 14.426 | −12.507 | 17.292 | 1.00 14.24 C |
| ATOM | 757 | CD | PRO | A | 99 | 14.448 | −10.992 | 17.356 | 1.00 13.23 C |
| ATOM | 758 | C | PRO | A | 99 | 15.431 | −12.083 | 14.087 | 1.00 13.28 C |
| ATOM | 759 | O | PRO | A | 99 | 16.284 | −12.423 | 13.259 | 1.00 14.28 O |
| ATOM | 760 | N | GLU | A | 100 | 14.141 | −11.995 | 13.765 | 1.00 13.11 N |
| ATOM | 761 | CA | GLU | A | 100 | 13.722 | −12.301 | 12.402 | 1.00 12.73 C |
| ATOM | 762 | CB | GLU | A | 100 | 12.195 | −12.290 | 12.296 | 1.00 13.10 C |
| ATOM | 763 | CG | GLU | A | 100 | 11.737 | −12.685 | 10.893 | 1.00 13.83 C |
| ATOM | 764 | CD | GLU | A | 100 | 10.257 | −12.894 | 10.778 | 1.00 15.02 C |
| ATOM | 765 | OE1 | GLU | A | 100 | 9.716 | −13.813 | 11.423 | 1.00 16.97 O |
| ATOM | 766 | OE2 | GLU | A | 100 | 9.637 | −12.123 | 10.023 | 1.00 14.34 O |
| ATOM | 767 | C | GLU | A | 100 | 14.306 | −11.318 | 11.377 | 1.00 12.68 C |
| ATOM | 768 | O | GLU | A | 100 | 14.843 | −11.720 | 10.320 | 1.00 12.94 O |
| ATOM | 769 | N | VAL | A | 101 | 14.219 | −10.040 | 11.684 | 1.00 12.96 N |
| ATOM | 770 | CA | VAL | A | 101 | 14.710 | −9.022 | 10.761 | 1.00 13.65 C |
| ATOM | 771 | CB | VAL | A | 101 | 14.283 | −7.602 | 11.213 | 1.00 13.29 C |
| ATOM | 772 | CG1 | VAL | A | 101 | 14.986 | −6.503 | 10.385 | 1.00 16.16 C |
| ATOM | 773 | CG2 | VAL | A | 101 | 12.773 | −7.457 | 11.127 | 1.00 13.75 C |
| ATOM | 774 | C | VAL | A | 101 | 16.220 | −9.148 | 10.611 | 1.00 14.67 C |
| ATOM | 775 | O | VAL | A | 101 | 16.722 | −9.083 | 9.509 | 1.00 15.13 O |
| ATOM | 776 | N | ARG | A | 102 | 16.932 | −9.347 | 11.713 | 1.00 15.37 N |
| ATOM | 777 | CA | ARG | A | 102 | 18.398 | −9.427 | 11.659 | 1.00 16.75 C |
| ATOM | 778 | CB | ARG | A | 102 | 18.965 | −9.395 | 13.087 | 1.00 17.79 C |
| ATOM | 779 | CG | ARG | A | 102 | 20.399 | −8.843 | 13.205 | 1.00 21.62 C |
| ATOM | 780 | CD | ARG | A | 102 | 20.645 | −7.684 | 12.236 | 1.00 23.24 C |
| ATOM | 781 | NE | ARG | A | 102 | 20.443 | −6.323 | 12.755 | 1.00 23.20 N |
| ATOM | 782 | CZ | ARG | A | 102 | 19.984 | −5.315 | 12.006 | 1.00 23.24 C |

TABLE 2-continued

| | | | | | | | | | |
|---|---|---|---|---|---|---|---|---|---|
| ATOM | 783 | NH1 | ARG | A | 102 | 19.599 | −5.551 | 10.751 | 1.00 23.30 N |
| ATOM | 784 | NH2 | ARG | A | 102 | 19.860 | −4.088 | 12.512 | 1.00 23.94 N |
| ATOM | 785 | C | ARG | A | 102 | 18.835 | −10.683 | 10.907 | 1.00 16.87 C |
| ATOM | 786 | O | ARG | A | 102 | 19.842 | −10.671 | 10.199 | 1.00 18.30 O |
| ATOM | 787 | N | HIS | A | 103 | 18.058 | −11.758 | 11.009 | 1.00 16.43 N |
| ATOM | 788 | CA | HIS | A | 103 | 18.377 | −12.966 | 10.286 | 1.00 17.48 C |
| ATOM | 789 | CB | HIS | A | 103 | 17.492 | −14.125 | 10.723 | 1.00 17.59 C |
| ATOM | 790 | CG | HIS | A | 103 | 17.809 | −15.400 | 10.004 | 1.00 21.53 C |
| ATOM | 791 | ND1 | HIS | A | 103 | 16.983 | −15.945 | 9.049 | 1.00 24.85 N |
| ATOM | 792 | CE1 | HIS | A | 103 | 17.538 | −17.042 | 8.559 | 1.00 26.32 C |
| ATOM | 793 | NE2 | HIS | A | 103 | 18.706 | −17.213 | 9.148 | 1.00 26.17 N |
| ATOM | 794 | CD2 | HIS | A | 103 | 18.906 | −16.193 | 10.047 | 1.00 23.34 C |
| ATOM | 795 | C | HIS | A | 103 | 18.249 | −12.767 | 8.783 | 1.00 16.88 C |
| ATOM | 796 | O | HIS | A | 103 | 19.135 | −13.160 | 8.025 | 1.00 17.24 O |
| ATOM | 797 | N | HIS | A | 104 | 17.139 | −12.181 | 8.345 | 1.00 16.36 N |
| ATOM | 798 | CA | HIS | A | 104 | 16.870 | −12.052 | 6.925 | 1.00 16.24 C |
| ATOM | 799 | CB | HIS | A | 104 | 15.363 | −12.094 | 6.675 | 1.00 16.12 C |
| ATOM | 800 | CG | HIS | A | 104 | 14.758 | −13.433 | 6.940 | 1.00 15.16 C |
| ATOM | 801 | ND1 | HIS | A | 104 | 14.797 | −14.464 | 6.024 | 1.00 17.29 N |
| ATOM | 802 | CE1 | HIS | A | 104 | 14.187 | −15.518 | 6.534 | 1.00 16.02 C |
| ATOM | 803 | NE2 | HIS | A | 104 | 13.770 | −15.213 | 7.751 | 1.00 16.75 N |
| ATOM | 804 | CD2 | HIS | A | 104 | 14.099 | −13.909 | 8.021 | 1.00 16.36 C |
| ATOM | 805 | C | HIS | A | 104 | 17.466 | −10.812 | 6.294 | 1.00 16.71 C |
| ATOM | 806 | O | HIS | A | 104 | 17.629 | −10.759 | 5.066 | 1.00 17.06 O |
| ATOM | 807 | N | CYS | A | 105 | 17.770 | −9.821 | 7.128 | 1.00 16.06 N |
| ATOM | 808 | CA | CYS | A | 105 | 18.278 | −8.524 | 6.690 | 1.00 16.59 C |
| ATOM | 809 | CB | CYS | A | 105 | 17.197 | −7.448 | 6.805 | 1.00 15.75 C |
| ATOM | 810 | SG | CYS | A | 105 | 15.584 | −7.864 | 6.090 | 1.00 17.37 S |
| ATOM | 811 | C | CYS | A | 105 | 19.456 | −8.140 | 7.573 | 1.00 18.00 C |
| ATOM | 812 | O | CYS | A | 105 | 19.388 | −7.172 | 8.319 | 1.00 17.69 O |
| ATOM | 813 | N | PRO | A | 106 | 20.554 | −8.899 | 7.482 | 1.00 18.97 N |
| ATOM | 814 | CA | PRO | A | 106 | 21.656 | −8.676 | 8.409 | 1.00 20.28 C |
| ATOM | 815 | CB | PRO | A | 106 | 22.677 | −9.754 | 8.005 | 1.00 20.67 C |
| ATOM | 816 | CG | PRO | A | 106 | 22.345 | −10.089 | 6.604 | 1.00 19.73 C |
| ATOM | 817 | CD | PRO | A | 106 | 20.853 | −9.998 | 6.545 | 1.00 19.37 C |
| ATOM | 818 | C | PRO | A | 106 | 22.299 | −7.282 | 8.418 | 1.00 22.24 C |
| ATOM | 819 | O | PRO | A | 106 | 22.809 | −6.871 | 9.462 | 1.00 24.24 O |
| ATOM | 820 | N | ASN | A | 107 | 22.276 | −6.559 | 7.304 | 1.00 23.21 N |
| ATOM | 821 | CA | ASN | A | 107 | 23.015 | −5.292 | 7.241 | 1.00 24.66 C |
| ATOM | 822 | CB | ASN | A | 107 | 23.979 | −5.303 | 6.062 | 1.00 26.10 C |
| ATOM | 823 | CG | ASN | A | 107 | 25.043 | −6.324 | 6.207 | 1.00 27.68 C |
| ATOM | 824 | OD1 | ASN | A | 107 | 25.261 | −7.119 | 5.296 | 1.00 29.64 O |
| ATOM | 825 | ND2 | ASN | A | 107 | 25.713 | −6.338 | 7.362 | 1.00 29.00 N |
| ATOM | 826 | C | ASN | A | 107 | 22.139 | −4.056 | 7.158 | 1.00 24.72 C |
| ATOM | 827 | O | ASN | A | 107 | 22.586 | −2.999 | 6.709 | 1.00 26.29 O |
| ATOM | 828 | N | THR | A | 108 | 20.910 | −4.195 | 7.632 | 1.00 23.11 N |
| ATOM | 829 | CA | THR | A | 108 | 19.828 | −3.246 | 7.386 | 1.00 22.12 C |
| ATOM | 830 | CB | THR | A | 108 | 18.561 | −4.066 | 7.011 | 1.00 22.14 C |
| ATOM | 831 | OG1 | THR | A | 108 | 18.807 | −4.802 | 5.813 | 1.00 25.06 O |
| ATOM | 832 | CG2 | THR | A | 108 | 17.318 | −3.190 | 6.815 | 1.00 24.17 C |
| ATOM | 833 | C | THR | A | 108 | 19.525 | −2.445 | 8.644 | 1.00 19.74 C |
| ATOM | 834 | O | THR | A | 108 | 19.311 | −3.049 | 9.695 | 1.00 19.19 O |
| ATOM | 835 | N | PRO | A | 109 | 19.470 | −1.102 | 8.550 | 1.00 16.40 N |
| ATOM | 836 | CA | PRO | A | 109 | 19.031 | −0.347 | 9.722 | 1.00 15.60 C |
| ATOM | 837 | CB | PRO | A | 109 | 19.143 | 1.114 | 9.282 | 1.00 15.76 C |
| ATOM | 838 | CG | PRO | A | 109 | 19.124 | 1.064 | 7.757 | 1.00 16.60 C |
| ATOM | 839 | CD | PRO | A | 109 | 19.824 | −0.211 | 7.423 | 1.00 15.88 C |
| ATOM | 840 | C | PRO | A | 109 | 17.592 | −0.663 | 10.112 | 1.00 15.49 C |
| ATOM | 841 | O | PRO | A | 109 | 16.750 | −0.973 | 9.252 | 1.00 14.97 O |
| ATOM | 842 | N | ILE | A | 110 | 17.340 | −0.577 | 11.416 | 1.00 14.61 N |
| ATOM | 843 | CA | ILE | A | 110 | 16.030 | −0.790 | 11.999 | 1.00 14.49 C |
| ATOM | 844 | CB | ILE | A | 110 | 16.068 | −1.905 | 13.054 | 1.00 15.01 C |
| ATOM | 845 | CG1 | ILE | A | 110 | 16.364 | −3.245 | 12.393 | 1.00 15.73 C |
| ATOM | 846 | CD1 | ILE | A | 110 | 16.593 | −4.392 | 13.368 | 1.00 19.39 C |
| ATOM | 847 | CG2 | ILE | A | 110 | 14.742 | −1.941 | 13.870 | 1.00 15.94 C |
| ATOM | 848 | C | ILE | A | 110 | 15.584 | 0.466 | 12.677 | 1.00 13.80 C |
| ATOM | 849 | O | ILE | A | 110 | 16.362 | 1.088 | 13.417 | 1.00 14.50 O |
| ATOM | 850 | N | ILE | A | 111 | 14.346 | 0.869 | 12.420 | 1.00 13.72 N |
| ATOM | 851 | CA | ILE | A | 111 | 13.734 | 1.920 | 13.209 | 1.00 13.09 C |
| ATOM | 852 | CB | ILE | A | 111 | 13.175 | 3.006 | 12.318 | 1.00 13.97 C |
| ATOM | 853 | CG1 | ILE | A | 111 | 14.392 | 3.647 | 11.608 | 1.00 18.10 C |
| ATOM | 854 | CD1 | ILE | A | 111 | 14.161 | 4.925 | 10.924 | 1.00 22.57 C |
| ATOM | 855 | CG2 | ILE | A | 111 | 12.345 | 4.022 | 13.119 | 1.00 14.53 C |
| ATOM | 856 | C | ILE | A | 111 | 12.653 | 1.279 | 14.075 | 1.00 12.70 C |
| ATOM | 857 | O | ILE | A | 111 | 11.822 | 0.520 | 13.559 | 1.00 12.11 O |
| ATOM | 858 | N | LEU | A | 112 | 12.674 | 1.558 | 15.377 | 1.00 12.35 N |
| ATOM | 859 | CA | LEU | A | 112 | 11.647 | 1.028 | 16.283 | 1.00 11.30 C |
| ATOM | 860 | CB | LEU | A | 112 | 12.251 | 0.756 | 17.660 | 1.00 12.08 C |
| ATOM | 861 | CG | LEU | A | 112 | 11.241 | 0.181 | 18.651 | 1.00 11.67 C |

TABLE 2-continued

| | | | | | | | | | | |
|---|---|---|---|---|---|---|---|---|---|---|
| ATOM | 862 | CD1 | LEU | A | 112 | 10.703 | −1.171 | 18.185 | 1.00 | 13.05 C |
| ATOM | 863 | CD2 | LEU | A | 112 | 11.879 | 0.073 | 20.040 | 1.00 | 13.53 C |
| ATOM | 864 | C | LEU | A | 112 | 10.535 | 2.043 | 16.383 | 1.00 | 11.41 C |
| ATOM | 865 | O | LEU | A | 112 | 10.776 | 3.209 | 16.709 | 1.00 | 11.83 O |
| ATOM | 866 | N | VAL | A | 113 | 9.301 | 1.612 | 16.081 | 1.00 | 11.11 N |
| ATOM | 867 | CA | VAL | A | 113 | 8.166 | 2.517 | 15.997 | 1.00 | 11.25 C |
| ATOM | 868 | CB | VAL | A | 113 | 7.568 | 2.562 | 14.555 | 1.00 | 11.45 C |
| ATOM | 869 | CG1 | VAL | A | 113 | 6.389 | 3.544 | 14.464 | 1.00 | 12.35 C |
| ATOM | 870 | CG2 | VAL | A | 113 | 8.653 | 2.966 | 13.533 | 1.00 | 11.84 C |
| ATOM | 871 | C | VAL | A | 113 | 7.081 | 2.122 | 16.997 | 1.00 | 10.54 C |
| ATOM | 872 | O | VAL | A | 113 | 6.545 | 1.010 | 16.912 | 1.00 | 10.85 O |
| ATOM | 873 | N | GLY | A | 114 | 6.795 | 3.003 | 17.953 | 1.00 | 10.72 N |
| ATOM | 874 | CA | GLY | A | 114 | 5.626 | 2.834 | 18.831 | 1.00 | 10.62 C |
| ATOM | 875 | C | GLY | A | 114 | 4.412 | 3.434 | 18.152 | 1.00 | 11.24 C |
| ATOM | 876 | O | GLY | A | 114 | 4.420 | 4.609 | 17.765 | 1.00 | 12.45 O |
| ATOM | 877 | N | THR | A | 115 | 3.365 | 2.633 | 17.972 | 1.00 | 10.04 N |
| ATOM | 878 | CA | THR | A | 115 | 2.156 | 3.038 | 17.267 | 1.00 | 10.46 C |
| ATOM | 879 | CB | THR | A | 115 | 1.711 | 1.939 | 16.291 | 1.00 | 10.43 C |
| ATOM | 880 | OG1 | THR | A | 115 | 1.467 | 0.771 | 17.063 | 1.00 | 11.87 O |
| ATOM | 881 | CG2 | THR | A | 115 | 2.800 | 1.638 | 15.237 | 1.00 | 11.11 C |
| ATOM | 882 | C | THR | A | 115 | 1.012 | 3.319 | 18.250 | 1.00 | 10.45 C |
| ATOM | 883 | O | THR | A | 115 | 1.107 | 2.999 | 19.452 | 1.00 | 11.66 O |
| ATOM | 884 | N | LYS | A | 116 | −0.075 | 3.847 | 17.703 | 1.00 | 10.99 N |
| ATOM | 885 | CA | LYS | A | 116 | −1.291 | 4.184 | 18.452 | 1.00 | 11.62 C |
| ATOM | 886 | CB | LYS | A | 116 | −1.996 | 2.939 | 18.986 | 1.00 | 11.39 C |
| ATOM | 887 | CG | LYS | A | 116 | −2.250 | 1.895 | 17.905 | 1.00 | 10.85 C |
| ATOM | 888 | CD | LYS | A | 116 | −3.303 | 0.882 | 18.343 | 1.00 | 11.77 C |
| ATOM | 889 | CE | LYS | A | 116 | −3.395 | −0.273 | 17.383 | 1.00 | 12.92 C |
| ATOM | 890 | NZ | LYS | A | 116 | −4.345 | −1.319 | 17.904 | 1.00 | 11.97 N |
| ATOM | 891 | C | LYS | A | 116 | −0.999 | 5.163 | 19.574 | 1.00 | 12.31 C |
| ATOM | 892 | O | LYS | A | 116 | −1.557 | 5.062 | 20.670 | 1.00 | 12.60 O |
| ATOM | 893 | N | LEU | A | 117 | −0.160 | 6.147 | 19.268 | 1.00 | 12.97 N |
| ATOM | 894 | CA | LEU | A | 117 | 0.210 | 7.158 | 20.249 | 1.00 | 14.06 C |
| ATOM | 895 | CB | LEU | A | 117 | 1.129 | 8.182 | 19.571 | 1.00 | 13.64 C |
| ATOM | 896 | CG | LEU | A | 117 | 1.521 | 9.443 | 20.352 | 1.00 | 14.58 C |
| ATOM | 897 | CD1 | LEU | A | 117 | 2.293 | 9.043 | 21.565 | 1.00 | 16.08 C |
| ATOM | 898 | CD2 | LEU | A | 117 | 2.368 | 10.351 | 19.496 | 1.00 | 16.13 C |
| ATOM | 899 | C | LEU | A | 117 | −1.014 | 7.851 | 20.851 | 1.00 | 13.77 C |
| ATOM | 900 | O | LEU | A | 117 | −0.992 | 8.227 | 22.041 | 1.00 | 15.02 O |
| ATOM | 901 | N | ASP | A | 118 | −2.055 | 8.024 | 20.047 | 1.00 | 13.75 N |
| ATOM | 902 | CA | ASP | A | 118 | −3.300 | 8.677 | 20.499 | 1.00 | 14.43 C |
| ATOM | 903 | CB | ASP | A | 118 | −4.271 | 8.865 | 19.330 | 1.00 | 14.70 C |
| ATOM | 904 | CG | ASP | A | 118 | −4.687 | 7.553 | 18.704 | 1.00 | 13.72 C |
| ATOM | 905 | OD1 | ASP | A | 118 | −3.846 | 6.912 | 18.028 | 1.00 | 14.20 O |
| ATOM | 906 | OD2 | ASP | A | 118 | −5.845 | 7.166 | 18.880 | 1.00 | 14.91 O |
| ATOM | 907 | C | ASP | A | 118 | −3.968 | 7.927 | 21.662 | 1.00 | 15.41 C |
| ATOM | 908 | O | ASP | A | 118 | −4.742 | 8.523 | 22.417 | 1.00 | 16.15 O |
| ATOM | 909 | N | LEU | A | 119 | −3.656 | 6.645 | 21.832 | 1.00 | 14.12 N |
| ATOM | 910 | CA | LEU | A | 119 | −4.297 | 5.853 | 22.873 | 1.00 | 14.41 C |
| ATOM | 911 | CB | LEU | A | 119 | −4.555 | 4.414 | 22.387 | 1.00 | 14.30 C |
| ATOM | 912 | CG | LEU | A | 119 | −5.555 | 4.218 | 21.247 | 1.00 | 14.14 C |
| ATOM | 913 | CD1 | LEU | A | 119 | −5.721 | 2.728 | 20.924 | 1.00 | 14.99 C |
| ATOM | 914 | CD2 | LEU | A | 119 | −6.917 | 4.854 | 21.569 | 1.00 | 14.15 C |
| ATOM | 915 | C | LEU | A | 119 | −3.542 | 5.866 | 24.191 | 1.00 | 15.31 C |
| ATOM | 916 | O | LEU | A | 119 | −4.098 | 5.437 | 25.213 | 1.00 | 15.58 O |
| ATOM | 917 | N | ARG | A | 120 | −2.294 | 6.333 | 24.191 | 1.00 | 15.71 N |
| ATOM | 918 | CA | ARG | A | 120 | −1.474 | 6.250 | 25.399 | 1.00 | 17.33 C |
| ATOM | 919 | CB | ARG | A | 120 | −0.005 | 6.632 | 25.178 | 1.00 | 16.86 C |
| ATOM | 920 | CG | ARG | A | 120 | 0.811 | 6.546 | 26.491 | 1.00 | 16.99 C |
| ATOM | 921 | CD | ARG | A | 120 | 2.296 | 6.428 | 26.273 | 1.00 | 16.57 C |
| ATOM | 922 | NE | ARG | A | 120 | 2.819 | 7.584 | 25.564 | 1.00 | 17.42 N |
| ATOM | 923 | CZ | ARG | A | 120 | 3.981 | 7.595 | 24.933 | 1.00 | 15.40 C |
| ATOM | 924 | NH1 | ARG | A | 120 | 4.746 | 6.503 | 24.897 | 1.00 | 15.17 N |
| ATOM | 925 | NH2 | ARG | A | 120 | 4.357 | 8.708 | 24.306 | 1.00 | 16.70 N |
| ATOM | 926 | C | ARG | A | 120 | −2.083 | 7.071 | 26.534 | 1.00 | 19.03 C |
| ATOM | 927 | O | ARG | A | 120 | −2.005 | 6.669 | 27.705 | 1.00 | 19.26 O |
| ATOM | 928 | N | ASP | A | 121 | −2.728 | 8.177 | 26.184 | 1.00 | 21.08 N |
| ATOM | 929 | CA | ASP | A | 121 | −3.414 | 8.964 | 27.211 | 1.00 | 23.85 C |
| ATOM | 930 | CB | ASP | A | 121 | −2.857 | 10.401 | 27.262 | 1.00 | 24.79 C |
| ATOM | 931 | CG | ASP | A | 121 | −3.016 | 11.149 | 25.950 | 1.00 | 28.79 C |
| ATOM | 932 | OD1 | ASP | A | 121 | −2.641 | 12.344 | 25.899 | 1.00 | 33.35 O |
| ATOM | 933 | OD2 | ASP | A | 121 | −3.514 | 10.559 | 24.974 | 1.00 | 32.10 O |
| ATOM | 934 | C | ASP | A | 121 | −4.953 | 8.886 | 27.147 | 1.00 | 24.43 C |
| ATOM | 935 | O | ASP | A | 121 | −5.637 | 9.704 | 27.777 | 1.00 | 26.11 O |
| ATOM | 936 | N | ASP | A | 122 | −5.477 | 7.881 | 26.427 | 1.00 | 23.95 N |
| ATOM | 937 | CA | ASP | A | 122 | −6.928 | 7.600 | 26.266 | 1.00 | 24.46 C |
| ATOM | 938 | CB | ASP | A | 122 | −7.177 | 6.663 | 25.068 | 1.00 | 24.33 C |
| ATOM | 939 | CG | ASP | A | 122 | −8.673 | 6.326 | 24.848 | 1.00 | 24.95 C |
| ATOM | 940 | OD1 | ASP | A | 122 | −9.439 | 7.225 | 24.431 | 1.00 | 27.49 O |

TABLE 2-continued

| | | | | | | | | | |
|---|---|---|---|---|---|---|---|---|---|
| ATOM | 941 | OD2 | ASP | A | 122 | −9.080 | 5.158 | 25.043 | 1.00 | 24.18 O |
| ATOM | 942 | C | ASP | A | 122 | −7.456 | 6.928 | 27.521 | 1.00 | 24.87 C |
| ATOM | 943 | O | ASP | A | 122 | −6.878 | 5.948 | 27.999 | 1.00 | 25.09 O |
| ATOM | 944 | N | LYS | A | 123 | −8.581 | 7.436 | 28.026 | 1.00 | 25.34 N |
| ATOM | 945 | CA | LYS | A | 123 | −9.105 | 7.041 | 29.328 | 1.00 | 25.83 C |
| ATOM | 946 | CB | LYS | A | 123 | −10.261 | 7.968 | 29.731 | 1.00 | 26.11 C |
| ATOM | 947 | CG | LYS | A | 123 | −9.831 | 9.405 | 30.013 | 1.00 | 28.80 C |
| ATOM | 948 | CD | LYS | A | 123 | −8.859 | 9.464 | 31.181 | 1.00 | 31.10 C |
| ATOM | 949 | CE | LYS | A | 123 | −8.804 | 10.839 | 31.826 | 1.00 | 33.04 C |
| ATOM | 950 | NZ | LYS | A | 123 | −8.546 | 10.688 | 33.283 | 1.00 | 33.17 N |
| ATOM | 951 | C | LYS | A | 123 | −9.525 | 5.585 | 29.406 | 1.00 | 25.13 C |
| ATOM | 952 | O | LYS | A | 123 | −9.068 | 4.857 | 30.289 | 1.00 | 25.32 O |
| ATOM | 953 | N | ASP | A | 124 | −10.366 | 5.152 | 28.467 | 1.00 | 25.18 N |
| ATOM | 954 | CA | ASP | A | 124 | −10.836 | 3.769 | 28.418 | 1.00 | 25.02 C |
| ATOM | 955 | CB | ASP | A | 124 | −11.861 | 3.580 | 27.302 | 1.00 | 25.90 C |
| ATOM | 956 | CG | ASP | A | 124 | −12.532 | 2.215 | 27.337 | 1.00 | 29.21 C |
| ATOM | 957 | OD1 | ASP | A | 124 | −13.297 | 1.943 | 28.292 | 1.00 | 32.53 O |
| ATOM | 958 | OD2 | ASP | A | 124 | −12.321 | 1.416 | 26.397 | 1.00 | 33.80 O |
| ATOM | 959 | C | ASP | A | 124 | −9.685 | 2.798 | 28.231 | 1.00 | 23.79 C |
| ATOM | 960 | O | ASP | A | 124 | −9.663 | 1.747 | 28.861 | 1.00 | 23.80 O |
| ATOM | 961 | N | THR | A | 125 | −8.723 | 3.160 | 27.374 | 1.00 | 22.32 N |
| ATOM | 962 | CA | THR | A | 125 | −7.581 | 2.290 | 27.125 | 1.00 | 20.76 C |
| ATOM | 963 | CB | THR | A | 125 | −6.716 | 2.824 | 25.974 | 1.00 | 20.70 C |
| ATOM | 964 | OG1 | THR | A | 125 | −7.526 | 2.972 | 24.801 | 1.00 | 22.33 O |
| ATOM | 965 | CG2 | THR | A | 125 | −5.602 | 1.832 | 25.674 | 1.00 | 19.54 C |
| ATOM | 966 | C | THR | A | 125 | −6.724 | 2.110 | 28.380 | 1.00 | 20.07 C |
| ATOM | 967 | O | THR | A | 125 | −6.333 | 0.993 | 28.712 | 1.00 | 18.81 O |
| ATOM | 968 | N | ILE | A | 126 | −6.459 | 3.207 | 29.085 | 1.00 | 19.39 N |
| ATOM | 969 | CA | ILE | A | 126 | −5.681 | 3.144 | 30.321 | 1.00 | 19.62 C |
| ATOM | 970 | CB | ILE | A | 126 | −5.364 | 4.532 | 30.887 | 1.00 | 19.40 C |
| ATOM | 971 | CG1 | ILE | A | 126 | −4.396 | 5.268 | 29.960 | 1.00 | 19.35 C |
| ATOM | 972 | CD1 | ILE | A | 126 | −4.362 | 6.779 | 30.214 | 1.00 | 22.93 C |
| ATOM | 973 | CG2 | ILE | A | 126 | −4.727 | 4.420 | 32.273 | 1.00 | 21.54 C |
| ATOM | 974 | C | ILE | A | 126 | −6.419 | 2.285 | 31.363 | 1.00 | 19.93 C |
| ATOM | 975 | O | ILE | A | 126 | −5.806 | 1.451 | 32.015 | 1.00 | 19.00 O |
| ATOM | 976 | N | GLU | A | 127 | −7.738 | 2.483 | 31.467 | 1.00 | 21.26 N |
| ATOM | 977 | CA | GLU | A | 127 | −8.583 | 1.729 | 32.397 | 1.00 | 23.21 C |
| ATOM | 978 | CB | GLU | A | 127 | −10.031 | 2.206 | 32.318 | 1.00 | 23.25 C |
| ATOM | 979 | CG | GLU | A | 127 | −10.360 | 3.475 | 33.104 | 1.00 | 25.80 C |
| ATOM | 980 | CD | GLU | A | 127 | −11.848 | 3.834 | 33.054 | 1.00 | 26.81 C |
| ATOM | 981 | OE1 | GLU | A | 127 | −12.633 | 3.114 | 32.387 | 1.00 | 32.68 O |
| ATOM | 982 | OE2 | GLU | A | 127 | −12.233 | 4.835 | 33.697 | 1.00 | 31.64 O |
| ATOM | 983 | C | GLU | A | 127 | −8.542 | 0.238 | 32.083 | 1.00 | 22.25 C |
| ATOM | 984 | O | GLU | A | 127 | −8.324 | −0.593 | 32.988 | 1.00 | 22.51 O |
| ATOM | 985 | N | LYS | A | 128 | −8.732 | −0.099 | 30.801 | 1.00 | 22.02 N |
| ATOM | 986 | CA | LYS | A | 128 | −8.708 | −1.499 | 30.345 | 1.00 | 23.13 C |
| ATOM | 987 | CB | LYS | A | 128 | −9.106 | −1.614 | 28.864 | 1.00 | 23.41 C |
| ATOM | 988 | CG | LYS | A | 128 | −10.556 | −1.981 | 28.639 | 1.00 | 26.63 C |
| ATOM | 989 | CD | LYS | A | 128 | −10.900 | −2.054 | 27.154 | 1.00 | 27.10 C |
| ATOM | 990 | CE | LYS | A | 128 | −12.342 | −2.503 | 26.951 | 1.00 | 32.09 C |
| ATOM | 991 | NZ | LYS | A | 128 | −12.819 | −2.188 | 25.566 | 1.00 | 34.87 N |
| ATOM | 992 | C | LYS | A | 128 | −7.382 | −2.201 | 30.607 | 1.00 | 21.64 C |
| ATOM | 993 | O | LYS | A | 128 | −7.351 | −3.373 | 30.992 | 1.00 | 21.72 O |
| ATOM | 994 | N | LEU | A | 129 | −6.274 | −1.492 | 30.390 | 1.00 | 19.65 N |
| ATOM | 995 | CA | LEU | A | 129 | −4.970 | −2.031 | 30.719 | 1.00 | 18.39 C |
| ATOM | 996 | CB | LEU | A | 129 | −3.826 | −1.147 | 30.159 | 1.00 | 17.50 C |
| ATOM | 997 | CG | LEU | A | 129 | −3.624 | −1.209 | 28.638 | 1.00 | 17.68 C |
| ATOM | 998 | CD1 | LEU | A | 129 | −2.705 | −0.084 | 28.182 | 1.00 | 17.69 C |
| ATOM | 999 | CD2 | LEU | A | 129 | −3.061 | −2.566 | 28.208 | 1.00 | 19.43 C |
| ATOM | 1000 | C | LEU | A | 129 | −4.818 | −2.218 | 32.220 | 1.00 | 18.22 C |
| ATOM | 1001 | O | LEU | A | 129 | −4.308 | −3.243 | 32.668 | 1.00 | 17.93 O |
| ATOM | 1002 | N | LYS | A | 130 | −5.281 | −1.239 | 32.999 | 1.00 | 18.30 N |
| ATOM | 1003 | CA | LYS | A | 130 | −5.138 | −1.281 | 34.448 | 1.00 | 19.99 C |
| ATOM | 1004 | CB | LYS | A | 130 | −5.657 | 0.019 | 35.077 | 1.00 | 19.61 C |
| ATOM | 1005 | CG | LYS | A | 130 | −5.327 | 0.161 | 36.563 | 1.00 | 22.48 C |
| ATOM | 1006 | CD | LYS | A | 130 | −5.971 | 1.394 | 37.175 | 1.00 | 23.21 C |
| ATOM | 1007 | CE | LYS | A | 130 | −5.621 | 1.505 | 38.650 | 1.00 | 28.22 C |
| ATOM | 1008 | NZ | LYS | A | 130 | −6.438 | 2.560 | 39.305 | 1.00 | 31.69 N |
| ATOM | 1009 | C | LYS | A | 130 | −5.835 | −2.500 | 35.066 | 1.00 | 19.55 C |
| ATOM | 1010 | O | LYS | A | 130 | −5.298 | −3.110 | 35.978 | 1.00 | 20.66 O |
| ATOM | 1011 | N | GLU | A | 131 | −7.002 | −2.844 | 34.534 | 1.00 | 19.98 N |
| ATOM | 1012 | CA | GLU | A | 131 | −7.762 | −4.027 | 34.993 | 1.00 | 21.82 C |
| ATOM | 1013 | CB | GLU | A | 131 | −8.989 | −4.225 | 34.127 | 1.00 | 22.37 C |
| ATOM | 1014 | CG | GLU | A | 131 | −10.065 | −3.208 | 34.295 | 1.00 | 25.39 C |
| ATOM | 1015 | CD | GLU | A | 131 | −11.267 | −3.528 | 33.423 | 1.00 | 27.20 C |
| ATOM | 1016 | OE1 | GLU | A | 131 | −11.173 | −4.443 | 32.570 | 1.00 | 28.48 O |
| ATOM | 1017 | OE2 | GLU | A | 131 | −12.305 | −2.868 | 33.584 | 1.00 | 32.18 O |
| ATOM | 1018 | C | GLU | A | 131 | −6.935 | −5.302 | 34.910 | 1.00 | 22.56 C |
| ATOM | 1019 | O | GLU | A | 131 | −7.151 | −6.244 | 35.678 | 1.00 | 22.48 O |

TABLE 2-continued

| | | | | | | | | | |
|---|---|---|---|---|---|---|---|---|---|
| ATOM | 1020 | N | LYS | A | 132 | −6.014 | −5.334 | 33.944 | 1.00 | 23.05 N |
| ATOM | 1021 | CA | LYS | A | 132 | −5.088 | −6.449 | 33.722 | 1.00 | 23.56 C |
| ATOM | 1022 | CB | LYS | A | 132 | −4.911 | −6.675 | 32.218 | 1.00 | 23.83 C |
| ATOM | 1023 | CG | LYS | A | 132 | −6.192 | −6.985 | 31.466 | 1.00 | 24.91 C |
| ATOM | 1024 | CD | LYS | A | 132 | −5.929 | −7.130 | 29.978 | 1.00 | 27.51 C |
| ATOM | 1025 | CE | LYS | A | 132 | −7.172 | −7.624 | 29.260 | 1.00 | 28.92 C |
| ATOM | 1026 | NZ | LYS | A | 132 | −6.986 | −7.606 | 27.778 | 1.00 | 31.70 N |
| ATOM | 1027 | C | LYS | A | 132 | −3.712 | −6.226 | 34.363 | 1.00 | 23.22 C |
| ATOM | 1028 | O | LYS | A | 132 | −2.764 | −7.003 | 34.114 | 1.00 | 23.85 O |
| ATOM | 1029 | N | LYS | A | 133 | −3.600 | −5.181 | 35.185 | 1.00 | 23.67 N |
| ATOM | 1030 | CA | LYS | A | 133 | −2.353 | −4.822 | 35.870 | 1.00 | 23.68 C |
| ATOM | 1031 | CB | LYS | A | 133 | −1.865 | −5.956 | 36.793 | 1.00 | 24.89 C |
| ATOM | 1032 | CG | LYS | A | 133 | −2.776 | −6.265 | 37.989 | 1.00 | 26.71 C |
| ATOM | 1033 | CD | LYS | A | 133 | −1.990 | −6.993 | 39.082 | 1.00 | 30.39 C |
| ATOM | 1034 | CE | LYS | A | 133 | −2.797 | −7.142 | 40.374 | 1.00 | 32.61 C |
| ATOM | 1035 | NZ | LYS | A | 133 | −1.962 | −7.691 | 41.489 | 1.00 | 34.46 N |
| ATOM | 1036 | C | LYS | A | 133 | −1.263 | −4.440 | 34.857 | 1.00 | 23.39 C |
| ATOM | 1037 | O | LYS | A | 133 | −0.074 | −4.726 | 35.058 | 1.00 | 23.85 O |
| ATOM | 1038 | N | LEU | A | 134 | −1.691 | −3.794 | 33.774 | 1.00 | 21.93 N |
| ATOM | 1039 | CA | LEU | A | 134 | −0.784 | −3.320 | 32.721 | 1.00 | 20.83 C |
| ATOM | 1040 | CB | LEU | A | 134 | −1.149 | −3.965 | 31.395 | 1.00 | 20.76 C |
| ATOM | 1041 | CG | LEU | A | 134 | −1.077 | −5.492 | 31.338 | 1.00 | 22.55 C |
| ATOM | 1042 | CD1 | LEU | A | 134 | −1.670 | −5.959 | 30.040 | 1.00 | 22.21 C |
| ATOM | 1043 | CD2 | LEU | A | 134 | 0.361 | −5.965 | 31.506 | 1.00 | 23.61 C |
| ATOM | 1044 | C | LEU | A | 134 | −0.889 | −1.817 | 32.584 | 1.00 | 20.05 C |
| ATOM | 1045 | O | LEU | A | 134 | −1.841 | −1.208 | 33.051 | 1.00 | 19.28 O |
| ATOM | 1046 | N | ILE | A | 135 | 0.086 | −1.233 | 31.891 | 1.00 | 18.39 N |
| ATOM | 1047 | CA | ILE | A | 135 | 0.162 | 0.198 | 31.682 | 1.00 | 18.18 C |
| ATOM | 1048 | CB | ILE | A | 135 | 1.028 | 0.856 | 32.786 | 1.00 | 19.88 C |
| ATOM | 1049 | CG1 | ILE | A | 135 | 0.682 | 2.322 | 32.955 | 1.00 | 22.25 C |
| ATOM | 1050 | CD1 | ILE | A | 135 | 0.371 | 2.670 | 34.398 | 1.00 | 26.92 C |
| ATOM | 1051 | CG2 | ILE | A | 135 | 2.501 | 0.581 | 32.588 | 1.00 | 20.81 C |
| ATOM | 1052 | C | ILE | A | 135 | 0.731 | 0.409 | 30.281 | 1.00 | 16.57 C |
| ATOM | 1053 | O | ILE | A | 135 | 1.407 | −0.483 | 29.770 | 1.00 | 16.98 O |
| ATOM | 1054 | N | PRO | A | 136 | 0.401 | 1.539 | 29.638 | 1.00 | 15.39 N |
| ATOM | 1055 | CA | PRO | A | 136 | 1.034 | 1.824 | 28.342 | 1.00 | 14.59 C |
| ATOM | 1056 | CB | PRO | A | 136 | 0.468 | 3.184 | 27.968 | 1.00 | 14.59 C |
| ATOM | 1057 | CG | PRO | A | 136 | −0.852 | 3.252 | 28.667 | 1.00 | 15.57 C |
| ATOM | 1058 | CD | PRO | A | 136 | −0.598 | 2.568 | 29.986 | 1.00 | 15.78 C |
| ATOM | 1059 | C | PRO | A | 136 | 2.550 | 1.891 | 28.388 | 1.00 | 15.06 C |
| ATOM | 1060 | O | PRO | A | 136 | 3.148 | 2.161 | 29.436 | 1.00 | 15.72 O |
| ATOM | 1061 | N | ILE | A | 137 | 3.165 | 1.615 | 27.245 | 1.00 | 13.89 N |
| ATOM | 1062 | CA | ILE | A | 137 | 4.600 | 1.756 | 27.119 | 1.00 | 13.54 C |
| ATOM | 1063 | CB | ILE | A | 137 | 5.107 | 1.026 | 25.857 | 1.00 | 13.19 C |
| ATOM | 1064 | CG1 | ILE | A | 137 | 4.725 | −0.467 | 25.896 | 1.00 | 14.05 C |
| ATOM | 1065 | CD1 | ILE | A | 137 | 5.097 | −1.217 | 27.175 | 1.00 | 16.84 C |
| ATOM | 1066 | CG2 | ILE | A | 137 | 6.610 | 1.212 | 25.703 | 1.00 | 13.91 C |
| ATOM | 1067 | C | ILE | A | 137 | 4.959 | 3.237 | 27.048 | 1.00 | 13.44 C |
| ATOM | 1068 | O | ILE | A | 137 | 4.387 | 4.003 | 26.304 | 1.00 | 13.44 O |
| ATOM | 1069 | N | THR | A | 138 | 5.933 | 3.618 | 27.867 | 1.00 | 13.55 N |
| ATOM | 1070 | CA | THR | A | 138 | 6.369 | 5.011 | 27.973 | 1.00 | 13.78 C |
| ATOM | 1071 | CB | THR | A | 138 | 6.930 | 5.314 | 29.379 | 1.00 | 14.14 C |
| ATOM | 1072 | OG1 | THR | A | 138 | 8.163 | 4.631 | 29.537 | 1.00 | 15.81 O |
| ATOM | 1073 | CG2 | THR | A | 138 | 5.955 | 4.861 | 30.469 | 1.00 | 15.66 C |
| ATOM | 1074 | C | THR | A | 138 | 7.490 | 5.285 | 26.980 | 1.00 | 13.92 C |
| ATOM | 1075 | O | THR | A | 138 | 8.163 | 4.354 | 26.514 | 1.00 | 14.34 O |
| ATOM | 1076 | N | TYR | A | 139 | 7.703 | 6.555 | 26.654 | 1.00 | 15.03 N |
| ATOM | 1077 | CA | TYR | A | 139 | 8.784 | 6.909 | 25.761 | 1.00 | 15.03 C |
| ATOM | 1078 | CB | TYR | A | 139 | 8.822 | 8.424 | 25.553 | 1.00 | 16.21 C |
| ATOM | 1079 | CG | TYR | A | 139 | 9.806 | 8.858 | 24.507 | 1.00 | 17.32 C |
| ATOM | 1080 | CD1 | TYR | A | 139 | 9.384 | 9.113 | 23.206 | 1.00 | 18.21 C |
| ATOM | 1081 | CE1 | TYR | A | 139 | 10.287 | 9.508 | 22.221 | 1.00 | 18.42 C |
| ATOM | 1082 | CZ | TYR | A | 139 | 11.623 | 9.663 | 22.535 | 1.00 | 19.94 C |
| ATOM | 1083 | OH | TYR | A | 139 | 12.503 | 10.051 | 21.534 | 1.00 | 21.13 O |
| ATOM | 1084 | CE2 | TYR | A | 139 | 12.079 | 9.414 | 23.821 | 1.00 | 19.28 C |
| ATOM | 1085 | CD2 | TYR | A | 139 | 11.159 | 9.015 | 24.815 | 1.00 | 18.75 C |
| ATOM | 1086 | C | TYR | A | 139 | 10.168 | 6.360 | 26.207 | 1.00 | 15.12 C |
| ATOM | 1087 | O | TYR | A | 139 | 10.919 | 5.797 | 25.404 | 1.00 | 14.95 O |
| ATOM | 1088 | N | PRO | A | 140 | 10.540 | 6.530 | 27.497 | 1.00 | 14.94 N |
| ATOM | 1089 | CA | PRO | A | 140 | 11.825 | 5.963 | 27.923 | 1.00 | 15.05 C |
| ATOM | 1090 | CB | PRO | A | 140 | 11.962 | 6.437 | 29.391 | 1.00 | 15.31 C |
| ATOM | 1091 | CG | PRO | A | 140 | 11.130 | 7.672 | 29.439 | 1.00 | 16.93 C |
| ATOM | 1092 | CD | PRO | A | 140 | 9.921 | 7.297 | 28.591 | 1.00 | 15.16 C |
| ATOM | 1093 | C | PRO | A | 140 | 11.934 | 4.454 | 27.796 | 1.00 | 14.68 C |
| ATOM | 1094 | O | PRO | A | 140 | 13.010 | 3.925 | 27.532 | 1.00 | 14.99 O |
| ATOM | 1095 | N | GLN | A | 141 | 10.821 | 3.755 | 27.992 | 1.00 | 14.91 N |
| ATOM | 1096 | CA | GLN | A | 141 | 10.831 | 2.321 | 27.795 | 1.00 | 15.32 C |
| ATOM | 1097 | CB | GLN | A | 141 | 9.504 | 1.709 | 28.260 | 1.00 | 15.84 C |
| ATOM | 1098 | CG | GLN | A | 141 | 9.408 | 1.695 | 29.805 | 1.00 | 17.42 C |

TABLE 2-continued

| ATOM | 1099 | CD  | GLN | A | 141 | 8.033  | 1.372  | 30.337 | 1.00 | 21.38 | C |
| ATOM | 1100 | OE1 | GLN | A | 141 | 7.048  | 1.409  | 29.613 | 1.00 | 19.25 | O |
| ATOM | 1101 | NE2 | GLN | A | 141 | 7.959  | 1.069  | 31.638 | 1.00 | 24.15 | N |
| ATOM | 1102 | C   | GLN | A | 141 | 11.100 | 1.970  | 26.329 | 1.00 | 14.71 | C |
| ATOM | 1103 | O   | GLN | A | 141 | 11.888 | 1.070  | 26.028 | 1.00 | 14.43 | O |
| ATOM | 1104 | N   | GLY | A | 142 | 10.450 | 2.704  | 25.432 | 1.00 | 14.86 | N |
| ATOM | 1105 | CA  | GLY | A | 142 | 10.638 | 2.471  | 23.988 | 1.00 | 14.98 | C |
| ATOM | 1106 | C   | GLY | A | 142 | 12.078 | 2.752  | 23.598 | 1.00 | 15.62 | C |
| ATOM | 1107 | O   | GLY | A | 142 | 12.702 | 1.979  | 22.871 | 1.00 | 15.98 | O |
| ATOM | 1108 | N   | LEU | A | 143 | 12.633 | 3.843  | 24.124 | 1.00 | 15.83 | N |
| ATOM | 1109 | CA  | LEU | A | 143 | 14.029 | 4.179  | 23.832 | 1.00 | 16.50 | C |
| ATOM | 1110 | CB  | LEU | A | 143 | 14.401 | 5.527  | 24.425 | 1.00 | 17.32 | C |
| ATOM | 1111 | CG  | LEU | A | 143 | 15.810 | 6.009  | 24.080 | 1.00 | 19.47 | C |
| ATOM | 1112 | CD1 | LEU | A | 143 | 16.041 | 6.135  | 22.575 | 1.00 | 21.78 | C |
| ATOM | 1113 | CD2 | LEU | A | 143 | 15.999 | 7.332  | 24.763 | 1.00 | 20.72 | C |
| ATOM | 1114 | C   | LEU | A | 143 | 14.988 | 3.100  | 24.327 | 1.00 | 15.76 | C |
| ATOM | 1115 | O   | LEU | A | 143 | 15.939 | 2.738  | 23.623 | 1.00 | 15.95 | O |
| ATOM | 1116 | N   | ALA | A | 144 | 14.747 | 2.576  | 25.529 | 1.00 | 15.60 | N |
| ATOM | 1117 | CA  | ALA | A | 144 | 15.579 | 1.489  | 26.048 | 1.00 | 15.89 | C |
| ATOM | 1118 | CB  | ALA | A | 144 | 15.176 | 1.128  | 27.474 | 1.00 | 16.77 | C |
| ATOM | 1119 | C   | ALA | A | 144 | 15.525 | 0.242  | 25.171 | 1.00 | 15.42 | C |
| ATOM | 1120 | O   | ALA | A | 144 | 16.529 | −0.409 | 24.935 | 1.00 | 15.80 | O |
| ATOM | 1121 | N   | MET | A | 145 | 14.329 | −0.085 | 24.695 | 1.00 | 15.04 | N |
| ATOM | 1122 | CA  | MET | A | 145 | 14.169 | −1.232 | 23.817 | 1.00 | 15.55 | C |
| ATOM | 1123 | CB  | MET | A | 145 | 12.690 | −1.461 | 23.547 | 1.00 | 15.20 | C |
| ATOM | 1124 | CG  | MET | A | 145 | 12.399 | −2.650 | 22.624 | 1.00 | 17.01 | C |
| ATOM | 1125 | SD  | MET | A | 145 | 12.861 | −4.261 | 23.305 | 1.00 | 18.66 | S |
| ATOM | 1126 | CE  | MET | A | 145 | 11.458 | −4.668 | 24.331 | 1.00 | 19.29 | C |
| ATOM | 1127 | C   | MET | A | 145 | 14.920 | −1.014 | 22.503 | 1.00 | 15.46 | C |
| ATOM | 1128 | O   | MET | A | 145 | 15.556 | −1.943 | 21.992 | 1.00 | 15.89 | O |
| ATOM | 1129 | N   | ALA | A | 146 | 14.853 | 0.203  | 21.971 | 1.00 | 15.90 | N |
| ATOM | 1130 | CA  | ALA | A | 146 | 15.560 | 0.543  | 20.729 | 1.00 | 16.14 | C |
| ATOM | 1131 | CB  | ALA | A | 146 | 15.283 | 1.978  | 20.323 | 1.00 | 16.29 | C |
| ATOM | 1132 | C   | ALA | A | 146 | 17.057 | 0.303  | 20.887 | 1.00 | 17.01 | C |
| ATOM | 1133 | O   | ALA | A | 146 | 17.708 | −0.245 | 19.997 | 1.00 | 16.87 | O |
| ATOM | 1134 | N   | LYS | A | 147 | 17.605 | 0.702  | 22.028 | 1.00 | 18.16 | N |
| ATOM | 1135 | CA  | LYS | A | 147 | 19.021 | 0.439  | 22.286 | 1.00 | 19.48 | C |
| ATOM | 1136 | CB  | LYS | A | 147 | 19.467 | 1.115  | 23.577 | 1.00 | 19.86 | C |
| ATOM | 1137 | CG  | LYS | A | 147 | 19.450 | 2.619  | 23.513 | 1.00 | 22.38 | C |
| ATOM | 1138 | CD  | LYS | A | 147 | 19.918 | 3.218  | 24.835 | 1.00 | 25.84 | C |
| ATOM | 1139 | CE  | LYS | A | 147 | 19.857 | 4.739  | 24.809 | 1.00 | 27.13 | C |
| ATOM | 1140 | NZ  | LYS | A | 147 | 20.013 | 5.289  | 26.179 | 1.00 | 29.52 | N |
| ATOM | 1141 | C   | LYS | A | 147 | 19.341 | −1.050 | 22.364 | 1.00 | 20.06 | C |
| ATOM | 1142 | O   | LYS | A | 147 | 20.356 | −1.501 | 21.828 | 1.00 | 19.99 | O |
| ATOM | 1143 | N   | GLU | A | 148 | 18.486 | −1.812 | 23.035 | 1.00 | 20.59 | N |
| ATOM | 1144 | CA  | GLU | A | 148 | 18.694 | −3.269 | 23.159 | 1.00 | 22.17 | C |
| ATOM | 1145 | CB  | GLU | A | 148 | 17.576 | −3.927 | 23.965 | 1.00 | 22.06 | C |
| ATOM | 1146 | CG  | GLU | A | 148 | 17.501 | −3.578 | 25.446 | 1.00 | 24.20 | C |
| ATOM | 1147 | CD  | GLU | A | 148 | 16.383 | −4.326 | 26.153 | 1.00 | 25.70 | C |
| ATOM | 1148 | OE1 | GLU | A | 148 | 16.031 | −5.439 | 25.711 | 1.00 | 31.32 | O |
| ATOM | 1149 | OE2 | GLU | A | 148 | 15.838 | −3.800 | 27.146 | 1.00 | 31.68 | O |
| ATOM | 1150 | C   | GLU | A | 148 | 18.773 | −3.977 | 21.809 | 1.00 | 21.83 | C |
| ATOM | 1151 | O   | GLU | A | 148 | 19.475 | −4.985 | 21.659 | 1.00 | 23.00 | O |
| ATOM | 1152 | N   | ILE | A | 149 | 18.024 | −3.473 | 20.833 | 1.00 | 20.08 | N |
| ATOM | 1153 | CA  | ILE | A | 149 | 17.978 | −4.121 | 19.519 | 1.00 | 19.47 | C |
| ATOM | 1154 | CB  | ILE | A | 149 | 16.519 | −4.318 | 18.997 | 1.00 | 18.75 | C |
| ATOM | 1155 | CG1 | ILE | A | 149 | 15.837 | −2.982 | 18.655 | 1.00 | 18.13 | C |
| ATOM | 1156 | CD1 | ILE | A | 149 | 14.511 | −3.149 | 17.895 | 1.00 | 18.17 | C |
| ATOM | 1157 | CG2 | ILE | A | 149 | 15.700 | −5.096 | 20.019 | 1.00 | 19.10 | C |
| ATOM | 1158 | C   | ILE | A | 149 | 18.834 | −3.408 | 18.492 | 1.00 | 19.23 | C |
| ATOM | 1159 | O   | ILE | A | 149 | 18.845 | −3.791 | 17.323 | 1.00 | 20.25 | O |
| ATOM | 1160 | N   | GLY | A | 150 | 19.558 | −2.381 | 18.927 | 1.00 | 18.35 | N |
| ATOM | 1161 | CA  | GLY | A | 150 | 20.482 | −1.680 | 18.039 | 1.00 | 17.82 | C |
| ATOM | 1162 | C   | GLY | A | 150 | 19.745 | −0.943 | 16.930 | 1.00 | 18.01 | C |
| ATOM | 1163 | O   | GLY | A | 150 | 20.273 | −0.782 | 15.825 | 1.00 | 18.92 | O |
| ATOM | 1164 | N   | ALA | A | 151 | 18.530 | −0.494 | 17.230 | 1.00 | 16.81 | N |
| ATOM | 1165 | CA  | ALA | A | 151 | 17.785 | 0.386  | 16.309 | 1.00 | 16.58 | C |
| ATOM | 1166 | CB  | ALA | A | 151 | 16.365 | 0.610  | 16.814 | 1.00 | 15.51 | C |
| ATOM | 1167 | C   | ALA | A | 151 | 18.502 | 1.727  | 16.150 | 1.00 | 17.00 | C |
| ATOM | 1168 | O   | ALA | A | 151 | 19.131 | 2.215  | 17.105 | 1.00 | 18.28 | O |
| ATOM | 1169 | N   | VAL | A | 152 | 18.430 | 2.329  | 14.964 | 1.00 | 16.92 | N |
| ATOM | 1170 | CA  | VAL | A | 152 | 19.067 | 3.619  | 14.731 | 1.00 | 17.25 | C |
| ATOM | 1171 | CB  | VAL | A | 152 | 19.465 | 3.825  | 13.238 | 1.00 | 17.70 | C |
| ATOM | 1172 | CG1 | VAL | A | 152 | 20.419 | 2.722  | 12.762 | 1.00 | 20.29 | C |
| ATOM | 1173 | CG2 | VAL | A | 152 | 18.251 | 3.882  | 12.357 | 1.00 | 17.61 | C |
| ATOM | 1174 | C   | VAL | A | 152 | 18.223 | 4.782  | 15.266 | 1.00 | 17.04 | C |
| ATOM | 1175 | O   | VAL | A | 152 | 18.718 | 5.881  | 15.513 | 1.00 | 17.43 | O |
| ATOM | 1176 | N   | LYS | A | 153 | 16.919 | 4.549  | 15.427 | 1.00 | 16.32 | N |
| ATOM | 1177 | CA  | LYS | A | 153 | 16.014 | 5.561  | 15.943 | 1.00 | 15.90 | C |

TABLE 2-continued

| | | | | | | | | | |
|---|---|---|---|---|---|---|---|---|---|
| ATOM | 1178 | CB | LYS | A | 153 | 15.424 | 6.391 | 14.792 | 1.00 17.62 C |
| ATOM | 1179 | CG | LYS | A | 153 | 16.374 | 7.355 | 14.069 | 1.00 21.36 C |
| ATOM | 1180 | CD | LYS | A | 153 | 16.886 | 8.472 | 14.985 | 1.00 26.36 C |
| ATOM | 1181 | CE | LYS | A | 153 | 15.779 | 9.375 | 15.496 | 1.00 29.00 C |
| ATOM | 1182 | NZ | LYS | A | 153 | 16.295 | 10.500 | 16.351 | 1.00 31.93 N |
| ATOM | 1183 | C | LYS | A | 153 | 14.867 | 4.871 | 16.657 | 1.00 14.89 C |
| ATOM | 1184 | O | LYS | A | 153 | 14.495 | 3.745 | 16.280 | 1.00 14.72 O |
| ATOM | 1185 | N | TYR | A | 154 | 14.316 | 5.562 | 17.655 | 1.00 14.38 N |
| ATOM | 1186 | CA | TYR | A | 154 | 13.031 | 5.224 | 18.255 | 1.00 13.82 C |
| ATOM | 1187 | CB | TYR | A | 154 | 13.164 | 5.052 | 19.779 | 1.00 14.86 C |
| ATOM | 1188 | CG | TYR | A | 154 | 11.808 | 4.874 | 20.433 | 1.00 14.08 C |
| ATOM | 1189 | CD1 | TYR | A | 154 | 11.018 | 3.754 | 20.142 | 1.00 15.57 C |
| ATOM | 1190 | CE1 | TYR | A | 154 | 9.763 | 3.594 | 20.695 | 1.00 15.86 C |
| ATOM | 1191 | CZ | TYR | A | 154 | 9.267 | 4.569 | 21.547 | 1.00 15.10 C |
| ATOM | 1192 | OH | TYR | A | 154 | 8.019 | 4.379 | 22.110 | 1.00 15.01 O |
| ATOM | 1193 | CE2 | TYR | A | 154 | 10.016 | 5.700 | 21.845 | 1.00 15.83 C |
| ATOM | 1194 | CD2 | TYR | A | 154 | 11.279 | 5.852 | 21.272 | 1.00 14.37 C |
| ATOM | 1195 | C | TYR | A | 154 | 12.087 | 6.372 | 17.980 | 1.00 13.73 C |
| ATOM | 1196 | O | TYR | A | 154 | 12.419 | 7.544 | 18.252 | 1.00 14.62 O |
| ATOM | 1197 | N | LEU | A | 155 | 10.917 | 6.062 | 17.427 | 1.00 12.95 N |
| ATOM | 1198 | CA | LEU | A | 155 | 9.902 | 7.055 | 17.068 | 1.00 13.09 C |
| ATOM | 1199 | CB | LEU | A | 155 | 9.914 | 7.303 | 15.564 | 1.00 13.61 C |
| ATOM | 1200 | CG | LEU | A | 155 | 11.217 | 7.832 | 14.961 | 1.00 15.78 C |
| ATOM | 1201 | CD1 | LEU | A | 155 | 11.156 | 7.731 | 13.448 | 1.00 16.92 C |
| ATOM | 1202 | CD2 | LEU | A | 155 | 11.464 | 9.258 | 15.437 | 1.00 16.38 C |
| ATOM | 1203 | C | LEU | A | 155 | 8.512 | 6.596 | 17.458 | 1.00 13.31 C |
| ATOM | 1204 | O | LEU | A | 155 | 8.231 | 5.400 | 17.429 | 1.00 13.15 O |
| ATOM | 1205 | N | GLU | A | 156 | 7.647 | 7.540 | 17.819 | 1.00 12.73 N |
| ATOM | 1206 | CA | GLU | A | 156 | 6.245 | 7.258 | 18.145 | 1.00 13.69 C |
| ATOM | 1207 | CB | GLU | A | 156 | 5.935 | 7.716 | 19.575 | 1.00 13.99 C |
| ATOM | 1208 | CG | GLU | A | 156 | 6.791 | 6.988 | 20.607 | 1.00 14.44 C |
| ATOM | 1209 | CD | GLU | A | 156 | 6.538 | 7.410 | 22.041 | 1.00 15.10 C |
| ATOM | 1210 | OE1 | GLU | A | 156 | 6.088 | 8.555 | 22.252 | 1.00 17.29 O |
| ATOM | 1211 | OE2 | GLU | A | 156 | 6.845 | 6.584 | 22.916 | 1.00 16.33 O |
| ATOM | 1212 | C | GLU | A | 156 | 5.315 | 7.948 | 17.162 | 1.00 13.28 C |
| ATOM | 1213 | O | GLU | A | 156 | 5.608 | 9.056 | 16.667 | 1.00 14.15 O |
| ATOM | 1214 | N | CYS | A | 157 | 4.173 | 7.332 | 16.869 | 1.00 12.48 N |
| ATOM | 1215 | CA | CYS | A | 157 | 3.248 | 7.946 | 15.935 | 1.00 12.25 C |
| ATOM | 1216 | CB | CYS | A | 157 | 3.685 | 7.653 | 14.491 | 1.00 12.28 C |
| ATOM | 1217 | SG | CYS | A | 157 | 3.426 | 5.920 | 13.944 | 1.00 13.16 S |
| ATOM | 1218 | C | CYS | A | 157 | 1.832 | 7.442 | 16.176 | 1.00 11.07 C |
| ATOM | 1219 | O | CYS | A | 157 | 1.635 | 6.467 | 16.913 | 1.00 11.61 O |
| ATOM | 1220 | N | SER | A | 158 | 0.883 | 8.110 | 15.530 | 1.00 11.86 N |
| ATOM | 1221 | CA | SER | A | 158 | −0.529 | 7.714 | 15.475 | 1.00 11.57 C |
| ATOM | 1222 | CB | SER | A | 158 | −1.400 | 8.639 | 16.344 | 1.00 11.46 C |
| ATOM | 1223 | OG | SER | A | 158 | −2.777 | 8.454 | 16.067 | 1.00 12.84 O |
| ATOM | 1224 | C | SER | A | 158 | −1.030 | 7.770 | 14.043 | 1.00 12.35 C |
| ATOM | 1225 | O | SER | A | 158 | −0.912 | 8.817 | 13.399 | 1.00 13.35 O |
| ATOM | 1226 | N | ALA | A | 159 | −1.565 | 6.671 | 13.515 | 1.00 12.23 N |
| ATOM | 1227 | CA | ALA | A | 159 | −2.230 | 6.704 | 12.210 | 1.00 12.91 C |
| ATOM | 1228 | CB | ALA | A | 159 | −2.548 | 5.283 | 11.741 | 1.00 12.63 C |
| ATOM | 1229 | C | ALA | A | 159 | −3.520 | 7.513 | 12.248 | 1.00 13.19 C |
| ATOM | 1230 | O | ALA | A | 159 | −3.945 | 8.058 | 11.223 | 1.00 13.32 O |
| ATOM | 1231 | N | LEU | A | 160 | −4.156 | 7.563 | 13.414 | 1.00 13.73 N |
| ATOM | 1232 | CA | LEU | A | 160 | −5.424 | 8.250 | 13.580 | 1.00 14.94 C |
| ATOM | 1233 | CB | LEU | A | 160 | −6.096 | 7.781 | 14.872 | 1.00 15.57 C |
| ATOM | 1234 | CG | LEU | A | 160 | −7.542 | 8.210 | 15.145 | 1.00 17.88 C |
| ATOM | 1235 | CD1 | LEU | A | 160 | −8.273 | 7.116 | 15.948 | 1.00 19.48 C |
| ATOM | 1236 | CD2 | LEU | A | 160 | −7.551 | 9.552 | 15.882 | 1.00 19.96 C |
| ATOM | 1237 | C | LEU | A | 160 | −5.253 | 9.781 | 13.525 | 1.00 14.74 C |
| ATOM | 1238 | O | LEU | A | 160 | −5.977 | 10.445 | 12.763 | 1.00 16.73 O |
| ATOM | 1239 | N | THR | A | 161 | −4.291 | 10.314 | 14.271 | 1.00 14.73 N |
| ATOM | 1240 | CA | THR | A | 161 | −4.076 | 11.779 | 14.312 | 1.00 15.61 C |
| ATOM | 1241 | CB | THR | A | 161 | −3.653 | 12.248 | 15.708 | 1.00 15.82 C |
| ATOM | 1242 | OG1 | THR | A | 161 | −2.357 | 11.718 | 16.027 | 1.00 15.63 O |
| ATOM | 1243 | CG2 | THR | A | 161 | −4.667 | 11.818 | 16.780 | 1.00 16.36 C |
| ATOM | 1244 | C | THR | A | 161 | −2.985 | 12.248 | 13.357 | 1.00 16.70 C |
| ATOM | 1245 | O | THR | A | 161 | −2.850 | 13.446 | 13.091 | 1.00 17.02 O |
| ATOM | 1246 | N | GLN | A | 162 | −2.203 | 11.288 | 12.859 | 1.00 15.83 N |
| ATOM | 1247 | CA | GLN | A | 162 | −0.997 | 11.511 | 12.035 | 1.00 16.95 C |
| ATOM | 1248 | CB | GLN | A | 162 | −1.294 | 12.308 | 10.764 | 1.00 17.58 C |
| ATOM | 1249 | CG | GLN | A | 162 | −2.244 | 11.634 | 9.840 | 1.00 20.45 C |
| ATOM | 1250 | CD | GLN | A | 162 | −2.105 | 12.156 | 8.438 | 1.00 24.07 C |
| ATOM | 1251 | OE1 | GLN | A | 162 | −2.089 | 11.398 | 7.477 | 1.00 25.85 O |
| ATOM | 1252 | NE2 | GLN | A | 162 | −1.965 | 13.465 | 8.314 | 1.00 23.76 N |
| ATOM | 1253 | C | GLN | A | 162 | 0.189 | 12.105 | 12.785 | 1.00 16.79 C |
| ATOM | 1254 | O | GLN | A | 162 | 1.225 | 12.404 | 12.176 | 1.00 16.94 O |
| ATOM | 1255 | N | ARG | A | 163 | 0.055 | 12.309 | 14.093 | 1.00 15.75 N |
| ATOM | 1256 | CA | ARG | A | 163 | 1.174 | 12.792 | 14.891 | 1.00 15.88 C |

TABLE 2-continued

| | | | | | | | | | |
|---|---|---|---|---|---|---|---|---|---|
| ATOM | 1257 | CB | ARG | A | 163 | 0.751 | 12.960 | 16.356 | 1.00 17.08 C |
| ATOM | 1258 | CG | ARG | A | 163 | 1.879 | 13.133 | 17.357 | 1.00 20.93 C |
| ATOM | 1259 | CD | ARG | A | 163 | 2.435 | 14.511 | 17.436 | 1.00 26.06 C |
| ATOM | 1260 | NE | ARG | A | 163 | 1.382 | 15.517 | 17.404 | 0.75 27.25 N |
| ATOM | 1261 | CZ | ARG | A | 163 | 1.616 | 16.822 | 17.415 | 1.00 28.54 C |
| ATOM | 1262 | NH1 | ARG | A | 163 | 2.865 | 17.266 | 17.462 | 1.00 29.24 N |
| ATOM | 1263 | NH2 | ARG | A | 163 | 0.602 | 17.670 | 17.354 | 1.00 27.89 N |
| ATOM | 1264 | C | ARG | A | 163 | 2.378 | 11.859 | 14.749 | 1.00 15.55 C |
| ATOM | 1265 | O | ARG | A | 163 | 2.258 | 10.640 | 14.947 | 0.50 12.27 O |
| ATOM | 1266 | N | GLY | A | 164 | 3.525 | 12.425 | 14.373 | 1.00 14.69 N |
| ATOM | 1267 | CA | GLY | A | 164 | 4.763 | 11.665 | 14.200 | 1.00 14.63 C |
| ATOM | 1268 | C | GLY | A | 164 | 4.863 | 10.804 | 12.950 | 1.00 13.55 C |
| ATOM | 1269 | O | GLY | A | 164 | 5.899 | 10.197 | 12.702 | 1.00 14.55 O |
| ATOM | 1270 | N | LEU | A | 165 | 3.797 | 10.762 | 12.162 | 1.00 13.31 N |
| ATOM | 1271 | CA | LEU | A | 165 | 3.707 | 9.782 | 11.084 | 1.00 13.13 C |
| ATOM | 1272 | CB | LEU | A | 165 | 2.261 | 9.658 | 10.595 | 1.00 13.76 C |
| ATOM | 1273 | CG | LEU | A | 165 | 1.980 | 8.553 | 9.573 | 1.00 14.86 C |
| ATOM | 1274 | CD1 | LEU | A | 165 | 2.309 | 7.157 | 10.106 | 1.00 16.12 C |
| ATOM | 1275 | CD2 | LEU | A | 165 | 0.535 | 8.633 | 9.149 | 1.00 14.31 C |
| ATOM | 1276 | C | LEU | A | 165 | 4.664 | 10.070 | 9.935 | 1.00 13.35 C |
| ATOM | 1277 | O | LEU | A | 165 | 5.419 | 9.185 | 9.497 | 1.00 13.32 O |
| ATOM | 1278 | N | LYS | A | 166 | 4.666 | 11.299 | 9.425 | 1.00 13.52 N |
| ATOM | 1279 | CA | LYS | A | 166 | 5.577 | 11.628 | 8.331 | 1.00 13.76 C |
| ATOM | 1280 | CB | LYS | A | 166 | 5.261 | 13.010 | 7.784 | 1.00 14.69 C |
| ATOM | 1281 | CG | LYS | A | 166 | 3.905 | 13.080 | 7.142 | 1.00 15.92 C |
| ATOM | 1282 | CD | LYS | A | 166 | 3.602 | 14.524 | 6.741 | 1.00 19.54 C |
| ATOM | 1283 | CE | LYS | A | 166 | 2.328 | 14.673 | 5.953 | 1.00 23.03 C |
| ATOM | 1284 | NZ | LYS | A | 166 | 1.129 | 14.415 | 6.801 | 1.00 27.33 N |
| ATOM | 1285 | C | LYS | A | 166 | 7.035 | 11.520 | 8.779 | 1.00 13.49 C |
| ATOM | 1286 | O | LYS | A | 166 | 7.892 | 11.110 | 7.995 | 1.00 14.34 O |
| ATOM | 1287 | N | THR | A | 167 | 7.327 | 11.841 | 10.038 | 1.00 13.55 N |
| ATOM | 1288 | CA | THR | A | 167 | 8.671 | 11.722 | 10.581 | 1.00 13.77 C |
| ATOM | 1289 | CB | THR | A | 167 | 8.710 | 12.319 | 11.997 | 1.00 14.09 C |
| ATOM | 1290 | OG1 | THR | A | 167 | 8.464 | 13.729 | 11.886 | 1.00 18.21 O |
| ATOM | 1291 | CG2 | THR | A | 167 | 10.041 | 12.057 | 12.697 | 1.00 15.51 C |
| ATOM | 1292 | C | THR | A | 167 | 9.211 | 10.297 | 10.528 | 1.00 13.82 C |
| ATOM | 1293 | O | THR | A | 167 | 10.397 | 10.080 | 10.290 | 1.00 13.73 O |
| ATOM | 1294 | N | VAL | A | 168 | 8.341 | 9.311 | 10.743 | 1.00 12.93 N |
| ATOM | 1295 | CA | VAL | A | 168 | 8.782 | 7.928 | 10.666 | 1.00 13.09 C |
| ATOM | 1296 | CB | VAL | A | 168 | 7.585 | 6.971 | 10.881 | 1.00 12.82 C |
| ATOM | 1297 | CG1 | VAL | A | 168 | 7.969 | 5.525 | 10.510 | 1.00 13.06 C |
| ATOM | 1298 | CG2 | VAL | A | 168 | 7.118 | 7.023 | 12.336 | 1.00 13.99 C |
| ATOM | 1299 | C | VAL | A | 168 | 9.458 | 7.652 | 9.316 | 1.00 12.52 C |
| ATOM | 1300 | O | VAL | A | 168 | 10.544 | 7.070 | 9.260 | 1.00 12.69 O |
| ATOM | 1301 | N | PHE | A | 169 | 8.807 | 8.071 | 8.244 | 1.00 12.32 N |
| ATOM | 1302 | CA | PHE | A | 169 | 9.301 | 7.796 | 6.904 | 1.00 12.53 C |
| ATOM | 1303 | CB | PHE | A | 169 | 8.129 | 7.771 | 5.926 | 1.00 12.31 C |
| ATOM | 1304 | CG | PHE | A | 169 | 7.176 | 6.663 | 6.252 | 1.00 12.91 C |
| ATOM | 1305 | CD1 | PHE | A | 169 | 7.521 | 5.355 | 5.938 | 1.00 12.66 C |
| ATOM | 1306 | CE1 | PHE | A | 169 | 6.701 | 4.291 | 6.307 | 1.00 14.90 C |
| ATOM | 1307 | CZ | PHE | A | 169 | 5.530 | 4.540 | 6.973 | 1.00 14.20 C |
| ATOM | 1308 | CE2 | PHE | A | 169 | 5.187 | 5.847 | 7.321 | 1.00 12.87 C |
| ATOM | 1309 | CD2 | PHE | A | 169 | 6.002 | 6.901 | 6.949 | 1.00 13.39 C |
| ATOM | 1310 | C | PHE | A | 169 | 10.469 | 8.680 | 6.503 | 1.00 13.15 C |
| ATOM | 1311 | O | PHE | A | 169 | 11.369 | 8.225 | 5.805 | 1.00 13.31 O |
| ATOM | 1312 | N | ASP | A | 170 | 10.488 | 9.913 | 7.016 | 1.00 13.64 N |
| ATOM | 1313 | CA | ASP | A | 170 | 11.672 | 10.784 | 6.859 | 1.00 14.87 C |
| ATOM | 1314 | CB | ASP | A | 170 | 11.524 | 12.080 | 7.651 | 1.00 16.28 C |
| ATOM | 1315 | CG | ASP | A | 170 | 10.543 | 13.048 | 7.058 | 1.00 19.88 C |
| ATOM | 1316 | OD1 | ASP | A | 170 | 10.119 | 12.892 | 5.896 | 1.00 21.00 O |
| ATOM | 1317 | OD2 | ASP | A | 170 | 10.202 | 14.002 | 7.798 | 1.00 23.66 O |
| ATOM | 1318 | C | ASP | A | 170 | 12.890 | 10.077 | 7.440 | 1.00 14.49 C |
| ATOM | 1319 | O | ASP | A | 170 | 13.957 | 10.021 | 6.826 | 1.00 14.33 O |
| ATOM | 1320 | N | GLU | A | 171 | 12.728 | 9.529 | 8.642 | 1.00 13.56 N |
| ATOM | 1321 | CA | GLU | A | 171 | 13.831 | 8.893 | 9.342 | 1.00 13.86 C |
| ATOM | 1322 | CB | GLU | A | 171 | 13.515 | 8.776 | 10.840 | 1.00 14.47 C |
| ATOM | 1323 | CG | GLU | A | 171 | 13.513 | 10.133 | 11.541 | 1.00 16.70 C |
| ATOM | 1324 | CD | GLU | A | 171 | 14.864 | 10.844 | 11.544 | 1.00 22.34 C |
| ATOM | 1325 | OE1 | GLU | A | 171 | 15.913 | 10.175 | 11.616 | 1.00 25.74 O |
| ATOM | 1326 | OE2 | GLU | A | 171 | 14.863 | 12.085 | 11.477 | 1.00 26.06 O |
| ATOM | 1327 | C | GLU | A | 171 | 14.221 | 7.564 | 8.716 | 1.00 13.90 C |
| ATOM | 1328 | O | GLU | A | 171 | 15.403 | 7.200 | 8.709 | 1.00 14.62 O |
| ATOM | 1329 | N | ALA | A | 172 | 13.246 | 6.838 | 8.180 | 1.00 13.38 N |
| ATOM | 1330 | CA | ALA | A | 172 | 13.546 | 5.622 | 7.432 | 1.00 13.23 C |
| ATOM | 1331 | CB | ALA | A | 172 | 12.252 | 5.014 | 6.897 | 1.00 14.03 C |
| ATOM | 1332 | C | ALA | A | 172 | 14.495 | 5.956 | 6.286 | 1.00 13.28 C |
| ATOM | 1333 | O | ALA | A | 172 | 15.493 | 5.250 | 6.050 | 1.00 14.11 O |
| ATOM | 1334 | N | ILE | A | 173 | 14.178 | 7.033 | 5.573 | 1.00 12.65 N |
| ATOM | 1335 | CA | ILE | A | 173 | 14.992 | 7.458 | 4.434 | 1.00 13.19 C |

TABLE 2-continued

| | | | | | | | | | |
|---|---|---|---|---|---|---|---|---|---|
| ATOM | 1336 | CB | ILE | A | 173 | 14.250 | 8.516 | 3.612 | 1.00 12.40 C |
| ATOM | 1337 | CG1 | ILE | A | 173 | 13.103 | 7.828 | 2.857 | 1.00 14.78 C |
| ATOM | 1338 | CD1 | ILE | A | 173 | 12.081 | 8.785 | 2.302 | 1.00 13.37 C |
| ATOM | 1339 | CG2 | ILE | A | 173 | 15.229 | 9.228 | 2.643 | 1.00 13.54 C |
| ATOM | 1340 | C | ILE | A | 173 | 16.370 | 7.940 | 4.916 | 1.00 13.03 C |
| ATOM | 1341 | O | ILE | A | 173 | 17.402 | 7.545 | 4.344 | 1.00 13.20 O |
| ATOM | 1342 | N | ARG | A | 174 | 16.382 | 8.744 | 5.977 | 1.00 13.62 N |
| ATOM | 1343 | CA | ARG | A | 174 | 17.674 | 9.196 | 6.521 | 1.00 14.74 C |
| ATOM | 1344 | CB | ARG | A | 174 | 17.494 | 10.195 | 7.646 | 1.00 15.41 C |
| ATOM | 1345 | CG | ARG | A | 174 | 16.882 | 11.488 | 7.168 | 1.00 15.94 C |
| ATOM | 1346 | CD | ARG | A | 174 | 16.629 | 12.458 | 8.320 | 1.00 20.70 C |
| ATOM | 1347 | NE | ARG | A | 174 | 16.118 | 13.738 | 7.823 | 1.00 22.87 N |
| ATOM | 1348 | CZ | ARG | A | 174 | 15.001 | 14.333 | 8.237 | 1.00 26.43 C |
| ATOM | 1349 | NH1 | ARG | A | 174 | 14.252 | 13.806 | 9.205 | 1.00 29.29 N |
| ATOM | 1350 | NH2 | ARG | A | 174 | 14.640 | 15.486 | 7.689 | 1.00 29.09 N |
| ATOM | 1351 | C | ARG | A | 174 | 18.557 | 8.055 | 6.972 | 1.00 15.31 C |
| ATOM | 1352 | O | ARG | A | 174 | 19.786 | 8.137 | 6.874 | 1.00 16.11 O |
| ATOM | 1353 | N | ALA | A | 175 | 17.955 | 6.974 | 7.463 | 1.00 15.52 N |
| ATOM | 1354 | CA | ALA | A | 175 | 18.750 | 5.836 | 7.925 | 1.00 16.05 C |
| ATOM | 1355 | CB | ALA | A | 175 | 17.848 | 4.791 | 8.567 | 1.00 16.64 C |
| ATOM | 1356 | C | ALA | A | 175 | 19.527 | 5.214 | 6.784 | 1.00 16.94 C |
| ATOM | 1357 | O | ALA | A | 175 | 20.554 | 4.546 | 6.996 | 1.00 17.87 O |
| ATOM | 1358 | N | VAL | A | 176 | 19.023 | 5.398 | 5.570 | 1.00 16.33 N |
| ATOM | 1359 | CA | VAL | A | 176 | 19.637 | 4.805 | 4.402 | 1.00 16.94 C |
| ATOM | 1360 | CB | VAL | A | 176 | 18.558 | 4.324 | 3.380 | 1.00 16.82 C |
| ATOM | 1361 | CG1 | VAL | A | 176 | 19.199 | 3.795 | 2.097 | 1.00 17.60 C |
| ATOM | 1362 | CG2 | VAL | A | 176 | 17.671 | 3.260 | 4.012 | 1.00 17.37 C |
| ATOM | 1363 | C | VAL | A | 176 | 20.608 | 5.811 | 3.770 | 1.00 18.02 C |
| ATOM | 1364 | O | VAL | A | 176 | 21.728 | 5.427 | 3.375 | 1.00 19.01 O |
| ATOM | 1365 | N | LEU | A | 177 | 20.209 | 7.085 | 3.716 | 1.00 18.56 N |
| ATOM | 1366 | CA | LEU | A | 177 | 20.959 | 8.112 | 2.960 | 1.00 19.99 C |
| ATOM | 1367 | CB | LEU | A | 177 | 19.995 | 9.076 | 2.262 | 1.00 19.32 C |
| ATOM | 1368 | CG | LEU | A | 177 | 19.084 | 8.466 | 1.202 | 1.00 19.69 C |
| ATOM | 1369 | CD1 | LEU | A | 177 | 18.245 | 9.570 | 0.570 | 1.00 21.53 C |
| ATOM | 1370 | CD2 | LEU | A | 177 | 19.869 | 7.693 | 0.137 | 1.00 20.62 C |
| ATOM | 1371 | C | LEU | A | 177 | 21.971 | 8.922 | 3.771 | 1.00 21.89 C |
| ATOM | 1372 | O | LEU | A | 177 | 22.858 | 9.576 | 3.198 | 1.00 22.03 O |
| ATOM | 1373 | N | CYS | A | 178 | 21.826 | 8.919 | 5.089 | 1.00 22.74 N |
| ATOM | 1374 | CA | CYS | A | 178 | 22.743 | 9.643 | 5.961 | 1.00 25.08 C |
| ATOM | 1375 | CB | CYS | A | 178 | 21.984 | 10.500 | 6.977 | 1.00 25.34 C |
| ATOM | 1376 | SG | CYS | A | 178 | 20.806 | 11.678 | 6.228 | 0.75 28.16 S |
| ATOM | 1377 | C | CYS | A | 178 | 23.648 | 8.648 | 6.661 | 1.00 26.11 C |
| ATOM | 1378 | O | CYS | A | 178 | 23.186 | 7.875 | 7.499 | 1.00 27.77 O |
| ATOM | 1379 | O6 | GDP | A | 191 | −3.009 | 5.022 | 15.369 | 1.00 12.24 O |
| ATOM | 1380 | C6 | GDP | A | 191 | −4.015 | 4.359 | 15.678 | 1.00 12.17 C |
| ATOM | 1381 | N1 | GDP | A | 191 | −4.860 | 4.763 | 16.631 | 1.00 11.86 N |
| ATOM | 1382 | C2 | GDP | A | 191 | −5.946 | 4.059 | 17.010 | 1.00 13.33 C |
| ATOM | 1383 | N3 | GDP | A | 191 | −6.335 | 2.908 | 16.446 | 1.00 12.94 N |
| ATOM | 1384 | C4 | GDP | A | 191 | −5.563 | 2.390 | 15.462 | 1.00 12.01 C |
| ATOM | 1385 | N2 | GDP | A | 191 | −6.728 | 4.592 | 17.968 | 1.00 14.08 N |
| ATOM | 1386 | C5 | GDP | A | 191 | −4.355 | 3.101 | 15.012 | 1.00 11.72 C |
| ATOM | 1387 | N7 | GDP | A | 191 | −3.778 | 2.354 | 14.043 | 1.00 11.60 N |
| ATOM | 1388 | C8 | GDP | A | 191 | −4.554 | 1.260 | 13.880 | 1.00 11.74 C |
| ATOM | 1389 | N9 | GDP | A | 191 | −5.622 | 1.293 | 14.713 | 1.00 11.13 N |
| ATOM | 1390 | C1* | GDP | A | 191 | −6.641 | 0.245 | 14.813 | 1.00 12.04 C |
| ATOM | 1391 | C2* | GDP | A | 191 | −7.274 | −0.146 | 13.495 | 1.00 13.49 C |
| ATOM | 1392 | O2* | GDP | A | 191 | −8.363 | 0.720 | 13.221 | 1.00 15.11 O |
| ATOM | 1393 | C3* | GDP | A | 191 | −7.655 | −1.573 | 13.776 | 1.00 13.18 C |
| ATOM | 1394 | O3* | GDP | A | 191 | −8.833 | −1.618 | 14.593 | 1.00 14.69 O |
| ATOM | 1395 | O4* | GDP | A | 191 | −5.970 | −0.930 | 15.291 | 1.00 11.20 O |
| ATOM | 1396 | C4* | GDP | A | 191 | −6.533 | −2.077 | 14.643 | 1.00 12.56 C |
| ATOM | 1397 | C5* | GDP | A | 191 | −5.462 | −2.819 | 13.842 | 1.00 10.91 C |
| ATOM | 1398 | O5* | GDP | A | 191 | −4.919 | −1.976 | 12.814 | 1.00 9.53 O |
| ATOM | 1399 | PA | GDP | A | 191 | −4.141 | −2.627 | 11.586 | 1.00 9.51 P |
| ATOM | 1400 | O1A | GDP | A | 191 | −3.619 | −1.488 | 10.785 | 1.00 9.65 O |
| ATOM | 1401 | O2A | GDP | A | 191 | −4.994 | −3.603 | 10.878 | 1.00 10.36 O |
| ATOM | 1402 | O3A | GDP | A | 191 | −2.961 | −3.377 | 12.352 | 1.00 9.19 O |
| ATOM | 1403 | PB | GDP | A | 191 | −1.946 | −4.469 | 11.696 | 1.00 8.75 P |
| ATOM | 1404 | O1B | GDP | A | 191 | −0.668 | −4.238 | 12.435 | 1.00 8.01 O |
| ATOM | 1405 | O3B | GDP | A | 191 | −2.522 | −5.850 | 12.023 | 1.00 9.28 O |
| ATOM | 1406 | O2B | GDP | A | 191 | −1.858 | −4.210 | 10.209 | 1.00 9.68 O |
| ATOM | 1407 | MG | MG | A | 192 | −2.167 | −5.353 | 8.526 | 1.00 8.83 MG |
| ATOM | 1408 | CBD | DRG | A | 193 | 0.406 | −14.451 | 2.136 | 1.00 20.00 C |
| ATOM | 1409 | CBB | DRG | A | 193 | 2.146 | −12.890 | 2.465 | 1.00 20.00 C |
| ATOM | 1410 | NBA | DRG | A | 193 | 3.529 | −12.690 | 2.960 | 1.00 20.00 N |
| ATOM | 1411 | CBC | DRG | A | 193 | 3.640 | −12.452 | 4.424 | 1.00 20.00 C |
| ATOM | 1412 | CBE | DRG | A | 193 | 2.434 | −11.812 | 5.143 | 1.00 20.00 C |
| ATOM | 1413 | CAZ | DRG | A | 193 | 4.116 | −11.597 | 2.155 | 1.00 20.00 C |
| ATOM | 1414 | CAY | DRG | A | 193 | 3.136 | −10.466 | 1.830 | 1.00 20.00 C |

TABLE 2-continued

| | | | | | | | | | | |
|---|---|---|---|---|---|---|---|---|---|---|
| ATOM | 1415 | CAW | DRG | A | 193 | 3.849 | −9.122 | 1.968 | 1.00 | 20.00 C |
| ATOM | 1416 | CAV | DRG | A | 193 | 4.966 | −8.927 | 0.931 | 1.00 | 20.00 C |
| ATOM | 1417 | CAX | DRG | A | 193 | 4.587 | −7.782 | −0.014 | 1.00 | 20.00 C |
| ATOM | 1418 | NAT | DRG | A | 193 | 5.170 | −10.167 | 0.151 | 1.00 | 20.00 N |
| ATOM | 1419 | C2 | DRG | A | 193 | 5.755 | −10.178 | −1.062 | 1.00 | 20.00 C |
| ATOM | 1420 | N1 | DRG | A | 193 | 6.881 | −10.908 | −1.294 | 1.00 | 20.00 N |
| ATOM | 1421 | N3 | DRG | A | 193 | 5.235 | −9.449 | −2.081 | 1.00 | 20.00 N |
| ATOM | 1422 | C4 | DRG | A | 193 | 5.792 | −9.433 | −3.311 | 1.00 | 20.00 C |
| ATOM | 1423 | CAU | DRG | A | 193 | 5.162 | −8.597 | −4.433 | 1.00 | 20.00 C |
| ATOM | 1424 | C5 | DRG | A | 193 | 7.151 | −10.382 | −3.474 | 1.00 | 20.00 C |
| ATOM | 1425 | C6 | DRG | A | 193 | 7.501 | −10.933 | −2.508 | 1.00 | 20.00 C |
| ATOM | 1426 | NAM | DRG | A | 193 | 8.587 | −11.713 | −2.703 | 1.00 | 20.00 N |
| ATOM | 1427 | CAJ | DRG | A | 193 | 9.598 | −11.432 | −3.564 | 1.00 | 20.00 C |
| ATOM | 1428 | CAF | DRG | A | 193 | 10.250 | −12.483 | −4.242 | 1.00 | 20.00 C |
| ATOM | 1429 | CAB | DRG | A | 193 | 11.209 | −12.178 | −5.237 | 1.00 | 20.00 C |
| ATOM | 1430 | CAA | DRG | A | 193 | 11.876 | −13.169 | −5.994 | 1.00 | 20.00 C |
| ATOM | 1431 | NAD | DRG | A | 193 | 11.681 | −14.479 | −5.807 | 1.00 | 20.00 N |
| ATOM | 1432 | CAC | DRG | A | 193 | 12.793 | −12.809 | −6.990 | 1.00 | 20.00 C |
| ATOM | 1433 | CAG | DRG | A | 193 | 13.025 | −11.443 | −7.223 | 1.00 | 20.00 C |
| ATOM | 1434 | CAK | DRG | A | 193 | 14.012 | −11.010 | −8.312 | 1.00 | 20.00 C |
| ATOM | 1435 | NAH | DRG | A | 193 | 12.390 | −10.511 | −6.483 | 1.00 | 20.00 N |
| ATOM | 1436 | CAE | DRG | A | 193 | 11.498 | −10.812 | −5.516 | 1.00 | 20.00 C |
| ATOM | 1437 | CAI | DRG | A | 193 | 10.871 | −9.762 | −4.834 | 1.00 | 20.00 C |
| ATOM | 1438 | CAL | DRG | A | 193 | 9.914 | −10.089 | −3.863 | 1.00 | 20.00 C |
| ATOM | 1439 | O | HOH | Z | 1 | −0.134 | −5.584 | 8.242 | 1.00 | 8.96 O |
| ATOM | 1440 | O | HOH | Z | 2 | −4.232 | −5.015 | 8.711 | 1.00 | 9.58 O |
| ATOM | 1441 | O | HOH | Z | 3 | −2.275 | −7.057 | 9.673 | 1.00 | 10.94 O |
| ATOM | 1442 | O | HOH | Z | 4 | 10.477 | −1.304 | −3.031 | 1.00 | 26.08 O |
| ATOM | 1443 | O | HOH | Z | 5 | 16.317 | −2.369 | −2.524 | 1.00 | 29.42 O |
| ATOM | 1444 | O | HOH | Z | 6 | 5.047 | −8.484 | 10.591 | 1.00 | 12.91 O |
| ATOM | 1445 | O | HOH | Z | 7 | 5.124 | −6.010 | 17.744 | 1.00 | 11.06 O |
| ATOM | 1446 | O | HOH | Z | 8 | 0.567 | −9.158 | 20.354 | 1.00 | 21.09 O |
| ATOM | 1447 | O | HOH | Z | 9 | 0.703 | −11.544 | 16.131 | 1.00 | 12.46 O |
| ATOM | 1448 | O | HOH | Z | 10 | 3.703 | −12.071 | 16.597 | 1.00 | 22.55 O |
| ATOM | 1449 | O | HOH | Z | 11 | −0.182 | −8.384 | 10.983 | 1.00 | 11.20 O |
| ATOM | 1450 | O | HOH | Z | 12 | −4.333 | −8.769 | 10.467 | 1.00 | 14.76 O |
| ATOM | 1451 | O | HOH | Z | 13 | −4.936 | −6.912 | 12.473 | 1.00 | 14.22 O |
| ATOM | 1452 | O | HOH | Z | 14 | −8.445 | 11.206 | 35.892 | 1.00 | 27.24 O |
| ATOM | 1453 | O | HOH | Z | 15 | −3.210 | −2.135 | 20.575 | 1.00 | 12.27 O |
| ATOM | 1454 | O | HOH | Z | 16 | −1.032 | 2.706 | 13.325 | 1.00 | 11.23 O |
| ATOM | 1455 | O | HOH | Z | 17 | 0.215 | 4.566 | 14.883 | 1.00 | 12.32 O |
| ATOM | 1456 | O | HOH | Z | 18 | 1.314 | 11.622 | 4.713 | 1.00 | 23.82 O |
| ATOM | 1457 | O | HOH | Z | 19 | 0.615 | 11.501 | 7.265 | 1.00 | 29.69 O |
| ATOM | 1458 | O | HOH | Z | 20 | −14.149 | 1.973 | 10.917 | 1.00 | 22.67 O |
| ATOM | 1459 | O | HOH | Z | 21 | −11.299 | −4.865 | 9.719 | 1.00 | 22.28 O |
| ATOM | 1460 | O | HOH | Z | 22 | −9.705 | −6.203 | 8.035 | 1.00 | 17.69 O |
| ATOM | 1461 | O | HOH | Z | 23 | 7.468 | 13.145 | −9.245 | 1.00 | 28.76 O |
| ATOM | 1462 | O | HOH | Z | 24 | −6.991 | −5.346 | 11.452 | 1.00 | 15.83 O |
| ATOM | 1463 | O | HOH | Z | 25 | 4.514 | 11.481 | −2.718 | 1.00 | 12.76 O |
| ATOM | 1464 | O | HOH | Z | 26 | 6.818 | 14.498 | 0.538 | 1.00 | 22.98 O |
| ATOM | 1465 | O | HOH | Z | 27 | −6.619 | −9.355 | 9.099 | 1.00 | 17.44 O |
| ATOM | 1466 | O | HOH | Z | 28 | 15.357 | 6.087 | −3.675 | 1.00 | 27.71 O |
| ATOM | 1467 | O | HOH | Z | 29 | 15.754 | 8.383 | −5.057 | 1.00 | 25.97 O |
| ATOM | 1468 | O | HOH | Z | 30 | −1.307 | −5.728 | 19.093 | 1.00 | 27.63 O |
| ATOM | 1469 | O | HOH | Z | 31 | −0.946 | −7.181 | 21.049 | 1.00 | 23.44 O |
| ATOM | 1470 | O | HOH | Z | 32 | −3.074 | −4.762 | 20.234 | 1.00 | 31.01 O |
| ATOM | 1471 | O | HOH | Z | 33 | 2.733 | 9.521 | 0.192 | 1.00 | 13.56 O |
| ATOM | 1472 | O | HOH | Z | 34 | 3.360 | 9.455 | −1.336 | 1.00 | 18.57 O |
| ATOM | 1473 | O | HOH | Z | 36 | 11.041 | −13.275 | −2.389 | 1.00 | 29.42 O |
| ATOM | 1474 | O | HOH | Z | 37 | −6.223 | 11.555 | 10.296 | 1.00 | 32.37 O |
| ATOM | 1475 | O | HOH | Z | 38 | −9.612 | −4.467 | 12.063 | 1.00 | 31.51 O |
| ATOM | 1476 | O | HOH | Z | 44 | 4.098 | −4.948 | −0.736 | 1.00 | 26.48 O |
| ATOM | 1477 | O | HOH | Z | 45 | 2.704 | −3.500 | 0.992 | 1.00 | 25.13 O |
| ATOM | 1478 | O | HOH | Z | 46 | 2.826 | −1.554 | 1.772 | 1.00 | 32.13 O |
| ATOM | 1479 | O | HOH | Z | 47 | −5.682 | 11.211 | −0.359 | 1.00 | 25.76 O |
| ATOM | 1480 | O | HOH | Z | 48 | −4.127 | −5.680 | −0.140 | 1.00 | 32.87 O |
| ATOM | 1481 | O | HOH | Z | 49 | 0.270 | −2.172 | −5.395 | 1.00 | 28.65 O |
| ATOM | 1482 | O | HOH | Z | 50 | −2.450 | −1.603 | −5.615 | 1.00 | 31.17 O |
| ATOM | 1483 | O | HOH | Z | 51 | 3.268 | −18.749 | 6.483 | 1.00 | 21.70 O |
| ATOM | 1484 | O | HOH | Z | 52 | 2.161 | −21.956 | 8.428 | 1.00 | 31.44 O |
| ATOM | 1485 | O | HOH | Z | 53 | −1.571 | −18.172 | 6.694 | 1.00 | 17.34 O |
| ATOM | 1486 | O | HOH | Z | 54 | −0.249 | −18.135 | 5.433 | 1.00 | 29.65 O |
| ATOM | 1487 | O | HOH | Z | 55 | 2.971 | 2.171 | −6.016 | 1.00 | 23.51 O |
| ATOM | 1488 | O | HOH | Z | 56 | 7.729 | 11.463 | 5.016 | 1.00 | 17.76 O |
| ATOM | 1489 | O | HOH | Z | 57 | 12.155 | 18.376 | 1.959 | 1.00 | 26.19 O |
| ATOM | 1490 | O | HOH | Z | 58 | 12.594 | 17.158 | 5.114 | 1.00 | 31.33 O |
| ATOM | 1491 | O | HOH | Z | 59 | −1.569 | 11.596 | 18.927 | 1.00 | 16.57 O |
| ATOM | 1492 | O | HOH | Z | 60 | 7.579 | 9.928 | 14.909 | 1.00 | 15.76 O |
| ATOM | 1493 | O | HOH | Z | 61 | 19.744 | −0.867 | 13.120 | 1.00 | 18.17 O |

TABLE 2-continued

| ATOM | 1494 | O | HOH | Z | 62 | 8.707 | 10.237 | 18.525 | 1.00 | 17.38 | O |
|---|---|---|---|---|---|---|---|---|---|---|---|
| ATOM | 1495 | O | HOH | Z | 63 | 21.457 | 20.231 | −3.910 | 1.00 | 19.88 | O |
| ATOM | 1496 | O | HOH | Z | 64 | 11.940 | −14.538 | 15.403 | 1.00 | 19.32 | O |
| ATOM | 1497 | O | HOH | Z | 65 | −3.012 | 1.332 | 32.662 | 1.00 | 17.87 | O |
| ATOM | 1498 | O | HOH | Z | 66 | 2.933 | 13.528 | 10.444 | 1.00 | 18.09 | O |
| ATOM | 1499 | O | HOH | Z | 67 | 5.511 | 13.684 | 11.621 | 1.00 | 18.83 | O |
| ATOM | 1500 | O | HOH | Z | 68 | −0.341 | −6.697 | 26.164 | 1.00 | 22.76 | O |
| ATOM | 1501 | O | HOH | Z | 69 | 15.508 | 4.752 | 28.264 | 1.00 | 19.65 | O |
| ATOM | 1502 | O | HOH | Z | 70 | 9.568 | −16.322 | 9.992 | 1.00 | 22.23 | O |
| ATOM | 1503 | O | HOH | Z | 71 | 15.958 | 7.636 | 18.742 | 1.00 | 23.87 | O |
| ATOM | 1504 | O | HOH | Z | 72 | −6.783 | 0.200 | 18.310 | 1.00 | 21.13 | O |
| ATOM | 1505 | O | HOH | Z | 73 | 11.447 | 9.949 | 19.027 | 1.00 | 19.55 | O |
| ATOM | 1506 | O | HOH | Z | 74 | 23.144 | 10.431 | 0.689 | 1.00 | 23.34 | O |
| ATOM | 1507 | O | HOH | Z | 75 | −7.996 | 8.406 | 20.020 | 1.00 | 25.41 | O |
| ATOM | 1508 | O | HOH | Z | 76 | 2.608 | 3.969 | 31.316 | 1.00 | 26.88 | O |
| ATOM | 1509 | O | HOH | Z | 77 | 2.425 | −3.227 | 31.617 | 1.00 | 27.72 | O |
| ATOM | 1510 | O | HOH | Z | 78 | 17.254 | −8.666 | 3.011 | 1.00 | 25.39 | O |
| ATOM | 1511 | O | HOH | Z | 79 | 12.918 | −15.190 | −0.608 | 1.00 | 34.94 | O |
| ATOM | 1512 | O | HOH | Z | 80 | 12.067 | −17.714 | −1.315 | 1.00 | 32.30 | O |
| ATOM | 1513 | O | HOH | Z | 81 | −10.581 | 2.386 | 3.590 | 1.00 | 25.93 | O |
| ATOM | 1514 | O | HOH | Z | 82 | 9.735 | −14.832 | −4.003 | 1.00 | 32.53 | O |
| ATOM | 1515 | O | HOH | Z | 83 | 11.835 | −6.311 | −3.598 | 1.00 | 32.48 | O |
| ATOM | 1516 | O | HOH | Z | 84 | 8.689 | 11.909 | 16.333 | 1.00 | 23.24 | O |
| ATOM | 1517 | O | HOH | Z | 85 | −6.601 | −3.539 | 17.808 | 1.00 | 23.91 | O |
| ATOM | 1518 | O | HOH | Z | 86 | 17.879 | 3.999 | 27.428 | 1.00 | 28.73 | O |
| ATOM | 1519 | O | HOH | Z | 87 | 12.222 | −16.863 | 9.403 | 1.00 | 23.77 | O |
| ATOM | 1520 | O | HOH | Z | 88 | 5.867 | 8.517 | 27.830 | 1.00 | 26.11 | O |
| ATOM | 1521 | O | HOH | Z | 89 | 17.094 | 7.930 | 10.841 | 1.00 | 29.44 | O |
| ATOM | 1522 | O | HOH | Z | 90 | −8.791 | −1.299 | 17.296 | 1.00 | 26.69 | O |
| ATOM | 1523 | O | HOH | Z | 91 | 4.804 | 0.800 | 30.972 | 1.00 | 28.06 | O |
| ATOM | 1524 | O | HOH | Z | 92 | 3.461 | 15.172 | 13.591 | 1.00 | 26.08 | O |
| ATOM | 1525 | O | HOH | Z | 93 | −14.826 | 5.257 | 33.876 | 1.00 | 28.68 | O |
| ATOM | 1526 | O | HOH | Z | 94 | 10.358 | −15.459 | 13.503 | 1.00 | 27.42 | O |
| ATOM | 1527 | O | HOH | Z | 95 | 21.417 | 4.120 | 9.561 | 1.00 | 25.75 | O |
| ATOM | 1528 | O | HOH | Z | 96 | −1.574 | −17.006 | 13.344 | 1.00 | 27.33 | O |
| ATOM | 1529 | O | HOH | Z | 97 | 3.802 | −20.213 | 9.738 | 1.00 | 26.02 | O |
| ATOM | 1530 | O | HOH | Z | 98 | 4.687 | −10.827 | 24.294 | 1.00 | 27.00 | O |
| ATOM | 1531 | O | HOH | Z | 99 | 18.579 | −0.462 | 26.775 | 1.00 | 28.17 | O |
| ATOM | 1532 | O | HOH | Z | 100 | 9.226 | 4.998 | 32.035 | 1.00 | 26.92 | O |
| ATOM | 1533 | O | HOH | Z | 101 | −0.655 | 6.897 | 29.980 | 1.00 | 28.47 | O |
| ATOM | 1534 | O | HOH | Z | 102 | 6.947 | 10.853 | 20.750 | 1.00 | 25.28 | O |
| ATOM | 1535 | O | HOH | Z | 103 | 18.739 | −13.365 | 14.310 | 1.00 | 28.79 | O |
| ATOM | 1536 | O | HOH | Z | 104 | 1.875 | 6.190 | 29.907 | 1.00 | 28.27 | O |
| ATOM | 1537 | O | HOH | Z | 105 | 11.693 | 3.613 | 32.212 | 1.00 | 34.50 | O |
| ATOM | 1538 | O | HOH | Z | 106 | −10.191 | 6.741 | 34.392 | 1.00 | 29.28 | O |
| ATOM | 1539 | O | HOH | Z | 107 | −6.667 | 8.319 | 32.568 | 1.00 | 35.78 | O |
| ATOM | 1540 | O | HOH | Z | 108 | 22.107 | −0.247 | 11.857 | 1.00 | 35.64 | O |
| ATOM | 1541 | O | HOH | Z | 109 | 5.419 | 11.752 | 18.009 | 1.00 | 33.54 | O |
| ATOM | 1542 | O | HOH | Z | 110 | 18.317 | 4.725 | 18.913 | 1.00 | 28.26 | O |
| ATOM | 1543 | O | HOH | Z | 111 | −19.579 | 1.950 | 5.342 | 1.00 | 33.46 | O |
| ATOM | 1544 | O | HOH | Z | 112 | −0.971 | −9.842 | 17.992 | 1.00 | 26.85 | O |
| ATOM | 1545 | O | HOH | Z | 113 | 18.991 | 1.782 | 28.143 | 1.00 | 32.15 | O |
| ATOM | 1546 | O | HOH | Z | 114 | −8.447 | 10.667 | 8.833 | 1.00 | 31.09 | O |
| ATOM | 1547 | O | HOH | Z | 115 | −7.957 | −5.784 | 38.341 | 1.00 | 33.78 | O |
| ATOM | 1548 | O | HOH | Z | 116 | 23.481 | 8.252 | −0.900 | 1.00 | 31.21 | O |
| ATOM | 1549 | O | HOH | Z | 117 | 16.296 | −11.718 | 2.686 | 1.00 | 25.55 | O |
| ATOM | 1550 | O | HOH | Z | 118 | −8.089 | 6.124 | 32.836 | 1.00 | 33.27 | O |
| ATOM | 1551 | O | HOH | Z | 119 | −18.899 | 1.773 | 9.908 | 1.00 | 28.82 | O |
| ATOM | 1552 | O | HOH | Z | 120 | −4.891 | 11.134 | 22.878 | 1.00 | 34.04 | O |
| ATOM | 1553 | O | HOH | Z | 121 | −3.879 | −6.962 | −3.653 | 1.00 | 25.64 | O |
| ATOM | 1554 | O | HOH | Z | 122 | 6.294 | −5.334 | 27.716 | 1.00 | 32.59 | O |
| ATOM | 1555 | O | HOH | Z | 123 | 19.061 | −12.417 | 17.639 | 1.00 | 35.78 | O |
| ATOM | 1556 | O | HOH | Z | 124 | 3.653 | 8.065 | 29.157 | 1.00 | 31.42 | O |
| ATOM | 1557 | O | HOH | Z | 125 | 20.626 | −6.832 | 4.898 | 1.00 | 30.71 | O |
| ATOM | 1558 | O | HOH | Z | 126 | −4.089 | 15.494 | 11.914 | 1.00 | 37.36 | O |
| ATOM | 1559 | O | HOH | Z | 127 | −5.505 | −1.483 | 22.141 | 1.00 | 33.40 | O |
| ATOM | 1560 | O | HOH | Z | 128 | 13.760 | −7.726 | 25.645 | 1.00 | 43.49 | O |
| ATOM | 1561 | O | HOH | Z | 129 | 11.225 | 13.014 | 16.204 | 1.00 | 31.87 | O |
| ATOM | 1562 | O | HOH | Z | 130 | −10.901 | 1.977 | 13.994 | 1.00 | 31.78 | O |
| ATOM | 1563 | O | HOH | Z | 131 | −1.232 | 15.529 | 13.872 | 1.00 | 31.18 | O |
| ATOM | 1564 | O | HOH | Z | 132 | −8.158 | 1.006 | 23.180 | 1.00 | 33.63 | O |
| ATOM | 1565 | O | HOH | Z | 133 | 3.948 | −1.576 | 30.415 | 1.00 | 43.32 | O |
| ATOM | 1566 | O | HOH | Z | 134 | −7.606 | 6.346 | 3.782 | 1.00 | 37.67 | O |
| ATOM | 1567 | O | HOH | Z | 135 | 20.292 | −7.467 | 0.209 | 1.00 | 31.70 | O |
| ATOM | 1568 | O | HOH | Z | 136 | 20.357 | 7.828 | 26.267 | 1.00 | 35.06 | O |
| ATOM | 1569 | O | HOH | Z | 137 | 20.649 | −0.024 | 1.228 | 1.00 | 31.80 | O |
| ATOM | 1570 | O | HOH | Z | 138 | −0.771 | 10.384 | 23.630 | 1.00 | 32.99 | O |
| ATOM | 1571 | O | HOH | Z | 139 | 17.801 | −7.406 | 25.546 | 1.00 | 33.06 | O |
| ATOM | 1572 | O | HOH | Z | 140 | −4.102 | −2.547 | −0.245 | 1.00 | 32.75 | O |

TABLE 2-continued

| ATOM | 1573 | O | HOH | Z | 141 | −9.581 | −5.177 | 30.449 | 1.00 | 32.14 | O |
|------|------|---|-----|---|-----|--------|--------|--------|------|-------|---|
| ATOM | 1574 | O | HOH | Z | 142 | 5.765 | −21.459 | 11.112 | 1.00 | 32.28 | O |
| ATOM | 1575 | O | HOH | Z | 143 | −7.145 | −10.843 | 13.347 | 1.00 | 38.51 | O |
| END | | | | | | | | | | | |

REFERENCES

Bastola, D. R., Pahwa, G. S., Lin, M. F., and Cheng, P. W. (2002). Downregulation of PTEN/MMAC/TEP1 expression in human prostate cancer cell line DU145 by growth stimuli. Mol. Cell. Biochem. 236, 75-81.

Clark, R. D., Strizhev, A., Leonard, J. M., Blake, J. F., and Matthew, J. B. (2002). Consensus scoring for ligand/protein interactions. J. Mol. Graph. Model. 20, 281-295.

Del Pozo, M. A., Price, L. S., Alderson, N. B., Ren, X. D., and Schwartz, M. A. (2000). Adhesion to the extracellular matrix regulates the coupling of the small GTPase Rac to its effector PAK. EMBO J. 19, 2008-2014.

Engers, R., Zwaka, T. P., Gohr, L., Weber, A., Gerharz, C. D., and Gabbert, H. E. (2000). Tiam1 mutations in human renal-cell carcinomas. Int. J. Cancer 88, 369-376.

Etienne-Manneville, S. and Hall, A. (2002). Rho GTPases in cell biology. Nature 420, 629-635. Fritz, G., Just, I., and Kaina, B. (1999). Rho GTPases are over-expressed in human tumors. Int. J. Cancer 81, 682-687.

Gao, Y., Xing, J., Streuli, M. Leto, T. L., and Zheng, Y. (2001). Trp(56) of rac1 specifies interaction with a subset of guanine nucleotide exchange factors. J. Biol. Chem. 276, 47530-47541.

Gruneberg, S., Wendt, B., and Klebe, G. (2001). Subnanomolar Inhibitors from Computer Screening: A Model Study Using Human Carbonic Anhydrase II Agnew. Chem. Int. Ed Engl. 40, 389-393.

Guo, F., Gao, Y. Wang, L., and Zheng, Y. (2003). p19ARF-p53 tumor suppressor pathway regulates cell motility by suppression of PI3 kinase and Rac1 GTPase activities. J. Biol. Chem. paper in press.

Hawkins, P. T., Eguinoa, A., Qiu, R. G., Stokoe, D., Cooke, F. T., Walters, R., Wennsstrom, S., Claesson-Welsh, L., Evans, T., Symons, M., and Stephens, L. (1995). PDGF stimulates an increase in GTP-Rac via activation of phosphoinostitide 3-kinase. Curr. Biol. 5, 393-403.

Hurst, T. (1994). Flexible 3D searching: the directed tweak technique. J. Chem. Inf. Comput. Sci. 34, 190-196.

Kaighn, M. E., Narayan, K. S., Ohnuki, Y., Lechner, J. F., and Jones, L. W. (1979). Establishment and characterization of a human prostatic carcinoma cell line (PC-3). Invest Urol. 17, 16-23.

Kamai, T., Arai, K., Tsujii, T., Honda, M., and Yoshida, K. (2001). Overexpression of RhoA mRNA is associated with advanced stage in testicular germ cell tumour. BJU. Int. 87, 227-231.

Karnoub, A. E., Worthylake, D. K., Rossman, K. L., Pruitt, W. M., Campbell, S. L., Sondek, J., and Der, C. J. (2001). Molecular basis for Rac1 recognition by guanine nucleotide exchange factors. Nat. Struct. Biol. 8, 1037-1041.

Kato-Stankiewicz, J., Hakimi, I., Zhi, G., Zhang, J., Serebriiskii, I., Guo, L., Edamatsu, H., Koike, H., Menon, S., Eckl, R., Sakamuri, S., Lu, Y., Chen, Q., Agarwal, S., Baumbach, W. R., Golemis, E. A., Tamanoi, F. and Khazak, V. (2002). Inhibitors of Ras/Raf-1 interaction identified by two-hybrid screening revert Ras-dependent transformation phenotypes in human cancer cells. 99, 14398-13303.

Khosravi-Far, R., Solski, P. A., Clark, G. J., Kinch, M. S., and Der, C. J. (1995). Activation of Rac1, RhoA, and mitogen-activated protein kinases is required for Ras transformation. Mol. Cell Biol. 15, 6443-6453.

Lang, S. H., Hyde, C., Reid, I. N., Hitchcock, I. S., Hart, C. A., Bryden, A. A., Villette, J. M., Stower, M. J., and Maitland, N. J. (2002). Enhanced expression of vimentin in momtile prostate cell lines in poorly differentiated and metastatic prostate carcinoma. Prostate 52, 253-263.

Liliental, J., Moon, S. Y., Lesche, R., Mamillapalli, R., Li, D., Zheng, Y., Sun, H., and Wu, H. (2000). Genetic deletion of the Pten tumor suppressor gene promotes cell motility by activation of Rac1 and Cdc42 GTPases. Curr. Bio. 10, 401-404.

Mira, J. P., Bernard, V., Groffen, J., Sanders, L. C., and Knaus, U. G. (2000). Endogenous, Hyperactive Rac3 controls proliferation of breast cancer cells by a p21-activated kinase-dependent pathway. Proc. Natl. Acad. Sci. U.S.A 97, 185-189.

Movilla, N., Doseil, M., Zheng, Y., and Bustelo, X. R. (2001). How Vav proteins discriminate the GTPases Rac1 and RhoA from Cdc42. Oncogene 20, 8057-8065.

Murshudov, G. N., Vagin, A. A., and Dodson, E. J. (1997) Acta Crystallogr. Biol. Crystallogr. D53, 240-255

Otwinowski, Z. and Minor, W. (1997) Processing of X-ray Diffraction Data Collected in Oscillation Mode *Methods in Enzymology* 276, 307-326

Otwinowski, Z., Borek, D., Majewski, W., and Minor, W. (2003) Multiparametric scaling of diffraction intensities *Acta Crystallogr.* A59, 228-234

Perola, E., Xu, K., Kollmeyer, T. M., Kaufmann, S. H., Prendergast, F. G., and Pang, Y. P. (2000). Successful virtual screening of a chemical database for farnesyltransferase inhibitor leads. J. Med. Chem. 43, 401-408.

Qiu, R. G., Abo, A., McCormick, F., and Symons, M. (1997). Cdc42 regulates anchorage-independent growth and is necessary for Ras transformation. Mol. Cell Biol. 17, 3449-3458.

Rarey, M., Kramer, B., Lengauer, T., and Klebe, G. (1996). A fast flexible docking method using an incremental construction algorithm. J. Mol. Biol. 261, 470-489.

Ridley, A. J., Paterson, H. F., Johnston, C. L., Diekmann, D., and Hall, A. (1992). The small GTP-binding protein rac regulates growth factor-induced membrane ruffling. Cell 70, 401-410.

Sahai, E. (2002). Rho-GTPases and cancer. Nature Reviews Cancer 2, 133-142.

Schmidt, A. and Hall, A. (2002). Guanine nucleotide exchange factors for Rho GTPases: turning on the switch. Genes Dev. 16, 1587-1609.

Schmitz, A. A., Govek, E. E., Bottner, B., and Van Aelst, L. (2000). Rho GtPases: signaling, migration, and invasion. Exp. Cell Res. 261, 1-12.

Schnelzer, A., Prechtel, D., Knaus, U., Dehne, K., Gerhard, M., Graeff, H., Harbeck, N., Schmitt, M., and Lengyel, E. (2000). Rac1 in human breast cancer: overexpression, mutation analysis, and characterization of a new isoform, Rac1b. Oncogene 19, 3013-3020.

Stepan, V. M., Tatewaki, M., Matsushima, M., Dickinson, D. J., del Valle, J., and Todisco, A. (1999). Gastrin induces c-fos gene transcription via multiple signaling pathways. Am. J. Physiol 276, G415-G424.

Suwa, H., Ohshio, G., Imamura, T., Watanabe, G., Arii, S., Imamura, M., Narumiya, S., Hiai, H., and Fukumoto, M. (1998). Overexpression of the rhoC gene correlates with progression of ductal adenocarcinoma of the pancreas. Br. J. Cancer 77, 147-152.

Worthlake, D. K., Rossman, K. L., and Sondek, J. (2000). Crystal structure of Rac1 in complex with the guanine nucleotide exchange region of Tiam1. Nature 408, 682-688.

Zhen, Y. (2001). Dbl family guanine nucleotide exchange factors. Trends Biochem. Sci. 26, 724-732.

Zheng, Y., Olson, M. F., Hall, A., Cerione, R. A., and Toksoz, D. (1995). Direct involvement of the small GTP-binding protein Rho in Ibc oncogene function. J. Biol. Chem. 270, 9031-9034.

SEQUENCE LISTING

```
<160> NUMBER OF SEQ ID NOS: 1

<210> SEQ ID NO 1
<211> LENGTH: 192
<212> TYPE: PRT
<213> ORGANISM: Human

<400> SEQUENCE: 1

Met Gln Ala Ile Lys Cys Val Val Val Gly Asp Gly Ala Val Gly Lys
 1               5                  10                  15

Thr Cys Leu Leu Ile Ser Tyr Thr Thr Asn Ala Phe Pro Gly Glu Tyr
                20                  25                  30

Ile Pro Thr Val Phe Asp Asn Tyr Ser Ala Asn Val Met Val Asp Gly
            35                  40                  45

Lys Pro Val Asn Leu Gly Leu Trp Asp Thr Ala Gly Gln Glu Asp Tyr
        50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
                100                 105                 110

Val Gly Thr Lys Leu Asp Leu Arg Asp Asp Lys Asp Thr Ile Glu Lys
            115                 120                 125

Leu Lys Glu Lys Lys Leu Thr Pro Ile Thr Tyr Pro Gln Gly Leu Ala
        130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu
                180                 185                 190
```

Symons, M. (2000). Adhesion signaling: PAK meets Rac on solid ground. Curr. Biol. 10, R535-R537.

Vagin, A. A. & Teplyakov, A. (1997). *J. Appl. Cryst.* 30, 1022-1025.

Van Aelst, L. and D'Souza-Schorey, C. (1997). Rho GTPases and signaling networks. Genes Dev. 11, 2295-2322.

Waszkowycz, B. (2001). Large-scale virtual screening for discovering leads in the postgenomic era. IBM systems J. 40, 360-376.

Winn, M. D., Isupov, M. N., and Murshudov, G. N. (2001) Use of TLS parameters to model anisotropic displacements in macromolecular refinement *Acta Crystallogr. Biol. Crystallogr.* D57, 122-133

What is claimed is:

1. A method for selecting chemical entities with an increased probability of associating with:

a) a molecule or molecular complex comprising a binding pocket defined by the structure coordinates of all atoms of Rac-1 GTPase amino acids Trp-56, Lys-5, Val-7, Ser-71, Val-36, Tyr-64, Arg-68, and Pro-73, as provided in Table 1 or Table 2; or b) a homolog of said molecule or molecular complex, wherein said homolog comprises a binding pocket that has all atoms of Rac-1 GTPase amino acids Trp-56, Lys-5, Val-7, Ser-71, Val-36, Tyr-64, Arg-68, and Pro-73, where the backbone atom positions in said homolog have a root mean square deviation from the backbone atom positions of said amino acids in Table 1 or Table 2 of not more than about 1.5 Angstrom, the method comprising:

(i) generating, on a computer, a three dimensional structure of the binding pocket of the molecule or molecular complex or the binding pocket of said homolog thereof;

(ii) performing a fitting operation between a three dimensional structure of a chemical entity and the three dimensional structure of the binding pocket of the molecule or molecular complex or the binding pocket of said homolog thereof;

(iii) analyzing the results of said fitting operation to quantify the association between the chemical entity and the binding pocket of the molecule or molecular complex or the binding pocket of said homolog thereof, wherein said analyzed results are indicative of the potential of the chemical entity to associate with the molecule or molecular complex or said homolog thereof; and (iv) selecting for those chemical entities with an increased probability of associating with said molecule or molecular complex or said homolog thereof.

\* \* \* \* \*